US010208025B2

(12) United States Patent
Chow et al.

(10) Patent No.: US 10,208,025 B2
(45) Date of Patent: Feb. 19, 2019

(54) ALKYNE-, AZIDE- AND TRIAZOLE-CONTAINING FLAVONOIDS AS MODULATORS FOR MULTIDRUG RESISTANCE IN CANCERS

(71) Applicants: The Hong Kong Polytechnic University, Hong Kong (CN); McGill University, Montreal (CA)

(72) Inventors: Larry Ming Cheung Chow, Hong Kong (CN); Tak Hang Chan, Hong Kong (CN); Kin Fai Chan, Hong Kong (CN); Iris Lai King Wong, Hong Kong (CN); Man Chun Law, Hong Kong (CN)

(73) Assignees: The Hong Kong Polytechnic University, Kowloon (HK); The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 15/296,471

(22) Filed: Oct. 18, 2016

(65) Prior Publication Data
US 2017/0044141 A1    Feb. 16, 2017

Related U.S. Application Data

(62) Division of application No. 14/378,869, filed as application No. PCT/CN2013/072058 on Mar. 1, 2013, now Pat. No. 9,611,256.

(60) Provisional application No. 61/605,299, filed on Mar. 1, 2012.

(51) Int. Cl.
| C07D 311/30 | (2006.01) |
| C07D 311/32 | (2006.01) |
| C07D 405/14 | (2006.01) |
| C07D 405/12 | (2006.01) |
| A61K 47/55 | (2017.01) |

(52) U.S. Cl.
CPC ............ *C07D 405/14* (2013.01); *A61K 47/55* (2017.08); *C07D 311/30* (2013.01); *C07D 405/12* (2013.01)

(58) Field of Classification Search
CPC ............................ C07D 311/30; C07D 311/32
See application file for complete search history.

(56) References Cited

FOREIGN PATENT DOCUMENTS

| CN | 1371372 A | 9/2002 |
| CN | 101454305 A | 6/2009 |
| WO | 2011/137516 A1 | 11/2011 |

OTHER PUBLICATIONS

Peng, May 6, 2011, ACS Appl. Mater. Interfaces, vol. 3, p. 1713-1720.*
Gosse, Micelles of Lipid-Oligonucleotide Conjugates: Implications for Membrane Anchoring and Base Pairing, 2004, J. Phys. Chem. B, vol. 108, p. 6485-6497. (Year: 2004).*
Chavan et al, Synthesis and Medicinal Significance of Chalcones—A Review, 2016, Asian Journal of Biomedical and Pharmaceutical Sciences, vol. 6, No. 56, p. 1-7. (Year: 2016).*
Barnes et al., "Steroid Transport, Accumulation, and Antagonism of P-Glycoprotein in Multidrug-Resistant Cells," *Biochemistry* 35:4820-4827, 1996.
Boechat et al., "Novel 1,2,3-Triazole Derivatives for Use against *Mycobacterium tuberculosis* H37Rv (ATCC 27294) Strain," *Journal of Medicinal Chemistry* 54:5988-5999, 2011.
de Castro et al., "Effect of Grapefruit Juice, Naringin, Naringenin, and Bergamottin on the Intestinal Carrier-Mediated Transport of Talinolol in Rats," *J. Agric. Food Chem.* 56:4840-4845, 2008.
Castro et al., "Inhibition of Drug Transport by Genistein in Multidrug-Resistant Cells Expressing P-Glycoprotein," *Biochemical Pharmacology* 53:89-93, 1997.
Chan et al., "Flavonoid Dimers as Bivalent Modulators for P-Glycoprotein-Based Multidrug Resistance: Structure-Activity Relationships," *ChemMedChem* 4:594-614, 2009.
Chan et al., "Flavonoid Dimers as Bivalent Modulators for P-Glycoprotein-Based Multidrug Resistance: Synthetic Apigenin Homodimers Linked with Defined-Length Poly(ethylene glycol) Spacers Increase Drug Retention and Enhance Chemosensitivity in Resistant Cancer Cells," *J. Med. Chem* 49:6742-6759, 2006.

(Continued)

*Primary Examiner* — Rebecca L Anderson
*Assistant Examiner* — Karen Cheng
(74) *Attorney, Agent, or Firm* — Seed IP Law Group LLP

(57) ABSTRACT

A triazole bridged flavonoid dimer compound library was efficiently constructed via the cycloaddition reaction of a series of flavonoid-containing azides (Az 1-15) and alkynes (Ac 1-17). These triazole bridged flavonoid dimers and their precursor alkyne- and azide-containing flavonoids were screened for their ability to modulate multidrug resistance (MDR) in P-gp-overexpressed cell line (LCC6MDR), MRP1-overexpressed cell line (2008/MRP1) and BCRP-overexpressed cell line (HEK293/R2 and MCF7-MX100). Generally, they displayed very promising MDR reversal activity against P-gp-, MRP1- and BCRP-mediated drug resistance. Moreover, they showed different levels of selectivity for various transporters. Overall, they can be divided into mono-selective, dual-selective and multi-selective modulators for the P-gp, MRP1 and BCRP transporters. The $EC_{50}$ values for reversing paclitaxel resistance (141-340 nM) of LCC6MDR cells, DOX (78-590 nM) and vincristine (82-550 nM) resistance of 2008/MRP1 cells and topotecan resistance (0.9-135 nM) of HEK293/R2 and MCF7-MX100 cells were at nanomolar range. Importantly, a number of compounds displayed $EC_{50}$ at or below 10 nM in BCRP-overexpressed cell lines, indicating that these bivalent triazoles more selectively inhibit BCRP transporter than the P-gp and MRP1 transporters. Most of the dimers are notably safe MDR chemosensitizers as indicated by their high therapeutic index values.

9 Claims, 31 Drawing Sheets

(56) References Cited

OTHER PUBLICATIONS

Chao et al., "Modulation of Etoposide (VP-16) Cytotoxicity by Verapamil or Cyclosporine in Multidrug-resistant Human Leukemic Cell Lines and Normal Bone Marrow," *Exp. Hematol.* 18:1193-1198, 1990.
Cooray et al., "Interaction of the breast cancer resistance protein with plant polyphenols," *Biochemical and Biophysical Research Communications* 317:269-275, 2004.
Draper et al., "Indomethacin-mediated reversal of multidrug resistance and drug efflux in human and murine cell lines overexpressing MRP, but not P-glycoprotein," *British Journal of Cancer* 75(6):810-815, 1997.
Duffy et al., "Enhancement of Chemotherapeutic Drug Toxicity to Human Tumour Cells In Vitro by a Subset of Non-steroidal Anti-inflammatory Drugs (NSAIDs)," *European Journal of Cancer* 34(8):1250-1259, 1998.
Eckford et al., "Abc Efflux Pump-Based Resistance to Chemotherapy Drugs," *Chem. Rev.* 109:2989-3011, 2009.
Ganapathi et al., "Correlation between Potency of Calmodulin Inhibitors and Effects on Cellular Levels and Cytotoxic Activity on Doxorubicin (Adriamycin) in Resistant P388 Mouse Leukemia Cells," *Eur J Cancer Clin Oncol* 20(6):799-806, 1984.
Gekeler et al., "The Leukotriene $LTD_4$ Receptor Antagonist MK571 Specifically Modulates MRP Associated Multidrug Resistance," *Biochemical and Biophysical Research Communications* 208(1):345-352, 1995.
Germann et al., "Cellular and biochemical characterization of VX-710 as a chemosensitizer: reversal of P-glycoprotein-mediated multidrug resistance in vitro," *Anti-Cancer Drugs* 8:125-140, 1997.
Germann et al., "Chemosensitization and drug accumulation effects of VX-710, verapamil, cyclosporine A, MS-209 and GF120918 in multidrug resistant HL60/ADR cells expressing the multidrug resistance-associated protein MRP," *Anti-Cancer Drugs* 8:141-155, 1997.
Gollapudi et al., "Probenecid reverses multidrug resistance in multidrug resistance-associated protein-overexpressing HL60/AR and H69/AR cells but not in P-glycoprotein-overexpressing HL60/Tax and P388/ADR cells," *Cancer Chemother Pharmacol* 40:150-158, 1997.
Gros et al., "Mammalian Multidrug Resistance Gene: Complete cDNA Sequence Indicates Strong Homology to Bacterial Transport Proteins," *Cell* 47: 371-380, 1986.
Gruol et al., "Reversal of Multidrug Resistance by RU 486," *Cancer Research* 54:3088-3091, 1994.
Gujadhur et al., "Formation of aryl-nitrogen bonds using a soluble copper(I) catalyst," *Tetrahedron Letters* 42:4791-4793, 2001.
Harbome, "Nature, Distribution and Function of Plant Flavonoids," *Prog Clin Biol Red* 213:15-24, 1986.
Hipfner et al., "Membrane Topology of the Multidrug Resistance Protein (MRP)," *The Journal of Biological Chemistry* 272(38):23623-23630, 1997.
Hofman et al., "Reversal of multidrug resistance by B859-35, a metabolite of B859-35, niguldipine, verapamil and nitrendipine," *J Cancer Res Clin Oncol* 118:361-366, 1992.
Höllt et al., "Stereoisomers of Calcium Antagonists Which Differ Markedly in Their Potencies as Calcium Blockers Are Equally Effective in Modulating Drug Transport by P-Glycoprotein," *Biochemical Pharmacology* 43(12):2601-2608, 1992.
Honjo et al., "Acquired Mutations in the MXR/BCRP/ABCP Gene Alter Substrate Specificity in MXR/BCRP/ABCP-overexpressing Cells," *Cancer Research* 61:6635-6639, 2001.
Honorat et al., "Multidrug Resistance ABC Transporter Structure Predictions by Homology Modeling Approaches," *Current Drug Metabolism* 12, 268-277, 2011.
Imai et al., "Phytoestrogens/Flavonoids Reverse Breast Cancer Resistance Protein/ABCG2-Mediated Multidrug Resistance," *Cancer Research* 64:4346-4352, 2004.

Kast et al., "Epitome Insertion Favors a Six Transmembrane Domain Model for the Carboxy-Terminal Portion of the Multidrug Resistance-Associated Protein," *Biochemistry* 37:2305-2313, 1998.
Klepsch et al., "Pharmacoinformatic Approaches to Design Natural Product Type Ligands of ABC-Transporters," *Current Pharmaceutical Design* 16:1742-1752, 2010.
Krishna et al., "Multidrug resistance (MDR) in cancer Mechanisms, reversal using modulators of Mdr and the role of MDR modulators in influencing the pharmacokinetics of anticancer drugs," *European Journal of Pharmaceutical Sciences* 11:265-283, 2000.
Kühnle et al., "Potent and Selective Inhibitors of Breast Cancer Resistance Protein (ABCG2) Derived from the p-Glycoprotein (ABCB1) Modulator Tariquidar," *J. Med. Chem* 52:1190-1197, 2009.
Kumar et al., "Recognition of HIV TAR RNA by triazole linked neomycin dimers," *Bioorg Med Chem Lett.* 21(16):4788-4792, 2011.
Leslie et al., "Modulation of Multidrug Resistance Protein 1 (MRP1/ABCC1) Transport and ATPase Activities by Interaction with Dietary Flavonoids," *Molecular Pharmacology* 59(5):1171-1180, 2001.
Li et al., "Synthesis of potent BCRP inhibitor-Ko143," *Tetrahedron Letters* 49:1480-1483, 2008.
Limtrakul et al., "Inhibition of P-Glycoprotein Function and Expression by Kaempferol and Quercetin," *Journal of Chemotherapy* 17(1):86-95, 2005.
Lockhart et al., "Pharmacogenetics of ATP-binding Cassette Transporters in Cancer and Chemotherapy," *Molecular Cancer Therapeutics* 2:685-698, 2003.
Loo et al., "Determining the Dimensions of the Drug-binding Domain of Human P-glycoprotein Using Thiol Cross-linking Compounds as Molecular Rulers," *The Journal of Biological Chemistry* 276(40):36877-36880, 2001.
Mao et al., "Role of the Breast Cancer Resistance Protein (ABCG2) in Drug Transport," *The AAPS Journal* 7(1):E118-E133, 2005.
McDevitt et al., "How can we best use structural information on P-glycoprotein to design inhibitors?" *Pharmacology & Therapeutics* 113:429-441, 2007.
McDevitt et al., "Purification and 3D Structural Analysis of Oligomeric Human Multidrug Transporter ABCG2," *Structure* 14:1623-1632, 2006.
Mitsunaga et al., "Effect of bioflavonoids on vincristine transport across blood-brain barrier," *European Journal of Pharmacology* 395:193-201, 2000.
Nguyen et al,. "Effect of Flavonoids on MRP1-Mediated Transport in Panc-1 Cells," *Journal of Pharmaceutical Sciences* 92(2):250-257, 2003.
Payen et al., "The sulphonylurea glibenclamide inhibits multidrug resistance protein (MRP1) activity in human lung cancer cells," *British Journal of Pharmacology* 132:778-784, 2001.
Pérez-Tomás, "Multidrug Resistance: Retrospect and Prospects in Anti-Cancer Drug Treatment," *Current Medicinal Chemistry* 13: 1859-1876, 2006.
Pirker et al., "Enhancement of the Activity of Immunotoxins by Analogues of Verapamil," *Cancer Research* 49:4791-4795, 1989.
Polgar et al., "ABCG2: structure, function and role in drug response," *Expert Opinion on Drug Metabolism & Toxicology* 4(1):1-15, 2008.
Rajakumar et al., "Synthesis and Characterization of Some Novel Dendritic Architectures Bearing Chalcone at the Periphery Through Click Approach," *Synthetic Communications* 39: 3888-3897, 2009.
Rasmussen et al., "Ruthenium-Catalyzed Cycloaddition of Aryl Azides and Alkynes," *Organic Letters* 9(26):5337-5339, 2007.
Rosenberg et al., "Structure of the Multidrug Resistance P-glycoprotein to 2.5 nm Resolution Determined by Electron Microscopy and Image Analysis," *The Journal of Biological Chemistry* 272(16):10685-10694, 1997.
Saito et al., "Emerging New Technology: QSAR Analysis and MO Calculation to Characterize Interaction of Protein Kinase Inhibitors with the Human ABC Transporter, ABCG2 (BCRP)," *Drug Metab. Pharmacokinet.* 25(1):72-83, 2010.
Slater et al., "Cyclosporin a corrects daunorubicin resistance in Ehrlich ascites carcinoma," *Br. J. Cancer* 54:235-238, 1986.

(56) References Cited

OTHER PUBLICATIONS

Slater et al., "Cyclosporin A Reverses Vincristine and Daunorubicin Resistance in Acute Lymphatic Leukemia in Vitro," *J Clin. Invest.* 77:1405-1408, 1986.

Soenen et al., "Multidrug Resistance Reversal Activity of Key Ningalin Analogues," *Bioorganic & Medicinal Chemistry Letters* 13:1777-1791, 2003.

Szakacs et al., "Targeting multidrug resistance in cancer," *Nature Reviews* 5:219-234, 2006.

Tao et al., "Multidrug resistance reversal activity of permethyl ningalin B amide derivatives," *Bioorganic & Medicinal Chemistry Letters*, 14:5979-5981, 2004.

Thomas et al., "Overcoming Multidrug Resistance in Cancer: An Update on the Clinical Strategy of Inhibiting P-Glycoprotein," *Cancer Control* 10(2):159-165, 2003.

Tsuruo et al., "Circumvention of Vincristine and Adriamycin Resistance in Vitro and in Vivo by Calcium Influx Blockers," *Cancer Research* 43:2905-2910, 1983.

Tsuruo et al., "Effects of Quinidine and Related Compounds on Cytotoxicity and Cellular Accumulation of Vincristine and Adriamycin in Drug-resistant Tumor Cells," *Cancer Research* 44:4303-4307, 1984.

Tsuruo., "Increased Accumulation of Vincristine and Adriamycin in Drug-resistant P388 Tumor Cells following Incubation with Calcium Antagonists and Calmodulin Inhibitors," *Cancer Research* 42:4730-4733, 1982.

Tsuruo et al., "Overcoming of Vincristine Resistance in P388 Leukemia in Vivo and in Vitro through Enhanced Cytotoxicity in Vincristine and Vinblastine by Verapamil," *Cancer Research* 41:1967-1972, 1981.

Twentyman et al., "Cyclosporin A and its analogues as modifiers of adriamycin and vincristine resistance in a multi-drug resistant human lung cancer cell line," *Br. J. Cancer* 56:55-57, 1987.

Twentyman et al., "Resistance Modification by PSC-833, a Novel Non-immunosuppressive Cyclosporin A," *Eur J Cancer* 27(12):1639-1642, 1991.

Ueda et al., "Human P-glycoprotein Transports Cortisol, Aldosterone, and Dexamethasone, but Not Progesterone," *The Journal of Biological Chemistry* 267(34):24248-24252, 1992.

Wang et al., "N-(4-[2-(1,2,3,4-Tetrahydro-6, 7-dimethoxy-2-isoquinolinypethyl]-phenyl)-9, 10-dihydro-5-methoxy-9-oxo-4-acridine Carboxamide (GF120918) as a Chemical ATP-Binding Cassette Transporter Family G Member 2 (Abcg2) Knockout Model to Study Nitrofurantoin Transfer into Milk," *Drug Metabolism and Disposition* 36(12):2591-2596, 2008.

Wängler et al., "DOTA derivatives for site-specific biomolecule-modification via click chemistry: Synthesis and comparison of reaction characteristics," *Bioorganic & Medicinal Chemistry* 19:3864-3874, 2011.

Wong et al., "Flavonoid Dimers as Bivalent Modulators for Pentamidine and Sodium Stiboglucanate Resistance in *Leishmania*," *Antimicrobial Agents and Chemotherapy* 51(3):930-940, 2007.

Wong et al,. "Modulation of Multidrug Resistance Protein 1 (MRP1/ABCC1)-Mediated Multidrug Resistance by Bivalent Apigenin Homodimers and Their Derivatives," *J. Med. Chem* 52:5311-5322, 2009.

Wong et al., "Quinacrine and a novel apigenin dimer can synergistically increase the pentamidine susceptibility of the protozoan parasite *Leishmania*," *Journal of Antimicrobial Chemotherapy* 63:1179-1190, 2009.

Xu et al., "Characterization of Oligomeric Human Half-ABC Transporter ATP-binding Cassette G2," *Journal of Biological Chemistry* 279(19): 19781-19789, 2004.

Yoshikawa et al., "Transport of SN-38 by the Wild Type of Human ABC Transporter ABCG2 and Its Inhibition by Quercetin, a Natural Flavonoid," *Journal of Experimental Therapeutics and Oncology* 4, 25-35, 2004.

van Zanden et al., "Quantitative structure activity relationship studies on the flavonoid mediated inhibition of multidrug resistance proteins 1 and 2," *Biochemical Pharmacology* 69:699-708, 2005.

Zhang et al., "Design and Syntheses of Permethyl Ningalin B Analogues: Potent Multidrug Resistance (MDR) Reversal Agents of Cancer Cells," *J. Med. Chem.* 53:5108-5120, 2010.

Zhang et al,. "Effect of the Flavonoids Biochanin A and Silymarin on the P-Glycoprotein-Mediated Transport of Digoxin and Vinblastine in Human Intestinal Caco-2 Cells," *Pharmaceutical Research* 20(8):1184-1191, 2003.

Zhang et al., "Flavonoids Are Inhibitors of Breast Cancer Resistance Protein (ABCG2)-Mediated Transport," *Molecular Pharmacology* 65(5):1208-1216, 2004.

Zhang et al., "Interactions Between the Flavonoid Biochanin A and P-Glycoprotein Substrates in Rats: In Vitro and In Vivo" *Journal of Pharmaceutical Sciences* 99(1):430-441, 2010.

Zhang et al., "Ruthenium-Catalyzed Cycloaddition of Alkynes and Organic Azides," *J. Am. Chem. Soc.* 127:15998-15999, 2005.

Zhang et al., "Synthesis of novel 6-triazologlycolipids via click chemistry and their preliminary cytotoxicity assessments," *Mol Divers* 15:889-900, 2011.

\* cited by examiner

Table 1

| Groups | Compounds[a] | Cytotoxicity (IC$_{50}$, mM) | | | | | MDR reversal activity of triazole compounds | | | | | | | | | | | | |
|---|---|---|---|---|---|---|---|---|---|---|---|---|---|---|---|---|---|---|---|
| | | LCC6 | LCC6MDR | 2008/P | 2008/MRP1 | L929 | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
| | | | | | | | IC$_{50}$ of paclitaxel (nM)[b] | RF[b] | (% of reversion)[b] | IC$_{50}$ of paclitaxel (nM)[c] | RF[c] | (% of reversion)[c] | IC$_{50}$ of DOX (nM)[b] | RF[b] | (% of reversion)[b] | IC$_{50}$ of vincristine (nM)[b] | RF[b] | (% of reversion)[b] | IC$_{50}$ of topotecan (nM)[b] | RF[b] | (% of reversion)[b] | IC$_{50}$ of topotecan (μM)[b] | RF[b] | (% of reversion)[b] |
| A[d] | Ac1 | >100 | >72 | ND | ND | >100 | 161.5 | 1.0 | (1.0) | 237.3 | 0.7 | (0.7) | 362.6±19.5 | 1.2 | (13.8) | ND | ND | ND | 107.9±13.0 | 4.7 | (14.6) | 7.0±0.1 | 4.8 | (4.6) |
| | Ac2 | >100 | >54 | ND | ND | >100 | 239.1 | 0.7 | (0.7) | 274.7 | 0.6 | (0.6) | 332.5±42.5 | 1.3 | (15.1) | ND | ND | ND | 135.2±16.5 | 3.8 | (11.7) | 7.0±0.9 | 4.8 | (4.6) |
| | Ac3 | >100 | >91 | ND | ND | >100 | 221.6 | 0.7 | (0.7) | 267.7 | 0.6 | (0.6) | 301.3±16.9 | 1.4 | (16.6) | ND | ND | ND | 59.7±1.4 | 8.5 | (26.5) | 2.8±0.5 | 11.9 | (11.4) |
| | Ac4 | >100 | >77 | ND | ND | >81 | 10.9±2.8 | 14.6 | (14.7) | 37.9 | 4.2 | (4.2) | 244.4±23.7 | 1.7 | (20.5) | ND | ND | ND | 37.5±3.6 | 13.5 | (42.1) | 1.1±0.2 | 30.4 | (29.1) |
| | Ac5 | ND | ND | ND | ND | ND | 174.9±21.7 | 0.9 | (0.9) | 187.5 | 0.8 | (0.9) | 368.8±178.7 | 1.1 | (13.6) | ND | ND | ND | 134.9±3.8 | 3.8 | (11.7) | ND | ND | ND |
| | Ac11 | >100 | >100 | ND | ND | >100 | 124.9±6.5 | 1.3 | (1.3) | ND | ND | ND | 380.4±6.3 | 1.1 | (13.2) | ND | ND | ND | 562.2±0.9 | 0.9 | (2.8) | 19.5±6.5 | 1.7 | (1.6) |

FIG. 1A

Table 1 (continued)

MDR reversal activity of triazole compounds

| Groups | Compounds[a] | Cytotoxicity (IC₅₀, mM) | | | | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
|---|---|---|---|---|---|---|---|---|---|---|---|---|---|---|---|---|---|---|---|---|---|---|---|
| | | LCC6 | LCC6MDR | 2008/P | 2008/MRP1 | L929 | IC₅₀ of paclitaxel (nM)[b] | RF[b] | (% of reversion)[b] | IC₅₀ of paclitaxel (nM)[c] | RF[c] | (% of reversion)[c] | IC₅₀ of DOX (nM)[b] | RF[b] | (% of reversion)[b] | IC₅₀ of vincristine (nM)[b] | RF[b] | (% of reversion)[b] | IC₅₀ of topotecan (μM)[b] | RF[b] | (% of reversion)[b] | IC₅₀ of topotecan (μM)[b] | RF[b] | (% of reversion)[b] |
| A[d] (cont'd) | Ac12 | >100 | >100 | >100 | >100 | >88 | 107.1 ± 0.9 | 1.5 | (1.5) | 129.0 ± 23.9 | 1.2 | (1.2) | 498.7 ± 76.4 | 0.8 | (10.0) | ND | ND | ND | 194.2 ± 2.6 | | (8.1) | ND | ND | ND |
| | Ac13 | 49.4 ± 16.1 | 54.8 ± 14.1 | 47.6 ± 8.0 | 56.0 ± 7.5 | 32.2 ± 5.2 | 74.8 ± 20.3 | 2.1 | (2.1) | 112.8 ± 35.6 | 1.4 | (1.4) | 561.2 ± 57.4 | 0.7 | (8.9) | ND | ND | ND | 131.8 ± 3.9 | | (12.0) | ND | ND | ND |
| | Ac16 | 53.8 ± 6.5 | 55.0 ± 9.7 | 62.7 ± 10.0 | 80.7 ± 1.5 | 58.2 ± 14.5 | 74.2 ± 8.1 | 2.1 | (2.2) | 110.6 ± 1.7 | 1.4 | (1.4) | 380.6 ± 109.5 | 1.1 | (13.2) | ND | ND | ND | 184.5 ± 17.7 | 2.8 | (8.6) | 6.5 | 5.1 | (4.9) |
| | Az1 | 74.2 ± 13.9 | 32.3 ± 6.1 | ND | ND | 8.9 ± 5.1 | 94.0 | 1.7 | (1.7) | 165.1 | 1.0 | (1.0) | 297.8 ± 17.2 | 1.4 | (16.8) | ND | ND | ND | 106.0 ± 13.7 | 4.8 | (14.9) | 5.4 ± 0.5 | 6.2 | (4.9) |
| B[d] | Az2 | 57.0 ± 17.8 | 39.9 | ND | ND | >33 | 32.7 | 4.9 | (4.9) | ND | ND | ND | 287.9 ± 110.9 | 1.5 | (17.4) | ND | ND | ND | 59.2 ± 6.2 | 8.6 | (26.7) | ND | ND | ND |
| | Az3 | 30.2 ± 0.3 | 18.1 | ND | ND | >33 | 23.6 | 6.7 | (6.8) | ND | ND | ND | 279.4 ± 105.2 | 1.5 | (17.9) | ND | ND | ND | 67.7 ± 1.4 | 7.5 | (23.3) | ND | ND | ND |

FIG. 1B

Table 1 (continued)

| Groups | Compounds[a] | Cytotoxicity (IC50, mM) | | | | | MDR reversal activity of triazole compounds | | | | | | | | | | | | | | |
|---|---|---|---|---|---|---|---|---|---|---|---|---|---|---|---|---|---|---|---|---|---|
| | | LCC6 | LCC6MDR | 2008/P | 2008/MRP1 | L929 | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
| | | | | | | | IC50 of paclitaxel (nM)[b] | RF[b] | (% of reversion)[b] | IC50 of paclitaxel (nM)[c] | RF[c] | (% of reversion)[c] | IC50 of DOX (nM)[b] | RF[b] | (% of reversion)[b] | IC50 of vincristine (nM)[b] | RF[b] | (% of reversion)[b] | IC50 of topotecan (nM)[b] | RF[b] | (% of reversion)[b] | IC50 of topotecan (μM)[b] | RF[b] | (% of reversion)[b] |
| B[d] (cont'd) | Az4 | 43.7 | 38.7 | ND | ND | 12.4 | 24.3 | 6.5 | (6.6) | ND | ND | ND | 329.2 ±96.4 | 1.3 | (15.2) | ND | ND | ND | 43.1 ±1.6 | 11.8 | (36.7) | ND | ND | ND |
| | Az5 | ND | ND | ND | ND | ND | 6.6 | 24.0 | (24.2) | ND | ND | ND | 176.6 ±59.8 | 2.4 | (28.4) | ND | ND | ND | 27.7 ±6.9 | 18.3 | (57.0) | ND | ND | ND |
| | Az6 | ND | ND | ND | ND | ND | 16.1 | 9.9 | (9.9) | ND | ND | ND | 260.6 ± 101.9 | 1.6 | (19.2) | ND | ND | ND | 30.0 ±6.2 | 16.9 | (52.7) | ND | ND | ND |
| | Az7 | ND | ND | ND | ND | ND | ND | ND | ND | ND | ND | ND | 385.9 ±97.2 | 1.1 | (13.0) | ND | ND | ND | 63.2 ±4.5 | 8.0 | (25.0) | ND | ND | ND |
| | Az8 | >100 | >100 | ND | ND | 67.5 | 63.1 | 2.5 | (2.5) | ND | ND | ND | 376.4 ± 136.8 | 1.1 | (13.3) | ND | ND | ND | 20.9 ±1.9 | 24.3 | (75.6) | 1.8± 0.5 | 18.6 | (17.8) |
| | Az9 | 32.4 | 34.8 | ND | ND | 20.6 | 7.3 | 21.7 | (21.9) | ND | ND | ND | 207.7 ±89.9 | 2.0 | (24.1) | ND | ND | ND | 15.8 ±1.4 | 32.2 | (100.0) | 0.7± 0.3 | 47.7 | (45.7) |
| | Az10 | >100 | 82.0 | ND | ND | 51.0 | 7.8 | 20.3 | (20.5) | ND | ND | ND | 187.3 ±79.1 | 2.2 | (26.7) | ND | ND | ND | 22.7 ±2.4 | 22.4 | (69.6) | 1.4± 0.6 | 23.9 | (22.9) |

FIG. 1C

Table 1 (continued)

| Groups | Compounds[a] | Cytotoxicity (IC₅₀, mM) | | | | | MDR reversal activity of triazole compounds | | | | | | | | | | | | |
|---|---|---|---|---|---|---|---|---|---|---|---|---|---|---|---|---|---|---|---|
| | | LCC6 | LCC6MDR | 2008/P | 2008/MRP1 | L929 | Pgp-overexpressed LCC6MDR | | | Pgp-overexpressed LCC6MDR | | | MRP1-overexpressed 2008/MRP1 | | | MRP1-overexpressed 2008/MRP1 | | BCRP-overexpressed HEK293/R2 | | | BCRP-overexpressed MCF7-MX100 | | |
| | | | | | | | IC₅₀ of paclitaxel (nM)[b] | RF[b] | (% of reversion)[b] | IC₅₀ of paclitaxel (nM)[c] | RF[c] | (% of reversion)[c] | IC₅₀ of DOX (nM)[b] | RF[b] | (% of reversion)[b] | IC₅₀ of vincristine (nM)[b] | RF[b] | (% of reversion)[b] | IC₅₀ of topotecan (nM)[b] | RF[b] | (% of reversion)[b] | IC₅₀ of topotecan (μM)[b] | RF[b] | (% of reversion)[b] |
| B[d] (cont'd) | Az11 | >66 | >63 | 54.7±1.8 | 53.6±10.6 | >48 | 107.2±10.2 | 1.5 | (1.5) | 141.6 | 1.1 | (1.1) | 353.2±124.9 | 1.2 | (14.2) | ND | ND | ND | 54.2±4.6 | 9.4 | (29.2) | ND | ND | ND |
| | Az12 | 75.6±6.4 | >62 | >77 | >72 | >49 | 67.0±4.3 | 2.4 | (2.4) | 90.7 | 1.7 | (1.8) | 358.1±143.8 | 1.2 | (14.0) | ND | ND | ND | 46.4±6.3 | 11.0 | (34.1) | ND | ND | ND |
| C | Ac1Az1 | >100 | >69 | ND | ND | 60.2±16.3 | 5.0±1.0 | 31.7 | (32.0) | 13.5±1.0 | 11.8 | (11.9) | 54.3±7.7 | 7.7 | (92.3) | ND | ND | ND | 23.1±6.1 | 22.0 | (68.4) | 0.9±0.1 | 37.1 | (35.6) |
| | Ac2Az1 | >100 | >81 | ND | ND | >100 | 8.3±1.1 | 19.1 | (19.3) | 34.4±0.1 | 4.6 | (4.7) | 30.9±1.3 | 13.6 | (162.1) | ND | ND | ND | 32.0±11.3 | 15.9 | (49.4) | 1.4±0.5 | 23.9 | (22.9) |
| | Ac3Az1 | >100 | >79 | ND | ND | >100 | 2.5±0.5 | 63.5 | (64.0) | 9.7±1.3 | 16.4 | (16.5) | 43.7±2.7 | 9.6 | (114.6) | ND | ND | ND | 24.1±9.5 | 21.1 | (65.6) | 0.6±0.1 | 55.7 | (53.3) |
| | Ac4Az1 | 1.3±0.2 | 2.3±0.7 | ND | ND | 1.1±0.1 | 4.4±1.1 | 36.1 | (36.4) | 46.2±10.1 | 3.4 | (3.5) | 108.9±3.9 | 3.9 | (46.0) | ND | ND | ND | 36.1±12.6 | 14.1 | (43.6) | 1.4±0.4 | 23.9 | (22.9) |
| | Ac4(5OH)Az1 | >100 | >77 | ND | ND | >100 | 4.4±1.2 | 36.1 | (36.4) | 14.9±2.9 | 10.7 | (10.7) | 47.8±0.6 | 8.8 | (104.8) | ND | ND | ND | 21.3±4.4 | 23.9 | (74.2) | 0.8±0.2 | 41.8 | (40.0) |

FIG. 1D

Table 1 (continued)

| Groups | Compounds[a] | Cytotoxicity (IC₅₀, mM) | | | | | MDR reversal activity of triazole compounds | | | | | | | | | | | |
|---|---|---|---|---|---|---|---|---|---|---|---|---|---|---|---|---|---|---|
| | | | | | | | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
| | | LCC6 | LCC6MDR | 2008/P | 2008/MRP1 | L929 | IC₅₀ of paclitaxel (nM)[b] | RF[b] | (% of reversion)[b] | IC₅₀ of paclitaxel (nM)[c] | RF[c] | (% of reversion)[c] | IC₅₀ of DOX (nM)[b] | RF[b] | (% of reversion)[b] | IC₅₀ of vincristine (nM)[b] | RF[b] | (% of reversion)[b] | IC₅₀ of topotecan (nM)[b] | RF[b] | (% of reversion)[b] | IC₅₀ of topotecan (nM)[b] | RF[b] | (% of reversion)[b] |
| C (cont'd) | Ac6Az1 | >100 | >100 | ND | ND | >100 | 3.7±0.3 | 42.9 | (43.2) | 14.8±3.1 | 10.7 | (10.8) | 116.7±7.8 | 3.6 | (42.9) | ND | ND | ND | 33.2±6.8 | 15.3 | (47.6) | 2.3±1.1 | 14.5 | (13.9) |
| | Ac7Az1 | >100 | >100 | ND | ND | >100 | 2.9±0.2 | 54.7 | (55.2) | 17.7±3.1 | 9.0 | (9.0) | 114.6±4.8 | 3.7 | (43.7) | ND | ND | ND | 40.5±4.6 | 12.5 | (39.0) | 3.3±1.6 | 10.1 | (9.7) |
| | Ac8Az1 | >100 | >100 | ND | ND | >100 | 56.5±11.1 | 2.8 | (2.8) | 74.8 | 2.1 | (2.1) | 95.4±6.7 | 4.4 | (52.5) | ND | ND | ND | 59.4±9.2 | 8.6 | (26.6) | 9.9±6.0 | 3.4 | (3.2) |
| | Ac9Az1 | 8.9±1.3 | 6.5±1.5 | ND | ND | >68 | 4.7±0.2 | 33.8 | (34.0) | 21.1±6.0 | 7.5 | (7.6) | 136.4±1.9 | 3.1 | (36.7) | ND | ND | ND | 36.8±6.5 | 13.8 | (42.9) | 2.0±0.6 | 16.7 | (16.0) |
| | Ac10Az1 | >33 | >33 | ND | ND | >100 | 5.2±0.1 | 30.5 | (30.8) | 19.4±6.5 | 8.2 | (8.2) | 91.4±8.6 | 4.6 | (54.8) | ND | ND | ND | 31.3±6.1 | 16.2 | (50.5) | 1.8±0.6 | 18.6 | (17.8) |
| | Ac11Az1 | >100 | >73 | ND | ND | >100 | 133.6±30.0 | 1.2 | (1.4) | 115.7±14.9 | 1.4 | (1.4) | 162.5±17.3 | 2.6 | (30.8) | ND | ND | ND | 23.9±5.9 | 21.3 | (66.1) | 1.1±0.2 | 30.4 | (29.1) |
| | Ac11Az2 | 2.7±0.4 | 3.4±0.2 | 2.8±0.2 | 3.4±0.5 | 2.5±0.3 | 95.7±11.2 | 1.7 | (1.7) | 140.8±17.0 | 1.1 | (1.1) | 320.6±23.8 | 1.3 | (15.6) | ND | ND | ND | 49.4±1.5 | 10.3 | (48.6) | ND | ND | ND |

FIG. 1E

Table 1 (continued)

| Groups | Compounds[a] | Cytotoxicity (IC$_{50}$, nM) | | | | | MDR reversal activity of triazole compounds | | | | | | | | | | | |
|---|---|---|---|---|---|---|---|---|---|---|---|---|---|---|---|---|---|---|
| | | | | | | | Pgp-overexpressed LCC6MDR | | | Pgp-overexpressed LCC6MDR | | | MRP1-overexpressed 2008/MRP1 | | | BCRP-overexpressed HEK293/R2 | | BCRP-overexpressed MCF7-MX100 |
| | | LCC6 | LCC6MDR | 2008/P | 2008/MRP1 | L929 | IC$_{50}$ of paclitaxel (nM)[b] | RF[b] | (% of reversion)[b] | IC$_{50}$ of paclitaxel (nM)[c] | RF[c] | (% of reversion)[c] | IC$_{50}$ of DOX (nM)[b] | RF[b] | (% of reversion)[b] | IC$_{50}$ of vincristine (nM)[b] | RF[b] | (% of reversion)[b] | IC$_{50}$ of topotecan (nM)[b] | RF[b] | (% of reversion)[b] |

Full data rows:

| Group | Compound | LCC6 | LCC6MDR | 2008/P | 2008/MRP1 | L929 | Pacl LCC6MDR IC50 | RF | %rev | Pacl Pgp IC50 | RF | %rev | DOX MRP1 IC50 | RF | %rev | Vincr MRP1 IC50 | RF | %rev | Topo HEK293/R2 IC50 | RF | %rev | Topo MCF7-MX100 IC50 | RF | %rev |
|---|---|---|---|---|---|---|---|---|---|---|---|---|---|---|---|---|---|---|---|---|---|---|---|---|
| C (cont'd) | Ac14Az1 | >11 | >100 | >100 | >100 | >100 | 145.8±11.0 | 1.1 | (1.1) | 140.1±13.0 | 1.1 | (1.1) | 420.2±143.1 | 1.0 | (11.9) | ND | ND | ND | 576.2±90.9 | 0.9 | (2.7) | 6.8 | 4.9 | (4.7) |
| D | Ac5Az1 syn | >100 | >100 | >100 | >100 | >57 | 2.3±0.2 | 69.0 | (69.6) | 9.9±0.1 | 16.0 | (16.2) | 104.9±14.7 | 4.0 | (47.8) | 42.6±7.0 | 2.9 | (118.5) | 47.9±1.8 | 10.6 | (33.0) | ND | ND | ND |
| D | Ac5Az2 | 2.7±0.5 | 6.7±0.2 | 5.5±2.9 | 8.7±3.0 | >50 | 5.2±0.9 | 30.5 | (30.8) | 29.2±10.5 | 5.4 | (5.5) | 114.0 | 3.7 | (43.9) | 25.7 | 4.8 | (196.5) | 43.9±2.8 | 11.6 | (36.0) | ND | ND | ND |
| D | Ac5Az2 syn | >100 | >100 | 81.5±3.3 | >100 | >50 | 3.3±0.6 | 48.1 | (48.5) | 23.1±0.4 | 6.9 | (6.9) | 66.9±8.9 | 6.3 | (74.9) | 13.9±1.1 | 8.9 | (363.3) | 37.5±1.9 | 13.5 | (42.1) | ND | ND | ND |
| D | Ac5Az3 | >100 | >100 | >100 | >100 | >50 | 52.6±17.7 | 3.0 | (3.0) | 101.0±20.0 | 1.6 | (1.6) | 158.6 | 2.6 | (31.6) | 28.3 | 4.4 | (178.4) | 54.4±2.5 | 9.3 | (29.0) | ND | ND | ND |
| D | Ac5Az4 | >100 | >100 | >100 | >100 | >50 | 2.7±0.7 | 58.8 | (59.3) | 19.8±0.5 | 8.0 | (8.1) | 93.0±14.4 | 4.5 | (53.9) | 17.6±0.1 | 7.0 | (286.9) | 41.5±2.1 | 12.2 | (38.1) | ND | ND | ND |
| D | Ac5Az4 | >100 | >100 | >100 | >100 | >100 | 1.6±0.3 | 99.2 | (100.0) | 8.2±1.7 | 19.4 | (19.5) | 52.3±4.8 | 8.0 | (95.8) | 6.5±0.3 | 19.0 | (776.9) | 28.8±3.7 | 17.6 | (54.9) | ND | ND | ND |

FIG. 1F

Table 1 (continued)

| Groups | Compounds[a] | Cytotoxicity (IC50, mM) | | | | | MDR reversal activity of triazole compounds | | | | | | | | | | | | | | |
|---|---|---|---|---|---|---|---|---|---|---|---|---|---|---|---|---|---|---|---|---|---|
| | | | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293R2 | | | BCRP-overexpressed MCF7-MX100 | | |
| | | LCC6 | LCC6MDR | 2008/P | 2008/MRP1 | L929 | IC50 of paclitaxel (nM)[b] | RF[b] | (% of reversion)[b] | IC50 of paclitaxel (nM)[c] | RF[c] | (% of reversion)[c] | IC50 of DOX (nM)[b] | RF[b] | (% of reversion)[b] | IC50 of vincristine (nM)[b] | RF[b] | (% of reversion)[b] | IC50 of topotecan (nM)[b] | RF[b] | (% of reversion)[b] | IC50 of topotecan (μM)[b] | RF[b] | (% of reversion)[b] |
| D (cont'd) | Ac5Az5 | >50 | >80 | >100 | >100 | >100 | 1.6±0.3 | 99.2 | (100.0) | 58.1±14.0 | 2.7 | (2.8) | 164.9±10.3 | 2.5 | (30.4) | 28.2±0.2 | 4.4 | (179.1) | 22.9±0.3 | 22.2 | (69.0) | ND | ND | ND |
| | Ac5Az5 OH | 1.4±0.3 | 1.5±0.3 | 5.4±1.4 | 6.0±0.7 | 2.4±0.2 | 3.5±1.0 | 45.3 | (45.7) | 9.5±4.6 | 16.7 | (16.8) | 177.1±2.9 | 2.4 | (28.3) | 37.9±8.6 | 3.3 | (133.2) | 98.7±39.3 | 5.1 | (16.0) | ND | ND | ND |
| | Ac5Az6 | >100 | >100 | >100 | >100 | >100 | 81.6±29.7 | 1.9 | (2.0) | 128.5±23.7 | 1.2 | (1.2) | 371.5±22.1 | 1.1 | (13.5) | 185.1±18.4 | 0.7 | (27.3) | 414.0±49.6 | 1.2 | (3.8) | ND | ND | ND |
| | Ac5Az7 | >100 | >100 | >100 | >100 | >100 | 1.6±0.2 | 99.2 | (100.0) | 6.3±0.1 | 25.2 | (25.4) | 50.4±4.9 | 8.3 | (99.4) | 47.1±14.0 | 2.6 | (107.2) | 32.0±5.8 | 15.9 | (49.4) | ND | ND | ND |
| | Ac5Az8 | >100 | >100 | >50 | >50 | >100 | 1.7±0.4 | 93.4 | (94.1) | 54.5±20.0 | 2.9 | (2.9) | 128.0±35.2 | 3.3 | (39.1) | 28.7±5.2 | 4.3 | (174.6) | 26.6±4.4 | 19.1 | (59.4) | 0.5±0.1 | 66.8 | (64.0) |
| | Ac5Az9 | >100 | >100 | >50 | >50 | >100 | 1.4±0.1 | 113.4 | (114.3) | 24.6±5.9 | 6.5 | (6.5) | 88.0±18.1 | 4.8 | (56.9) | 27.8±5.3 | 4.4 | (181.7) | 25.0 | 20.3 | (63.2) | 0.5±0.0 | 66.8 | (64.0) |
| | Ac5Az10 | >100 | >100 | >100 | >100 | >100 | 7.9±0.1 | 20.1 | (20.3) | 87.6±11.8 | 1.8 | (1.8) | 258.9±12.4 | 1.6 | (19.4) | 55.3±8.0 | 2.2 | (91.3) | 26.1±0.7 | 19.5 | (60.5) | 0.4±0.0 | 83.5 | (80.0) |

FIG. 1G

Table 1 (continued)

| Groups | Compounds[a] | Cytotoxicity (IC$_{50}$, mM) | | | | | MDR reversal activity of triazole compounds | | | | | | | | | | | | |
|---|---|---|---|---|---|---|---|---|---|---|---|---|---|---|---|---|---|---|---|
| | | | | | | | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
| | | LCC6 | LCC6MDR | 2008/P | 2008/MRP1 | L929 | IC$_{50}$ of paclitaxel (nM)[b] | RF[b] | (% of reversion)[b] | IC$_{50}$ of paclitaxel (nM)[c] | RF[c] | (% of reversion)[c] | IC$_{50}$ of DOX (nM)[b] | RF[b] | (% of reversion)[b] | IC$_{50}$ of vincristine (nM)[b] | RF[b] | (% of reversion)[b] | IC$_{50}$ of topotecan (nM)[b] | RF[b] | (% of reversion)[b] | IC$_{50}$ of topotecan (μM)[b] | RF[b] | (% of reversion)[b] |
| D (cont'd) | Ac5Az1 OOH | 1.2± 0.3 | 0.9± 0.2 | 3.4± 2.0 | 1.7± 0.2 | 2.2± 0.6 | Toxic | ND | ND | 2.6± 1.2 | 61.0 | (61.5) | 336.4 ±54.0 | 1.2 | (14.9) | 103.4 ± 40.2 | 1.2 | (48.8) | 40.2± 3.9 | 12.6 | (39.3) | ND | ND | ND |
| | Ac5Az1 1 | >100 | >100 | >100 | >100 | >100 | 2.9± 0.2 | 54.7 | (55.2) | 6.7± 0.8 | 23.7 | (23.9) | 110.5 ±17.3 | 3.8 | (45.3) | 22.6 ±1.8 | 5.5 | (223.5) | 20.3± 0.8 | 25.0 | (77.8) | ND | ND | ND |
| | Ac5Az1 2 | >100 | >100 | >100 | >100 | >100 | 3.9± 0.3 | 40.7 | (41.0) | 17.9± 4.0 | 8.9 | (8.9) | 116.8 ±24.5 | 3.6 | (42.9) | 18.5 ±1.3 | 6.7 | (273.0) | 19.7± 0.6 | 25.8 | (80.2) | ND | ND | ND |
| | Ac5Az1 4 | >100 | >100 | >100 | >100 | >100 | 24.1 ± 14.0 | 6.6 | (6.6) | 113.6 ±3.2 | 1.4 | (1.4) | 102.3 ±11.6 | 4.1 | (49.0) | 18.9 ±2.2 | 6.5 | (267.2) | 43.6± 7.2 | 11.7 | (36.2) | 2.1± 0.5 | 15.9 | (15.2) |
| | Ac5Az1 5 | >100 | >100 | >100 | >100 | >100 | 2.4± 0.0 | 66.1 | (66.7) | 61.1± 12.0 | 2.6 | (2.6) | 52.7± 7.2 | 8.0 | (95.1) | 8.2± 0.8 | 15.0 | (615.9) | 39.8± 7.4 | 12.8 | (39.7) | 1.6± 0.4 | 20.9 | (20.0) |
| E[e] | Ac5 + Az4 | ND | ND | ND | ND | ND | ND | ND | ND | ND | ND | ND | 470.1 ±60.5 | 0.9 | (10.7) | ND | ND | ND | ND | ND | ND | ND | ND | ND |
| | Ac5 + Az5 | ND | ND | ND | ND | ND | ND | ND | ND | ND | ND | ND | ND | ND | ND | ND | ND | ND | 43.2± 4.8 | 11.8 | (36.6) | ND | ND | ND |

FIG. 1H

Table 1 (continued)

MDR reversal activity of triazole compounds

| Groups | Compounds[a] | Cytotoxicity (IC50, mM) | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
|---|---|---|---|---|---|---|---|---|---|---|---|---|---|---|---|---|---|---|---|---|---|---|---|---|
| | | LCC6 | LCC6MDR | 2008/P | 2008/MRP1 | L929 | IC50 of paclitaxel (nM)[b] | RF[b] | (% of reversion)[b] | IC50 of paclitaxel (nM)[c] | RF[c] | (% of reversion)[c] | IC50 of DOX (nM)[b] | RF[b] | (% of reversion)[b] | IC50 of vincristine (nM)[b] | RF[b] | (% of reversion)[b] | IC50 of topotecan (nM)[b] | RF[b] | (% of reversion)[b] | IC50 of topotecan (nM)[b] | RF[b] | (% of reversion)[b] |
| E[e] (cont'd) | Ac5+Az7 | ND | ND | ND | ND | ND | ND | ND | ND | ND | ND | ND | 541.1±113.3 | 0.8 | (9.3) | ND | ND | ND | ND | ND | ND | ND | ND | ND |
| | Ac5+Az8 | ND | ND | ND | ND | ND | ND | ND | ND | ND | ND | ND | ND | ND | ND | ND | ND | ND | 45.0±4.5 | 11.3 | (35.1) | 3.7 | 9.0 | (8.6) |
| | Ac5+Az9 | ND | ND | ND | ND | ND | ND | ND | ND | ND | ND | ND | ND | ND | ND | ND | ND | ND | ND | ND | ND | 0.5 | 66.8 | (64.0) |
| | Ac5+Az10 | ND | ND | ND | ND | ND | ND | ND | ND | ND | ND | ND | ND | ND | ND | ND | ND | ND | ND | ND | ND | 1.6 | 20.9 | (20.0) |
| F | Ac12Az1 | >50 | >50 | >10 | >100 | >100 | 8.0±2.1 | 19.8 | (20.0) | 30.6±5.2 | 5.2 | (5.2) | 49.9±7.1 | 8.4 | (100.4) | 8.2±1.0 | 15.0 | (615.9) | 25.8±4.5 | 19.7 | (61.2) | ND | ND | ND |
| | Ac12Az2 | >33 | >33 | 9.7±1.5 | >100 | >50 | 4.2±0.6 | 37.8 | (38.1) | 36.1±13.2 | 4.4 | (4.4) | 53.0±2.8 | 7.9 | (94.5) | 6.5±0.4 | 19.0 | (776.9) | 24.3±4.0 | 20.9 | (65.0) | ND | ND | ND |
| | Ac12Az3 | >33 | >33 | >10 | >100 | >50 | 2.2±0.2 | 72.1 | (72.7) | 16.5±5.0 | 9.6 | (9.7) | 48.1±5.9 | 8.7 | (104.2) | 5.0±0.2 | 24.6 | (1010.0) | 21.9±3.0 | 23.2 | (72.1) | ND | ND | ND |
| | Ac12Az4 | >33 | >33 | >10 | >100 | >100 | 3.4±0.3 | 46.7 | (47.1) | 23.5±6.6 | 6.8 | (6.8) | 55.1±6.6 | 7.6 | (90.9) | 6.4±0.7 | 19.3 | (789.1) | 21.3±3.9 | 23.9 | (74.2) | ND | ND | ND |

FIG. 1I

Table 1 (continued)

| Groups | Compounds[a] | Cytotoxicity (IC$_{50}$, mM) | | | | | MDR reversal activity of triazole compounds | | | | | | | | | | | | |
|---|---|---|---|---|---|---|---|---|---|---|---|---|---|---|---|---|---|---|---|
| | | | | | | | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
| | | LCC6 | LCC6MDR | 2008/P | 2008/MRP1 | L929 | IC$_{50}$ of paclitaxel (nM)[b] | RF[b] | (% of reversion)[b] | IC$_{50}$ of paclitaxel (nM)[c] | RF[c] | (% of reversion)[c] | IC$_{50}$ of DOX (nM)[b] | RF[b] | (% of reversion)[b] | IC$_{50}$ of vincristine (nM)[b] | RF[b] | (% of reversion)[b] | IC$_{50}$ of topotecan (nM)[b] | RF[b] | (% of reversion)[b] | IC$_{50}$ of topotecan (μM)[b] | RF[b] | (% of reversion)[b] |
| F (cont'd) | Ac12Az5 | >50 | >50 | >10 | >100 | >100 | 2.0±0.3 | 79.4 | (80.0) | 23.3±7.2 | 6.8 | (6.9) | 96.8±33.0 | 4.3 | (51.8) | 18.9±1.0 | 6.5 | (267.2) | 16.2±1.5 | 31.4 | (97.5) | ND | ND | ND |
| | Ac12Az7 | >33 | >33 | >10 | >100 | >100 | 4.7±0.3 | 33.8 | (34.0) | 22.7±6.9 | 7.0 | (7.0) | 62.3±6.7 | 6.7 | (80.4) | 8.8±0.5 | 14.0 | (573.9) | 20.3±2.6 | 25.0 | (77.8) | ND | ND | ND |
| | Ac12Az8 | >50 | >50 | >10 | >100 | >100 | 3.0±0.6 | 52.9 | (53.3) | 30.6±13.2 | 5.2 | (5.2) | 89.8±24.4 | 4.7 | (55.8) | 20.0±3.6 | 6.2 | (252.5) | 14.4±1.0 | 35.3 | (109.7) | 0.4±0.0 | 83.5 | (80.0) |
| | Ac12Az9 | >50 | >50 | >10 | >100 | >100 | 1.8±0.3 | 88.2 | (88.9) | 26.5±7.7 | 6.0 | (6.0) | 85.9±30.7 | 4.9 | (58.3) | 18.5±0.1 | 6.7 | (273.0) | 12.9±0.6 | 39.4 | (122.5) | 0.4±0.0 | 83.5 | (80.0) |
| | Ac12Az10 | >50 | >50 | >10 | >100 | >100 | 2.6±1.0 | 61.0 | (61.5) | 19.1±6.2 | 8.3 | (8.4) | 136.0±40.7 | 3.1 | (36.8) | 31.6±2.7 | 3.9 | (159.8) | 18.8±1.7 | 27.0 | (84.0) | 0.5±0.1 | 66.8 | (64.0) |
| | Ac12Az11 | 14.6±6.8 | 6.6±1.6 | >95 | >100 | >100 | 10.7±0.1 | 14.8 | (15.0) | 42.6±3.5 | 3.7 | (3.8) | 59.0±18.9 | 7.1 | (84.9) | 17.0±2.9 | 7.2 | (297.1) | 18.7±1.3 | 27.2 | (84.5) | ND | ND | ND |
| | Ac12Az12 | 10.7±1.0 | 9.5±0.7 | >86 | >100 | ND | 8.0±0.2 | 19.8 | (20.0) | 39.2±6.6 | 4.0 | (4.1) | 51.8±10.4 | 8.1 | (96.7) | 11.2±1.6 | 11.0 | (450.9) | 19.6±0.4 | 25.9 | (80.6) | ND | ND | ND |
| G[e] | Ac12 + Az2 | ND | ND | ND | ND | ND | 113.1 | 1.4 | (1.4) | ND | ND | ND | 408.3 | 1.0 | (12.3) | 105.7±19.5 | 1.2 | (47.8) | ND | ND | ND | ND | ND | ND |
| | Ac12 + Az3 | ND | ND | ND | ND | ND | ND | ND | | ND | ND | ND | 388.4 | 1.1 | (12.9) | 104.4±15.1 | 1.2 | (48.4) | ND | ND | ND | ND | ND | ND |

FIG. 1J

Table 1 (continued)

| Groups | Compounds[a] | Cytotoxicity (IC$_{50}$, mM) | | | | | MDR reversal activity of triazole compounds | | | | | | | | | | | | | | | |
|---|---|---|---|---|---|---|---|---|---|---|---|---|---|---|---|---|---|---|---|---|---|---|
| | | | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
| | | LCC6 | LCC6MDR | 2008/P | 2008/MRP1 | L929 | IC$_{50}$ of paclitaxel (nM)[b] | RF[c] | (% of reversion)[c] | IC$_{50}$ of paclitaxel (nM)[c] | RF[c] | (% of reversion)[c] | IC$_{50}$ of DOX (nM)[b] | RF | (% of reversion)[b] | IC$_{50}$ of vincristine (nM)[b] | RF | (% of reversion)[b] | IC$_{50}$ of topotecan (nM)[b] | RF | (% of reversion)[b] | IC$_{50}$ of topotecan (µM)[b] | RF | (% of reversion)[b] |
| G[e] (cont'd) | Ac12 + Az4 | ND | ND | ND | ND | ND | ND | ND | ND | ND | ND | ND | 477.9 | 0.9 | ND | 99.2±15.6 | 1.2 | (50.9) | ND | ND | ND | ND | ND | ND |
| | Ac12 + Az7 | ND | ND | ND | ND | ND | ND | ND | ND | ND | ND | ND | 421.9 | 1.0 | ND | ND | ND | ND | ND | ND | ND | ND | ND | ND |
| | Ac12 + Az8 | ND | ND | ND | ND | ND | 18.0±2.4 | 8.8 | (8.9) | ND | ND | ND | ND | ND | ND | ND | ND | ND | 33.9±7.6 | 15.0 | (46.6) | 1.3±0.1 | 25.7 | (24.6) |
| | Ac12 + Az9 | ND | ND | ND | ND | ND | 15.6±2.4 | 10.2 | (10.3) | ND | ND | ND | ND | ND | ND | ND | ND | ND | 19.4±0.2 | 26.2 | (81.4) | 0.5±0.1 | 66.8 | (64.0) |
| | Ac12 + Az10 | ND | ND | ND | ND | ND | 48.7±9.8 | 3.3 | (3.3) | 105.5±22.9 | 1.5 | (1.5) | 142.4±30.5 | 2.9 | (35.2) | 39.7±15.0 | 3.1 | (127.2) | 41.0±6.4 | 12.4 | (38.5) | 1.1±0.2 | 30.4 | (29.1) |
| H | Ac13Az1 | >33 | >33 | >10 | >100 | >50 | 41.6±3.8 | 3.8 | (3.8) | 93.9±13.6 | 1.7 | (1.7) | 156.6±20.3 | 2.7 | (32.0) | 34.0±9.3 | 3.6 | (148.5) | 47.9±3.7 | 10.6 | (33.0) | ND | ND | ND |
| | Ac13Az2 | >11 | >11 | 13.0±6.3 | >33 | >11 | 22.5±2.4 | 7.1 | (7.1) | 85.9±11.7 | 1.8 | (1.9) | 156.3±25.0 | 2.7 | (32.1) | 27.7±10.7 | 4.4 | (182.3) | 45.9±4.0 | 11.1 | (34.4) | ND | ND | ND |
| | Ac13Az3 | >11 | >11 | >10 | >100 | >100 | 30.5±2.3 | 5.2 | (5.2) | 86.8±8.0 | 1.8 | (1.8) | 133.4±11.0 | 3.1 | (37.6) | 23.9±4.1 | 5.2 | (211.3) | 38.7±5.6 | 13.1 | (40.8) | ND | ND | ND |
| | Ac13Az4 | >50 | >50 | >10 | >100 | >50 | ND | ND | ND | ND | ND | ND | ND | ND | ND | ND | ND | ND | 35.3±7.0 | 14.4 | (44.8) | ND | ND | ND |

FIG. 1K

Table 1 (continued)

MDR reversal activity of triazole compounds

| Groups | Compounds[a] | Cytotoxicity (IC50, mM) | | | | | Pgp-over-expressed LCC6MDR | | | Pgp-over-expressed LCC6MDR | | | MRP1-over-expressed 2008/MRP1 | | | MRP1-over-expressed 2008/MRP1 | | | BCRP-over-expressed HEK293/R2 | | | BCRP-over-expressed MCF7-MX100 | | |
|---|---|---|---|---|---|---|---|---|---|---|---|---|---|---|---|---|---|---|---|---|---|---|---|---|
| | | LCC6 | LCC6MDR | 2008/P | 2008/MRP1 | L929 | IC50 of paclitaxel (nM)[b] | RF[c] | (% of reversion)[b] | IC50 of paclitaxel (nM)[c] | RF[c] | (% of reversion)[c] | IC50 of DOX (nM)[b] | RF[c] | (% of reversion)[b] | IC50 of vincristine (nM)[b] | RF[c] | (% of reversion)[b] | IC50 of topotecan (nM)[b] | RF[c] | (% of reversion)[b] | IC50 of topotecan (nM)[b] | RF[c] | (% of reversion)[b] |
| H (cont'd) | Ac13Az5 | >33 | >33 | >10 | >100 | >100 | 3.4± 0.3 | 46.7 | (47.1) | 35.4± 10.2 | 4.5 | (4.5) | 113.1 ±15.4 | 3.7 | (44.3) | 24.8± 4.2 | 5.0 | (203.6) | 18.4± 3.2 | 27.6 | (85.9) | ND | ND | ND |
| | Ac13Az7 | >33 | >50 | >10 | >100 | >100 | 43.1± 8.3 | 3.7 | (3.7) | 98.1± 14.7 | 1.6 | (1.6) | 176.5 ±36.8 | 2.4 | (28.4) | 36.6± 0.3 | 3.4 | (138.0) | 35.1± 6.2 | 14.5 | (45.0) | ND | ND | ND |
| | Ac13Az8 | >50 | >50 | >10 | >100 | >100 | 9.2± 2.2 | 17.3 | (17.4) | 64.5± 25.1 | 2.5 | (2.5) | 89.6± 12.2 | 4.7 | (55.9) | 24.3± 0.5 | 5.1 | (207.8) | 13.5± 1.3 | 37.6 | (117.0) | 0.4± 0.0 | 83.5 | (80.0) |
| | Ac13Az9 | >50 | >50 | 6.3± 1.4 | >100 | >100 | 2.7± 0.5 | 58.8 | (59.3) | 28.4± 6.2 | 5.6 | (5.6) | 121.7 ±16.9 | 3.5 | (41.2) | 25.1± 2.0 | 4.9 | (201.2) | 13.9± 1.1 | 36.6 | (113.7) | 0.4± 0.0 | 83.5 | (80.0) |
| | Ac13Az10 | >10 | >100 | >10 | >100 | >100 | 3.2± 1.0 | 49.6 | (50.0) | 14.9± 3.9 | 10.7 | (10.7) | 136.1 ±9.2 | 3.1 | (36.8) | 18.0± 3.5 | 6.8 | (280.6) | 17.9± 2.5 | 28.4 | (88.3) | 0.6± 0.1 | 55.7 | (53.3) |
| | Ac13Az11 | 14.4 ±3.6 | 16.8± 8.2 | 15.9 ±6.6 | 16.6± 5.1 | 12.1± 2.3 | 78.5± 3.6 | 2.0 | (2.0) | 113.3 ±18.8 | 1.4 | (1.4) | 170.6 ±9.2 | 2.5 | (29.4) | 50.1± 4.5 | 2.5 | (100.8) | 28.0± 4.6 | 18.1 | (56.4) | ND | ND | ND |
| | Ac13Az12 | 11.7 ±1.5 | 11.6± 1.0 | 15.9 ±6.6 | 16.6± 5.1 | 12.1± 2.3 | 59.0± 5.6 | 2.7 | (2.7) | 104.1 ±10.5 | 1.5 | (1.5) | 132.8 ±3.2 | 3.2 | (37.7) | 154.5 ± 115.5 | 0.8 | (32.7) | 23.2± 2.1 | 21.9 | (68.1) | ND | ND | ND |

FIG. 1L

Table 1 (continued)

MDR reversal activity of triazole compounds

| Groups | Compounds[a] | Cytotoxicity (IC$_{50}$, mM) | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
|---|---|---|---|---|---|---|---|---|---|---|---|---|---|---|---|---|---|---|---|---|---|---|---|---|
| | | LCC6 | LCC6MDR | 2008/P | 2008/MRP1 | L929 | IC$_{50}$ of paclitaxel (nM)[b] | RF[b] | % of reversion[b] | IC$_{50}$ of paclitaxel (nM)[c] | RF[c] | % of reversion[c] | IC$_{50}$ of DOX (nM)[b] | RF[b] | % of reversion[b] | IC$_{50}$ of vincristine (nM)[b] | RF[b] | % of reversion[b] | IC$_{50}$ of topotecan (nM)[b] | RF[b] | % of reversion[b] | IC$_{50}$ of topotecan (nM)[b] | RF[b] | % of reversion[b] |
| I[e] | Ac13 + Az8 | ND | ND | ND | ND | ND | 24.6±13.0 | 6.5 | (6.5) | ND | ND | ND | ND | ND | ND | ND | ND | ND | 38.5±7.2 | 13.2 | (41.0) | 1.0±0.1 | 33.4 | (32.0) |
| | Ac13 + Az9 | ND | ND | ND | ND | ND | 26.1±9.4 | 6.1 | (6.1) | ND | ND | ND | ND | ND | ND | ND | ND | ND | 18.0±1.1 | 28.2 | (87.8) | 0.5±0.1 | 66.8 | (64.0) |
| | Ac13 + Az10 | ND | ND | ND | ND | ND | 9.1±1.8 | 17.4 | (17.6) | 51.6±31.4 | 3.1 | (3.1) | ND | ND | ND | ND | ND | ND | 43.5±5.1 | 11.7 | (36.3) | 1.3±0.1 | 25.8 | (24.6) |
| J | Ac15Az1 | >100 | >100 | >100 | >100 | >100 | 40.8±22.2 | 3.9 | (3.9) | 79.1±39.6 | 2.0 | (2.0) | 50.8±5.6 | 8.3 | (98.6) | 30.1±4.7 | 4.1 | (167.8) | 18.1±0.9 | 28.1 | (87.3) | ND | ND | ND |
| | Ac15Az2 | >100 | >100 | >100 | >100 | >100 | 14.8±9.0 | 10.7 | (10.8) | 61.1±28.5 | 2.6 | (2.6) | 45.0±14.3 | 9.3 | (111.3) | 47.6±14.8 | 2.6 | (106.1) | Toxic | ND | ND | ND | ND | ND |
| | Ac15Az3 | >100 | >100 | >100 | >100 | >100 | 14.4±5.6 | 11.0 | (11.1) | 34.6±20.0 | 4.6 | (4.6) | 33.4±0.3 | 12.6 | (150.0) | 12.8±2.4 | 9.6 | (394.5) | 15.9±1.0 | 32.0 | (99.4) | ND | ND | ND |
| | Ac15Az5 | >100 | >100 | >100 | >100 | >100 | 14.4±5.6 | 11.0 | (11.1) | 34.6±20.0 | 4.6 | (4.6) | 111.6±1.3 | 3.8 | (44.9) | 33.7±14.5 | 3.7 | (149.9) | 14.3±1.2 | 35.5 | (110.5) | ND | ND | ND |
| | Ac15Az8 | >100 | >100 | >100 | >100 | >100 | 98.7±28.9 | 1.6 | (1.6) | 116.3±23.5 | 1.4 | (1.4) | 174.9±3.3 | 2.4 | (28.6) | 66.3±13.5 | 1.9 | (76.2) | 14.5±1.2 | 35.0 | (109.0) | 0.5 | 66.8 | (64.0) |
| | Ac15Az9 | >100 | >100 | >100 | >100 | >100 | 100.2±42.3 | 1.6 | (1.6) | 96.0±28.4 | 1.7 | (1.7) | 179.1±3.5 | 2.3 | (28.0) | 55.4±16.8 | 2.2 | (91.2) | 15.0±1.1 | 33.9 | (105.3) | 0.5 | 66.8 | (64.0) |

FIG. 1M

Table 1 (continued)

| Groups | Compounds[a] | Cytotoxicity (IC$_{50}$, mM) | | | | | MDR reversal activity of triazole compounds | | | | | | | | | | | | | | |
|---|---|---|---|---|---|---|---|---|---|---|---|---|---|---|---|---|---|---|---|---|---|
| | | | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
| | | LCC6 | LCC6MDR | 2008/P | 2008/MRP1 | L929 | IC$_{50}$ of paclitaxel (nM)[b] | RF[c] | (% of reversion)[b] | IC$_{50}$ of paclitaxel (nM)[c] | RF[c] | (% of reversion)[c] | IC$_{50}$ of DOX (nM)[b] | RF[c] | (% of reversion)[b] | IC$_{50}$ of vincristine (nM)[b] | RF[c] | (% of reversion)[b] | IC$_{50}$ of topotecan (nM)[b] | RF[c] | (% of reversion)[b] | IC$_{50}$ of topotecan (μM)[b] | RF[c] | (% of reversion)[b] |
| J (cont'd) | Ac15Az11 | >100 | >100 | >100 | >100 | >100 | 86.0±33.5 | 1.8 | (1.9) | 96.7±32.3 | 1.6 | (1.7) | 201.3±0.8 | 2.1 | (24.9) | 92.1±16.3 | 1.3 | (54.8) | 20.4±0.9 | 24.9 | (77.5) | ND | ND | ND |
| | Ac15Az12 | >100 | >100 | >100 | >100 | >100 | 80.3±35.4 | 2.0 | (2.0) | 99.6±45.3 | 1.6 | (1.6) | 198.9±19.5 | 2.1 | (25.2) | 82.6±17.4 | 1.5 | (61.1) | 19.9±1.2 | 25.5 | (79.4) | ND | ND | ND |
| | Ac15Az13 | >100 | >100 | >100 | >100 | >100 | 88.5±41.9 | 1.8 | (1.8) | 91.7±35.0 | 1.7 | (1.7) | 190.4±1.4 | 2.2 | (26.3) | 85.0±15.1 | 1.4 | (59.4) | 31.9±3.2 | 15.9 | (49.5) | ND | ND | ND |
| K | Ac16Az1 | >100 | >100 | >100 | >100 | >100 | 4.1±0.8 | 38.7 | (39.0) | 33.1±4.7 | 4.8 | (4.8) | 16.7±1.1 | 25.1 | (300.0) | ND | ND | ND | 39.9±4.0 | 12.7 | (39.6) | 0.4 | 83.5 | (80.0) |
| | Ac16Az2 | >100 | >100 | >100 | >100 | >100 | 5.0±0.4 | 31.7 | (32.0) | 42.6±8.4 | 3.7 | (3.8) | 16.9±1.3 | 24.8 | (296.4) | ND | ND | ND | 47.9±2.5 | 10.6 | (33.0) | 0.5 | 66.8 | (64.0) |
| | Ac16Az3 | >100 | >100 | >100 | >100 | >100 | 6.5±0.5 | 24.4 | (24.6) | 35.1±2.7 | 4.5 | (4.6) | 20.3±4.3 | 20.7 | (246.8) | ND | ND | ND | 43.5±6.1 | 11.7 | (36.3) | 0.6 | 55.7 | (53.3) |
| | Ac16Az5 | >100 | >100 | >100 | >100 | >100 | 62.6±20.4 | 2.5 | (2.6) | 136.9±10.5 | 1.2 | (1.2) | 64.4±16.1 | 6.5 | (77.8) | ND | ND | ND | 36.3±4.5 | 14.0 | (43.5) | 0.5 | 66.8 | (64.0) |
| | Ac16Az7 | >100 | >100 | >100 | >100 | >100 | 6.0±1.0 | 26.5 | (26.7) | 55.2±11.0 | 2.9 | (2.9) | 21.1±5.2 | 19.9 | (237.4) | ND | ND | ND | 40.0±5.7 | 12.7 | (39.5) | 0.6 | 55.7 | (53.3) |

FIG. 1N

Table 1 (continued)

MDR reversal activity of triazole compounds

| Groups | Compounds[a] | Cytotoxicity (IC₅₀, mM) | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
|---|---|---|---|---|---|---|---|---|---|---|---|---|---|---|---|---|---|---|---|---|---|---|---|---|
| | | LCC6 | LCC6MDR | 2008/P | 2008/MRP1 | L929 | IC₅₀ of paclitaxel (nM)[b] | RF[b] | % of reversion[b] | IC₅₀ of paclitaxel (nM)[c] | RF[c] | % of reversion[c] | IC₅₀ of DOX (nM)[b] | RF[b] | % of reversion[b] | IC₅₀ of vincristine (nM)[b] | RF[b] | % of reversion[b] | IC₅₀ of topotecan (nM)[b] | RF[b] | % of reversion[b] | IC₅₀ of topotecan (μM)[b] | RF[b] | % of reversion[b] |
| K (cont'd) | Ac16Az1 2 | >10 | >100 | >10 | >100 | >100 | 5.4±1.3 | 29.4 | (29.6) | 51.1±7.0 | 3.1 | (3.1) | 24.5±7.7 | 17.1 | (204.5) | ND | ND | ND | 51.2±3.0 | 9.9 | (30.9) | 0.5 | 66.8 | (64.0) |
| | Ac16Az1 3 | >10 | >100 | >10 | >100 | >100 | 8.6±1.4 | 18.5 | (18.6) | 91.5±8.6 | 1.7 | (1.7) | 106.2±32.5 | 4.0 | (47.2) | ND | ND | ND | 54.5±3.5 | 9.3 | (29.0) | 0.9 | 37.1 | (35.6) |
| | Verpamil | 63.9±1.7 | 63.8±0.1 | ND | ND | 89.2±8.2 | 43.9±5.2 | 3.6 | (3.6) | ND | ND | ND | ND | ND | ND | ND | ND | ND | ND | ND | ND | ND | ND | ND |
| | PSC833 | 14.6±2.2 | 25.3±4.3 | ND | ND | >100 | 1.8±0.3 | 88.2 | (88.9) | ND | ND | ND | ND | ND | ND | ND | ND | ND | ND | ND | ND | ND | ND | ND |
| | Cyclosporine A | 2.8±0.6 | 8.3±1.5 | ND | ND | 33.9±5.2 | 2.0±0.2 | 79.4 | (80.0) | ND | ND | ND | 64.7 | 6.5 | (77.4) | ND | ND | ND | ND | ND | ND | ND | ND | ND |
| | 1d(5,7H-6Me) n=5 | ND | ND | ND | ND | ND | ND | ND | ND | ND | ND | ND | ND | ND | ND | 11.5±2.2 | 10.7 | (439.1) | ND | ND | ND | ND | ND | ND |
| | Ko143 | ND | ND | ND | ND | 29.2±1.6 | ND | ND | ND | ND | ND | ND | ND | ND | ND | ND | ND | ND | 24.0±1.9 | 21.2 | (65.8) | 0.48±0.03 | 69.6 | (66.7) |
| | Controls[f] | | | | | | 158.7±6.1 | 1.0 | ND | ND | ND | ND | 419.9±17.4 | 1.0 | ND | 123.2±15.8 | 1.0 | ND | 508.1±31.1 | 1.0 | ND | 33.4±2.1 | 1.0 | ND |

FIG. 10

Table 1 (continued)

MDR reversal activity of triazole compounds

| Groups | Compounds[a] | Cytotoxicity (IC$_{50}$, mM) | | | | | Pgp-overexpressed LCC6MDR | | | Pgp-overexpressed LCC6MDR | | | MRP1-overexpressed 2008/MRP1 | | | MRP1-overexpressed 2008/MRP1 | | | BCRP-overexpressed HEK293/R2 | | | BCRP-overexpressed MCF7-MX100 | | |
|---|---|---|---|---|---|---|---|---|---|---|---|---|---|---|---|---|---|---|---|---|---|---|---|---|
| | | LCC6 | LCC6MDR | 2008/P | 2008/MRP1 | L929 | IC$_{50}$ of paclitaxel (nM)[b] | RF[b] | (% of reversion)[b] | IC$_{50}$ of paclitaxel (nM)[c] | RF[c] | (% of reversion)[c] | IC$_{50}$ of DOX (nM)[b] | RF[b] | (% of reversion)[b] | IC$_{50}$ of vincristine (nM)[b] | RF[b] | (% of reversion)[b] | IC$_{50}$ of topotecan (nM)[b] | RF[b] | (% of reversion)[b] | IC$_{50}$ of topotecan (μM)[b] | RF[b] | (% of reversion)[b] |
| | LCC6[g] | | | | | | 1.6±0.3 | 99.2 | ND | ND | ND | ND | ND | ND | ND | ND | ND | ND | ND | ND | ND | ND | ND | ND |
| | 2008/P[g] | | | | | | ND | ND | ND | ND | ND | ND | 50.1±3.9 | 8.4 | ND | 50.5±6.4 | 2.4 | ND | ND | ND | ND | ND | ND | ND |
| | HEK293/pcDNA3.1[g] | | | | | | ND | ND | ND | ND | ND | ND | ND | ND | ND | ND | ND | ND | 15.8±1.5 | 32.2 | ND | ND | ND | ND |
| | MCF7[g] | | | | | | ND | ND | ND | ND | ND | ND | ND | ND | ND | ND | ND | ND | ND | ND | ND | 0.32±0.07 | 104.4 | ND |
| | > 80 % reversion | | | | | | | | | | | | | | | | | | | | | | | |
| | 79-50 % reversion | | | | | | | | | | | | | | | | | | | | | | | |
| | 49-10 % reversion | | | | | | | | | | | | | | | | | | | | | | | |
| | <10 % reversion | | | | | | | | | | | | | | | | | | | | | | | |

FIG. 1P

Table 2

| Groups | Active compounds | P-gp-selectivity (LCC6MDR) | MRP1-selectivity (2008/MRP1) | BCRP-selectivity (HEK293/R2) |
|---|---|---|---|---|
| B | Az5 | | | √ |
| | Az6 | | | √ |
| | Az8 | | | √ |
| | Az9 | | | √√ |
| | Az10 | | | √ |
| C | Ac1Az1 | | √ | √ |
| | Ac2Az1 | | √√ | |
| | Ac3Az1 | √ | √√ | |
| | Ac4(5OH)Az1 | √ | √√ | |
| | Ac7Az1 | | √ | √ |
| | Ac8Az1 | | √ | |
| | Ac10Az1 | | | √ |
| | Ac11Az1 | | | √ |

*FIG. 2A*

Table 2 (continued)

| Groups | Active compounds | P-gp-selectivity (LCC6MDR) | MRP1-selectivity (2008/MRP1) | BCRP-selectivity (HEK293/R2) |
|---|---|---|---|---|
| D | Ac5Az1 | √ | | |
| | Ac5Az2 | | √ | |
| | Ac5Az3 | √ | √ | |
| | Ac5Az4 | √√ | √√ | √ |
| | Ac5Az5 | √√ | | √ |
| | Ac5Az7 | √√ | √√ | |
| | Ac5Az8 | √√ | | √ |
| | Ac5Az9 | √√ | √ | √ |
| | Ac5Az10 | | | √ |
| | Ac5Az11 | √ | | √ |
| | Ac5Az12 | | | √√ |
| | Ac5Az15 | √ | √√ | √ |
| F | Ac12Az1 | | √√ | √ |
| | Ac12Az2 | | √√ | √ |
| | Ac12Az3 | √ | √√ | √ |
| | Ac12Az4 | | √ | √√ |
| | Ac12Az5 | √√ | √√ | √√ |
| | Ac12Az7 | | √ | √√ |
| | Ac12Az8 | √ | | √√ |
| | Ac12Az9 | √√ | | √√ |
| | Ac12Az10 | √ | | √√ |
| | Ac12Az11 | | | √√ |
| | Ac12Az12 | | √√ | √√ |

FIG. 2B

Table 2 (continued)

| Groups | Active compounds | P-gp-selectivity (LCC6MDR) | MRP1-selectivity (2008/MRP1) | BCRP-selectivity (HEK293/R2) |
|---|---|---|---|---|
| H | Ac13Az5 | | | √√ |
| H | Ac13Az8 | | √ | √√ |
| H | Ac13Az9 | √ | | √√ |
| H | Ac13Az10 | √ | | √√ |
| H | Ac13Az11 | | | √ |
| H | Ac13Az12 | | | √√ |
| J | Ac15Az1 | | √√ | √√ |
| J | Ac15Az2 | | √√ | |
| J | Ac15Az3 | | √√ | √√ |
| J | Ac15Az5 | | | √√ |
| J | Ac15Az8 | | | √√ |
| J | Ac15Az9 | | | √√ |
| J | Ac15Az11 | | | √ |
| J | Ac15Az12 | | | √ |

*FIG. 2C*

Table 2 (continued)

| Groups | Active compounds | P-gp-selectivity (LCC6MDR) | MRP1-selectivity (2008/MRP1) | BCRP-selectivity (HEK293/R2) |
|---|---|---|---|---|
| K | Ac16Az1 | | | |
| | Ac16Az2 | | √√ | |
| | Ac16Az3 | | √√ | |
| | Ac16Az5 | | √ | |
| | Ac16Az7 | | √√ | |
| | Ac16Az12 | | √√ | |
| Total no. of active cpds (%) | 56 | 18 (32.1%) | 32 (57.1%) | 41 (73.2%) |

√√: > 80% of reversion
√: 79-50% of reversion

FIG. 2D

Table 3

| Compounds | Cytotoxicity (IC$_{50}$, mM) | | Paclitaxel resistance of LCC6MDR | | DOX resistance of 2008/MRP1 | | Vincristine resistance of 2008/MRP1 | | Topotecan resistance of HEK293/R2 | | Topotecan resistance of MCF7-MX100 | |
|---|---|---|---|---|---|---|---|---|---|---|---|---|
| | L929 | Raw264.7 | EC$_{50}$ (nM) | Therapeutic index | EC$_{50}$ (nM) | Therapeutic index | EC$_{50}$ (nM) | Therapeutic index | EC$_{50}$ (nM) | Therapeutic index | EC$_{50}$ (nM) | Therapeutic index |
| Ac1Az1 | 60.2±16.3 | ND | ND | ND | 127.5±32.5 | 472.2 | ND | ND | 12.3±4.8 | 4894.3 | 23.1±10.8 | 2606.1 |
| Ac2Az1 | >100 | ND | ND | ND | 145.0±25.0 | >689.7 | ND | ND | ND | ND | ND | ND |
| Ac3Az1 | >100 | ND | ND | ND | 137.0±16.2 | >730.0 | ND | ND | 5.4±1.6 | >18518.5 | 17.5±8.1 | >5714.3 |
| Ac4(5OH)Az1 | >100 | ND | ND | ND | 110.0±15.0 | >909.1 | ND | ND | 12.6±4.6 | >7936.5 | 51.0±29.1 | >1960.8 |
| Ac11AZ1 | >100 | ND | ND | ND | ND | ND | ND | ND | 48.0±10.0 | >2083.3 | 31.0 | >3225.8 |
| Ac5Az1 | >57 | ND | ND | ND | 250.0 | >228.0 | ND | ND | ND | ND | ND | ND |
| Ac5Az4 | >100 | ND | ND | ND | 161.7±10.9 | >618.4 | 117.0±16.0 | >854.7 | 18.0 | >5555.6 | ND | ND |
| Ac5Az5 | >100 | ND | ND | ND | ND | ND | 115.0 | >869.6 | 33.0 | >3030.3 | ND | ND |
| Ac5Az7 | >100 | ND | 157.0 | >636.9 | 191.7±33.5 | >521.6 | ND | ND | ND | ND | ND | ND |
| Ac5Az8 | >100 | ND | ND | ND | ND | ND | ND | ND | 3.6±0.2 | >27777.8 | 4.0±2.3 | >25000.0 |
| Ac5Az9 | >100 | ND | ND | ND | ND | ND | ND | ND | 2.8±0.7 | >35714.3 | 0.9±0.3 | >111111.1 |
| Ac5Az10 | >100 | ND | ND | ND | ND | ND | ND | ND | 16.0 | >6250.0 | 7.5±1.0 | >13333.3 |
| Ac5Az11 | >100 | ND | 160.0±21.0 | >625.0 | 175.0±17.6 | >571.4 | 135.0±10.0 | >740.7 | 28.0±2.0 | >3571.4 | 135.0±25.1 | >740.7 |
| Ac5Az12 | >100 | ND | 141.0±1.0 | >709.2 | 131.7±38.4 | >759.3 | 92.5±2.5 | >1081.1 | 32.0±4.0 | >3125.0 | 62.5 | >1600.0 |

FIG. 3A

Table 3 (continued)

| Compounds | Cytotoxicity (IC₅₀, mM) | | Paclitaxel resistance of LCC6MDR | | DOX resistance of 2008/MRP1 | | Vincristine resistance of 2008/MRP1 | | Topotecan resistance of HEK293/R2 | | Topotecan resistance of MCF7-MX100 | |
|---|---|---|---|---|---|---|---|---|---|---|---|---|
| | L929 | Raw264.7 | EC₅₀ (nM) | Therapeutic index | EC₅₀ (nM) | Therapeutic index | EC₅₀ (nM) | Therapeutic index | EC₅₀ (nM) | Therapeutic index | EC₅₀ (nM) | Therapeutic index |
| Ac12Az1 | >100 | ND | ND | ND | ND | ND | 84.0±11.0 | >1190.5 | ND | ND | ND | ND |
| Ac12Az2 | >50 | ND | ND | ND | 167.5±12.5 | >298.5 | 132.3±19.2 | >377.9 | ND | ND | ND | ND |
| Ac12Az3 | >50 | ND | 190.0 | >263.2 | 149.8±15.8 | >333.8 | 81.5±20.6 | >613.5 | ND | ND | ND | ND |
| Ac12Az4 | >100 | ND | ND | ND | 190.3±5.2 | >525.5 | 135.7±17.6 | >736.9 | ND | ND | ND | ND |
| Ac12Az7 | >100 | ND | ND | ND | 172.3±31.1 | >580.4 | 93.3±20.5 | >1071.8 | ND | ND | ND | ND |
| Ac12Az8 | >100 | ND | ND | ND | ND | ND | ND | ND | 3.9 | >25641.0 | 5.6±1.7 | >17857.1 |
| Ac12Az9 | >100 | ND | ND | ND | ND | ND | ND | ND | 0.9±0.1 | >111111.1 | 1.4±0.6 | >71428.6 |
| Ac12Az10 | >100 | ND | 330.0 | >303.0 | ND | ND | ND | ND | 20.0±5.0 | >5000.0 | 34.2±12.0 | >2924.0 |
| Ac12Az11 | >100 | ND | ND | ND | 114.0±11.0 | >877.2 | 169.0 | >591.7 | 30.0 | >3333.3 | ND | ND |
| Ac12Az12 | >100 | ND | ND | ND | 135.0±10.0 | >740.7 | 168.0 | >595.2 | 34.0 | >2941.2 | ND | ND |
| Ac13Az8 | >100 | ND | ND | ND | ND | ND | ND | ND | 4.1±0.5 | >24390.2 | 6.0 | >16666.7 |
| Ac13Az9 | >100 | ND | ND | ND | ND | ND | ND | ND | 1.7±0.4 | >58823.5 | 2.0±0.7 | >50000.0 |
| Ac13Az10 | >100 | ND | 340.0 | >294.1 | ND | ND | ND | ND | 16.5±2.5 | >6060.6 | 118.3±35.7 | >845.3 |

FIG. 3B

Table 3 (continued)

| Compounds | Cytotoxicity (IC$_{50}$, mM) | | Paclitaxel resistance of LCC6MDR | | DOX resistance of 2008/MRP1 | | Vincristine resistance of 2008/MRP1 | | Topotecan resistance of HEK293/R2 | | Topotecan resistance of MCF7-MX100 | |
|---|---|---|---|---|---|---|---|---|---|---|---|---|
| | L929 | Raw264.7 | EC$_{50}$ (nM) | Therapeutic index | EC$_{50}$ (nM) | Therapeutic index | EC$_{50}$ (nM) | Therapeutic index | EC$_{50}$ (nM) | Therapeutic index | EC$_{50}$ (nM) | Therapeutic index |
| Ac15Az1 | >100 | ND | ND | ND | ND | ND | ND | ND | 111.0±9.0 | >900.9 | ND | ND |
| Ac15Az2 | >100 | ND | ND | ND | 530.0±120.4 | >188.7 | 550.0 | >181.8 | ND | ND | ND | ND |
| Ac15Az3 | >100 | ND | ND | ND | 475.0±25.1 | >210.5 | 535.0±62.6 | >186.9 | 36.0±4.0 | >2777.8 | ND | ND |
| Ac15Az5 | >100 | ND | ND | ND | ND | ND | ND | ND | 48.0 | >2083.3 | ND | ND |
| Ac15Az8 | >100 | ND | ND | ND | ND | ND | ND | ND | 4.5±3.5 | >22222.2 | 1.3±0.7 | >76923.1 |
| Ac15Az9 | >100 | ND | ND | ND | ND | ND | ND | ND | 2.4±1.5 | >41666.7 | 2.0±0.6 | >50000.0 |
| Ac16Az1 | >100 | ND | ND | ND | 77.7±16.5 | >1287.0 | ND | ND | ND | ND | ND | ND |
| Ac16Az2 | >100 | ND | ND | ND | 98.8±18.3 | >1012.1 | ND | ND | ND | ND | ND | ND |
| Ac16Az3 | >100 | ND | ND | ND | 137.7±21.4 | >726.2 | ND | ND | ND | ND | ND | ND |
| Ac16Az5 | >100 | ND | ND | ND | 301.7±93.0 | >331.5 | ND | ND | ND | ND | ND | ND |
| Ac16Az7 | >100 | ND | ND | ND | 123.0±13.0 | >813.0 | ND | ND | ND | ND | ND | ND |
| Ac16Az12 | >100 | ND | ND | ND | 208.0±32.0 | >480.8 | ND | ND | ND | ND | ND | ND |
| Ac16Az13 | >100 | ND | ND | ND | 590.0 | >169.5 | ND | ND | ND | ND | ND | ND |
| Az8 | 67.5 | ND | ND | ND | ND | ND | ND | ND | 80.3±24.1 | 840.6 | 120.0 | 562.5 |
| Az9 | 20.6 | ND | ND | ND | ND | ND | ND | ND | 8.5±1.3 | 2423.5 | 10.2±1.6 | 2019.6 |
| Az10 | 51.0 | ND | ND | ND | ND | ND | ND | ND | 32.0 | 1593.8 | ND | ND |

*FIG. 3C*

Table 3 (continued)

| Compounds | Cytotoxicity (IC$_{50}$, mM) | | Paclitaxel resistance of LCC6MDR | | DOX resistance of 2008/MRP1 | | Vincristine resistance of 2008/MRP1 | | Topotecan resistance of HEK293/R2 | | Topotecan resistance of MCF7-MX100 | |
|---|---|---|---|---|---|---|---|---|---|---|---|---|
| | L929 | Raw264.7 | EC$_{50}$ (nM) | Therapeutic index | EC$_{50}$ (nM) | Therapeutic index | EC$_{50}$ (nM) | Therapeutic index | EC$_{50}$ (nM) | Therapeutic index | EC$_{50}$ (nM) | Therapeutic index |
| Verapamil | 89.2±8.2 | ND | 445.7±40.7 | 200.1 | ND | ND | ND | ND | ND | ND | ND | ND |
| PSC833 | >100 | ND | 2.3±0.5 | >43478.3 | ND | ND | ND | ND | ND | ND | ND | ND |
| Cyclosporine A | 33.9±5.2 | ND | 32.0±1.0 | 1059.4 | ND | ND | ND | ND | ND | ND | ND | ND |
| 1d(5,7H-6Me)n=5 | ND | >100 | ND | ND | 110.7±24.6 | >903.3 | 120.0±13.2 | >833.3 | ND | ND | ND | ND |
| Ko143 | 29.2±1.6 | ND | ND | ND | ND | ND | ND | ND | 11.4±2.4 | 2561.4 | 9.0±1.5 | 3244.4 |

*FIG. 3D*

Table 4

| | RF/P-gp/Paclitaxel | Az1 | Az2 | Az3 | Az4 | Az5 | Az5 (OH) | Az6 | Az7 | Az8 | Az9 | Az10 | Az10 (OH) | Az11 | Az12 | Az13 | Az14 | Az15 |
|---|---|---|---|---|---|---|---|---|---|---|---|---|---|---|---|---|---|---|
| Ac1 | 1.0 | 1.7 | 4.9 | 6.7 | 6.5 | 24.0 | ND | 9.9 | ND | 2.5 | 21.7 | 20.3 | ND | 1.5 | 2.4 | ND | ND | ND |
| Ac2 | 0.7 | 31.7 | | | | | | | | | | | | | | | | |
| Ac3 | 0.7 | 19.1 | | | | | | | | | | | | | | | | |
| Ac4 | 14.6 | 63.5 | | | | | | | | | | | | | | | | |
| Ac4 (5OH) | ND | 36.1 | | | | | | | | | | | | | | | | |
| Ac5 | 0.9 | 36.1 | 48.1 | 58.8 | 99.2 | 99.2 | 45.3 | 1.9 | 99.2 | 93.4 | 113.4 | 20.1 | toxic | 54.7 | 40.7 | | 6.6 | 66.1 |
| Ac6 | 1.0 | 69.0 | | | | | | | | | | | | | | | | |
| Ac7 | 1.1 | 42.9 | | | | | | | | | | | | | | | | |
| Ac8 | 0.9 | 54.7 | | | | | | | | | | | | | | | | |
| Ac9 | 1.1 | 2.8 | | | | | | | | | | | | | | | | |
| Ac10 | 1.2 | 33.8 | | | | | | | | | | | | | | | | |
| Ac11 | 1.3 | 30.5 | 1.7 | | | | | | | | | | | | | | | |
| Ac12 | 1.5 | 1.2 | 37.8 | 72.1 | 46.7 | 79.4 | | | 33.8 | 52.9 | 88.2 | 61.0 | | 14.8 | 19.8 | | | |
| Ac13 | 2.1 | 19.8 | 3.8 | 7.1 | 5.2 | 46.7 | | | 3.7 | 17.3 | 58.8 | 49.6 | | 2.0 | 2.7 | | | |
| Ac14 | ND | 3.3 | | | | | | | | | | | | | | | | |
| Ac15 | ND | 1.1 | 3.9 | 10.7 | | 11.0 | | | | 1.6 | 1.6 | | | 1.8 | 2.0 | 1.8 | | |
| Ac16 | 2.1 | 17.4 | 31.7 | 24.4 | | 2.5 | | | 26.5 | | | | | | 29.7 | 18.5 | | |

FIG. 4A

Table 4 (continued)

| RF/P-gp/Paclitaxel | Az1 | Az2 | Az3 | Az4 | Az5 | Az5 (OH) | Az6 | Az7 | Az8 | Az9 | Az10 | Az10 (OH) | Az11 | Az12 | Az13 | Az14 | Az15 |
|---|---|---|---|---|---|---|---|---|---|---|---|---|---|---|---|---|---|
| | 1.7 | 4.9 | 6.7 | 6.5 | 24.0 | ND | 9.9 | ND | 2.5 | 21.7 | 20.3 | ND | 1.5 | 2.4 | ND | ND | ND |
| Verapamil | 3.6 | | | | | | | | | | | | | | | | |
| PSC833 | 88.2 | | | | | | | | | | | | | | | | |
| Cyclosporine A | 79.4 | | | | | | | | | | | | | | | | |

*FIG. 4B*

Table 5

| RF/MRP1/DOX | Az1 | Az2 | Az3 | Az4 | Az5 | Az5 (OH) | Az6 | Az7 | Az8 | Az9 | Az10 | Az10 (OH) | Az11 | Az12 | Az13 | Az14 | Az15 |
|---|---|---|---|---|---|---|---|---|---|---|---|---|---|---|---|---|---|
| | 1.2 | 1.4 | 1.5 | 1.5 | 1.3 | 2.4 | ND | 1.6 | 1.1 | 1.1 | 2.0 | 2.2 | ND | 1.2 | 1.2 | ND | ND | ND |
| Ac1 | 1.2 | 7.7 | | | | | | | | | | | | | | | | |
| Ac2 | 1.3 | 13.6 | | | | | | | | | | | | | | | | |
| Ac3 | 1.4 | 9.6 | | | | | | | | | | | | | | | | |
| Ac4 | 1.7 | 3.9 | | | | | | | | | | | | | | | | |
| Ac4 (5OH) | ND | 8.8 | | | | | | | | | | | | | | | | |
| Ac5 | 1.1 | 4.0 | 6.3 | 4.5 | 8.0 | 2.5 | 2.4 | 1.1 | 8.3 | 3.3 | 4.8 | 1.6 | 1.2 | 3.8 | 3.6 | | 4.1 | 8.0 |
| Ac6 | 1.2 | 3.6 | | | | | | | | | | | | | | | | |
| Ac7 | 1.2 | 3.7 | | | | | | | | | | | | | | | | |
| Ac8 | 1.2 | 4.4 | | | | | | | | | | | | | | | | |
| Ac9 | 1.2 | 3.1 | | | | | | | | | | | | | | | | |
| Ac10 | 1.3 | 4.6 | | | | | | | | | | | | | | | | |
| Ac11 | 1.1 | 2.6 | 1.3 | | | | | | | | | | | | | | | |
| Ac12 | 0.8 | 8.4 | 7.9 | 8.7 | 7.6 | 4.3 | | | 6.7 | 4.7 | 4.9 | 3.1 | | 7.1 | 8.1 | | | |
| Ac13 | 0.7 | 2.9 | 2.7 | 2.7 | 3.1 | 3.7 | | | 2.4 | 4.7 | 3.5 | 3.1 | | 2.5 | 3.2 | | | |
| Ac14 | ND | 1.0 | | | | | | | | | | | | | | | | |
| Ac15 | ND | 8.3 | 9.3 | 12.6 | | 3.8 | | | | 2.4 | 2.3 | | | 2.1 | 2.1 | 2.2 | | |
| Ac16 | 1.1 | 25.1 | 24.8 | 20.7 | | 6.5 | | | 19.9 | | | | | | 17.1 | 4.0 | | |
| 4e | 6.5 | | | | | | | | | | | | | | | | | |

*FIG. 5*

Table 6

| RF/MRP1/Vincristine | Az1 | Az2 | Az3 | Az4 | Az5 | Az5(OH) | Az6 | Az7 | Az8 | Az9 | Az10 | Az10(OH) | Az11 | Az12 | Az13 | Az14 | Az15 |
|---|---|---|---|---|---|---|---|---|---|---|---|---|---|---|---|---|---|
| Ac1 | ND | ND | | | | | | | | | | | | | | | |
| Ac2 | ND | ND | | | | | | | | | | | | | | | |
| Ac3 | ND | ND | | | | | | | | | | | | | | | |
| Ac4 | ND | ND | | | | | | | | | | | | | | | |
| Ac4(5OH) | ND | | | | | | | | | | | | | | | | |
| Ac5 | ND | 2.9 | 8.9 | 7.0 | 19.0 | 4.4 | 3.3 | 0.7 | 2.6 | 4.3 | 4.4 | 2.2 | 1.2 | 5.5 | 6.7 | | |
| Ac6 | ND | ND | | | | | | | | | | | | | | | |
| Ac7 | ND | ND | | | | | | | | | | | | | | | |
| Ac8 | ND | ND | | | | | | | | | | | | | | | |
| Ac9 | ND | ND | | | | | | | | | | | | | | | |
| Ac10 | ND | ND | | | | | | | | | | | | | | | |
| Ac11 | ND | ND | ND | | | | | | | | | | | | | | |
| Ac12 | ND | 15.0 | 19.0 | 24.6 | 19.3 | 6.5 | | | 14.0 | 6.2 | 6.7 | 3.9 | | 7.2 | 11.0 | | | |
| Ac13 | ND | 3.1 | 3.6 | 4.4 | 5.2 | 5.0 | | | 3.4 | 5.1 | 4.9 | 6.8 | | 2.5 | 0.8 | | | |
| Ac14 | ND | ND | | | | | | | ND | | | | | | | | | |
| Ac15 | ND | 4.1 | 2.6 | 9.6 | | 3.7 | | | | 1.9 | 2.2 | | | 1.3 | 1.5 | 1.4 | 6.5 | 15.0 |
| Ac16 | ND | ND | ND | ND | | ND | | | | | | | | | ND | ND | | |
| 4e | 10.7 | | | | | | | | | | | | | | | | | |

*FIG. 6*

Table 7

| RF/BCRP/topotecan/HEK293/R2 | | Az1 | Az2 | Az3 | Az4 | Az5 | Az5(OH) | Az6 | Az7 | Az8 | Az9 | Az10 | Az10(OH) | Az11 | Az12 | Az13 | Az14 | Az15 |
|---|---|---|---|---|---|---|---|---|---|---|---|---|---|---|---|---|---|---|
| Ac1 | 4.7 | 4.8 | 8.6 | 7.5 | 11.8 | 18.3 | ND | 16.9 | 8.0 | 24.3 | 32.2 | 22.4 | ND | 9.4 | 11.0 | ND | ND | ND |
| Ac2 | 3.8 | 22.0 | | | | | | | | | | | | | | | | |
| Ac3 | 8.5 | 15.9 | | | | | | | | | | | | | | | | |
| Ac4 | 13.5 | 21.1 | | | | | | | | | | | | | | | | |
| Ac4(5OH) | ND | 14.1 | | | | | | | | | | | | | | | | |
| Ac5 | 1.2 | 23.9 | 13.5 | 12.2 | 17.6 | 22.2 | 5.1 | 1.2 | 15.9 | 19.1 | 20.3 | 19.5 | 12.6 | 25.0 | 25.8 | | 11.7 | 12.8 |
| Ac6 | 1.2 | 10.6 | | | | | | | | | | | | | | | | |
| Ac7 | 0.7 | 15.3 | | | | | | | | | | | | | | | | |
| Ac8 | 0.5 | 12.5 | | | | | | | | | | | | | | | | |
| Ac9 | 0.7 | 8.6 | | | | | | | | | | | | | | | | |
| Ac10 | 1.0 | 13.8 | | | | | | | | | | | | | | | | |
| Ac11 | 0.9 | 16.2 | 10.3 | | | | | | | | | | | | | | | |
| Ac12 | 2.6 | 21.3 | 20.9 | 23.2 | 23.9 | 31.4 | | | 25.0 | 35.3 | 39.4 | 27.0 | | 27.2 | 25.9 | | | |
| Ac13 | 3.9 | 19.7 | 11.1 | 13.1 | 14.4 | 27.6 | | | 14.5 | 37.6 | 36.6 | 28.4 | | 18.1 | 21.9 | | | |
| Ac14 | ND | 10.6 | toxic | | | | | | 12.7 | 35.0 | 33.9 | | | | | | | |
| Ac15 | ND | 0.9 | | 32.0 | | 35.5 | | | | | | | | 24.9 | 25.5 | 15.9 | | |
| Ac16 | 2.8 | 28.1 | 10.6 | 11.7 | | 14.0 | | | | | | | | | 9.9 | 9.3 | | |
| Ko143 | 21.2 | 12.7 | | | | | | | | | | | | | | | | |

*FIG. 7*

Table 8

| RF/BCRP/topotecan/MCF7-MX100 | Az1 | Az2 | Az3 | Az4 | Az5 | Az5(OH) | Az6 | Az7 | Az8 | Az9 | Az10 | Az10(OH) | Az11 | Az12 | Az13 | Az14 | Az15 |
|---|---|---|---|---|---|---|---|---|---|---|---|---|---|---|---|---|---|
| Ac1 | 4.8 | 6.2 | ND | ND | ND | ND | ND | ND | ND | 18.6 | 47.7 | 23.9 | ND | ND | ND | ND | ND | ND |
| Ac2 | 4.8 | 37.1 | | | | | | | | | | | | | | | |
| Ac3 | 11.9 | 23.9 | | | | | | | | | | | | | | | |
| Ac4 | 30.4 | 55.7 | | | | | | | | | | | | | | | |
| Ac4(5OH) | ND | 23.9 | | | | | | | | | | | | | | | |
| Ac5 | ND | 41.8 | ND | ND | ND | ND | ND | ND | ND | 66.8 | 66.8 | 83.5 | ND | ND | ND | ND | 16.5 | 21.1 |
| Ac6 | ND | 14.5 | | | | | | | | | | | | | | | |
| Ac7 | ND | 10.1 | | | | | | | | | | | | | | | |
| Ac8 | ND | 3.4 | | | | | ND | ND | | 83.5 | 83.5 | 66.8 | | | | | | |
| Ac9 | ND | 16.7 | | | ND | ND | ND | | ND | 83.5 | 83.5 | 55.7 | | | | | | |
| Ac10 | ND | 18.6 | | | ND | | ND | | | 66.8 | 66.8 | | | | | | | |
| Ac11 | 1.7 | 30.4 | ND | ND | | | | | 55.7 | | | | | ND | | | | |
| Ac12 | ND | ND | ND | ND | | | | | | | | | | ND | ND | | | |
| Ac13 | ND | ND | ND | ND | | | | | | | | | | ND | ND | | | |
| Ac14 | ND | 4.9 | | | | | | | | | | | | | ND | ND | | |
| Ac15 | ND | ND | ND | ND | ND | | | | | | | | | | | 66.8 | | |
| Ac16 | 5.1 | 83.5 | 66.8 | 55.7 | | 66.8 | | | | | | | | | | | | |
| Ko143 | 69.6 | | | | | | | | | | | | | | | | | |

*FIG. 8*

Table 9

| triazole bridge flavonoid dimers synthesized | Az1 | Az2 | Az3 | Az4 | Az5 | Az6 | Az7 | Az8 | Az9 | Az10 | Az11 | Az12 | Az13 | Az14 | Az15 |
|---|---|---|---|---|---|---|---|---|---|---|---|---|---|---|---|
| Ac1 | Y | | | | | | | | | | | | | | |
| Ac2 | Y | | | | | | | | | | | | | | |
| Ac3 | Y | | | | | | | | | | | | | | |
| Ac4 | Y | | | | | | | | | | | | | | |
| Ac5 | Y | Y | Y | Y | Y | Y | Y | Y | Y | Y | Y | Y | | | |
| Ac6 | Y | | | | | | | | | | | | | | |
| Ac7 | Y | | | | | | | | | | | | | | |
| Ac8 | Y | | | | | | | | | | | | | | |
| Ac9 | Y | | | | | | | | | | | | | | |
| Ac10 | Y | | | | | | | | | | | | | | |
| Ac11 | Y | Y | | | | | | | | | | | | | |
| Ac12 | Y | Y | Y | Y | Y | | Y | Y | Y | Y | Y | Y | | | |
| Ac13 | Y | Y | Y | Y | Y | | Y | Y | Y | Y | Y | Y | Y | | |
| Ac16 | Y | Y | Y | | | | Y | | | | | | | | |
| Ac14 | Y | | | | | | | | | | | | | | |
| Ac15 | Y | Y | Y | | Y | | | Y | Y | | Y | Y | Y | Y | Y |
| Ac17 | Y | Y | | | | | | | | | | | | | |

FIG. 9

ALKYNE-, AZIDE- AND TRIAZOLE-CONTAINING FLAVONOIDS AS MODULATORS FOR MULTIDRUG RESISTANCE IN CANCERS

CROSS-REFERENCE TO RELATED APPLICATIONS

This application is a divisional of U.S. patent application Ser. No. 14/378,869, filed Aug. 14, 2014 (pending); which is a U.S. National Phase Application of International Application No. PCT/CN2013/072058, filed Mar. 1, 2013; which claims the benefit of U.S. Provisional Patent Application No. 61/605,299, filed Mar. 1, 2012. These applications are incorporated herein by reference in their entirety.

FIELD OF THE INVENTION

The invention relates to novel alkyne-, azide- and triazole-containing flavonoid compounds, methods of preparing the same, and use of these compounds for reducing multidrug resistance caused by overexpression of ABC transporters.

This invention relates to a new method of generating a new series of compounds that can be used to reverse cancer drug resistance.

This invention relates to the novelty of structure of the alkyne-, azide- and triazole-containing flavonoids that show highly potent activities toward P-gp, MPR1 and BCRP, thereby reversing cancer drug resistance.

BACKGROUND OF THE INVENTION

The extensive multidrug resistance (MDR) in cancer cells has been a major obstacle to successful cancer chemotherapy. An important mechanism for MDR is the enhanced cellular efflux of anticancer agents due to over-expression of ATP-binding cassette. (ABC) transporter proteins.[1] Among the 48 ABC transporters identified so far, P-glycoprotein (P-gp, ABCB1), multidrug resistance protein (MRP1, ABCC1) and breast cancer resistance protein (BCRP, ABCG2) are three main efflux transporters associated with MDR.[2] The structures and functions of ABC transporters have been studied extensively by scientists. It is known that all ABC proteins consist of transmembrane domains (TMDs), and nucleotide-binding domains (NBDs).[3] P-gp has been identified to possess cytosolic N- and C-termini, two TMDs of 6 helices each, and two NBDs in a single 1280-residue polypeptide.[3-6]

The structure of the 1531-residue MRP1 is similar to that of P-gp, but the protein possesses an extra N-terminal TMD with 5 transmembrane (TM) helices, termed $TMD_0$, whose function remains unclear.[3,5,7,8] BCRP is a 655-residue half-transporter that possesses an N-terminal NBD and a 6-helix TMD. The functional protein of BCRP is assumed to operate as a homodimer.[3,5,9,10]

However, the binding modes and binding sites of these three transporter proteins with their substrates are not clear. There is no common "pharmacophore" that can be used to function as an inhibitor of these three ABC transporters.[3] Structurally diverse inhibitors or modulators of ABC multidrug efflux pumps have been identified by homology modeling, combinatorial chemistry, QSAR analysis, and utilization of protein structure information.[11-14] There have been three generations of P-gp inhibitors. The first generation P-gp inhibitors include calcium channel blocker verapamil,[15-17] antimalarial drug quinidine,[18] calmodulin antagonists,[19,20] the immunosuppressant cyclosporine A[21-24] and some steroids.[25-27] The second generation P-gp chemosensitizer include dexverapamil,[28] PSC833 (valspodar),[26,29] dexniguldipine,[30] and VX-710 (biricodar).[31,32]

The third generation MDR modulators developed by structure-activity relationships and combinatorial chemistry approaches include zosuquidar LY335979, tariquidar XR9576, laniquidar R101933, elacridar GF120918 and the substituted diarylimidazole ONT-090.[33,34] Among them, only a very few were selected for clinical trial and none of them has been approved yet for clinical application.

Fewer MRP1 inhibitors have been identified. Most MRP1 substrates, as well as inhibitors, are anionic compounds that enter cells poorly, thus making it difficult to design a good inhibitor for MRP1 compared to P-gp. The Leukotriene C4 (LTC4) analogue (MK571),[3,35] glibenclamide,[36] probenecid[37] and some non-specific inhibitors of organic anion transporters like NSAIDs (e.g. indomethacin)[38,39] have been described as MRP1 modulators. Pantoprazole, fumitremorgin C, and its derivatives Ko132, Ko134 and Ko143[3,40] are specific ABCG2 inhibitors. Besides, some third generation P-gp inhibitors such as elacridar[41] and tariquidar[42] also modulate ABCG2 activity.

Flavonoids are polyphenolic compounds commonly found in fruits, vegetables, and plant-derived products of the human diet.[43] Because humans consume large amounts of flavonoids daily, it is generally accepted that flavonoids are not toxic. Moreover, it has been reported that some flavonoids have been found to reverse cancer MDR. Some flavonoids like genistein, chrysin, biochanin, quercetin, kaempferol and naringenin have inhibitory activity on P-gp mediated transport of.[44-49]

Other flavonoids like aglycones and glycosides have been shown to inhibit MRP1-mediated transport to various degree.[50-52] Many flavonoids have also been shown to interact with BCRP transporter. They significantly inhibit the BCRP-mediated transport of topotecan and mitoxantrone in BCRP-overexpressing cancer cells.[53-56] Flavonoids are therefore promising candidates for development of novel modulators of MDR.

OBJECTS OF THE INVENTION

It is an object of the invention to develop novel flavonoid derivatives having improved activities and/or selectivity to resolve or ameliorate at least one or more of the problems associated with the prior art. As a minimum, it is an object of this invention to provide the public with a useful choice.

SUMMARY OF THE INVENTION

In a first aspect, the present invention provides a compound of formula I:

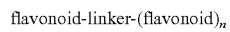

I wherein
the flavonoid is selected from the group consisting of chalcone, flavone, flavonol, flavanone, anthocyanin, and isoflavonoid;
n is 1 or 2; and
the linker is a group having at least one triazole bridged unit.

The linker may have 1 to 10 triazole bridged unit, and more preferably a 1 to 5 triazole bridged unit or a 1 to 3 triazole bridged unit.

The at least one triazole bridged unit may further comprises at least one polyethylene glycol unit.

In a second aspect, the present invention provides a compound of formula II comprising of a flavonoid containing an acetylene group:

flavonoid-linker-CCH    II wherein
the flavonoid is selected from the group consisting of chalcone, flavone, flavonol, flavanone, anthocyanin, and isoflavonoid; and
the linker is a group having at least one carbon atom.

Preferably, the linker is selected from the group consisting of alkylene group, group having a plurality of ethylene glycol units, group having a plurality of propylene glycol units, group having a plurality of amino alkyl units, and combinations thereof.

In a third aspect, the present invention provides a compound of formula III comprising of a flavonoid containing an azide group:

Flavonoid-linker-$N_3$    III wherein
the flavonoid is selected from the group consisting of chalcone, flavone, flavonol, flavanone, anthocyanin, and isoflavonoid; and
the linker is a group having at least one carbon atom.

Preferably the linker is selected from the group consisting of alkylene group, group having a plurality of ethylene glycol units, group having a plurality of propylene glycol units, group having a plurality of amino alkyl units, and combinations thereof.

In a fourth aspect, the present invention provides a process of synthesizing a compound of the formula I as defined in the first aspect, comprising reacting a compound of formula II as defined in the second aspect with a compound of formula III as defined by the third aspect by catalytic 1,3-dipolar cycloaddition.

The catalytic 1,3-dipolar cycloaddition may be regioselective, and the catalytic 1,3-dipolar cycloaddition may be Cu(I) catalyzed or Ru catalyzed.

In a fifth aspect, the present invention provides a method of reducing P-glycoprotein based multidrug resistance including the step of administering an effective amount of a compound of formula I as defined in the first aspect or a compound of formula II as defined in the second aspect or a compound of formula III as defined in the third aspect.

In a sixth aspect, the present invention provides a method of reducing MRP1-based multidrug resistance including the step of administering an effective amount of a compound of formula I as defined in the first aspect or a compound of formula II as defined in the second aspect or a compound of formula III as defined in the third aspect.

In a seventh aspect, the present invention provides a method of reducing BCRP-based multidrug resistance including the step of administering an effective amount of a compound of formula I as defined in the first aspect or a compound of formula II as defined in the second aspect or a compound of formula III as defined in the third aspect.

In an eighth aspect, the present invention provides a method of reducing resistance of a drug caused by overexpression of ABC transporters including the step of administering an effective amount of a compound of formula I as defined in the first aspect or a compound of formula II as defined in the second aspect or a compound of formula III as defined in the third aspect.

In a ninth aspect, the present invention provides a method of treating drug-resistance cancers caused by overexpression of ABC transporters including the step of administering an effective amount of a compound of formula I as defined in the first aspect or a compound of formula II as defined in the third aspect or a compound of formula III as defined in the third aspect.

In a tenth aspect, the present invention provides a use of an effective amount of a compound of formula I as defined in the first aspect or a compound of formula II as defined in the second aspect or a compound of formula III as defined in the third aspect, in the manufacturing of a medicament for reducing P-glycoprotein based multidrug resistance.

In a further aspect, the present invention provides a use of an effective amount of a compound of formula I as defined in the first aspect or a compound of formula II as defined in the second aspect or a compound of formula III as defined in the third aspect in the manufacturing of a medicament for reducing MRP-1 based multidrug resistance.

In another aspect, the present invention provides a use of an effective amount of a compound of formula I as defined in the first aspect or a compound of formula II as defined in the second aspect or a compound of formula III as defined in the third aspect in the manufacturing of a medicament for reducing BCRP-based multidrug resistance.

In yet a further aspect, the present invention provides a use of an effective amount of a compound of formula I as defined in the first aspect or a compound of formula II as defined in the second aspect or a compound of formula III as defined in the third aspect in the manufacturing of a medicament for reducing resistance of a drug caused by overexpression of ABC transporters.

In yet another aspect, the present invention provides a use of an effective amount of a compound of formula I or a compound of formula II as defined in the second aspect or a compound of formula III as defined in the third aspect in the manufacturing of a medicament for treating drug-resistant cancers caused by overexpression of ABC transporters.

In still another aspect, the present invention provides a medicament for reducing P-glycoprotein based multidrug resistance or for reducing MRP-1 based multidrug resistance or for reducing BCRP-based multidrug resistance, said medicament including a compound of formula I as defined in the first aspect or a compound of formula II as defined in the second aspect or a compound of formula III as defined in the third aspect.

In still a further aspect, the present invention provides a medicament for reducing resistance of a drug caused by overexpression of ABC transporter, said medicament including a compound of formula I as defined in the first aspect or a compound of formula II as defined in the second aspect or a compound of formula III as defined in the third aspect.

In yet still another aspect, the present invention provides a medicament for treating drug-resistant cancers caused by overexpression of ABC transporter, said medicament including a compound of formula I defined in the first aspect or a compound of formula II as defined in the second aspect or a compound of formula III as defined in the third aspect.

In yet still a further aspect, the present invention provides a method of generating a library of a predetermined number of compounds of the formula I as defined in the first aspect comprising:

a) providing a flavonoid containing an acetylene group of formula II as defined in the second aspect;

b) selectively reacting the flavonoid containing an acetylene group of formula II as defined in the second aspect with the flavonoid containing an azido group of formula III as defined in the third aspect; and c) repeating steps (a) and (b) a predetermined number of times to obtain a predetermined number of compounds of the formula I as defined in the first aspect.

In still yet an alternate aspect, the present invention provides a use of a library of compounds of formula I as defined in the first aspect made by a method as defined in the yet still a further aspect above to screen the modulating potency of multidrug resistance caused by overexpression of ABC transporter of each compound within the library.

It is a preferred feature of the present invention to provide a new class of modulators of P-gp, MRP1 and BCRP, based on alkyne-, azide- and triazole-containing flavonoids and have completely new chemical structure.

It is another preferred feature of the present invention to provide a combinatorial library of triazole-bridged flavonoid heterodimers that allows rapid screening of P-gp, MRP1 and BCRP-modulating activities.

These newly synthesized compounds are highly potent in reversing cancer drug resistance in vitro and can be used in the future to reverse cancer drug resistance in cancer patients.

These newly synthesized compounds have different levels of selectivity towards the three major transporters responsible for cancer drug resistance. Such wide range of selectivity will increase the versatility of applications that these new compounds can be applied.

For example, dual-selective compounds (towards P-gp and BCRP) may be useful in targeting these drug transporters in the blood brain barrier, thereby increasing the cancer drug concentration in the brain. This is extremely important for treating brain tumor which would otherwise be very difficult due to the lack of uptake of cancer drug in the brain.

The present invention is more advantageous over the existing technology for the following reasons:

(1) Highly potent for reversing P-gp-mediated paclitaxel resistance ($EC_{50}$=141-340 nM) and doxorubicin resistance ($EC_{50}$=114-530 nM), MRP1-mediated vincristine resistance ($EC_{50}$=82-550 nM) and BCRP-mediated topotecan and mitoxantrone resistance ($EC_{50}$=0.9-135 nM)

(2) A highly efficient and inexpensive method to develop a large combinatorial library of flavonoid dimers with different flavonoid moieties for in vitro screening for P-gp, MRP1 and BCRP modulating activity.

(3) Most triazole flavonoid dimers are very safe to use, with very low in vitro cytotoxicity towards normal fibroblast cells ($IC_{50}$>100 μM). This compares favorably to Ko143, the most potent BCRP modulator in the literature ($IC_{50}$=29 μM). Therapeutic indexes of some triazole flavonoid dimers are 43-fold higher than the best BCRP modulator in the literature, Ko143.

(4) Some triazole flavonoid dimers have extremely potent BCRP-modulating activity which 12-fold more potent than Ko143, the most potent BCRP-modulator in the literature.

(5) A wide range of selectivity towards P-gp, MRP1 and BCRP, therefore affording a versatile application of these new flavonoid dimers in different situation, including the reversal of cancer drug resistance or increase bioavailability of cancer or epileptic drugs in the brain, just to name a few.

Thus, it is a preferred feature of the invention to design novel alkyne-, azide- and triazole-containing flavonoids, synthesis and characterization of the activity in inhibiting P-gp, MRP 1 and BCRP in cancer cells in vitro.

BRIEF DESCRIPTION OF THE DRAWINGS

FIGS. 1A-1P show Table 1 which summarizes cytotoxicity and MDR reversal activity of triazole dimers and their monomers.

FIGS. 2A-2D show Table 2 which summarizes selectivity of triazole dimers and their monomers for various ABC transporters.

FIGS. 3A-3D show Table 3 which summarizes $EC_{50}$ and therapeutic index of triazole dimers and their monomers.

FIGS. 4A and 4B show Table 4 which summarizes triazoles for the P-gp mediated paclitaxel resistance reversal potency in LCC6MDR.

FIG. 5 shows Table 5 which summarizes triazoles for the MRP1-mediated DOX resistance reversal potency in 2008/MRP1.

FIG. 6 shows Table 6 which summarizes triazoles for the MRP1-mediated vincristine resistance reversal potency in 2008MRP1.

FIG. 7 shows Table 7 which summarizes triazoles for BCRP-mediated topotecan resistance reversal potency in HEK293/R2.

FIG. 8 shows Table 8 which summarizes triazoles for the BCRP-mediated topotecan resistance reversal potency in MCF7-MX100.

FIG. 9 shows Table 9 which summarizes anti-triazole bridged flavonoid dimers synthesized (Y, 65 compounds).

MATERIALS AND METHODS

General.

All NMR spectra were recorded on a Bruker MHz DPX400 spectrometer at 400 MHz for $^1$H and 100 MHz for $^{13}$C or Varian Unity Inova 500 NB NMR Spectrometer at 500 MHz for $^1$H and 125 MHz for $^{13}$C. All NMR measurements were carried out at room temperature and the chemical shifts are reported as parts per million (ppm) in unit relative to the resonance of $CDCl_3$ (7.26 ppm in the $^1$H, 77.0 ppm for the central line of the triplet in the $^{13}$C modes, respectively). Low-resolution and high-resolution mass spectra were obtained on a Micromass Q-TOF-2 by electron spray ionization (ESI) mode or on Finnigan MAT95 ST by electron ionization (EI) mode. Melting points were measured using Electrothermal IA9100 digital melting point apparatus and were uncorrected. All reagents and solvents were reagent grade and were used without further purification unless otherwise stated. The plates used for thin-layer chromatography (TLC) were E. Merck Silica Gel 60F$_{254}$ (0.25-mm thickness) and they were visualized under short (254-nm) and long (365-nm) UV light. Chromatographic purifications were carried out using MN silica gel 60 (230-400 mesh). Substituted 4' or 7-hydroxyflavones 1a-h were prepared as reported previously.[58] The purity of tested compounds was determined by HPLC, which was performed by using Agilent 1100 series installed with an analytic column of Agilent Prep-Sil Scalar column (4.6 mm×250 mm, 5-μm) at UV detection of 320 nm (reference at 450 nm) with isocratic elution of hexane (50%)/ethyl acetate (25%)/methanol (25%) at a flow rate of 1.0 mL/min. All tested compounds were shown to >95% purity according to HPLC.

General Procedure for the Synthesis of Ac1 to Ac16 (Scheme 1)

(i) To a round-bottom flask was charged with corresponding 4'-hydroxyflavones or 7-hydroxyflavones 1a-e (1 equiv.), 5-chloropent-1-yne or 6-chlorohex-1-yne (1.2 equiv.), $K_2CO_3$ (1.5 equiv.) and DMF (3 ml per equiv (mmol)). The reaction mixture was stirred at refluxing temperature for 2 h. When TLC indicated complete consumption of starting material, the reaction mixture was poured into a separating funnel containing water. The mixture was continuously extracted with DCM. If the mixture could not be separated into two layers, small amount of 1M HCl was added. The combined organic layers were dried over MgSO$_4$, filtered and evaporated to give a brown crude reaction mixture. Purification was performed by flash column chromatography on silica gel with acetone in DCM as eluent to furnish desired product.

(ii) Excess KOH (3M solution in 96% EtOH, 3-4 equiv) was added to a mixture of 4-(hex-5-yn-1-yloxy)benzaldehyde (2a) (1.0 equiv) and the substituted 2'-hydroxyacetophenone 3a-e (1.0 equiv). The mixture was stirred at room temperature for 16 h. When TLC indicated complete consumption of starting material, the reaction mixture was acidified to pH 5 with 1M HCl at ice-bath temperature. The yellow precipitate formed was collected by suction filtration. The yellow solid was washed with n-hexane and subjected to crystallization from MeOH to afford the desired chalcones. If no precipitate was formed after the addition of 1M HCl, then the mixture was continuously extracted with DCM. The combined organic layers were dried over MgSO$_4$, filtered, and evaporated under reduced pressure to give a crude mixture, which was subjected to flash column chromatography using 15% EtOAc in hexane as eluent to furnish the desired chalcones.

2-(4-(Pent-4-yn-1-yloxy)phenyl)-4H-chromen-4-one (Ac1)

This compound (0.53 g, 82%) was obtained from 2-(4-hydroxyphenyl)-4H-chromen-4-one (1a) and 5-chloropent-1-yne according to the general procedure (i) described above. $^1$H NMR (400 MHz, CHLOROFORM-d) δ ppm 1.98-2.06 (m, 3H), 2.40-2.44 (m, 2H), 4.13 (t, J=6.40 Hz, 2H), 6.71 (s, 1H), 7.00 (d, J=8.80 Hz, 2H), 7.38 (dd, J=7.60, 7.20 Hz, 1H), 7.52 (d, J=8.40 Hz, 1H), 7.65 (ddd, J=7.60, 7.20, 1.60 Hz, 1H), 7.85 (d, J=8.80 Hz, 2H), 8.21 (dd, J=7.60, 1.60 Hz, 1H); $^{13}$C NMR (100 MHz, CHLOROFORM-d) δ ppm 15.07, 27.92, 66.32, 69.12, 83.11, 106.07, 114.87, 117.91, 123.86, 123.92, 125.02, 125.57, 127.94, 133.51, 156.10, 161.68, 163.33, 178.32; LRMS (ESI) m/z 305 [M+H]$^+$; HRMS (ESI) calcd for C$_{20}$H$_{17}$O$_3$ [M+H]$^+$ 305.1178, found 305.1180.

7-(Pent-4-yn-1-yloxy)-2-phenyl-4H-chromen-4-one (Ac2)

This compound (0.33 g, 79%) was obtained from 7-hydroxy-2-phenyl-4H-chromen-4-one (1e) and 5-chloropent-1-yne according to the general procedure (i) described above. $^1$H NMR (400 MHz, CHLOROFORM-d) δ ppm 1.99-2.07 (m, 3H), 2.40-2.44 (m, 2H), 4.16 (t, J=6.40 Hz, 2H), 6.71 (s, 1H), 6.93-6.95 (m, 2H), 7.47-7.49 (m, 3H), 7.84-7.86 (m, 2H), 8.09 (dd, J=7.20, 2.80 Hz, 1H); $^{13}$C NMR (100 MHz, CHLOROFORM-d) δ ppm 15.06, 27.78, 66.74, 69.27, 82.97, 100.87, 107.38, 114.67, 117.74, 126.06, 126.93, 128.94, 131.36, 131.73, 157.87, 162.90, 163.39, 177.77; LRMS (ESI) m/z 305 [M+H]$^+$; HRMS (ESI) calcd for C$_{20}$H$_{17}$O$_3$ [M+H]$^+$ 305.1178, found 305.1181.

7-Fluoro-2-(4-(pent-4-yn-1-yloxy)phenyl)-4H-chromen-4-one (Ac3)

This compound (0.31 g, 89%) was obtained from 7-fluoro-2-(4-hydroxyphenyl)-4H-chromen-4-one (1b) and 5-chloropent-1-yne according to the general procedure (i) described above. $^1$H NMR (400 MHz, CHLOROFORM-d) δ ppm 1.98-2.06 (m, 3H), 2.40-2.44 (m, 2H), 4.14 (t, J=6.00 Hz, 2H), 6.68 (s, 1H), 6.99 (d, J=8.80 Hz, 2H), 7.08-7.13 (m, 1H), 7.20 (dd, J=9.20, 2.40 Hz, 1H), 7.81 (t, J=8.80 Hz, 2H), 8.20 (dd, J=6.40, 6.40 Hz, 1H); $^{13}$C NMR (100 MHz, CHLOROFORM-d) δ ppm 15.06, 27.91, 66.35, 69.12, 83.08, 104.50, 104.75, 106.04, 113.58, 113.79, 114.93, 120.70, 123.52, 127.89, 156.98, 157.11, 161.80, 163.61, 164.26, 166.79, 177.27; LRMS (ESI) m/z 323 [M+H]$^+$; HRMS (ESI) calcd for C$_{20}$H$_{16}$FO$_3$ [M+H]$^+$ 323.1083, found 323.1086.

5-(Benzyloxy)-7-(methoxymethoxy)-2-(4-(pent-4-yn-1-yloxy)phenyl)-4H-chromen-4-one (Ac4)

This compound (0.11 g, 71%) was obtained from 5-(benzyloxy)-2-(4-hydroxyphenyl)-7-(methoxymethoxy)-4H-chromen-4-one (1c) and 5-chloropent-1-yne according to the general procedure (i) described above. $^1$H NMR (400 MHz, CHLOROFORM-d) δ ppm 1.97-2.03 (m, 3H), 2.38-2.42 (m, 2H), 3.47 (s, 3H), 4.09 (t, J=6.00 Hz, 2H), 5.20 (s, 2H), 5.21 (s, 2H), 6.47 (d, J=1.60 Hz, 1H), 6.54 (s, 1H), 6.73 (d, J=1.60 Hz, 1H), 6.95 (d, J=8.80 Hz, 2H), 7.26-7.40 (m, 3H), 7.62 (d, J=7.20 Hz, 2H), 7.77 (d, J=8.40 Hz, 2H); $^{13}$C NMR (100 MHz, CHLOROFORM-d) δ ppm 15.07, 27.94, 56.39, 66.28, 69.11, 70.66, 83.16, 94.29, 95.97, 98.69, 107.48, 110.18, 114.75, 123.71, 126.60, 127.55, 128.50, 136.44, 159.38, 159.55, 160.68, 161.19, 161.32, 177.32; LRMS (ESI) m/z 471 [M+H]$^+$; HRMS (ESI) calcd for C$_{29}$H$_{27}$O$_6$ [M+H]$^+$ 471.1808, found 471.1815.

2-(4-(Hex-5-yn-1-yloxy)phenyl)-6-methyl-4H-chromen-4-one (Ac5)

This compound (0.22 g, 73%) was obtained from 2-(4-hydroxyphenyl)-6-methyl-4H-chromen-4-one (1d) and 6-chloropent-1-yne according to the general procedure (i) described above. $^1$H NMR (500 MHz, CHLOROFORM-d) δ ppm 1.67-1.76 (m, 2H), 1.86-1.96 (m, 2H), 1.97 (br. s., 1H), 2.23-2.31 (m, 2H), 2.41 (s, 3H), 4.02 (t, J=6.10 Hz, 2H), 6.67 (s, 1H), 6.95 (d, J=8.30 Hz, 2H), 7.37-7.46 (m, 2H), 7.80 (d, J=8.79 Hz, 2H), 7.95 (s, 1H); $^{13}$C NMR (126 MHz, CHLOROFORM-d) δ ppm 18.06, 20.81, 24.87, 28.05, 67.49, 68.72, 83.81, 105.82, 114.77, 117.60, 123.45, 123.87, 124.88, 127.80, 134.61, 134.86, 154.32, 161.67, 163.15, 178.31; LRMS (ESI) m/z 333 [M+H]$^+$; HRMS (ESI) calcd for C$_{22}$H$_{21}$O$_3$ [M+H]$^+$ 333.1491, found 333.1495.

(E)-3-(4-(Hex-5-yn-1-yloxy)phenyl)-1-(2-hydroxyphenyl)prop-2-en-1-one (Ac6)

This compound (0.36 g, 75%) was obtained from 4-(hex-5-yn-1-yloxy)benzaldehyde (2a) and 2'-hydroxyacetophenone (3a) according to the general procedure (ii) described above. $^1$H NMR (400 MHz, CHLOROFORM-d) δ ppm 1.82-1.85 (m, 2H), 1.93-2.01 (m, 3H), 2.31-2.35 (m, 2H), 4.09 (t, J=6.00 Hz, 2H), 6.94-7.05 (m, 3H), 7.48-7.62 (m, 2H), 7.64-7.95 (m, 2H), 12.97 (s, 1H); $^{13}$C NMR (100 MHz, CHLOROFORM-d) δ ppm 18.16, 24.97, 28.15, 67.71, 68.84, 83.96, 114.74, 114.99, 117.52, 118.59, 118.75, 120.14, 127.26, 129.54, 130.57, 131.99, 136.13, 145.40, 161.50, 163.56, 193.67; LRMS (ESI) m/z 321 [M+H]$^+$; HRMS (ESI) calcd for C$_{21}$H$_{21}$O$_3$ [M+H]$^+$ 321.1491, found 321.1492.

(E)-1-(5-Ethyl-2-hydroxyphenyl)-3-(4-(hex-5-yn-1-yloxy)phenyl)prop-2-en-1-one (Ac7)

This compound (0.23 g, 61%) was obtained from 4-(hex-5-yn-1-yloxy)benzaldehyde (2a) and 2'-hydroxy-5'-ethylacetophenone (3b) according to the general procedure (ii) described above. $^1$H NMR (400 MHz, CHLOROFORM-d) δ ppm 1.26 (t, J=6.00 Hz, 3H), 1.74-1.78 (m, 2H), 1.93-2.01 (m, 3H), 2.63-2.69 (m, 2H), 4.09 (t, J=6.00 Hz, 2H), 6.94-6.98 (m, 3H), 7.35 (dd, J=2.00, 7.20 Hz, 1H), 7.53-7.71 (m, 3H), 7.91 (d, J=7.20 Hz, 1H), 12.84 (s, 1H); $^{13}$C NMR (100 MHz, CHLOROFORM-d) δ ppm 15.94, 18.17, 24.99, 28.17, 67.52, 68.84, 83.99, 114.96, 117.61, 118.41, 119.82, 127.32, 128.17, 130.57, 134.37, 136.09, 145.18, 161.45, 161.69, 193.59; LRMS (ESI) m/z 349 [M+H]$^+$; HRMS (ESI) calcd for $C_{23}H_{25}O_3$ [M+H]$^+$ 349.1804, found 349.1806.

(E)-3-(4-(Hex-5-yn-1-yloxy)phenyl)-1-(2-hydroxy-5-methylphenyl)prop-2-en-1-one (Ac8)

This compound (0.25 g, 70%) was obtained from 4-(hex-5-yn-1-yloxy)benzaldehyde (2a) and 2'-hydroxy-5'-methylacetophenone (3c) according to the general procedure (ii) described above. $^1$H NMR (400 MHz, CHLOROFORM-d) δ ppm 1.75-1.79 (m, 2H), 1.94-2.01 (m, 3H), 2.29 (t, J=6.00 Hz, 2H), 2.43 (s, 3H), 4.08 (t, J=6.00 Hz, 2H), 6.95 (d, J=8.70 Hz, 2H), 7.46 (d, J=15.40 Hz, 1H), 7.64 (d, J=8.70 Hz, 2H), 7.89-8.01 (m, 3H), 13.45 (s, 1H); $^{13}$C NMR (100 MHz, CHLOROFORM-d) δ ppm 18.15, 20.36, 24.96, 28.12, 67.59, 68.80, 83.92, 115.08, 118.08, 124.29, 126.85, 128.00, 130.93, 131.02, 136.09, 137.23, 146.98, 154.72, 161.95, 192.34; LRMS (ESI) m/z 335 [M+H]$^+$; HRMS (ESI) calcd for $C_{22}H_{23}O_3$ [M+H]$^+$ 335.1647, found 335.1649.

(E)-3-(4-(Hex-5-yn-1-yloxy)phenyl)-1-(2-hydroxy-4-methylphenyl)prop-2-en-1-one (Ac9)

This compound (0.31 g, 65%) was obtained from 4-(hex-5-yn-1-yloxy)benzaldehyde (2a) and 2'-hydroxy-4'-methylacetophenone (3d) according to the general procedure (ii) described above. $^1$H NMR (400 MHz, CHLOROFORM-d) δ ppm 1.74-1.78 (m, 2H), 1.93-2.01 (m, 3H), 2.30-2.34 (m, 2H), 2.39 (s, 3H), 4.08 (t, J=6.00 Hz, 2H), 6.78 (d, J=7.20 Hz, 1H), 6.85 (s, 1H), 6.97 (d, J=8.00 Hz, 2H), 7.55 (d, J=7.20 Hz, 1H), 7.64 (d, J=8.00 Hz, 2H), 7.82 (d, J=7.20 Hz, 1H), 7.92 (d, J=7.20 Hz, 2H), 13.02 (s, 1H); $^{13}$C NMR (100 MHz, CHLOROFORM-d) δ ppm 18.15, 21.97, 24.98, 28.16, 67.52, 68.75, 83.94, 114.97, 115.74, 117.94, 118.65, 120.05, 127.40, 129.41, 130.46, 144.86, 147.77, 161.38, 163.75, 193.11; LRMS (ESI) m/z 335 [M+H]$^+$; HRMS (ESI) calcd for $C_{22}H_{23}O_3$ [M+H]$^+$ 335.1647, found 335.1650.

(E)-1-(4-Fluoro-2-hydroxyphenyl)-3-(4-(hex-5-yn-1-yloxy)phenyl)prop-2-en-1-one (Ac10)

This compound (0.33 g, 69%) was obtained from 4-(hex-5-yn-1-yloxy)benzaldehyde (2a) and 2'-hydroxy-5'-fluoroacetophenone (3e) according to the general procedure (ii) described above. $^1$H NMR (400 MHz, CHLOROFORM-d) δ ppm 1.74-1.78 (m, 2H), 1.93-2.01 (m, 3H), 2.30-2.33 (m, 2H), 4.07 (t, J=6.00 Hz, 2H), 6.64-6.73 (m, 4H), 6.94 (d, J=8.00 Hz, 2H), 7.47 (d, J=15.40 Hz, 1H), 7.63 (d, J=8.00 Hz, 2H), 7.89-7.96 (m, 2H), 13.37 (s, 1H); $^{13}$C NMR (100 MHz, CHLOROFORM-d) δ ppm 18.15, 24.94, 28.14, 67.55, 68.81, 83.95, 104.98, 105.21, 106.86, 107.08, 114.74, 115.01, 117.20, 127.11, 130.61, 131.74, 131.86, 145.66, 161.60, 166.02, 166.06, 166.20, 192.49; LRMS (ESI) m/z 339 [M+H]$^+$; HRMS (ESI) calcd for $C_{21}H_{20}FO_3$ [M+H]$^+$ 339.1396, found 339.1398.

2-(4-(Pent-4-yn-1-yloxy)phenyl)quinazolin-4(3H)-one (Ac11)

To a well stirred solution of 4-(pent-4-yn-1-yloxy)benzaldehyde (2b) and 2-aminobenzamide (4) in DMSO at 150° C., was added catalytic amount of iodine. The reaction mixture was further heated for 3 h. When TLC indicated complete consumption of starting material, the reaction mixture was poured into a beaker containing water ice-bath temperature. The white precipitate formed was collected by suction filtration. The white solid was washed with n-hexane and subjected to crystallization from MeOH to afford the desired compound Ac11 (0.33 g, 65%). $^1$H NMR (400 MHz, DMSO-d$_6$) δ ppm 1.87-1.93 (m, 2H), 2.31-2.35 (m, 2H), 2.81 (s, 1H), 4.10 (t, J=6.00 Hz, 2H), 7.06 (d, J=8.80 Hz, 2H), 7.46 (dd, J=7.60, 7.60 Hz, 1H), 7.68 (d, J=7.60 Hz, 1H), 7.78 (dd, J=7.60, 7.60 Hz, 1H), 8.10-8.17 (m, 3H), 12.38 (s, 1H); $^{13}$C NMR (100 MHz, DMSO-d$_6$) δ ppm 14.87, 28.03, 66.67, 72.09, 83.98, 114.82, 121.08, 125.26, 126.23, 126.50, 127.63, 129.89, 134.91, 152.30, 161.51, 162.77; LRMS (ESI) m/z 305 [M+H]$^+$; HRMS (ESI) calcd for $C_{19}H_{17}N_2O_2$ [M+H]$^+$ 305.1290, found 305.1296.

7-(Hex-5-yn-1-yloxy)-2-phenyl-4H-chromen-4-one (Ac12)

This compound (0.13 g, 69%) was obtained from 7-hydroxy-2-phenyl-4H-chromen-4-one (1e) and 6-chloropent-1-yne according to the general procedure (i) described above. $^1$H NMR (500 MHz, CHLOROFORM-d) δ ppm 1.71-1.81 (m, 3H), 1.95-2.04 (m, 3H), 2.31 (td, J=7.08, 2.44 Hz, 2H), 4.12 (t, J=6.34 Hz, 3H), 6.77 (s, 1H), 6.95-7.01 (m, 2H), 7.49-7.55 (m, 3H), 7.89-7.94 (m, 2H), 8.13 (d, J=8.79 Hz, 1H); $^{13}$C NMR (101 MHz, CHLOROFORM-d) δ ppm 18.01, 24.79, 27.87, 67.91, 68.81, 83.71, 100.78, 107.34, 114.58, 117.63, 125.99, 126.83, 128.86, 131.25, 131.72, 157.81, 162.78, 163.44, 177.63; LRMS (ESI) m/z 319 [M+H]$^+$; HRMS (ESI) calcd for $C_{21}H_{19}O_3$ [M+H]$^+$ 319.1334, found 319.1328.

2-Phenyl-7-(2-(prop-2-yn-1-yloxy)ethoxy)-4H-chromen-4-one (Ac13)

To a round-bottom flask was charged with corresponding 7-hydroxyflavones 1e (0.021 mol, 5 g), 2-bromoethanol (0.022 mol, 1.6 ml), $K_2CO_3$ (0.021 mol, 2.9 g) and anhydrous DMF (20 ml). The reaction mixture was stirred at refluxing temperature for 3 h. The reaction mixture was poured into a beaker containing ice water followed by filtration and washing (50 ml hexane). This (3.2 g, 54%) was used without further purification. The obtained compound (7.1 mmol, 2 g) was then dissolved in anhydrous THF (10 ml). To this solution at room temperature, was added excess sodium hydride (8.5 mmol, 0.2 g) and propargyl bromide (80% in xylene) (7.1 mmol, 0.79 ml) solution successively at 0° C. for 1 hr. The reaction mixture was then stirred for 3 h at RT. When TLC indicated complete consumption of starting material, the reaction mixture was poured into a separating funnel containing water. The mixture was continuously extracted with DCM. The combined organic layers were dried over $MgSO_4$, filtered and evaporated to give a brown crude reaction mixture. Purification was performed by flash column chromatography on silica gel with acetone in DCM (1:10) as eluent to furnish titled compound (1.7 g, 75%). $^1$H NMR (500 MHz, CHLOROFORM-d) δ ppm 2.49 (t, J=2.44 Hz, 1H), 3.97-3.99 (m, 2H), 4.24-4.33 (m, 4H), 6.78 (s, 1H), 7.00 (d, J=2.44 Hz, 1H), 7.03 (dd, J=8.79, 2.44

Hz, 1H), 7.49-7.57 (m, 3H), 7.88-7.94 (m, 2H), 8.15 (d, J=8.79 Hz, 1H); $^{13}$C NMR (101 MHz, CHLOROFORM-d) δ ppm 58.47, 67.68, 74.92, 79.13, 101.01, 107.30, 114.56, 117.83, 125.95, 126.84, 128.81, 131.24, 131.62, 157.65, 162.79, 163.06, 177.50; LRMS (ESI) m/z 321 [M+H]$^+$; HRMS (ESI) calcd for $C_{20}H_{17}O_4$ [M+H]$^+$ 321.1127, found 321.1121.

2-(2-(di(prop-2-yn-1-yl)amino)ethoxy)ethanol (Ac14)

To a solution of 2-(2-aminoethoxy)ethanol (0.048 mol, 4.74 ml) in acetone (25 ml) at room temperature, was added excess propargyl bromide (0.1 mol, 11.6 ml) solution. The reaction mixture was then stirred at room temperature for 12 h. evaporated to give a brown crude reaction mixture. The oily substance was obtained after evaporation. Purification was performed by flash column chromatography on silica gel with acetone in DCM (1:3) as eluent to furnish titled compound (0.012 mol, 2.2 g, 25%). $^1$H NMR (500 MHz, CHLOROFORM-d) δ ppm 2.23 (br. s., 2H), 2.78 (t, J=5.12 Hz, 2H), 3.49 (s, 4H), 3.54-3.59 (m, 2H), 3.62 (t, J=5.37 Hz, 2H), 3.66-3.73 (m, 2H); $^{13}$C NMR (125 MHz, CHLOROFORM-d) δ ppm 42.45, 52.12, 61.68, 68.69, 72.30, 73.36, 78.36; LRMS (ESI) calcd for $C_{10}H_{16}NO_2$, 182, found m/z 182 [M+H]$^+$.

N-Benzyl-N,N-di(prop-2-yn-1-yl)amine (Ac15)

This compound was commercially available.

7-(2-(Benzyl(prop-2-yn-1-yl)amino)ethoxy)-2-phenyl-4H-chromen-4-one (Ac16)

To a well stirred solution of 7-hydroxyflavones 1e (2.9 mmol, 0.7 g), 2-(benzyl(prop-2-yn-1-yl)amino)ethanol (2.9 mmol, 0.56 g) and PPh$_3$ (0.77 g, 1 equiv.) in THF (10 ml) at room temperature, was added DIAD (0.58 ml, 1 equiv.) dropwise. The reaction mixture was then stirred for 12 h. The reaction mixture was evaporated to give a brown crude reaction mixture. Purification was performed by flash column chromatography on silica gel with acetone in DCM (1:50) as eluent to furnish titled compound (0.42 g, 35%). $^1$H NMR (500 MHz, CHLOROFORM-d) δ ppm 2.30 (t, J=2.20 Hz, 1H), 3.07 (t, J=5.61 Hz, 2H), 3.48 (d, J=2.44 Hz, 2H), 3.79 (s, 2H), 4.21 (t, J=5.61 Hz, 2H), 6.77 (s, 1H), 6.95-7.01 (m, 2H), 7.27-7.29 (m, 1H), 7.31-7.35 (m, 2H), 7.37-7.40 (m, 2H), 7.50-7.55 (m, 3H), 7.88-7.93 (m, 2H), 8.13 (d, J=8.78 Hz, 1H); $^{13}$C NMR (101 MHz, CHLOROFORM-d) ppm 42.61, 51.72, 58.53, 67.22, 70.04, 101.11, 107.54, 114.72, 117.93, 126.16, 127.07, 127.46, 128.42, 128.98, 129.12, 131.39, 131.89, 157.93, 163.03, 163.26, 177.82; LRMS (ESI) m/z 410 [M+H]$^+$; HRMS (ESI) calcd for $C_{27}H_{24}NO_3$ [M+H]$^+$ 410.1756, found 410.1750.

Tri(prop-2-yn-1-yl)amine (Ac17)

This compound was commercially available.
General Procedure for Synthesis of Az1 to Az15 (Scheme 2).
(i) To a round-bottom flask was charged with 4'-hydroxyflavones (1a, d, f, g, h) or 7-hydroxyflavones (1e) (1 equiv.), 2-bromoethanol or 2-(2-chloroethoxy)ethanol or 2-(2-(2-chloroethoxy)ethoxy)ethanol (1.2 equiv.), K$_2$CO$_3$ (1.5 equiv.) and DMF (3 mL per equiv.). The reaction mixture was stirred at refluxing temperature. When TLC indicated complete consumption of starting material, the reaction mixture was poured into a separating funnel containing water. The mixture was continuously extracted with DCM. If the mixture could not be separated into two layers, small amount of 1M HCl was added. The combined organic layers were dried over MgSO$_4$, filtered and evaporated to give a brown crude reaction mixture. Purification was performed by flash column chromatography on silica gel with acetone in DCM as eluent to furnish desired product.

(ii) The hydroxylated flavone obtained from (i) above was then dissolved in a solution of DCM (1 ml per equiv.) and triethylamine (1 mL per equiv.) at 0° C. Methanesulfonyl chloride (1.2 equiv.) was then added dropwise and stirred for 1 hr at room temperature. When TLC indicated complete consumption of the starting material, the white precipitate formed was removed by passing through a short pad of silica gel to furnish the mesylated product which was sufficiently pure for the next step. To a solution of the mesylate in ACN (2 ml per equiv.) was added excess of sodium azide (3 equiv.). The solution was kept for reflux at 80° C. for 15 h. The resulting solution was treated with water and then extracted with DCM. The combined organic layer was dried over MgSO$_4$ and concentrated at reduced pressure to give pale yellow viscous liquid. Purification was performed by flash column chromatography on silica gel with acetone in DCM as eluent to furnish desired product.

2-(4-(2-(2-Azidoethoxy)ethoxy)phenyl)-4H-chromen-4-one (Az1)

This compound (0.62 g, 45%) was obtained from 2-(4-hydroxyphenyl)-4H-chromen-4-one (1a) and 2-(2-chloroethoxy)ethanol according to the general procedure (i) and (ii) described above. $^1$H NMR (400 MHz, CHLOROFORM-d) δ ppm 3.32 (t, J=4.80 Hz, 2H), 3.65 (t, J=4.80 Hz, 2H), 3.77 (t, J=4.80 Hz, 2H), 4.06 (t, J=4.80 Hz, 2H), 6.56 (s, 1H), 6.86 (d, J=8.80 Hz, 2H), 7.26 (dd, J=7.60, 7.20 Hz, 1H), 7.37 (d, J=8.40 Hz, 1H), 7.53 (ddd, J=7.60, 7.20, 1.60 Hz, 1H), 7.68 (d, J=8.80 Hz, 2H), 8.05 (dd, J=7.60, 1.60 Hz, 1H); $^{13}$C NMR (100 MHz, CHLOROFORM-d) δ ppm 50.54, 67.46, 69.38, 70.17, 105.83, 114.85, 117.87, 123.69, 123.83, 124.92, 125.32, 127.76, 133.46, 155.91, 161.40, 163.05, 178.03; LRMS (ESI) m/z 352 [M+H]$^+$; HRMS (ESI) calcd for $C_{19}H_{18}N_3O_4$ [M+H]$^+$ 352.1297, found 352.1295.

2-(4-(2-(2-(2-Azidoethoxy)ethoxy)ethoxy)phenyl)-4H-chromen-4-one (Az2)

This compound (0.36 g, 41%) was obtained from 2-(4-hydroxyphenyl)-4H-chromen-4-one (1a) and 2-(2-chloroethoxy)ethanol according to the general procedure (i) and (ii) described above. $^1$H NMR (500 MHz, CHLOROFORM-d) δ ppm 3.40 (t, J=5.12 Hz, 2H), 3.68-3.73 (m, 4H), 3.74-3.78 (m, 2H), 3.91-3.93 (m, 2H), 4.20-4.25 (m, 2H), 6.75 (s, 1H), 7.05 (d, J=10 Hz, 2H), 7.41 (t, J=7.57 Hz, 1H), 7.55 (d, J=8.30 Hz, 1H), 7.66-7.71 (m, 1H), 7.88 (d, J=10 Hz, 2H), 8.23 (d, J=7.81 Hz, 1H); $^{13}$C NMR (126 MHz, CHLOROFORM-d) δ ppm 50.56, 67.54, 69.51, 69.98, 70.62, 70.79, 106.01, 114.93, 117.83, 123.78, 123.97, 124.92, 125.46, 127.81, 133.42, 156.01, 161.51, 163.19, 163.20, 178.15; LRMS (ESI) m/z 396 [M+H]$^+$, 418 [M+Na]$^+$; HRMS (ESI) calcd for $C_{21}H_{22}N_3O_5$ [M+H]$^+$ 396.1559, found 396.1544; calcd for $C_{21}H_{21}N_3O_5Na$ [M+Na]$^+$418.1379, found 418.1378.

2-(4-(2-(2-(2-Azidoethoxy)ethoxy)ethoxy)phenyl)-6-methyl-4H-chromen-4-one (Az3)

This compound (0.21 g, 36%) was obtained from 2-(4-hydroxyphenyl)-6-methyl-4H-chromen-4-one (1d) and 2-(2-(2-chloroethoxy)ethoxy)ethanol according to the general procedure (i) and (ii) described above. $^1$H NMR (500 MHz, CHLOROFORM-d) δ ppm 2.33 (s, 3H), 3.30 (t, J=4.88 Hz, 2H), 3.58-3.64 (m, 4H), 3.64-3.69 (m, 2H), 3.80 (t, J=4.64 Hz, 2H), 4.09 (t, J=4.64 Hz, 2H), 6.57 (s, 1H), 6.90 (d, J=10.0 Hz, 2H), 7.26-7.38 (m, 2H), 7.71 (d, J=10.0 Hz, 2H), 7.85 (s, 1H); $^{13}$C NMR (126 MHz, CHLOROFORM-d) δ ppm 20.58, 50.38, 67.35, 69.32, 69.77, 70.41, 70.59, 76.73, 76.99, 77.25, 105.57, 114.69, 117.40, 123.19, 123.82, 124.57, 127.52, 134.39, 134.61, 154.04, 161.25, 162.77, 177.93. LRMS (ESI) m/z 410 [M+H]$^+$, 432 [M+Na]$^+$; HRMS (ESI) calcd for $C_{22}H_{24}N_3O_5$ [M+H]$^+$ 410.1716, found 410.1709; calcd for $C_{22}H_{23}N_3O_5Na$ [M+Na]$^+$ 432.1535, found 432.1544.

2-(4-(2-(2-(2-Azidoethoxy)ethoxy)ethoxy)phenyl)-6-fluoro-4H-chromen-4-one (Az4)

This compound (0.23 g, 31%) was obtained from 6-fluoro-2-(4-hydroxyphenyl)-4H-chromen-4-one (1f) and 2-(2-(2-chloroethoxy)ethoxy)ethanol according to the general procedure (i) and (ii) described above. $^1$H NMR (500 MHz, CHLOROFORM-d) δ ppm 3.39 (t, J=4.88 Hz, 2H), 3.67-3.72 (m, 4H), 3.74-3.78 (m, 2H), 3.90-3.93 (m, 2H), 4.20-4.24 (m, 2H), 6.73 (s, 1H), 7.05 (d, J=10.0 Hz, 2H), 7.40 (ddd, J=9.03, 7.57, 2.93 Hz, 1H), 7.53-7.58 (m, 1H), 7.84-7.89 (m, 3H); $^{13}$C NMR (126 MHz, CHLOROFORM-d) δ ppm 50.35, 67.37, 69.25, 69.72, 69.73, 70.37, 70.55, 104.91, 110.07 (d, J=23.25 Hz, C5), 114.72, 119.74 (d, J=8.25 Hz, C8), 121.22 (d, J=25.63 Hz, C7), 123.28, 124.72 (d, J=7.25 Hz, C10), 127.56, 151.90 (d, J=1.25 Hz, C9), 159.64 (d, J=244.88 Hz, C6), 161.46, 163.15, 176.85 (d, J=2.50 Hz, C4); LRMS (ESI) m/z 414 [M+H]$^+$, 436 [M+]$^+$; HRMS (ESI) calcd for $C_{21}H_{21}N_3O_5F$ [M+H]$^+$ 414.1465, found 414.1472; calcd for $C_{21}H_{20}N_3O_5FNa$ [M+Na]$^+$ 436.1285, found 436.1299.

2-(4-(2-(2-(2-Azidoethoxy)ethoxy)ethoxy)phenyl)-3-(benzyloxy)-4H-chromen-4-one (Az5)

This compound (0.17 g, 32%) was obtained from 3-(benzyloxy)-2-(4-hydroxyphenyl)-4H-chromen-4-one (1 g) and 2-(2-(2-chloroethoxy)ethoxy)ethanol according to the general procedure (i) and (ii) described above. $^1$H NMR (500 MHz, CHLOROFORM-d) δ ppm 3.29 (t, J=4.88 Hz, 2H), 3.56-3.64 (m, 4H), 3.64-3.69 (m, 2H), 3.77-3.83 (m, 2H), 4.06-4.12 (m, 2H), 5.05 (s, 2H), 6.89 (d, J=10.0 Hz, 2H), 7.17-7.24 (m, 3H), 7.28 (t, J=7.50 Hz, 1H), 7.32-7.34 (m, 2H), 7.38 (d, J=8.30 Hz, 1H), 7.50-7.55 (m, 1H), 7.95 (d, J=10.0 Hz, 2H), 8.18 (d, J=10.0 Hz, 1H); $^{13}$C NMR (126 MHz, CHLOROFORM-d) δ ppm 50.22, 67.12, 69.19, 69.62, 70.24, 70.42, 73.39, 113.94, 117.49, 122.92, 123.70, 124.10, 125.12, 127.65, 127.80, 128.33, 130.01, 132.79, 136.43, 138.83, 154.63, 155.63, 160.27, 174.31; LRMS (ESI) m/z 502 [M+H]$^+$, 524 [M+Na]$^+$; HRMS (ESI) calcd for $C_{28}H_{28}N_3O_6$ [M+H]$^+$502.1978, found 502.1989; calcd for $C_{28}H_{27}N_3O_6Na$ [M+Na]$^+$524.1798, found 524.1797.

2-(4-(2-(2-(2-Azidoethoxy)ethoxy)ethoxy)phenyl)-6,8-dichloro-4H-chromen-4-one (Az6)

This compound (0.25 g, 34%) was obtained from 6,8-dichloro-2-(4-hydroxyphenyl)-4H-chromen-4-one (1h) and 2-(2-(2-chloroethoxy)ethoxy)ethanol according to the general procedure (i) and (ii) described above. $^1$H NMR (500 MHz, CHLOROFORM-d) δ ppm 3.39 (t, J=5.0 Hz, 2H), 3.67-3.73 (m, 4H), 3.74-3.78 (m, 2H), 3.92 (t, J=5.0 Hz, 2H), 4.23 (t, J=5.0 Hz, 2H), 6.77 (s, 1H), 7.06 (d, J=9.0 Hz, 2H), 7.72 (dd, J=2.44, 0.98 Hz, 1H), 7.93 (d, J=9.0 Hz, 2H), 8.09 (d, J=2.44, 1H); $^{13}$C NMR (101 MHz, CHLOROFORM-d) δ ppm 50.73, 67.78, 69.65, 70.14, 70.79, 70.97, 105.80, 115.31, 123.33, 123.91, 124.34, 125.78, 128.23, 130.72, 133.56, 150.45, 162.17, 163.51, 176.35; LRMS (ESI) m/z 464 [M+H]$^+$, 486 [M+Na]$^+$; HRMS (ESI) calcd for $C_{21}H_{20}N_3O_5Cl_2$ [M+H]$^+$ 464.0780, found 464.0783; calcd for $C_{21}H_{19}N_3O_5NaCl_2$ [M+Na]$^+$486.0599, found 486.0598.

2-(4-(2-(2-Azidoethoxy)ethoxy)phenyl)-6-fluoro-4H-chromen-4-one (Az7)

This compound (0.18 g, 37%) was obtained from 6-fluoro-2-(4-hydroxyphenyl)-4H-chromen-4-one (10 and 2-(2-chloroethoxy)ethanol according to the general procedure (i) and (ii) described above. $^1$H NMR (500 MHz, CHLOROFORM-d) δ ppm 3.42 (t, J=4.88 Hz, 2H), 3.73-3.79 (m, 2H), 3.88-3.93 (m, 2H), 4.19-4.24 (m, 2H), 6.71 (s, 1H), 7.03 (d, J=9.0, 2H), 7.35-7.42 (m, 1H), 7.54 (dd, J=9.03, 4.15 Hz, 1H), 7.81-7.88 (m, 3H); $^{13}$C NMR (126 MHz, CHLOROFORM-d) δ ppm 50.47, 67.43, 69.31, 70.09, 105.10, 110.22 (d, J=23.75 Hz, C5), 114.85, 119.84 (d, J=8.25 Hz, C8), 121.37 (d, J=25.13 Hz, C7), 123.53, 124.83 (d, J=7.83 Hz, C10), 127.72, 152.04, 159.27 (d, J=244.88 Hz, C6), 161.48, 163.29, 177.07, 177.09; LRMS (ESI) m/z 370 [M+H]$^+$; HRMS (ESI) calcd for $C_{19}H_{17}N_3O_4F$ [M+H]$^+$ 370.1203, found 370.1218.

Methyl 3-(((2-(4-(2-(2-azidoethoxy)ethoxy)phenyl)-4-oxo-4H-chromen-3-yl)oxy)methyl)benzoate (Az8)

A round-bottom flask was charged with 3-(benzyloxy)-2-(4-(2-(2-hydroxyethoxy)ethoxy)phenyl)-4H-chromen-4-one (5a) (5 mmol, 2.2 g), a catalytic amount of Pd(OH)$_2$ and THF/MeOH (1:1-10 ml). The reaction mixture was stirred vigorously under H$_2$ atmosphere at balloon pressure and room temperature for 14 h. When TLC indicated complete consumption of the starting material, the charcoal was removed by suction filtration. The pale-yellow filtrate was purified by passing through a short pad of silica gel to furnish debenzylated product 3-hydroxy-2-(4-(2-(2-hydroxyethoxy)ethoxy)phenyl)-4H-chromen-4-one (6a) (76%, 1.3 g). To a round-bottom flask was charged with the debenzylated product 6a, methyl 3-(bromomethyl)benzoate (4 mmol, 0.92 g), K$_2$CO$_3$ (4 mmol, 0.55 g) and acetone (10 ml). The reaction mixture was stirred at refluxing temperature for 12 h. When TLC indicated complete consumption of starting material, Solvent was rotary evaporated to dryness. Purification was performed by flash column chromatography on silica gel with acetone in DCM as eluent to furnish methyl 3-(((2-(4-(2-(2-hydroxyethoxy)ethoxy)phenyl)-4-oxo-4H-chromen-3-yl)oxy)methyl)benzoate (7a) (86%, 1.6 g). The titled compound Az8 (0.29 g, 57%) was obtained from 7a (1 mmol) according to the general procedure (ii) described above. $^1$H NMR (500 MHz, CHLOROFORM-d) δ ppm 3.44 (t, J=4.88 Hz, 2H), 3.76-3.79 (m, 2H), 3.89 (s, 3H), 3.90-3.94 (m, 2H), 4.20-4.25 (m, 2H), 5.15 (s, 2H), 6.99 (d, J=8.79 Hz, 2H), 7.35 (t, J=7.81 Hz, 1H), 7.41 (t, J=7.57 Hz, 1H), 7.52 (d, J=8.30 Hz, 1H), 7.59 (d, J=7.32 Hz, 1H), 7.65-7.71 (m, 1H), 7.93 (d, J=7.81 Hz, 1H), 7.96-8.01 (m, 3H), 8.29 (dd, J=7.81, 1.46 Hz, 1H); $^{13}$C NMR (101 MHz, CHLOROFORM-d) δ ppm 50.73, 52.03, 67.52, 69.64, 70.31, 73.36, 114.41, 117.93, 123.46, 124.19, 124.65, 125.77, 128.29, 129.27, 129.81, 130.13, 130.54, 133.24, 133.30, 137.18, 139.07, 155.22, 156.51, 160.62, 166.82, 174.87; LRMS (ESI) m/z 516 [M+H]$^+$, 538 [M+Na]$^+$; HRMS (ESI) calcd for $C_{28}H_{26}N_3O_7$ [M+H]$^+$ 516.1771, found 516.1783; calcd for $C_{28}H_{24}N_3O_7Na$ [M+Na]$^+$ 538.1590, found 538.1583.

Methyl 3-(((2-(4-(2-(2-(2-azidoethoxy)ethoxy) ethoxy)phenyl)-4-oxo-4H-chromen-3-yl)oxy) methyl)benzoate (Az9)

The titled compound Az9 (0.62 g, 37%) was obtained from 3-(benzyloxy)-2-(4-(2-(2-(2-hydroxyethoxy)ethoxy) ethoxy)phenyl)-4H-chromen-4-one (5b) (3 mmol, 1.5 g) according to the procedure for the synthesis of Az8 described above. $^1$H NMR (500 MHz, CHLOROFORM-d) δ ppm 3.40 (t, J=4.39 Hz, 2H), 3.67-3.74 (m, 5H), 3.74-3.79 (m, 2H), 3.89 (s, 3H), 3.92 (t, J=4.15 Hz, 2H), 4.22 (t, J=4.15 Hz, 2H), 5.15 (s, 2H), 6.98 (d, J=8.79 Hz, 2H), 7.35 (t, J=7.81 Hz, 1H), 7.42 (t, J=7.57 Hz, 1H), 7.52 (d, J=8.79 Hz, 1H), 7.59 (d, J=6.34 Hz, 1H), 7.65-7.70 (m, 1H), 7.93 (d, J=7.50 Hz, 1H), 7.96-8.01 (m, 3H), 8.29 (d, J=8.30 Hz, 1H); $^{13}$C NMR (101 MHz, CHLOROFORM-d) δ ppm 50.71, 52.04, 67.55, 69.71, 70.12, 70.78, 70.94, 73.35, 114.41, 117.92, 123.36, 124.20, 124.64, 125.78, 128.29, 129.28, 129.80, 130.14, 130.52, 133.23, 133.30, 137.19, 139.07, 155.23, 156.53, 160.73 166.82, 174.87; LRMS (ESI) m/z 560 [M+H]$^+$, 582 [M+Na]$^+$; HRMS (ESI) calcd for $C_{30}H_{30}N_3O_8$ [M+H]$^+$ 560.2033, found 560.2028; calcd for $C_{30}H_{29}N_3O_8Na$ [M+Na]$^+$ 582.1852, found 582.1831.

2-(4-(2-(2-Azidoethoxy)ethoxy)phenyl)-3-(benzyloxy)-4H-chromen-4-one (Az10)

This compound (0.23 g, 31%) was obtained from 3-(benzyloxy)-2-(4-hydroxyphenyl)-4H-chromen-4-one (1 g) and 2-(2-chloroethoxy)ethanol according to the general procedure (i) and (ii) described above. $^1$H NMR (500 MHz, CHLOROFORM-d) δ ppm 3.43-3.45 (m, 2H), 3.77-3.79 (m, 2H), 3.91-3.93 (m, 2H), 4.22-4.24 (m, 2H), 5.12 (s, 2H), 6.99 (d, J=8.79 Hz, 2H), 7.26-7.28 (m, 3H), 7.34-7.44 (m, 3H), 7.52 (d, J=8.30 Hz, 1H), 7.67 (t, J=7.81 Hz, 1H), 8.04 (d, J=8.79 Hz, 2H), 8.29 (d, J=7.81 Hz, 1H); $^{13}$C NMR (126 MHz, CHLOROFORM-d) δ ppm 50.49, 67.34, 69.39, 70.09, 73.70, 114.18, 117.72, 123.34, 123.97, 124.36, 125.45, 127.88, 128.03, 128.60, 130.31, 133.03, 136.62, 139.10, 154.93, 155.97, 160.39, 174.68; LRMS (ESI) m/z 458 [M+H]$^+$, 480 [M+Na]$^+$; HRMS (ESI) calcd for $C_{26}H_{24}N_3O_5$ [M+H]$^+$ 458.1716, found 458.1738; calcd for $C_{26}H_{23}N_3O_5Na$ [M+Na]$^+$ 480.1535, found 480.1527.

7-(2-(2-Azidoethoxy)ethoxy)-2-phenyl-4H-chromen-4-one (Az11)

This compound (0.12 g, 32%) was obtained from 7-hydroxy-2-phenyl-4H-chromen-4-one (1e) and 2-(2-chloroethoxy)ethanol according to the general procedure (i) and (ii) described above. $^1$H NMR (500 MHz, CHLOROFORM-d) δ ppm 3.43 (t, J=5.0 Hz, 2H), 3.78 (t, J=5.0 Hz, 2H), 3.93 (t, J=5.0 Hz, 2H), 4.27 (t, J=5.0 Hz, 2H), 6.79 (s, 1H), 6.99-7.04 (m, 2H), 7.49-7.56 (m, 3H), 7.88-7.93 (m, 2H), 8.14 (d, J=8.30 Hz, 1H); $^{13}$C NMR (101 MHz, CHLOROFORM-d) δ ppm 50.32, 67.68, 69.00, 69.98, 100.79, 106.92, 114.37, 117.52, 125.69, 126.49, 128.60, 131.06, 131.27, 157.39, 162.50, 162.87, 177.25; LRMS (ESI) m/z 352 [M+H]$^+$; HRMS (ESI) calcd for $C_{19}H_{18}N_3O_4$ [M+H]$^+$ 352.1297, found 352.1288.

7-(2-(2-(2-Azidoethoxy)ethoxy)ethoxy)-2-phenyl-4H-chromen-4-one (Az12)

This compound (0.14 g, 38%) was obtained from 7-hydroxy-2-phenyl-4H-chromen-4-one (1e) and 2-(2-(2-chloroethoxy)ethoxy)ethanol according to the general procedure (i) and (ii) described above. $^1$H NMR (500 MHz, CHLOROFORM-d) δ ppm 3.39 (t, J=4.88 Hz, 2H), 3.67-3.72 (m, 4H), 3.75-3.78 (m, 2H), 3.93-3.95 (m, 2H), 4.26 (t, J=5.0 Hz, 2H), 6.77 (s, 1H), 6.98-7.04 (m, 2H), 7.49-7.56 (m, 3H), 7.88-7.93 (m, 2H), 8.13 (d, J=8.78 Hz, 1H); $^{13}$C NMR (101 MHz, CHLOROFORM-d) δ ppm 50.53, 67.95, 69.33, 69.96, 70.59, 70.79, 101.00, 107.28, 114.64, 117.73, 125.97, 126.80, 128.83, 131.25, 131.61, 157.70, 162.86, 163.22, 177.63; LRMS (ESI) m/z 396 [M+H]$^+$; HRMS (ESI) calcd for $C_{21}H_{22}N_3O_5$ [M+H]$^+$ 396.1559, found 396.1544.

7-(2-Azidoethoxy)-2-phenyl-4H-chromen-4-one (Az13)

This compound (0.11 g, 29%) was obtained from 7-hydroxy-2-phenyl-4H-chromen-4-one (1e) and 2-bromoethanol according to the general procedure (i) and (ii) described above. $^1$H NMR (500 MHz, CHLOROFORM-d) δ ppm 3.68 (t, J=4.88 Hz, 2H), 4.26 (t, J=4.64 Hz, 2H), 6.74-6.80 (m, 1H), 6.96-7.05 (m, 2H), 7.47-7.56 (m, 3H), 7.85-7.93 (m, 2H), 8.11-8.19 (m, 1H); $^{13}$C NMR (101 MHz, CHLOROFORM-d) δ ppm 49.91, 67.48, 101.38, 107.52, 114.37, 118.30, 126.15, 127.31, 129.0, 131.47, 131.74, 157.80, 162.64, 163.15, 177.70; LRMS (ESI) m/z 308 [M+H]$^+$; HRMS (ESI) calcd for $C_{17}H_{14}N_3O_3$ [M+H]$^+$ 308.1035, found 308.1037.

2-(4-(2-((2-Azidoethyl)(benzyl)amino)ethoxy)phenyl)-4H-chromen-4-one (Az14)

To a well stirred solution of 4'-hydroxyflavones 1a (3 mmol, 0.71 g), N-benzyl-N,N-di(2-hydroxyethyl)amine (3 mmol, 0.6 g) and PPh$_3$ (3 mmol, 0.79 g) in THF (20 ml) at room temperature was added DIAD (3 mmol, 0.59 ml) dropwise. The reaction mixture was then stirred for 12 h at room temperature. When TLC indicated complete consumption of starting material, the reaction mixture was evaporated to give a brown crude reaction mixture. Purification was performed by flash column chromatography on silica gel with acetone in DCM (1:10) as eluent to furnish intermediate compound 2-(4-(2-(benzyl(2-hydroxyethyl)amino) ethoxy)phenyl)-4H-chromen-4-one (0.13 g, 10.4%). The titled compound Az14 (64.9 mg, 47%) was obtained from the intermediate compound according to the general procedure (ii) described above. $^1$H NMR (500 MHz, CHLORO FORM-d) δ ppm 2.91 (br. s., 2H), 3.03 (br. s., 2H), 3.32 (br. s., 2H), 3.80 (br. s., 2H), 4.15 (br. s., 2H), 6.77 (s, 1H), 6.92-6.96 (m, 2H), 7.27-7.37 (m, 5H), 7.49-7.56 (m, 3H), 7.89-7.93 (m, 2H), 8.13 (d, J=8.30 Hz, 1H); LRMS (ESI) m/z 441 [M+H]$^+$; HRMS (ESI) calcd for $C_{26}H_{25}N_4O_3$ [M+H]$^+$ 441.1927, found 441.1909.

7-(2-((2-Azidoethyl)(benzyl)amino)ethoxy)-2-phenyl-4H-chromen-4-one (Az15)

The titled compound Az15 (96 mg, 42%) was obtained from 7-hydroxyflavone 1e according to the procedure for the synthesis of Ac14 described above. $^1$H NMR (500 MHz, CHLOROFORM-d) δ ppm 2.90 (br. s., 2H), 3.00 (br. s., 2H), 3.32 (br. s., 2H), 3.79 (s, 2H), 4.11 (br. s., 2H), 6.75 (s, 1H), 6.98 (m, J=8.79 Hz, 2H), 7.26-7.44 (m, 6H), 7.54-7.58 (m, 1H), 7.66-7.71 (m, 1H), 7.84-7.91 (m, 2H), 8.23 (dd, J=7.81, 1.46 Hz, 1H); LRMS (ESI) m/z 441 [M+H]$^+$; HRMS (ESI) calcd for $C_{26}H_{25}N_4O_3$ [M+H]$^+$ 441.1927, found 441.1908.

Synthesis of anti-triazole bridged flavonoid dimers (Scheme 3 and Table 1 in FIGS. 1A-1P)

General Procedure for the Synthesis of Anti-Triazole Bridged Flavonoid Dimers Catalyzed by Cu(I).

The Cu(PPh$_3$)$_3$Br catalyst (MW=929) (0.05 mmol), prepared according to literature[66], was added to a THF solution (2 mL) containing the azide (Az 0.1 mmol) and the alkyne (Ac, 0.1 mmol). For Ac14- or Ac15, 0.2 mmol of azide was added. For Ac17, 0.3 mmol of azide was added. The reaction mixture was stirred overnight under reflux condition. Solvent was removed by evaporation and the resulting crude mixture showed the product to be only the anti-regioisomer except Ac13Az4 (anti:syn=97:3) and Ac13Az7 (anti:syn=85:15). The crude residue was purified by flash chromatography on silica gel using gradient of 10-50% of acetone with $CH_2Cl_2$ to afford the desired compound.

Ac1Az1

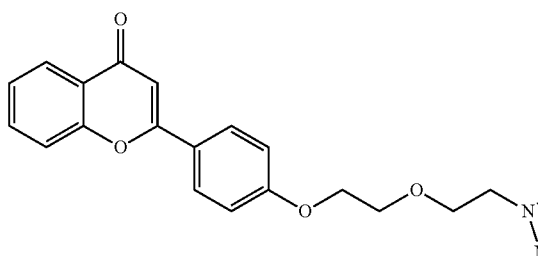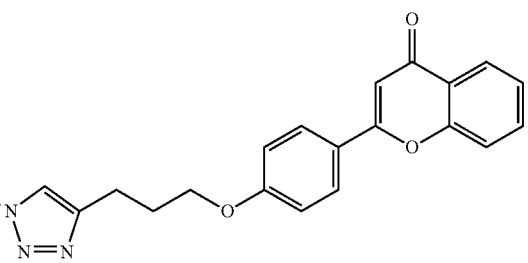

2-(4-(3-(1-(2-(2-(4-(4-Oxo-4H-chromen-2-yl)phenoxy)ethoxy)ethyl)-1H-1,2,3-triazol-4-yl)propoxy)phenyl)-4H-chromen-4-one (Ac1Az1)

This compound (90 mg) was obtained from Ac1 and Az1 in 81% yield according to the general procedure described above. $^1$H NMR (400 MHz, CHLOROFORM-d) δ ppm 2.08 (t, J=6.40 Hz, 2H), 2.82 (t, J=6.40 Hz, 2H), 3.75 (t, J=6.40 Hz, 2H), 3.87-3.96 (m, 4H), 4.04 (t, J=6.40 Hz, 2H), 4.50 (t, J=6.40 Hz, 2H), 6.57 (s, 1H), 6.60 (s, 1H), 6.85 (d, J=8.40 Hz, 2H), 6.89 (d, J=8.40 Hz, 2H), 7.25-7.28 (m, 2H), 7.39 (dd, J=7.20, 7.20 Hz, 2H), 7.48 (s, 1H), 7.55-7.56 (m, 2H), 7.69 (d, J=8.40 Hz, 2H), 7.74 (d, J=8.40 Hz, 2H), 8.08 (dd, J=7.20, 7.20 Hz, 2H); $^{13}$C NMR (100 MHz, CHLOROFORM-d) δ ppm 21.99, 28.66, 50.05, 67.07, 67.32, 69.40, 69.71, 105.81, 105.98, 114.72, 114.80, 117.86, 117.89, 122.16, 123.58, 123.70, 124.08, 124.98, 125.37, 127.80, 127.87, 133.49, 146.81, 155.93, 161.27, 161.66, 162.96, 163.16, 178.09, 178.14; LRMS (ESI) m/z 656 [M+H]$^+$; HRMS (ESI) calcd for $C_{39}H_{34}N_3O_7$ [M+H]$^+$ 656.2397, found 656.2394.

Ac2Az1

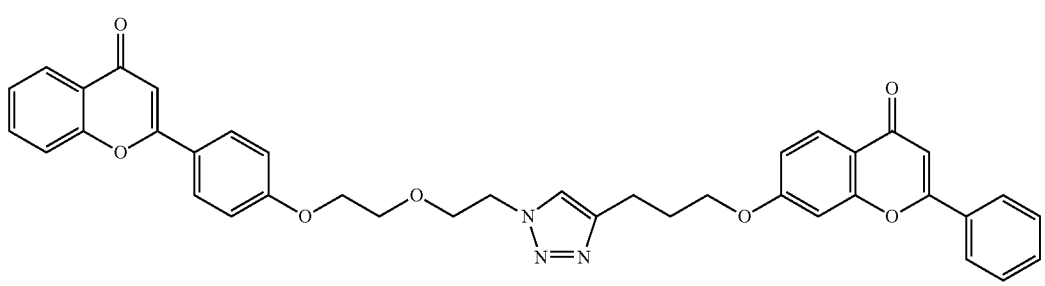

7-(3-(1-(2-(2-(4-(4-Oxo-4H-chromen-2-yl)phenoxy) ethoxy)ethyl)-1H-1,2,3-triazol-4-yl)propoxy)-2-phenyl-4H-chromen-4-one (Ac2Az1)

This compound (82 mg) was obtained from Ac2 and Az1 in 85% yield according to the general procedure described above. $^1$H NMR (400 MHz, CHLOROFORM-d) δ ppm 2.13 (t, J=6.40 Hz, 2H), 2.84 (t, J=6.40 Hz, 2H), 3.76 (t, J=6.40 Hz, 2H), 3.89 (t, J=6.40 Hz, 2H), 3.99-4.06 (m, 4H), 4.51 (t, J=6.40 Hz, 2H), 6.61 (s, 1H), 6.63 (s, 1H), 6.81-6.91 (m, 4H), 7.28 (dd, J=7.20, 7.20 Hz, 1H), 7.38-7.42 (m, 4H), 7.49 (s, 1H), 7.50 (dd, J=7.20, 7.20 Hz, 1H), 7.74-7.79 (m, 4H), 7.99 (d, J=7.20 Hz, 1H), 8.01 (d, J=7.20 Hz, 1H); $^{13}$C NMR (100 MHz, CHLOROFORM-d) δ ppm 21.94, 28.53, 50.08, 67.34, 67.55, 69.41, 69.71, 100.81, 106.00, 107.22, 114.56, 114.81, 117.57, 117.84, 122.16, 123.70, 124.13, 125.01, 125.36, 125.99, 126.78, 127.89, 128.90, 131.34, 131.57, 133.53, 146.69, 155.95, 157.76, 161.26, 162.80, 162.98, 163.39, 177.64, 178.12; LRMS (ESI) m/z 656 [M+H]$^+$; HRMS (ESI) calcd for $C_{39}H_{34}N_3O_7$ [M+H]$^+$ 656.2397, found 656.2401.

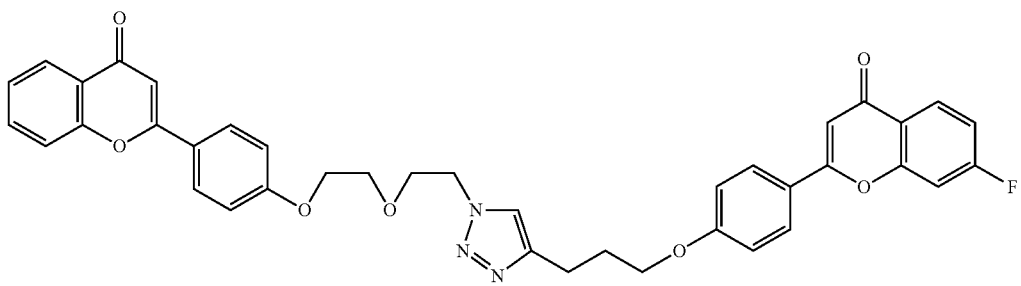 [SMILES: O=c1cc(-c2ccc(OCCOCCn3cc(CCCOc4ccc(-c5cc(=O)c6ccc(F)cc6o5)cc4)nn3)cc2)oc2ccccc12]

7-Fluoro-2-(4-(3-(1-(2-(2-(4-(4-oxo-4H-chromen-2-yl)phenoxy)ethoxy)ethyl)-1H-1,2,3-triazol-4-yl)propoxy)phenyl)-4H-chromen-4-one (Ac3Az1)

This compound (92 mg) was obtained from Ac3 and Az1 in 91% yield according to the general procedure described above. $^1$H NMR (400 MHz, CHLOROFORM-d) δ ppm 2.09 (t, J=6.40 Hz, 2H), 2.82 (t, J=6.40 Hz, 2H), 3.76 (t, J=4.80 Hz, 2H), 3.89 (t, J=4.80 Hz, 2H), 3.95 (t, J=6.40 Hz, 2H), 4.05 (t, J=6.40 Hz, 2H), 4.51 (t, J=6.40 Hz, 2H), 6.53 (s, 1H), 6.59 (s, 1H), 6.84 (d, J=8.20 Hz, 2H), 6.89 (d, J=8.20 Hz, 2H), 6.98-7.02 (m, 2H), 7.25-7.27 (m, 2H), 7.48 (d, J=7.40 Hz, 1H), 7.48 (s, 1H), 7.55 (dd, J=7.20, 7.20 Hz, 1H), 7.65 (d, J=8.20 Hz, 2H), 7.74 (d, J=8.20 Hz, 2H), 8.06-8.09 (m, 2H); $^{13}$C NMR (100 MHz, CHLOROFORM-d) δ ppm 21.98, 28.66, 50.05, 67.12, 67.33, 69.40, 69.71, 105.77, 105.98, 114.77, 114.79, 117.84, 120.57, 122.13, 123.17, 123.70, 124.09, 124.98, 125.37, 127.75, 127.86, 133.50, 146.80, 155.93, 156.82, 156.95, 161.27, 161.78, 162.93, 163.44, 164.14, 166.67, 177.10, 178.05; LRMS (ESI) m/z 674 [M+H]$^+$; HRMS (ESI) calcd for $C_{39}H_{33}N_3O_7$ [M+H]$^+$ 674.2303, found 674.2309.

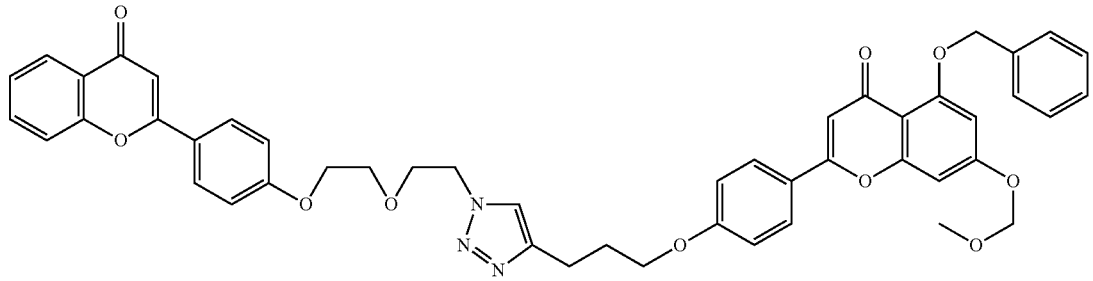 [SMILES: COCOc1cc(OCc2ccccc2)c2c(=O)cc(-c3ccc(OCCCc4cn(CCOCCOc5ccc(-c6cc(=O)c7ccccc7o6)cc5)nn4)cc3)oc2c1]

5-(Benzyloxy)-7-(methoxymethoxy)-2-(4-(3-(1-(2-(2-(4-(4-oxo-4H-chromen-2-yl)phenoxy)ethoxy)ethyl)-1H-1,2,3-triazol-4-yl)propoxy)phenyl)-4H-chromen-4-one (Ac4Az1)

This compound (120 mg) was obtained from Ac4 and Az1 in 85% yield according to the general procedure described above. $^1$H NMR (400 MHz, CHLOROFORM-d) δ ppm 2.09 (t, J=6.40 Hz, 2H), 2.83 (t, J=6.40 Hz, 2H), 3.44 (s, 3H), 3.75 (t, J=6.40 Hz, 2H), 3.88 (t, J=6.40 Hz, 2H), 3.96 (t, J=6.40 Hz, 2H), 4.04 (t, J=6.40 Hz, 2H), 4.49 (t, J=6.40 Hz, 2H), 5.16 (s, 2H), 5.17 (s, 2H), 6.43 (d, J=2.00 Hz, 1H), 6.46 (s, 1H), 6.63 (s, 1H), 6.68 (d, J=2.00 Hz, 1H), 6.86 (d, J=8.20 Hz, 2H), 6.92 (d, J=8.20 Hz, 2H), 7.24-7.35 (m, 5H), 7.46 (s, 1H), 7.58-7.67 (m, 5H), 7.78 (d, J=7.40 Hz, 2H), 8.13 (t, J=7.40 Hz, 2H); $^{13}$C NMR (100 MHz, CHLOROFORM-d) δ ppm 22.00, 28.67, 50.05, 56.37, 67.03, 67.33, 69.40, 69.72, 70.59, 94.27, 95.95, 98.64, 106.02, 107.34, 110.07, 114.63, 114.83, 117.88, 122.16, 123.48, 123.74, 124.15, 125.00, 126.57, 127.52, 127.90, 128.47, 133.53, 136.42, 146.82, 155.98, 159.29, 159.47, 160.58, 161.18, 161.28, 161.33, 163.00, 177.23, 178.13; LRMS (ESI) m/z 822 [M+H]$^+$; HRMS (ESI) calcd for $C_{48}H_{44}N_3O_{10}$ [M+H]$^+$ 822.3027, found 822.3034.

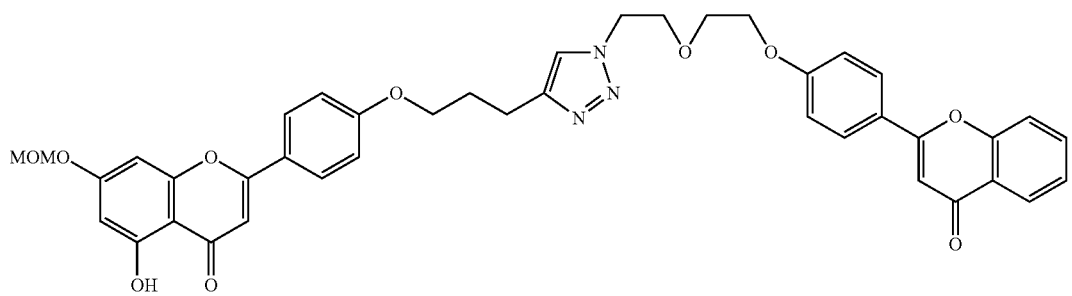

5-Hydroxy-7-(methoxymethoxy)-2-(4-(3-(1-(2-(2-(4-(4-oxo-4H-chromen-2-yl)phenoxy)ethoxy)ethyl)-1H-1,2,3-triazol-4-yl)propoxy)phenyl)-4H-chromen-4-one (Ac4Az1(5OH))

A round-bottom flask was charged with compound Ac4Az1 (25 mg, 0.03 mmol), a catalytic amount of Pd (20 mg, 10% on activated charcoal) and MeOH (20 mL). The reaction mixture was stirred vigorously under H$_2$ atmosphere at balloon pressure and room temperature for 14 h. When TLC indicated complete consumption of the starting material, the charcoal was removed by suction filtration. The pale-yellow filtrate was purified by passing through a short pad of silica gel to furnish the titled product (18 mg, 82%) as a white foam: $^1$H NMR (400 MHz, CHLOROFORM-d) δ ppm 2.12 (t, J=4.80 Hz, 2H), 2.85 (t, J=4.80 Hz, 2H), 3.46 (s, 3H), 3.79 (t, J=4.80 Hz, 2H), 3.91-3.98 (m, 4H), 4.09 (t, J=4.80 Hz, 2H), 4.52 (t, J=4.80 Hz, 2H), 5.19 (s, 2H), 6.38 (d, J=2.00 Hz, 1H), 6.44 (s, 1H), 6.57 (d, J=1.60 Hz, 1H), 6.65 (s, 1H), 6.85-6.94 (m, 4H), 7.26-7.48 (m, 3H), 7.66-7.79 (m, 5H), 8.11 (d, J=6.40 Hz, 1H), 12.71 (s, 1H); $^{13}$C NMR (100 MHz, CHLOROFORM-d) δ ppm 21.99, 28.67, 50.08, 56.37, 67.13, 67.35, 69.44, 69.74, 94.15, 94.22, 99.90, 104.02, 106.02, 106.05, 114.77, 114.84, 117.85, 122.15, 123.10, 123.75, 124.19, 125.01, 125.47, 127.88, 133.53, 146.81, 156.00, 157.35, 161.29, 161.84, 161.90, 162.78, 162.99, 163.89, 178.14, 182.30; LRMS (ESI) m/z 732 [M+H]$^+$; HRMS (ESI) calcd for $C_{41}H_{38}N_3O_{10}$ [M+H]$^+$ 732.2557, found 732.2563.

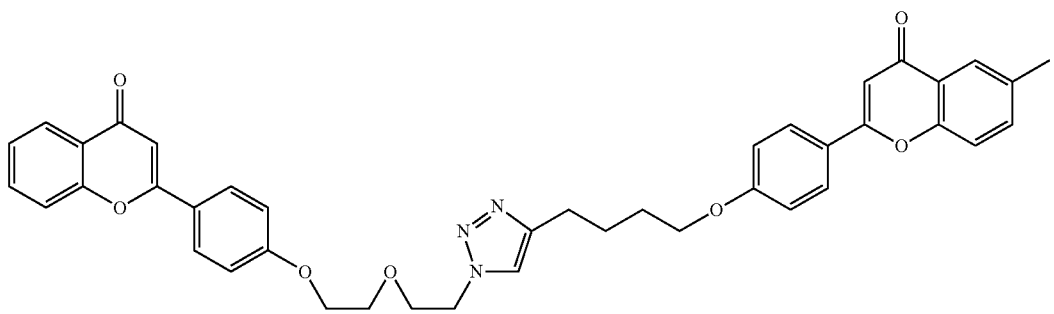 [SMILES: Cc1ccc2oc(-c3ccc(OCCCCc4cn(CCOCCOc5ccc(-c6cc(=O)c7ccccc7o6)cc5)nn4)cc3)cc(=O)c2c1]

6-Methyl-2-(4-(4-(1-(2-(2-(4-(4-oxo-4H-chromen-2-yl)phenoxy)ethoxy)ethyl)-1H-1,2,3-triazol-4-yl)butoxy)phenyl)-4H-chromen-4-one (Ac5Az1)

This compound (52 mg) was obtained from Ac5 and Az1 in 76% yield according to the general procedure described above. $^1$H NMR (500 MHz, CHLOROFORM-d) δ ppm 1.82 (br. s., 4H), 2.39 (s, 3H), 2.71-2.77 (m, 2H), 3.77-3.82 (m, 2H), 3.89-3.97 (m, 4H), 4.08-4.14 (m, 2H), 4.52 (t, J=5.12 Hz, 2H), 6.61 (s, 1H), 6.65 (s, 1H), 6.87 (d, J=10.0 Hz, 2H), 6.94 (d, J=10.0 Hz, 2H), 7.31 (t, J=10.0 Hz, 1H), 7.35 (d, J=8.79 Hz, 1H), 7.41 (dd, J=8.54, 2.20 Hz, 1H), 7.44 (d, J=8.30 Hz, 1H), 7.47 (s, 1H), 7.59 (t, J=7.5 Hz, 1H), 7.73 (d, J=10.0 Hz, 2H), 7.78 (d, J=10.0 Hz, 2H), 7.91 (s, 1H), 8.11 (dd, J=5.0 Hz, 1H); $^{13}$C NMR (126 MHz, CHLOROFORM-d) δ ppm 20.77, 25.21, 25.75, 28.50, 49.97, 67.35, 67.68, 69.40, 69.71, 105.71, 106.05, 114.66, 114.82, 117.57, 117.76, 121.81, 123.38, 123.72, 124.19, 124.77, 124.91, 125.42, 127.70, 127.81, 133.41, 134.56, 134.79, 147.46, 154.23, 155.93, 161.24, 161.60, 162.91, 163.00, 178.00, 178.18; LRMS (ESI) m/z 684 [M+H]$^+$; HRMS (ESI) calcd for $C_{41}H_{38}N_3O_7$ [M+H]$^+$ 684.2710, found 684.2727.

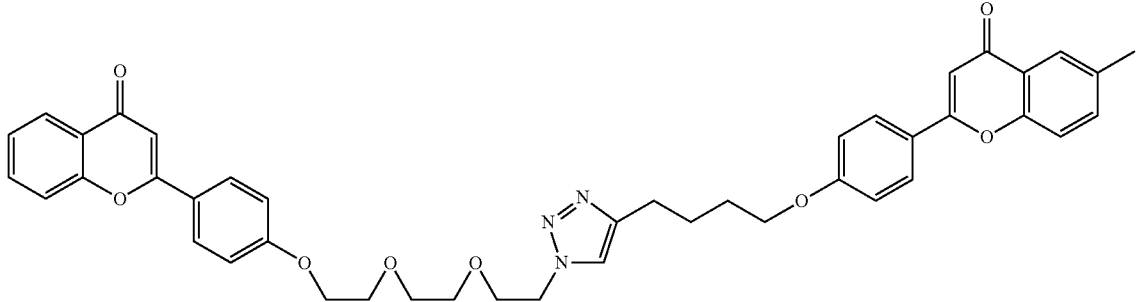 [SMILES: Cc1ccc2oc(-c3ccc(OCCCCc4cn(CCOCCOCCOc5ccc(-c6cc(=O)c7ccccc7o6)cc5)nn4)cc3)cc(=O)c2c1]

6-Methyl-2-(4-(4-(1-(2-(2-(2-(4-(4-oxo-4H-chromen-2-yl)phenoxy)ethoxy) ethoxy)ethyl)-1H-1,2,3-triazol-4-yl)butoxy)phenyl)-4H-chromen-4-one (Ac5Az2)

This compound (63 mg) was obtained from Ac5 and Az2 in 86% yield according to the general procedure described above. $^1$H NMR (500 MHz, CHLOROFORM-d) δ ppm 1.86 (br. s., 3H), 2.42-2.47 (m, 2H), 2.78 (br. s., 1H), 3.63-3.66 (m, 2H), 3.68-3.72 (m, 2H), 3.86 (dt, J=17.81, 4.76 Hz, 4H), 3.99-4.03 (m, 1H), 4.15-4.19 (m, 2H), 4.52 (t, J=5.12 Hz, 1H), 6.68 (s, 1H), 6.71 (s, 1H), 6.94 (d, J=8.79 Hz, 2H), 7.00 (d, J=8.79 Hz, 2H), 7.34-7.40 (m, 1H), 7.40-7.43 (m, 1H), 7.44-7.48 (m, 1H), 7.48-7.53 (m, 2H), 7.63-7.68 (m, 1H), 7.80 (d, J=8.79 Hz, 2H), 7.85 (d, J=9.27 Hz, 2H), 7.97 (s, 1H), 8.19 (dd, J=7.81, 1.46 Hz, 1H); $^{13}$C NMR (101 MHz, CHLOROFORM-d) δ ppm 20.73, 25.18, 25.77, 28.48, 49.94, 67.44, 67.65, 69.35, 69.44, 70.36, 70.45, 70.55, 71.15, 105.66, 105.93, 114.63, 114.80, 117.52, 117.76, 121.80, 123.35, 123.66, 123.70, 123.99, 124.73, 124.87, 125.36, 127.68, 127.76, 133.38, 134.55, 134.77, 147.38, 154.19, 155.91, 161.33, 161.57, 162.97, 163.00, 178.16; LRMS (ESI) m/z 728 [M+H]$^+$, 750 [M+Na]$^+$; HRMS (ESI) calcd for $C_{43}H_{42}N_3O_8$ [M+H]$^+$ 728.2972, found 728.2955; calcd for $C_{43}H_{41}N_3O_8Na$ [M+Na]$^+$ 750.2791, found 750.2815.

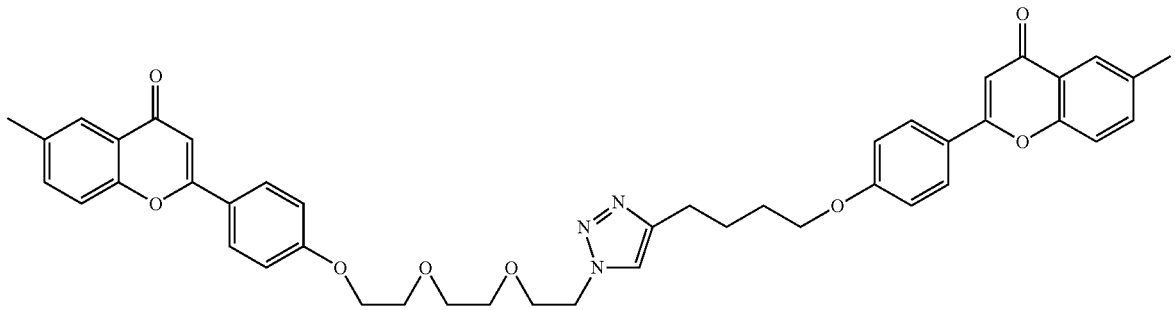

6-Methyl-2-(4-(2-(2-(2-(4-(4-(6-methyl-4-oxo-4H-chromen-2-yl)phenoxy)butyl)-1H-1,2,3-triazol-1-yl)ethoxy)ethoxy)ethoxy)phenyl)-4H-chromen-4-one (Ac5Az3)

This compound (68 mg) was obtained from Ac5 and Az3 in 92% yield according to the general procedure described above. $^1$H NMR (500 MHz, CHLOROFORM-d) δ ppm 1.85-1.87 (m, 4H), 2.45 (s, 3H), 2.43 (s, 3H), 2.77-2.79 (m, 2H), 3.63-3.67 (m, 2H), 3.67-3.72 (m, 2H), 3.85 (t, J=4.39 Hz, 2H), 3.88 (t, J=4.88 Hz, 2H), 3.99-4.03 (m, 2H), 4.17 (t, J=4.64 Hz, 2H), 4.52 (t, J=4.88 Hz, 2H), 6.69 (s, 1H), 6.70 (s, 1H), 6.94 (d, J=8.79 Hz, 2H), 7.00 (m, J=7.81 Hz, 2H), 7.41 (t, J=9.03 Hz, 2H), 7.47 (t, J=8.79 Hz, 2H), 7.51 (s, 1H), 7.84 (d, J=8.79 Hz, 2H), 7.81 (d, J=8.79 Hz, 2H), 7.97 (s, 1H), 7.97 (s, 1H); $^{13}$C NMR (101 MHz, CHLOROFORM-d) δ ppm 20.85, 25.32, 25.91, 28.61, 29.24, 50.06, 67.56, 67.77, 69.50, 69.58, 70.50, 70.69, 105.88, 106.04, 114.76, 114.89, 117.61, 117.64, 121.87, 123.54, 123.87, 124.36, 124.92, 127.81, 127.86, 134.66, 134.70, 134.90, 134.96, 154.36, 161.36, 161.69, 162.95, 163.13; LRMS (ESI) m/z 742 [M+H]$^+$; HRMS (ESI) calcd for $C_{44}H_{44}N_3O_8$ [M+H]$^+$ 742.3128, found 742.3103.

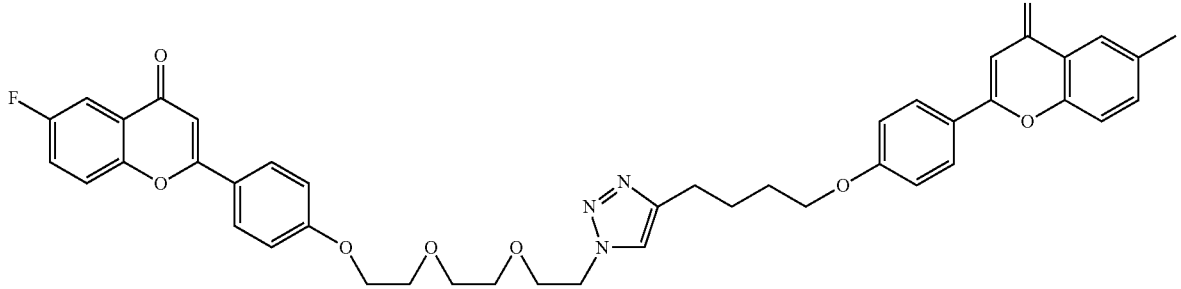

6-Fluoro-2-(4-(2-(2-(2-(4-(4-(4-(6-methyl-4-oxo-4H-chromen-2-yl)phenoxy)butyl)-1H-1,2,3-triazol-1-yl)ethoxy)ethoxy)ethoxy)phenyl)-4H-chromen-4-one (Ac5Az4)

This compound (59 mg) was obtained from Ac5 and Az4 in 79% yield according to the general procedure described above. $^1$H NMR (500 MHz, CHLOROFORM-d) δ ppm 1.84-1.89 (m, 4H), 2.44 (s, 3H), 2.75-2.81 (m, 2H), 3.62-3.67 (m, 2H), 3.67-3.72 (m, 2H), 3.82-3.86 (m, 2H), 3.88 (t, J=5.12 Hz, 2H), 3.99-4.04 (m, 2H), 4.13-4.18 (m, 2H), 4.52 (t, J=5.12 Hz, 2H), 6.69 (s, 1H), 6.69 (s, 1H), 6.94 (d, J=10 Hz, 2H), 6.70 (d, J=10 Hz, 2H), 7.37 (ddd, J=9.15, 7.69, 3.17 Hz, 1H), 7.41 (d, J=8.30 Hz, 1H), 7.47 (dd, J=8.54, 2.20 Hz, 1H), 7.49-7.53 (m, 2H), 7.78-7.85 (m, 5H), 7.97 (s, 1H); $^{13}$C NMR (126 MHz, CHLOROFORM-d) δ ppm 20.73, 25.20, 25.79, 28.49, 49.95, 67.47, 67.67, 69.35, 69.45, 70.38, 70.58, 105.21, 105.65, 110.29 (d, J=23.38 Hz, C5), 114.63, 114.84, 117.51, 119.85 (d, J=7.75 Hz, C8), 121.41 (d, J=25.63 Hz, C7), 121.76, 123.33, 123.67, 124.73, 124.88 (d, J=7.38 Hz, C10), 127.66, 127.78, 134.53, 134.77, 147.37, 152.07, 154.17, 159.31 (d, J=244.88 Hz, C6), 161.49, 161.57, 162.94, 163.22, 177.12, 178.12; LRMS (ESI) m/z 746 [M+H]$^+$, 768 [M+Na]$^+$; HRMS (ESI) calcd for $C_{43}H_{41}N_3O_8F$ [M+H]$^+$ 746.2878, found 746.2845; calcd for $C_{43}H_{40}N_3O_8FNa$ [M+Na]$^+$ 768.2697, found 768.2685.

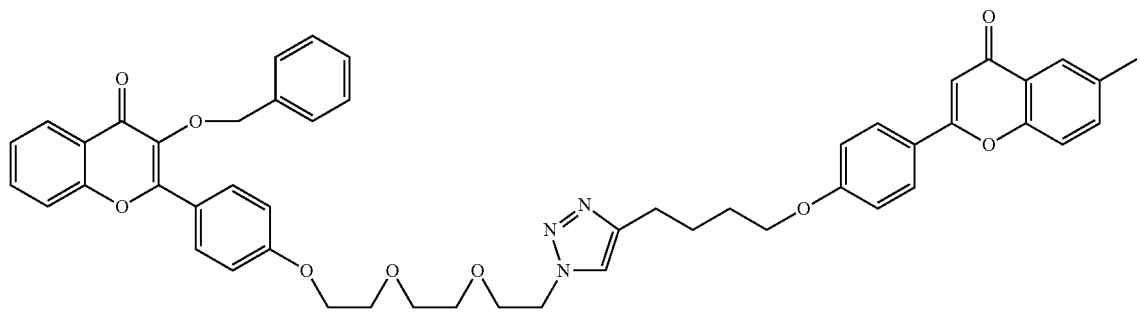 [SMILES: Cc1ccc2oc(-c3ccc(OCCCCc4cn(CCOCCOCCOc5ccc(-c6oc7ccccc7c(=O)c6OCc6ccccc6)cc5)nn4)cc3)cc(=O)c2c1]

3-(Benzyloxy)-2-(4-(2-(2-(2-(4-(4-(6-methyl-4-oxo-4H-chromen-2-yl)phenoxy)butyl)-1H-1,2,3-triazol-1-yl)ethoxy)ethoxy)ethoxy)phenyl)-4H-chromen-4-one (Ac5Az5)

This compound (56 mg) was obtained from Ac5 and Az5 in 63% yield according to the general procedure described above. $^1$H NMR (400 MHz, CHLOROFORM-d) δ ppm 1.81 (br. s., 4H), 2.38 (s, 3H), 2.74 (br. s., 2H), 3.59-3.63 (m, 2H), 3.78-3.82 (m, 2H), 3.84 (t, J=5.07 Hz, 2H), 3.91-3.97 (m, 2H), 4.09-4.15 (m, 2H), 4.48 (t, J=4.88 Hz, 2H), 5.07 (s, 2H), 6.62 (s, 1H), 6.85-6.93 (m, 4H), 7.20-7.26 (m, 3H), 7.28-7.37 (m, 4H), 7.38-7.44 (m, 2H), 7.50 (br. s., 1H), 7.58 (ddd, J=8.59, 7.03, 1.56 Hz, 1H), 7.70-7.77 (m, 2H), 7.91 (br. s., 1H), 7.98 (d, J=8.0, 2H), 8.19 (dd, J=8.20, 1.56 Hz, 1H); $^{13}$C NMR (101 MHz, CHLOROFORM-d) δ ppm 20.74, 25.21, 25.76, 28.49, 49.98, 67.36, 67.66, 69.44, 70.38, 70.56, 73.70, 105.70, 114.14, 114.66, 117.54, 117.71, 121.80, 123.37, 123.40, 123.70, 123.97, 124.40, 124.75, 125.48, 127.69, 127.91, 128.06, 128.60, 130.34, 133.08, 134.54, 134.76, 136.65, 139.14, 154.21, 154.93, 155.81, 160.39, 161.58, 163.01, 174.69, 178.18; LRMS (ESI) m/z 834 [M+H]$^+$, 856 [M+Na]$^+$; HRMS (ESI) calcd for C$_{50}$H$_{48}$N$_3$O$_9$ [M+H]$^+$ 834.3391, found 834.3367; calcd for C$_{50}$H$_{47}$N$_3$O$_9$Na [M+Na]$^+$ 856.3210, found 856.3195.

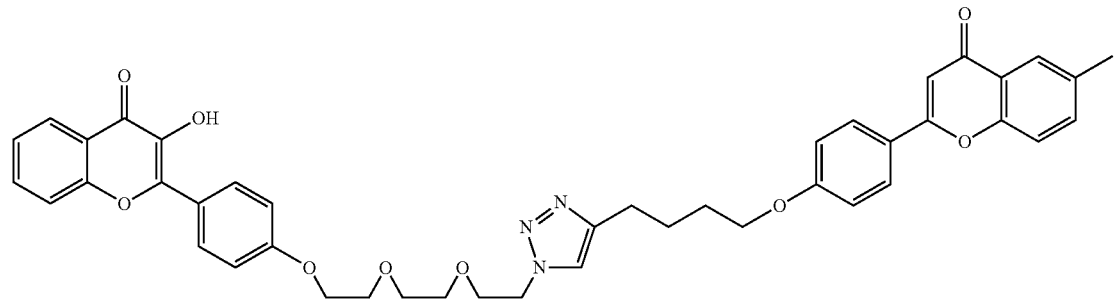 [SMILES: Cc1ccc2oc(-c3ccc(OCCCCc4cn(CCOCCOCCOc5ccc(-c6oc7ccccc7c(=O)c6O)cc5)nn4)cc3)cc(=O)c2c1]

3-Hydroxy-2-(4-(2-(2-(2-(4-(4-(6-methyl-4-oxo-4H-chromen-2-yl)phenoxy)butyl)-1H-1,2,3-triazol-1-yl)ethoxy)ethoxy)ethoxy)phenyl)-4H-chromen-4-one (Ac5Az5(OH))

A round-bottom flask was charged with compound Ac5Az5 (15 mg, 0.02 mmol), a catalytic amount of Pd (10 mg, 10% on activated charcoal), and MeOH (10 mL). The reaction mixture was stirred vigorously under H$_2$ atmosphere at balloon pressure and room temperature for 14 h. When TLC indicated complete consumption of the starting material, the charcoal was removed by suction filtration. The pale-yellow filtrate was purified by passing through a short pad of silica gel to furnish the titled product (12 mg, 92%): $^1$H NMR (500 MHz, CHLOROFORM-d) δ ppm 1.81-1.89 (m, 4H), 2.43 (s, 3H), 2.76-2.78 (m, 2H), 3.62-3.67 (m, 2H), 3.67-3.73 (m, 2H), 3.83-3.86 (m, 2H), 3.87 (t, J=5.12 Hz, 2H), 3.96-4.01 (m, 2H), 4.15-4.20 (m, 2H), 4.52 (t, J=5.12 Hz, 2H), 6.67 (s, 1H), 6.92 (d, J=10 Hz, 2H), 7.02-7.00 (m, 3H), 7.36 (t, J=7.57 Hz, 1H), 7.40 (d, J=8.30 Hz, 1H), 7.45 (dd, J=8.30, 1.95 Hz, 1H), 7.50-7.55 (m, 2H), 7.65 (t, J=8.30, 1H), 7.78 (d, J=10 Hz, 2H), 7.97 (s, 1H), 8.16-8.24 (m, 3H); $^{13}$C NMR (101 MHz, CHLOROFORM-d) δ ppm 20.89, 25.35, 25.94, 28.65, 50.10, 67.49, 67.82, 69.61, 70.55, 70.72, 105.92, 114.60, 114.78, 117.66, 118.09, 120.65, 121.91, 123.55, 123.84, 123.91, 124.36, 124.98, 125.34, 127.84, 129.47, 133.33, 134.67, 134.94, 137.65, 144.98, 147.56, 154.40, 155.20, 160.13, 161.73, 163.18, 173.06, 178.40; LRMS (ESI) m/z 744 [M+H]$^+$, 766 [M+Na]$^+$; HRMS (ESI) calcd for C$_{43}$H$_{42}$N$_3$O$_9$ [M+H]$^+$ 744.2921, found 744.2892; calcd for C$_{43}$H$_{41}$N$_3$O$_9$Na [M+Na]$^+$ 766.2741, found 766.2736.

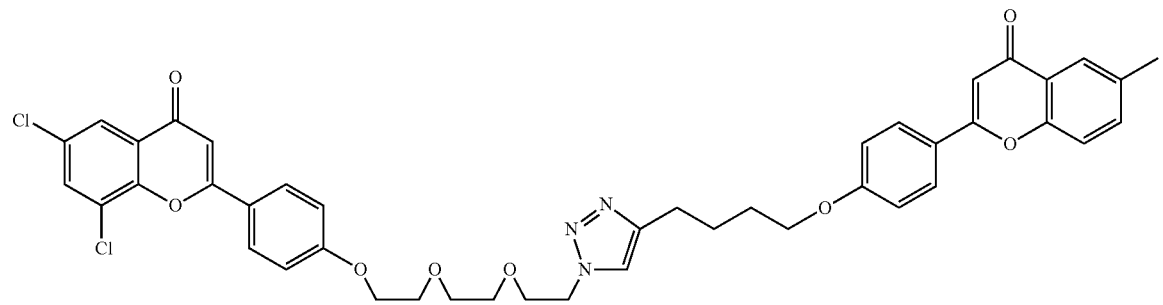 [SMILES: Cc1ccc2oc(-c3ccc(OCCCCc4cn(CCOCCOCCOc5ccc(-c6cc(=O)c7cc(Cl)cc(Cl)c7o6)cc5)nn4)cc3)cc(=O)c2c1]

6,8-Dichloro-2-(4-(2-(2-(2-(4-(4-(4-(6-methyl-4-oxo-4H-chromen-2-yl)phenoxy)butyl)-1H-1,2,3-triazol-1-yl)ethoxy)ethoxy)ethoxy)phenyl)-4H-chromen-4-one (Ac5Az6)

This compound (46 mg) was obtained from Ac5 and Az6 in 58% yield according to the general procedure described above. $^1$H NMR (500 MHz, CHLOROFORM-d) δ ppm 1.86 (br. s., 4H), 2.46 (s, 3H), 2.75-2.80 (m, 2H), 3.62-3.67 (m, 2H), 3.70 (d, J=2.44 Hz, 2H), 3.84-3.86 (m, 2H), 3.89 (t, J=4.88 Hz, 2H), 4.00 (br. s., 2H), 4.17-4.19 (m, 2H), 4.53 (t, J=4.88 Hz, 2H), 6.69 (s, 1H), 6.73 (s, 1H), 6.93 (d, J=10 Hz, 2H), 7.02 (d, J=10 Hz, 2H), 7.42 (d, J=8.30 Hz, 1H), 7.47 (d, J=8.79 Hz, 1H), 7.51 (s, 1H), 7.79-7.81 (d, J=10 Hz, 2H), 7.88-7.90 (d, J=10 Hz, 2H), 7.98 (s, 1H), 8.01-8.05 (m, 1H); LRMS (ESI) m/z 796 [M+H]$^+$, 818 [M+Na]$^+$; HRMS (ESI) calcd for $C_{43}H_{40}N_3O_8Cl_2$ [M+H]$^+$ 796.2192, found 796.2206; calcd for $C_{43}H_{39}N_3O_8NaCl_2$ [M+Na]$^+$ 818.2012, found 818.1998.

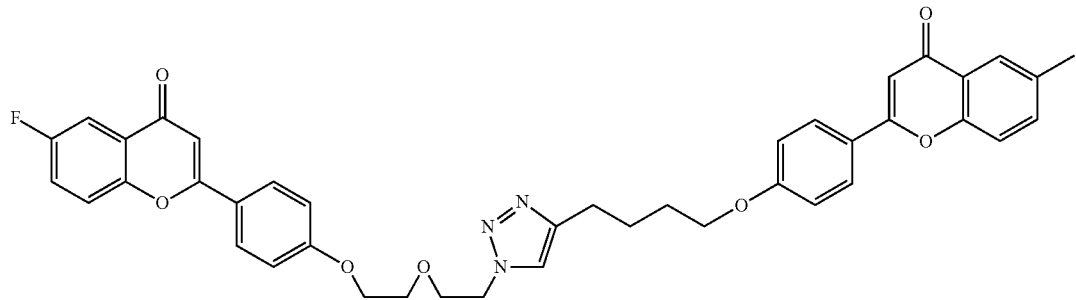 [SMILES: Cc1ccc2oc(-c3ccc(OCCCCc4cn(CCOCCOc5ccc(-c6cc(=O)c7cc(F)ccc7o6)cc5)nn4)cc3)cc(=O)c2c1]

6-Fluoro-2-(4-(2-(2-(4-(4-(4-(6-methyl-4-oxo-4H-chromen-2-yl)phenoxy) butyl)-1H-1,2,3-triazol-1-yl)ethoxy)ethoxy)phenyl)-4H-chromen-4-one (Ac5Az7)

This compound (61 mg) was obtained from Ac5 and Az7 in 87% yield according to the general procedure described above. $^1$H NMR (500 MHz, CHLOROFORM-d) δ ppm 1.85 (br. s., 4H), 2.43 (s, 3H), 2.77 (br. s., 2H), 3.81-3.85 (m, 2H), 3.94 (t, J=4.88 Hz, 2H), 3.99 (br. s., 2H), 4.11-4.16 (m, 2H), 4.54 (t, J=4.88 Hz, 2H), 6.65 (s, 1H), 6.67 (s, 1H), 6.91 (d, J=8.79 Hz, 2H), 6.97 (d, J=8.79 Hz, 2H), 7.30-7.36 (m, 1H), 7.37-7.41 (m, 1H), 7.43-7.50 (m, 3H), 7.74-7.82 (m, 5H), 7.95 (s, 1H); $^{13}$C NMR (126 MHz, CHLOROFORM-d) δ ppm 20.85, 25.28, 25.84, 28.57, 50.08, 67.44, 67.77, 69.48, 69.81, 105.49, 105.85, 110.51 (d, J=23.75 Hz, C5) 114.76, 114.94, 117.63, 119.89 (d, J=7.75 Hz, C8), 121.58 (d, J=25.75 Hz, C7), 121.89, 123.47, 123.89, 124.05, 124.90, 125.02 (d, J=7.38 Hz, C10), 127.80, 127.96, 134.66, 134.93, 147.60, 152.21, 152.22, 154.33, 159.47 (d, J=245.25 Hz, C6), 161.46, 161.67, 163.09, 163.30, 177.27, 178.31; LRMS (ESI) m/z 702 [M+H]$^+$; HRMS (ESI) calcd for $C_{42}H_{37}N_3O_8F$ [M+H]$^+$ 702.2503, found 702.2534.

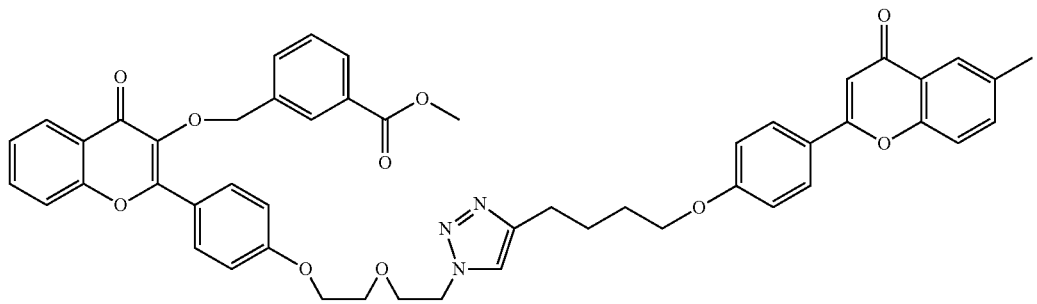 [SMILES: COC(=O)c1cccc(COc2c(-c3ccc(OCCOCCn4cc(CCCCOc5ccc(-c6cc(=O)c7cc(C)ccc7o6)cc5)nn4)cc3)oc3ccccc3c2=O)c1]

Methyl 3-(((2-(4-(2-(2-(4-(4-(4-(6-methyl-4-oxo-4H-chromen-2-yl) phenoxy)butyl)-1H-1,2,3-triazol-1-yl)ethoxy)ethoxy)phenyl)-4-oxo-4H-chromen-3-yl) oxy)methyl)benzoate (Ac5Az8)

This compound (44 mg) was obtained from Ac5 and Az8 in 51% yield according to the general procedure described above. $^1$H NMR (500 MHz, CHLOROFORM-d) δ ppm 1.84 (br. s., 4H), 2.43 (s, 3H), 2.77 (br. s., 2H), 3.82-3.84 (m, 2H), 3.86 (s, 3H), 3.94 (t, J=4.88 Hz, 2H), 3.98 (br. s., 2H), 4.11-4.17 (m, 2H), 4.54 (t, J=4.88 Hz, 2H), 5.13 (s, 2H), 6.65 (s, 1H), 6.92 (t, J=8.30 Hz, 4H), 7.32-7.37 (m, 2H), 7.40 (d, J=5 Hz, 1H), 7.45 (d, J=8.79 Hz, 2H), 7.50 (br. s., 1H), 7.58 (d, J=6.83 Hz, 1H), 7.60-7.64 (m, 1H), 7.77 (d, J=8.30 Hz, 2H), 7.86-8.01 (m, 5H), 8.22 (d, J=7.81 Hz, 1H); $^{13}$C NMR (101 MHz, CHLOROFORM-d) δ ppm 20.86, 25.29, 25.83, 28.58, 50.07, 51.98, 67.29, 67.76, 69.56, 69.79, 73.26, 105.86, 114.25, 114.77, 117.65, 117.81, 121.88, 123.51, 123.86, 124.07, 124.61, 124.91, 125.66, 127.81, 128.25, 129.20, 129.73, 130.07, 130.49, 133.15, 133.29, 134.65, 134.90, 137.15, 139.03, 147.58, 154.35, 155.08, 156.15, 160.40, 161.68, 163.13, 166.72, 174.72, 178.33; LRMS (ESI) m/z 848 [M+H]$^+$, 870 [M+Na]$^+$; HRMS (ESI) calcd for $C_{50}H_{46}N_3O_{10}$ [M+H]$^+$ 848.3183, found 848.3145; calcd for $C_{50}H_{45}N_3O_{10}Na$ [M+Na]$^+$ 870.3003, found 870.2966.

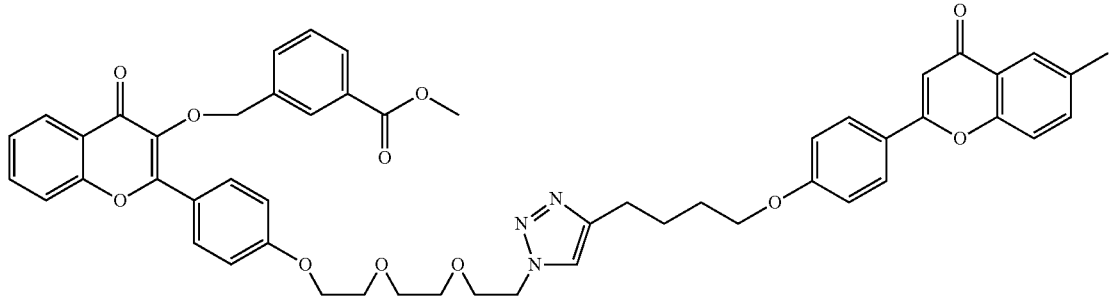 [SMILES: COC(=O)c1cccc(COc2c(-c3ccc(OCCOCCOCCn4cc(CCCCOc5ccc(-c6cc(=O)c7cc(C)ccc7o6)cc5)nn4)cc3)oc3ccccc3c2=O)c1]

Methyl 3-(((2-(4-(2-(2-(2-(4-(4-(4-(6-methyl-4-oxo-4H-chromen-2-yl) phenoxy)butyl)-1H-1,2,3-triazol-1-yl)ethoxy)ethoxy)ethoxy)phenyl)-4-oxo-4H-chromen-3-yl)oxy)methyl)benzoate (Ac5Az9)

This compound (83 mg) was obtained from Ac5 and Az9 in 93% yield according to the general procedure described above. $^1$H NMR (500 MHz, CHLOROFORM-d) δ ppm 1.86 (br. s., 4H), 2.44 (s, 3H), 2.78 (br. s., 2H), 3.62-3.67 (m, 2H), 3.68-3.72 (m, 2H), 3.81-3.90 (m, 7H), 4.01 (br. s., 2H), 4.17 (t, J=4.39 Hz, 2H), 4.52 (t, J=4.88 Hz, 2H), 5.14 (s, 2H), 6.69 (s, 1H), 6.91-6.97 (m, 4H), 7.34 (t, J=7.81 Hz, 1H), 7.36-7.40 (m, 1H), 7.42 (d, J=10 Hz, 1H), 7.44-7.50 (m, 2H), 7.51 (br. s., 1H), 7.60 (d, J=5 Hz, 1H), 7.61-7.68 (m, 1H), 7.80-7.82 (d, J=10 Hz, 2H), 7.87-8.02 (m, 5H), 8.25 (d, J=10, 1H); $^{13}$C NMR (101 MHz, CHLOROFORM-d) δ ppm 20.76, 25.22, 25.79, 28.51, 29.17, 49.99, 51.91, 67.36, 67.69, 69.45, 69.49, 70.41, 70.59, 73.15, 105.74, 114.20, 114.68, 117.56, 117.77, 121.81, 123.26, 123.40, 123.74, 123.97, 124.50, 124.79, 125.53, 127.72, 128.17, 129.12, 129.61, 129.99, 130.36, 133.05, 133.19, 134.56, 134.80, 137.08, 138.92, 154.24, 154.99, 156.11, 160.46, 161.61, 163.04, 166.63, 174.62, 178.20; LRMS (ESI) m/z 892 [M+H]$^+$, 914 [M+Na]$^+$; HRMS (ESI) calcd for $C_{52}H_{50}N_3O_{11}$ [M+H]$^+$ 892.3445, found 892.3410; calcd for $C_{52}H_{49}N_3O_{11}Na$ [M+Na]$^+$ 914.3265, found 914.3301.

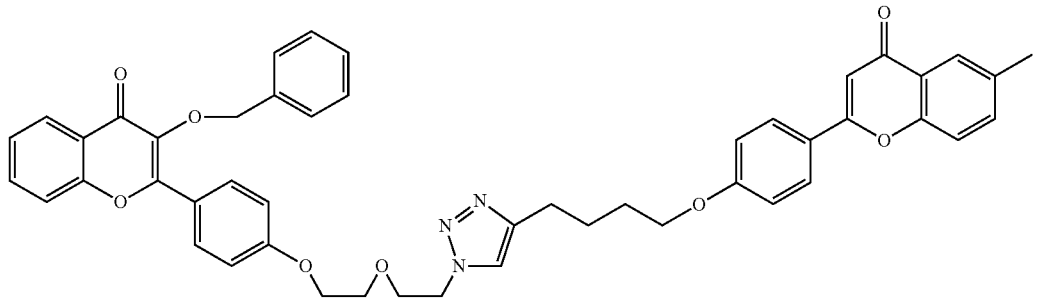 [SMILES: Cc1ccc2oc(-c3ccc(OCCCCc4cn(CCOCCOc5ccc(-c6oc7ccccc7c(=O)c6OCc6ccccc6)cc5)nn4)cc3)cc(=O)c2c1]

3-(Benzyloxy)-2-(4-(2-(2-(4-(4-(4-(6-methyl-4-oxo-4H-chromen-2-yl)phenoxy)butyl)-1H-1,2,3-triazol-1-yl)ethoxy)ethoxy)phenyl)-4H-chromen-4-one (Ac5Az10)

This compound (77 mg) was obtained from Ac5 and Az10 in 98% yield according to the general procedure described above. $^1$H NMR (400 MHz, CHLOROFORM-d) δ ppm 1.83 (br. s., 3H), 2.41 (s, 2H), 2.67-2.81 (m, 2H), 3.78-3.85 (m, 2H), 3.89-3.98 (m, 4H), 4.09-4.17 (m, 2H), 4.53 (t, J=5.07 Hz, 2H), 5.09 (s, 2H), 6.63 (s, 1H), 6.92 (d, J=9.37 Hz, 2H), 6.89 (d, J=8.98 Hz, 2H), 7.22-7.28 (m, 3H), 7.29-7.46 (m, 6H), 7.48 (s, 1H), 7.59 (ddd, J=8.59, 7.03, 1.56 Hz, 1H), 7.75 (d, J=10 Hz, 2H), 7.95 (s, 1H), 8.0 (d, J=10 Hz, 2H), 8.21 (d, J=10.0 Hz, 1H); $^{13}$C NMR (101 MHz, CHLOROFORM-d) δ ppm 20.84, 25.27, 25.81, 28.56, 50.05, 67.29, 67.73, 69.53, 69.76, 73.81, 105.83, 114.20, 114.75, 117.63, 117.76, 121.89, 123.47, 123.67, 123.82, 124.07, 124.51, 124.87, 125.62, 127.79, 128.01, 128.15, 128.68, 130.46, 133.18, 134.63, 134.87, 136.74, 139.27, 147.55, 154.32, 155.02, 155.81, 160.34, 161.66, 163.11, 174.78, 178.30; LRMS (ESI) m/z 790 [M+H]$^+$, 812 [M+Na]$^+$; HRMS (ESI) calcd for $C_{48}H_{44}N_3O_8$ [M+H]$^+$ 790.3128, found 790.3140; calcd for $C_{48}H_{43}N_3O_8Na$ [M+Na]$^+$ 812.2948, found 812.2961.

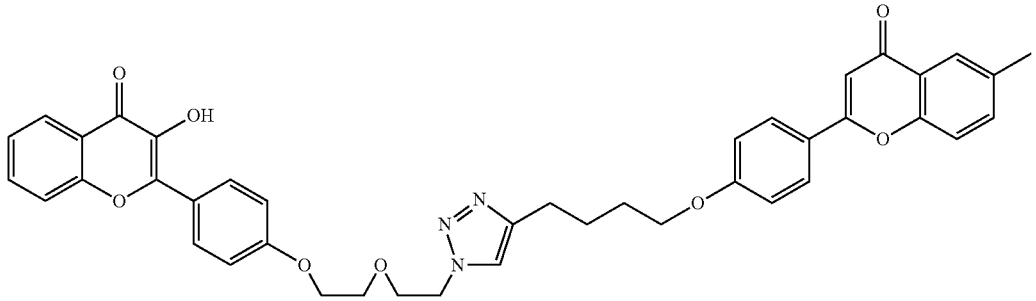 [SMILES: Cc1ccc2oc(-c3ccc(OCCCCc4cn(CCOCCOc5ccc(-c6oc7ccccc7c(=O)c6O)cc5)nn4)cc3)cc(=O)c2c1]

3-Hydroxy-2-(4-(2-(2-(4-(4-(4-(6-methyl-4-oxo-4H-chromen-2-yl)phenoxy)butyl)-1H-1,2,3-triazol-1-yl)ethoxy)ethoxy)phenyl)-4H-chromen-4-one (Ac5Az10(OH))

A round-bottom flask was charged with compound Ac5Az10 (17 mg, 0.03 mmol), a catalytic amount of Pd (15 mg, 10% on activated charcoal), and MeOH (10 mL). The reaction mixture was stirred vigorously under H$_2$ atmosphere at balloon pressure and room temperature for 14 h. When TLC indicated complete consumption of the starting material, the charcoal was removed by suction filtration. The pale-yellow filtrate was purified by passing through a short pad of silica gel to furnish the titled product (14 mg, 90%). $^1$H NMR (500 MHz, CHLOROFORM-d) δ ppm 1.82-1.87 (m, 4H), 2.45 (s, 3H), 2.76-2.81 (m, 2H), 3.83-3.86 (m, 2H), 3.95 (t, J=5.0 Hz, 2H), 3.97-4.01 (m, 2H), 4.17 (dd, J=5.12, 3.66 Hz, 2H), 4.55 (t, J=5.0 Hz, 2H), 6.67 (s, 1H), 6.92 (d, J=10.0 Hz, 2H), 6.97 (br. s., 1H), 7.03 (d, J=10.0 Hz, 2H), 7.36 (t, J=7.32 Hz, 1H), 7.41 (d, J=8.30 Hz, 1H), 7.47 (dd, J=8.30, 1.95 Hz, 1H), 7.50 (s, 1H), 7.51-7.54 (m, 1H), 7.62-7.68 (m, 1H), 7.78 (d, J=8.79 Hz, 2H), 7.98 (s, 1H), 8.19 (d, J=7.81 Hz, 1H), 8.22 (d, J=9.27 Hz, 2H); $^{13}$C NMR (101 MHz, CHLOROFORM-d) δ ppm 20.92, 25.34, 25.88, 28.63, 50.15, 67.37, 67.83, 69.67, 69.88, 105.94, 114.61, 114.81, 117.69, 118.08, 120.65, 121.99, 123.57, 123.93, 124.00, 124.42, 125.02, 125.38, 127.85, 129.52, 133.39, 134.70, 134.97, 137.67, 144.90, 147.66, 154.42, 155.23, 160.04, 161.75, 163.21, 173.08, 178.43; LRMS (ESI) m/z 700 [M+H]$^+$; HRMS (ESI) calcd for $C_{41}H_{38}N_3O_8$ [M+H]$^+$ 700.2659, found 700.2672.

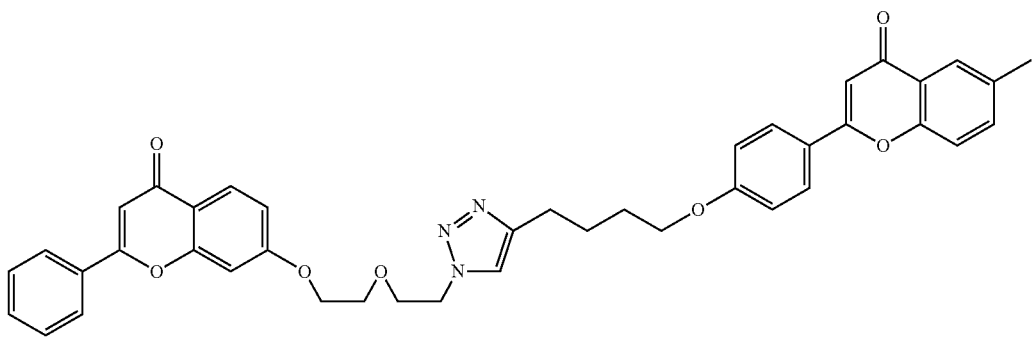 [SMILES: Cc1ccc2oc(-c3ccc(OCCCCc4cn(CCOCCOc5ccc6c(=O)cc(-c7ccccc7)oc6c5)nn4)cc3)cc(=O)c2c1]

6-Methyl-2-(4-(4-(1-(2-(2-((4-oxo-2-phenyl-4H-chromen-7-yl)oxy)ethoxy) ethyl)-1H-1,2,3-triazol-4-yl)butoxy)phenyl)-4H-chromen-4-one (Ac5Az11)

This compound (40 mg) was obtained from Ac5 and Az11 in 59% yield according to the general procedure described above. $^1$H NMR (500 MHz, CHLOROFORM-d) δ ppm 1.85 (br. s., 4H), 2.45 (s, 3H), 2.78 (br. s., 2H), 3.84-3.88 (m, 2H), 3.95-4.01 (m, 4H), 4.17-4.21 (m, 2H), 4.55-4.75 (m, 2H), 6.69 (s, 1H), 6.75 (s, 1H), 6.90-7.00 (m, 4H), 7.40-7.54 (m, 6H), 7.81 (d, J=9.0 Hz, 2H), 7.83-7.90 (m, 2H), 7.97-8.00 (m, 1H), 8.13 (d, J=8.79 Hz, 1H); $^{13}$C NMR (101 MHz, CHLOROFORM-d) δ ppm 20.80, 25.20, 25.74, 28.51, 50.10, 67.69, 67.75, 69.27, 69.74, 101.05, 105.74, 107.35, 114.42, 114.70, 117.60, 117.96, 123.43, 123.75, 124.82, 125.96, 127.00, 127.75, 128.88, 131.36, 131.54, 134.60, 134.83, 154.28, 157.71, 161.63, 162.90, 162.98, 163.11, 177.50, 178.26; LRMS (ESI) m/z 684 [M+H]$^+$; HRMS (ESI) calcd for $C_{41}H_{38}N_3O_7$ [M+H]$^+$ 684.2710, found 684.2692.

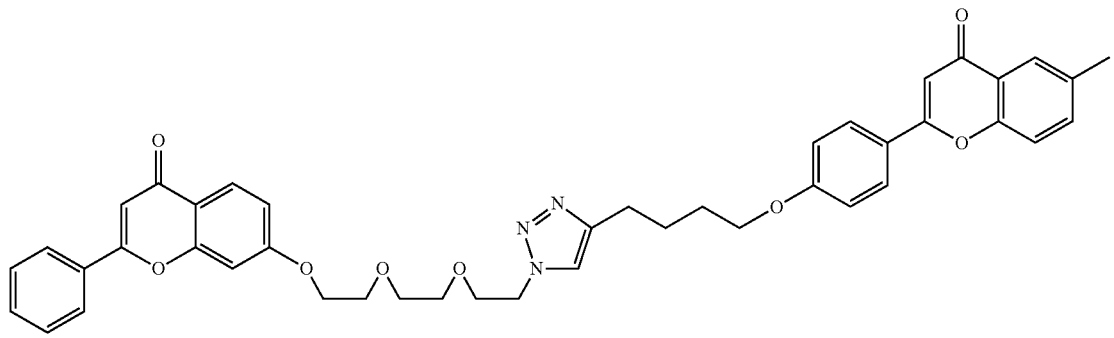 [SMILES: Cc1ccc2oc(-c3ccc(OCCCCc4cn(CCOCCOCCOc5ccc6c(=O)cc(-c7ccccc7)oc6c5)nn4)cc3)cc(=O)c2c1]

6-Methyl-2-(4-(4-(1-(2-(2-(2-((4-oxo-2-phenyl-4H-chromen-7-yl)oxy)ethoxy)ethoxy)ethyl)-1H-1,2,3-triazol-4-yl)butoxy)phenyl)-4H-chromen-4-one (Ac5Az12)

This compound (33 mg) was obtained from Ac5 and Az12 in 46% yield according to the general procedure described above. $^1$H NMR (500 MHz, CHLOROFORM-d) δ ppm 1.83-1.89 (m, 4H), 2.45 (s, 3H), 2.76-2.81 (m, 2H), 3.62-3.67 (m, 2H), 3.68-3.73 (m, 2H), 3.86-3.90 (m, 4H), 4.00-4.02 (m, 2H), 4.19-4.24 (m, 2H), 4.52 (t, J=4.88 Hz, 2H), 6.70 (s, 1H), 6.74 (s, 1H), 6.91-7.02 (m, 4H), 7.40-7.54 (m, 6H), 7.82 (d, J=9.0 Hz, 2H), 7.87 (dd, J=7.57, 1.71 Hz, 2H), 7.99 (s, 1H), 8.13 (d, J=8.79 Hz, 1H); $^{13}$C NMR (101 MHz, CHLOROFORM-d) δ ppm 20.90, 25.21, 25.89, 28.62, 50.29, 67.80, 68.07, 69.41, 69.55, 70.56, 70.78, 101.19, 105.94, 107.53, 114.59, 114.84, 117.68, 118.04, 122.03, 123.54, 123.97, 125.00, 126.12, 127.15, 127.91, 128.99, 131.44, 131.76, 134.73, 135.00, 154.44, 157.87, 161.74, 163.06, 163.23, 163.27, 177.70, 178.44; LRMS (ESI) m/z 728 [M+H]$^+$; HRMS (ESI) calcd for $C_{43}H_{42}N_3O_8$ [M+H]$^+$ 728.2972, found 728.3006.

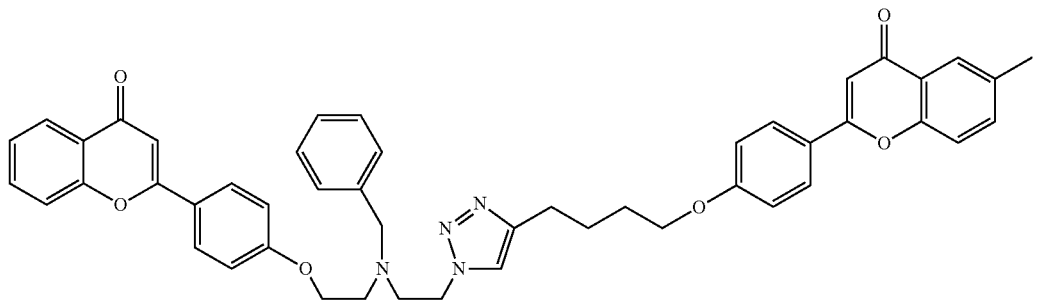 [SMILES: Cc1ccc2oc(-c3ccc(OCCCCc4cn(CCN(CCOc5ccc(-c6cc(=O)c7ccccc7o6)cc5)Cc5ccccc5)nn4)cc3)cc(=O)c2c1]

2-(4-(4-(1-(2-(Benzyl(2-(4-(4-oxo-4H-chromen-2-yl)phenoxy)ethyl)amino)ethyl)-1H-1,2,3-triazol-4-yl)butoxy)phenyl)-6-methyl-4H-chromen-4-one (Ac5Az14)

This compound (38 mg) was obtained from Ac5 and Az14 in 49% yield according to the general procedure described above. $^1$H NMR (400 MHz, CHLOROFORM-d) δ ppm 1.81 (br. s., 4H), 2.44 (s, 3H), 2.71 (br. s., 2H), 2.97-3.00 (m, 2H), 3.11 (br. s., 2H), 3.76 (s, 2H), 3.89-4.03 (m, 4H), 4.40 (br. s., 2H), 6.66 (s, 1H), 6.72 (s, 1H), 6.84-6.94 (m, 4H), 7.20-7.32 (m, 5H), 7.33-7.53 (m, 6H), 7.74-7.81 (m, 2H), 7.82-7.88 (m, 2H), 7.97 (d, J=0.78 Hz, 1H), 8.09 (d, J=8.98 Hz, 1H); $^{13}$C NMR (101 MHz, CHLOROFORM-d) δ ppm 20.88, 25.29, 25.88, 28.61, 48.65, 52.89, 54.75, 59.79, 67.14, 67.75, 100.97, 105.90, 107.46, 114.48, 114.78, 117.66, 117.97, 121.48, 123.55, 123.89, 124.96, 126.08, 127.10, 127.47, 127.85, 128.46, 128.69, 128.95, 131.41, 131.69, 134.67, 134.94, 138.36, 154.40, 157.87, 161.70, 162.98, 163.03, 163.22, 177.63, 178.39; LRMS (ESI) m/z 773 [M+H]$^+$; HRMS (ESI) calcd for $C_{48}H_{45}N_4O_6$ [M+H]$^+$ 773.3339, found 773.3314.

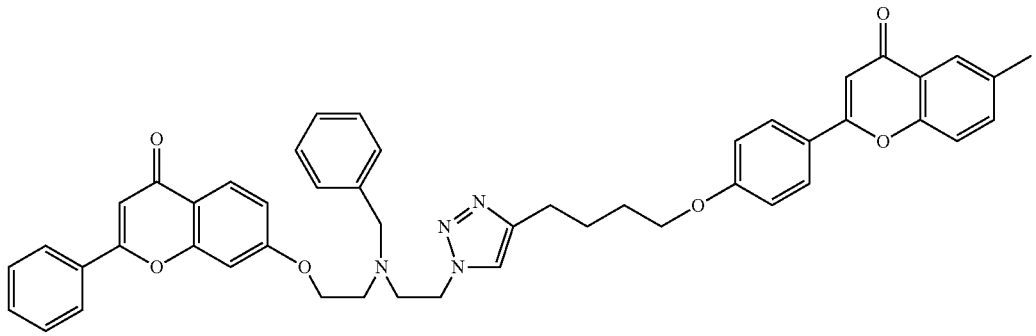 [SMILES: Cc1ccc2oc(-c3ccc(OCCCCc4cn(CCN(CCOc5ccc6c(=O)cc(-c7ccccc7)oc6c5)Cc5ccccc5)nn4)cc3)cc(=O)c2c1]

2-(4-(4-(1-(2-(Benzyl(2-((4-oxo-2-phenyl-4H-chromen-7-yl)oxy)ethyl)amino)ethyl)-1H-1,2,3-triazol-4-yl)butoxy)phenyl)-6-methyl-4H-chromen-4-one (Ac5Az15)

This compound (41 mg) was obtained from Ac5 and Az15 in 53% yield according to the general procedure described above. $^1$H NMR (500 MHz, CHLOROFORM-d) δ ppm 1.84 (br. s., 4H), 2.46 (s, 3H), 2.73 (br. s., 2H), 2.97 (br. s., 2H), 3.11 (br. s., 2H), 3.77 (br. s., 2H), 3.89-4.05 (m, 4H), 4.40 (br. s., 2H), 6.68 (s, 1H), 6.72 (s, 1H), 6.88-6.97 (m, 4H), 7.21-7.33 (m, 5H), 7.33-7.40 (m, 2H), 7.40-7.44 (m, 1H), 7.45-7.52 (m, 2H), 7.61-7.67 (m, 1H), 7.76-7.81 (m, 2H), 7.84 (d, J=8.79 Hz, 2H), 7.99 (s, 1H), 8.18 (dd, J=8.05, 1.71 Hz, 1H); $^{13}$C NMR (101 MHz, CHLOROFORM-d) δ ppm 20.92, 25.33, 25.92, 28.68, 48.70, 53.06, 54.79, 59.87, 66.78, 67.82, 105.97, 106.26, 114.82, 114.87, 117.71, 117.90, 123.59, 123.92, 123.99, 124.29, 125.01, 125.07, 125.65, 127.47, 127.88, 128.03, 128.48, 128.73, 133.55, 134.72, 134.99, 154.44, 156.14, 161.33, 161.74, 163.18, 163.21, 178.26, 178.44; LRMS (ESI) m/z 773 [M+H]$^+$; HRMS (ESI) calcd for $C_{48}H_{45}N_4O_6$ [M+H]$^+$ 773.3339, found 773.3353.

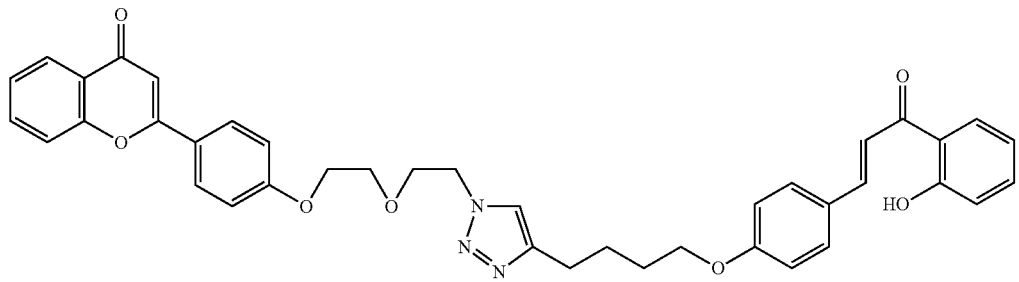 [SMILES: O=C(/C=C/c1ccc(OCCCCc2cn(CCOCCOc3ccc(-c4cc(=O)c5ccccc5o4)cc3)nn2)cc1)c1ccccc1O]

(E)-2-(4-(2-(2-(4-(4-(4-(3-(2-Hydroxyphenyl)-3-oxoprop-1-en-1-yl)phenoxy)butyl)-1H-1,2,3-triazol-1-yl)ethoxy)ethoxy)phenyl)-4H-chromen-4-one (Ac6Az1)

This compound (44 mg) was obtained from Ac6 and Az1 in 53% yield according to the general procedure described above. $^1$H NMR (400 MHz, CHLOROFORM-d) δ ppm 2.06-2.08 (m, 4H), 2.81 (t, J=6.40 Hz, 2H), 3.74 (t, J=6.40 Hz, 2H), 3.84-3.94 (m, 4H), 4.03 (t, J=6.40 Hz, 2H), 4.45 (t, J=6.40 Hz, 2H), 6.57 (s, 1H), 6.85 (d, J=8.40 Hz, 2H), 6.89 (d, J=8.40 Hz, 2H), 7.25-7.28 (m, 3H), 7.39 (dd, J=7.20, 7.20 Hz, 2H), 7.48 (s, 1H), 7.55-7.56 (m, 3H), 7.69 (d, J=8.40 Hz, 2H), 7.74 (d, J=8.40 Hz, 2H), 8.08 (dd, J=7.20, 7.20 Hz, 2H), 13.50 (s, 1H); LRMS (ESI) m/z 673 [M+H]$^+$.

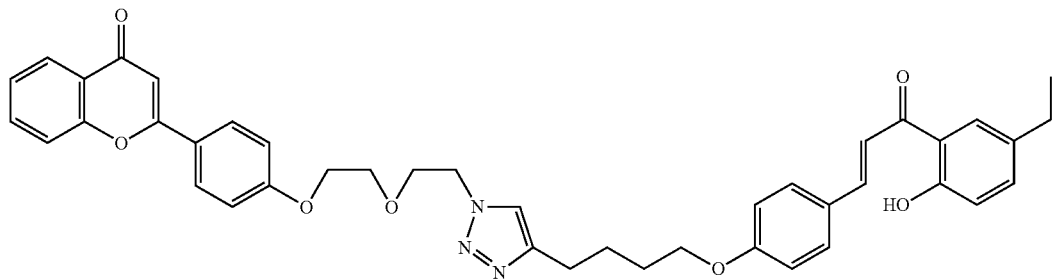 [SMILES: CCc1ccc(O)c(C(=O)/C=C/c2ccc(OCCCCc3cn(CCOCCOc4ccc(-c5cc(=O)c6ccccc6o5)cc4)nn3)cc2)c1]

(E)-2-(4-(2-(2-(4-(4-(4-(3-(5-Ethyl-2-hydroxyphenyl)-3-oxoprop-1-en-1-yl)phenoxy)butyl)-1H-1,2,3-triazol-1-yl)ethoxy)ethoxy)phenyl)-4H-chromen-4-one (Ac7Az1)

This compound (53 mg) was obtained from Ac7 and Az1 in 59% yield according to the general procedure described above. $^1$H NMR (400 MHz, CHLOROFORM-d) δ ppm 1.63 (t, J=6.00, 3H), 2.06-2.08 (m, 4H), 2.81-2.86 (m, 4H), 3.75 (t, J=6.40 Hz, 2H), 3.84-3.95 (m, 4H), 4.02 (t, J=6.40 Hz, 2H), 4.47 (t, J=6.40 Hz, 2H), 6.57 (s, 1H), 6.86 (d, J=8.40 Hz, 2H), 6.89 (d, J=8.40 Hz, 2H), 7.25-7.28 (m, 2H), 7.39 (dd, J=7.20, 7.20 Hz, 2H), 7.48 (s, 1H), 7.55-7.56 (m, 3H), 7.69 (d, J=8.40 Hz, 2H), 7.74 (d, J=8.40 Hz, 2H), 8.08 (dd, J=7.20, 7.20 Hz, 2H), 13.60 (s, 1H); LRMS (ESI) m/z 701 [M+H]$^+$.

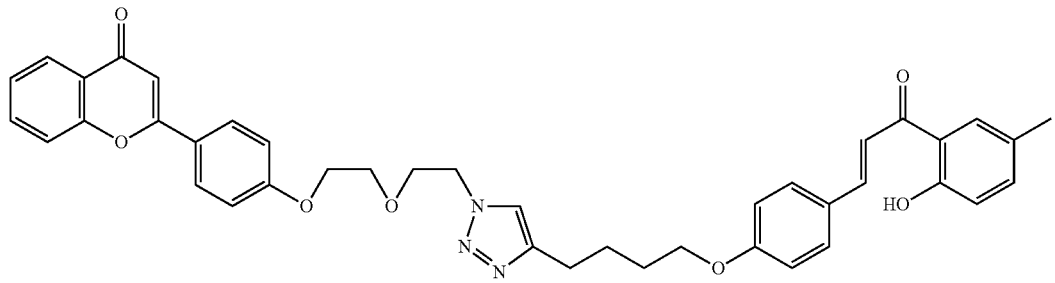 [SMILES: Cc1ccc(O)c(C(=O)/C=C/c2ccc(OCCCCc3cn(CCOCCOc4ccc(-c5cc(=O)c6ccccc6o5)cc4)nn3)cc2)c1]

(E)-2-(4-(2-(2-(4-(4-(4-(3-(2-Hydroxy-5-methylphenyl)-3-oxoprop-1-en-1-yl)phenoxy)butyl)-1H-1,2,3-triazol-1-yl)ethoxy)ethoxy)phenyl)-4H-chromen-4-one (Ac8Az1)

This compound (63 mg) was obtained from Ac8 and Az1 in 63% yield according to the general procedure described above. $^1$H NMR (400 MHz, CHLOROFORM-d) δ ppm 2.06-2.08 (m, 2H), 2.43 (s, 3H), 2.81-2.86 (m, 4H), 3.75 (t, J=6.40 Hz, 2H), 3.84-3.95 (m, 4H), 4.02 (t, J=6.40 Hz, 2H), 4.47 (t, J=6.40 Hz, 2H), 6.57 (s, 1H), 6.86 (d, J=8.40 Hz, 2H), 6.89 (d, J=8.40 Hz, 2H), 7.25-7.28 (m, 2H), 7.39 (dd, J=7.20, 7.20 Hz, 2H), 7.48 (s, 1H), 7.55-7.56 (m, 3H), 7.69 (d, J=8.40 Hz, 2H), 7.74 (d, J=8.40 Hz, 2H), 8.08 (dd, J=7.20, 7.20 Hz, 2H), 13.60 (s, 1H); LRMS (ESI) m/z 687 [M+H]$^+$.

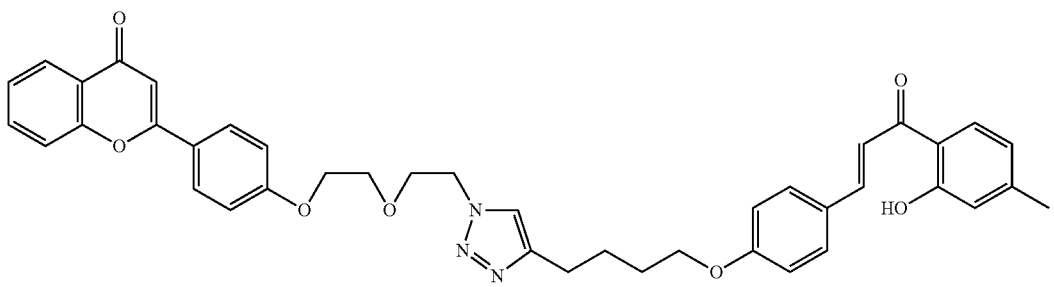 [SMILES: Cc1ccc(C(=O)/C=C/c2ccc(OCCCCc3cn(CCOCCOc4ccc(-c5cc(=O)c6ccccc6o5)cc4)nn3)cc2)c(O)c1]

(E)-2-(4-(2-(2-(4-(4-(4-(3-(2-Hydroxy-4-methylphenyl)-3-oxoprop-1-en-1-yl)phenoxy)butyl)-1H-1,2,3-triazol-1-yl)ethoxy)ethoxy)phenyl)-4H-chromen-4-one (Ac9Az1)

This compound (48 mg) was obtained from Ac9 and Az1 in 56% yield according to the general procedure described above. $^1$H NMR (400 MHz, CHLOROFORM-d) δ ppm 2.06-2.08 (m, 2H), 2.39 (s, 3H), 2.82-2.86 (m, 4H), 3.76 (t, J=6.40 Hz, 2H), 3.84-3.95 (m, 4H), 4.02 (t, J=6.40 Hz, 2H), 4.47 (t, J=6.40 Hz, 2H), 6.57 (s, 1H), 6.86 (d, J=8.40 Hz, 2H), 6.89 (d, J=8.40 Hz, 2H), 7.25-7.28 (m, 2H), 7.39 (dd, J=7.20, 7.20 Hz, 2H), 7.48 (s, 1H), 7.55-7.56 (m, 3H), 7.69 (d, J=8.40 Hz, 2H), 7.74 (d, J=8.40 Hz, 2H), 8.08 (dd, J=7.20, 7.20 Hz, 2H), 13.55 (s, 1H); LRMS (ESI) m/z 687 [M+H]$^+$.

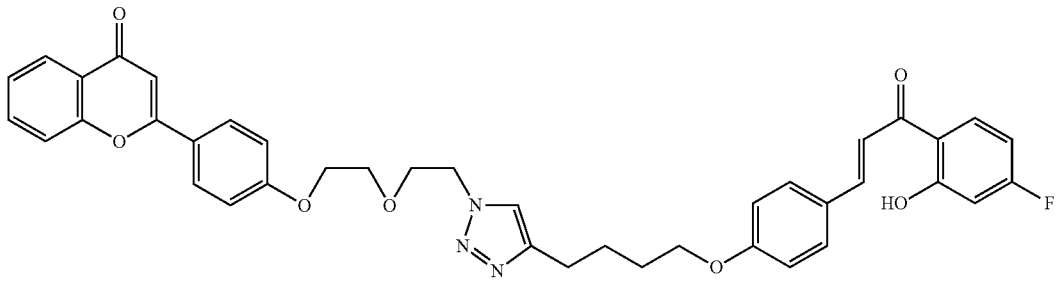 [SMILES: O=C(/C=C/c1ccc(OCCCCc2cn(CCOCCOc3ccc(-c4cc(=O)c5ccccc5o4)cc3)nn2)cc1)c1ccc(F)cc1O]

(E)-2-(4-(2-(2-(4-(4-(4-(3-(4-Fluoro-2-hydroxyphenyl)-3-oxoprop-1-en-1-yl)phenoxy)butyl)-1H-1,2,3-triazol-1-yl)ethoxy)ethoxy)phenyl)-4H-chromen-4-one (Ac10Az1)

This compound (41 mg) was obtained from Ac10 and Az1 in 51% yield according to the general procedure described above. $^1$H NMR (400 MHz, CHLOROFORM-d) δ ppm 2.04-2.08 (m, 2H), 2.83-2.86 (m, 4H), 3.79 (t, J=6.40 Hz, 2H), 3.84-3.96 (m, 4H), 4.02 (t, J=6.40 Hz, 2H), 4.47 (t, J=6.40 Hz, 2H), 6.57 (s, 1H), 6.86 (m, 4H), 7.25-7.28 (m, 2H), 7.39 (dd, J=7.20, 7.20 Hz, 2H), 7.48 (s, 1H), 7.55-7.56 (m, 3H), 7.69 (m, 4H), 8.08 (dd, J=7.20, 7.20 Hz, 2H), 13.40 (s, 1H); LRMS (ESI) m/z 691 [M+H]$^+$.

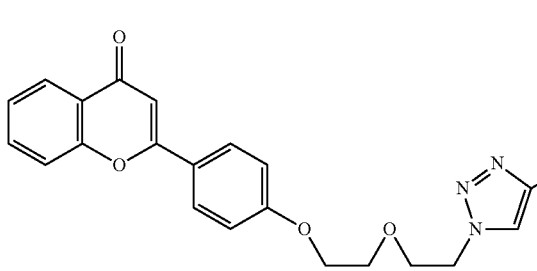
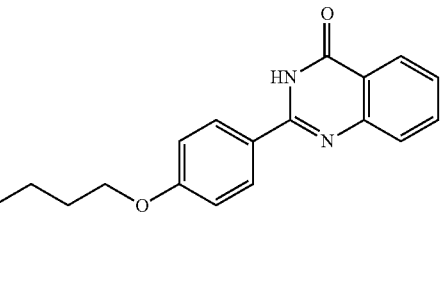

2-(4-(3-(1-(2-(2-(4-(4-Oxo-4H-chromen-2-yl)phenoxy)ethoxy)ethyl)-1H-1,2,3-triazol-4-yl)propoxy)phenyl)quinazolin-4(3H)-one (Ac11Az1)

This compound (48 mg) was obtained from Ac11 and Az1 in 59% yield according to the general procedure described above. $^1$H NMR (400 MHz, CHLOROFORM-d) δ ppm 2.05-2.20 (m, 4H), 3.78 (s, 2H), 3.94 (s, 2H), 4.05-4.08 (m, 4H), 4.57 (s, 2H), 6.65 (s, 1H), 6.93-6.99 (m, 4H), 7.25-7.81 (m, 8H), 8.11-8.26 (m, 4H), 11.56 (s, 1H); LRMS (ESI) m/z 657 [M+H]$^+$.

7-(4-(1-(2-(2-(4-(4-Oxo-4H-chromen-2-yl)phenoxy)ethoxy)ethyl)-1H-1,2,3-triazol-4-yl)butoxy)-2-phenyl-4H-chromen-4-one (Ac12Az1)

This compound (63 mg) was obtained from Ac12 and Az1 in 91% yield according to the general procedure described above. $^1$H NMR (500 MHz, CHLOROFORM-d) δ ppm 1.79-1.91 (m, 4H), 2.74-2.77 (m, 2H), 3.77-3.83 (m, 2H), 3.92 (t, J=4.88 Hz, 2H), 3.98-4.04 (m, 2H), 4.08-4.15 (m, 2H), 4.52 (t, J=4.88 Hz, 2H), 6.66 (s, 1H), 6.67 (s, 1H), 6.82-6.89 (m, 2H), 6.92-6.98 (m, 2H), 7.33 (t, J=7.32 Hz, 1H), 7.41-7.50 (m, 5H), 7.59-7.62 (m, 1H), 7.77-7.85 (m, 4H), 8.03 (d, J=8.75 Hz, 1H), 8.13 (dd, J=7.75, 1.45 Hz,

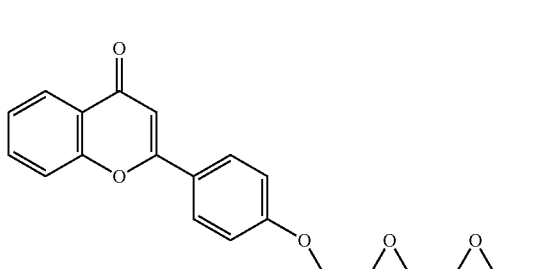

2-(4-(3-(1-(2-(2-(2-(4-(4-oxo-4H-chromen-2-yl)phenoxy)ethoxy)ethoxy)ethyl)-1H-1,2,3-triazol-4-yl)propoxy)phenyl)quinazolin-4(3H)-one (Ac11Az2)

This compound (39 mg) was obtained from Ac11 and Az2 in 45% yield according to the general procedure described above. $^1$H NMR (400 MHz, CHLOROFORM-d) δ ppm 2.04-2.20 (m, 6H), 3.76 (s, 2H), 3.93 (s, 2H), 4.05-4.09 (m, 4H), 4.59 (s, 2H), 6.66 (s, 1H), 6.43-6.98 (m, 4H), 7.26-7.82 (m, 8H), 8.13-8.27 (m, 4H), 11.66 (s, 1H); LRMS (ESI) m/z 701 [M+H]$^+$.

1H); $^{13}$C NMR (101 MHz, CHLOROFORM-d) δ ppm 25.17, 25.74, 28.36, 50.00, 67.36, 68.17, 69.43, 69.73, 100.70, 106.08, 107.29, 114.58, 114.84, 117.57, 117.78, 121.84, 123.74, 124.23, 124.96, 125.45, 125.97, 126.76, 127.83, 128.84, 131.25, 131.66, 133.45, 147.41, 155.96, 157.79, 161.25, 162.77, 162.93, 163.42, 177.58, 178.04; LRMS (ESI) m/z 670 [M+H]$^+$, 692 [M+Na]$^+$; HRMS (ESI) calcd for $C_{40}H_{36}N_3O_7$ [M+H]$^+$ 670.2553, found 670.2525; calcd for $C_{40}H_{35}N_3O_7Na$ [M+Na]$^+$ 692.2373, found 692.2357.

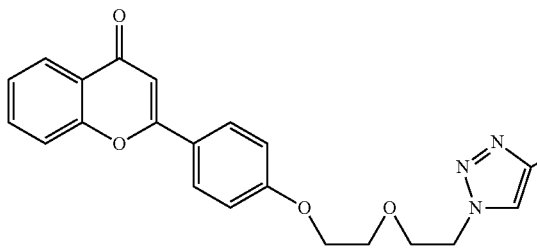
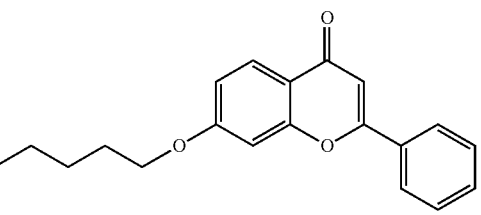

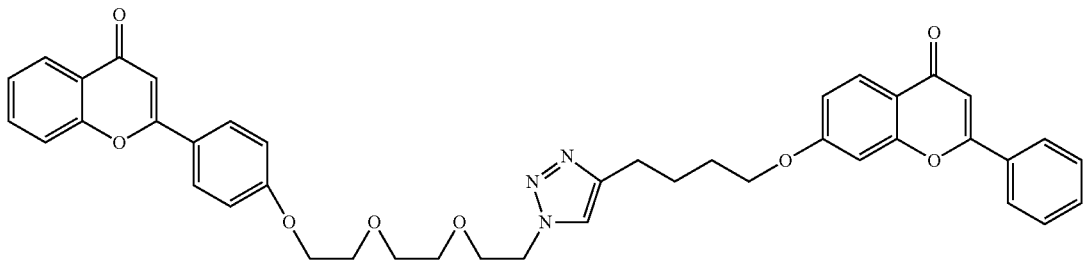 [SMILES: O=c1cc(-c2ccc(OCCOCCOCCn3cc(CCCCOc4ccc5c(=O)cc(-c6ccccc6)oc5c4)nn3)cc2)oc2ccccc12]

7-(4-(1-(2-(2-(2-(4-(4-Oxo-4H-chromen-2-yl)phenoxy)ethoxy)ethoxy)ethyl)-1H-1,2,3-triazol-4-yl)butoxy)-2-phenyl-4H-chromen-4-one (Ac12Az2)

This compound (70 mg) was obtained from Ac12 and Az2 in 98% yield according to the general procedure described above. $^1$H NMR (500 MHz, CHLOROFORM-d) δ ppm 1.89 (br. s., 4H), 2.80 (br. s., 2H), 3.62-3.68 (m, 2H), 3.68-3.75 (m, 2H), 3.85 (t, J=4.15 Hz, 2H), 3.89 (t, J=5.12 Hz, 2H), 4.07 (br. s., 2H), 4.18 (t, J=4.39 Hz, 2H), 4.53 (t, J=4.88 Hz, 2H), 6.72 (s, 1H), 6.74 (s, 1H), 6.91 (s, 1H), 6.94 (dd, J=9.03, 1.22 Hz, 1H), 7.01 (d, J=8.30 Hz, 2H), 7.39 (t, J=7.57 Hz, 1H), 7.52 (d, J=4.88 Hz, 5H), 7.66 (t, J=7.57 Hz, 1H), 7.82-7.93 (m, 4H), 8.10 (d, J=8.79 Hz, 1H), 8.20 (d, J=7.81 Hz, 1H); $^{13}$C NMR (101 MHz, CHLOROFORM-d) δ ppm 25.13, 25.73, 28.31, 49.93, 67.44, 68.13, 69.35, 69.44, 70.35, 70.55, 100.65, 105.92, 107.19, 114.52, 114.79, 117.48, 117.74, 121.76, 123.67, 123.98, 124.86, 125.35, 125.89, 126.67, 127.74, 128.78, 131.20, 131.56, 133.36, 147.28, 155.89, 157.71, 161.33, 162.68, 162.94, 163.36, 177.50, 177.98; LRMS (ESI) m/z 714 [M+H]$^+$, 736 [M+Na]$^+$; HRMS (ESI) calcd for $C_{42}H_{40}N_3O_8$ [M+H]$^+$ 714.2815, found 714.2804; calcd for $C_{42}H_{39}N_3O_8Na$ [M+Na]$^+$ 736.2635, found 736.2625.

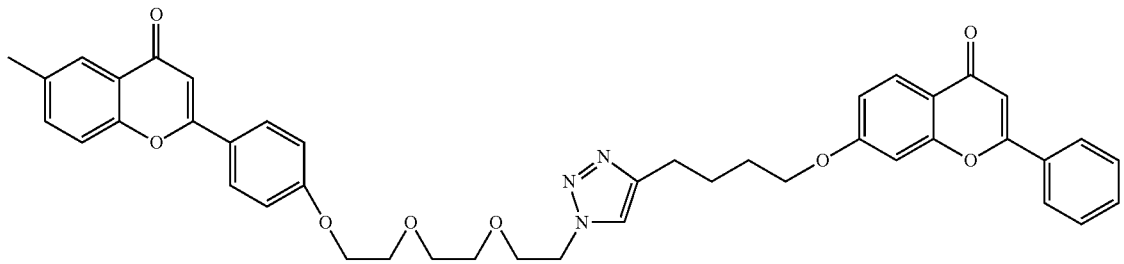 [SMILES: Cc1ccc2oc(-c3ccc(OCCOCCOCCn4cc(CCCCOc5ccc6c(=O)cc(-c7ccccc7)oc6c5)nn4)cc3)cc(=O)c2c1]

6-Methyl-2-(4-(2-(2-(2-(4-(4-((4-oxo-2-phenyl-4H-chromen-7-yl)oxy)butyl)-1H-1,2,3-triazol-1-yl)ethoxy)ethoxy)ethoxy)phenyl)-4H-chromen-4-one (Ac12Az3)

This compound (62 mg) was obtained from Ac12 and Az3 in 85% yield according to the general procedure described above. $^1$H NMR (500 MHz, CHLOROFORM-d) δ ppm 1.83 (br. s., 4H), 2.37 (s, 3H), 2.74 (br. s., 2H), 3.61 (br. s., 2H), 3.63-3.70 (m, 2H), 3.80 (br. s., 2H), 3.84 (t, J=4.88 Hz, 2H), 4.00 (br. s., 2H), 4.12 (br. s., 2H), 4.48 (t, J=4.88 Hz, 2H), 6.63 (s, 1H), 6.67 (s, 1H), 6.83 (s, 1H), 6.86 (d, J=9.27 Hz, 1H), 6.94 (d, J=8.30 Hz, 2H), 7.33 (d, J=8.30 Hz, 1H), 7.39 (d, J=8.79 Hz, 1H), 7.41-7.48 (m, 3H), 7.50 (s, 1H), 7.77 (d, J=8.30 Hz, 2H), 7.81 (d, J=6.83 Hz, 2H), 7.90 (s, 1H), 8.02 (d, J=8.79 Hz, 1H); $^{13}$C NMR (101 MHz, CHLOROFORM-d) δ ppm 20.76, 25.18, 25.77, 28.36, 49.96, 67.48, 68.17, 69.40, 69.48, 70.39, 70.59, 100.70, 105.85, 107.24, 114.55, 114.81, 117.53, 121.80, 123.36, 124.21, 124.79, 125.95, 126.74, 127.75, 128.82, 131.23, 131.62, 134.61, 134.86, 147.32, 154.22, 157.77, 161.28, 162.75, 162.85, 163.41, 177.57, 178.18; LRMS (ESI) m/z 728 [M+H]$^+$, 750 [M+Na]$^+$; HRMS (ESI) calcd for $C_{43}H_{42}N_3O_8$ [M+H]$^+$ 728.2972, found 728.2949; calcd for $C_{43}H_{41}N_3O_8Na$ [M+Na]$^+$ 750.2791, found 750.2790.

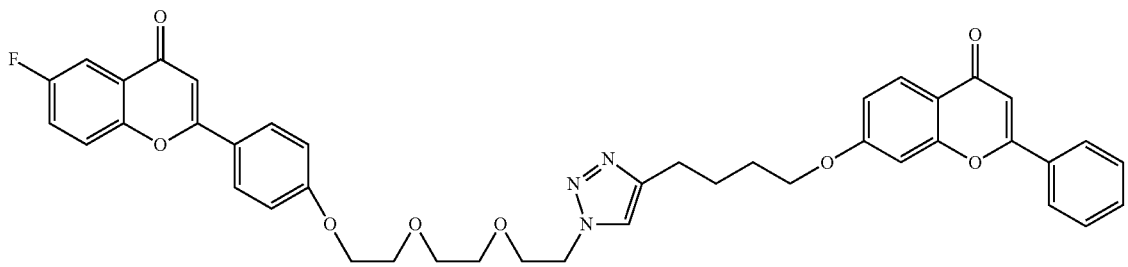 [SMILES: O=c1cc(-c2ccccc2)oc2cc(OCCCCc3cn(CCOCCOCCOc4ccc(-c5cc(=O)c6cc(F)ccc6o5)cc4)nn3)ccc12]

6-Fluoro-2-(4-(2-(2-(2-(4-(4-((4-oxo-2-phenyl-4H-chromen-7-yl)oxy)butyl)-1H-1,2,3-triazol-1-yl)ethoxy)ethoxy)ethoxy)phenyl)-4H-chromen-4-one (Ac12Az4)

This compound (53 mg) was obtained from Ac12 and Az4 in 73% yield according to the general procedure described above. $^1$H NMR (500 MHz, CHLOROFORM-d) δ ppm 1.89 (br. s., 4H), 2.79 (br. s., 2H), 3.61-3.67 (m, 2H), 3.67-3.71 (m, 2H), 3.81-3.86 (m, 2H), 3.88 (t, J=5.12 Hz, 2H), 4.06 (br. s., 2H), 4.13-4.20 (m, 2H), 4.52 (t, J=4.39 Hz, 2H), 6.69 (s, 1H), 6.73 (s, 1H), 6.90 (s, 1H), 6.93 (d, J=8.79 Hz, 1H), 6.99 (d, J=8.79 Hz, 2H), 7.34-7.40 (m, 1H), 7.46-7.55 (m, 5H), 7.80-7.85 (m, 3H), 7.85-7.90 (m, 2H), 8.09 (d, J=8.79 Hz, 1H); $^{13}$C NMR (101 MHz, CHLOROFORM-d) δ ppm 25.07, 25.63, 28.22, 49.94, 67.38, 68.05, 69.24, 69.31, 70.26, 70.47, 100.56, 105.04, 107.03, 110.13 (d, J=23.63 Hz, C5), 114.42, 114.73, 117.37, 119.77 (d, J=8.08 Hz, C8), 121.30 (d, J=25.15 Hz, C7), 123.49, 124.75 (d, J=6.67 Hz, C10), 125.77, 126.52, 127.67, 128.68, 131.11, 131.40, 151.94 (d, J=2.02 Hz, C9), 157.59, 159.18 (d, J=247.85 Hz, C6), 161.39, 162.54, 163.11, 163.26, 176.94 (d, J=3.03 Hz, C4), 177.32; LRMS (ESI) m/z 732 [M+H]$^+$, 754 [M+Na]$^+$; HRMS (ESI) calcd for C$_{42}$H$_{39}$N$_3$O$_8$F [M+H]$^+$ 732.2721, found 732.2712; calcd for C$_{42}$H$_{38}$N$_3$O$_8$FNa [M+Na]$^+$ 754.2541, found 754.2524.

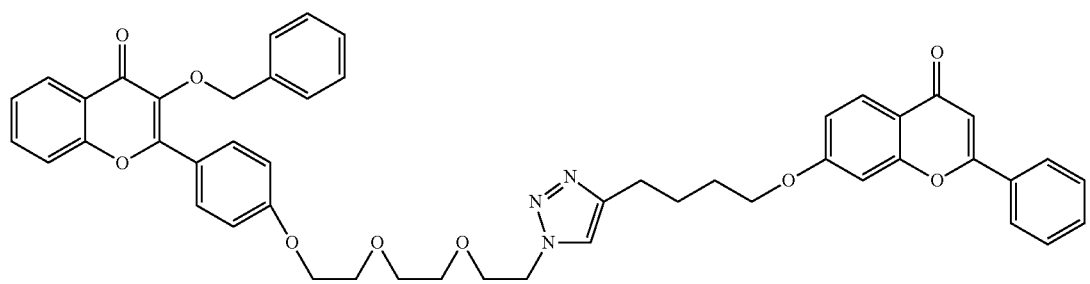 [SMILES: O=c1cc(-c2ccccc2)oc2cc(OCCCCc3cn(CCOCCOCCOc4ccc(-c5oc6ccccc6c(=O)c5OCc5ccccc5)cc4)nn3)ccc12]

3-(Benzyloxy)-2-(4-(2-(2-(2-(4-(4-((4-oxo-2-phenyl-4H-chromen-7-yl)oxy) butyl)-1H-1,2,3-triazol-1-yl)ethoxy)ethoxy)ethoxy)phenyl)-4H-chromen-4-one (Ac12Az5)

This compound (58 mg) was obtained from Ac12 and Az5 in 71% yield according to the general procedure described above. $^1$H NMR (500 MHz, CHLOROFORM-d) δ ppm 1.83-1.94 (m, 4H), 2.77-2.80 (m, 2H), 3.62-3.68 (m, 2H), 3.68-3.74 (m, 2H), 3.84-3.86 (m, 2H), 3.88 (t, J=5.12 Hz, 2H), 4.01-4.08 (m, 2H), 4.17-4.19 (m, 2H), 4.52 (t, J=5.12 Hz, 2H), 5.11 (s, 2H), 6.74 (s, 1H), 6.89-6.97 (m, 4H), 7.25-7.30 (m, 3H), 7.34-7.41 (m, 3H), 7.45-7.54 (m, 5H), 7.61-7.67 (m, 1H), 7.85-7.91 (m, 2H), 8.00-8.05 (m, 2H), 8.09 (d, J=8.79 Hz, 1H), 8.26 (dd, J=8.30, 1.46 Hz, 1H); $^{13}$C NMR (101 MHz, CHLOROFORM-d) δ ppm 25.13, 25.73, 28.32, 49.94, 67.35, 68.14, 69.42, 69.44, 70.36, 70.56, 73.71, 100.68, 107.24, 114.14, 114.55, 117.49, 117.71, 121.79, 123.40, 123.95, 124.41, 125.48, 125.94, 126.71, 127.91, 128.05, 128.58, 128.79, 130.33, 131.21, 131.60, 133.08, 136.64, 139.13, 147.30, 154.91, 155.84, 157.75, 160.38, 162.74, 162.76, 163.39, 174.71, 177.58; LRMS (ESI) m/z 820 [M+H]$^+$, 842 [M+Na]$^+$; HRMS (ESI) calcd for C$_{49}$H$_{46}$N$_3$O$_9$ [M+H]$^+$ 820.3234, found 820.3246; calcd for C$_{49}$H$_{45}$N$_3$O$_9$Na [M+Na]$^+$ 842.3054, found 842.3068.

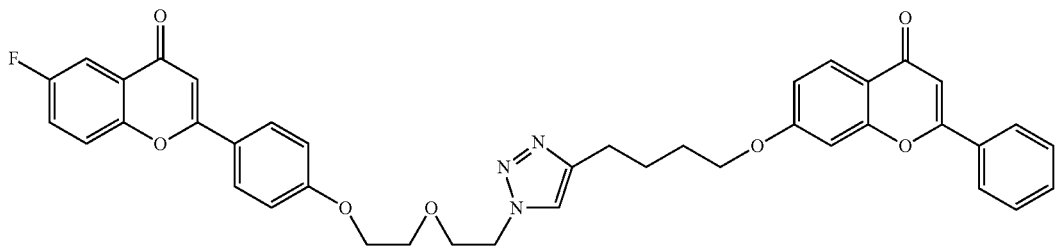

6-Fluoro-2-(4-(2-(2-(4-(4-((4-oxo-2-phenyl-4H-chromen-7-yl)oxy)butyl)-1H-1,2,3-triazol-1-yl)ethoxy)ethoxy)phenyl)-4H-chromen-4-one (Ac12Az7)

This compound (63 mg) was obtained from Ac12 and Az7 in 91% yield according to the general procedure described above. $^1$H NMR (500 MHz, CHLOROFORM-d) δ ppm 1.82-1.94 (m, 5H), 2.78-2.80 (m, 2H), 3.80-3.86 (m, 2H), 3.95 (t, J=5.00, 2H), 4.01-4.09 (m, 2H), 4.15-4.16 (m, 2H), 4.55 (t, J=5.12 Hz, 2H), 6.70 (s, 1H), 6.73 (s, 1H), 6.88-6.93 (m, 2H), 6.97-7.02 (m, 2H), 7.37 (ddd, J=9.15, 7.69, 3.17 Hz, 1H), 7.47-7.54 (m, 5H), 7.78-7.89 (m, 5H), 8.09 (d, J=8.79 Hz, 1H); $^{13}$C NMR (101 MHz, CHLOROFORM-d) δ ppm 25.07, 25.64, 28.24, 49.89, 67.28, 68.08, 69.28, 69.61, 100.58, 105.15, 107.08, 110.16 (d, J=23.23 Hz, C5), 114.48, 114.76, 117.39, 119.78 (d, J=8.08 Hz, C8), 121.38 (d, J=25.25 Hz, C7), 121.77, 123.67, 124.78 (d, J=6.06 Hz, C10), 125.82, 126.57, 127.73, 128.73, 131.17, 131.44, 147.29, 151.97, 157.63, 159.23 (d, J=248.46 Hz, C6), 161.31, 162.61, 163.09, 163.30, 177.00, 177.41; LRMS (ESI) m/z 688 [M+H]$^+$, 710 [M+Na]$^+$; HRMS (ESI) calcd for $C_{40}H_{35}N_3O_7F$ [M+H]$^+$ 688.2459, found 688.2454; calcd for $C_{40}H_{34}N_3O_7FNa$ [M+Na]$^+$ 710.2278, found 710.2261.

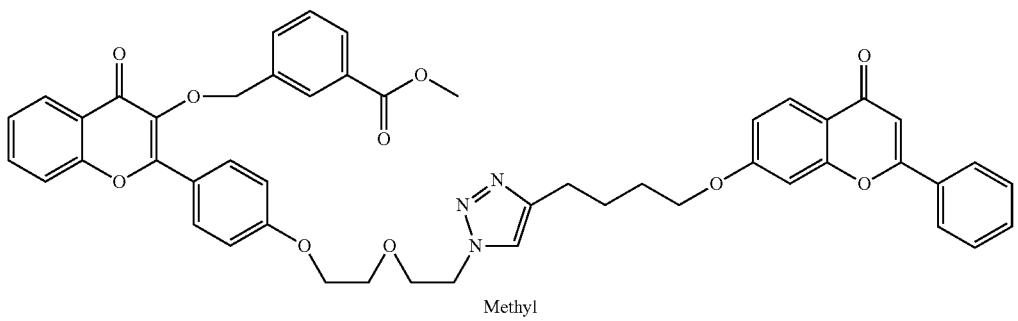 [SMILES: COC(=O)c1cccc(COc2c(-c3ccc(OCCOCCn4cc(CCCCOc5ccc6c(=O)cc(-c7ccccc7)oc6c5)nn4)cc3)oc3ccccc3c2=O)c1]

3-(((4-oxo-2-(4-(2-(2-(4-(4-((4-oxo-2-phenyl-4H-chromen-7-yl)oxy)butyl)-1H-1,2,3-triazol-1-yl)ethoxy)ethoxy)phenyl)-4H-chromen-3-yl)oxy)methyl)benzoate (Ac12Az8)

This compound (63 mg) was obtained from Ac12 and Az8 in 76% yield according to the general procedure described above. $^1$H NMR (500 MHz, CHLOROFORM-d) δ ppm 1.84-1.92 (m, 4H), 2.77-2.80 (m, 2H), 3.82-3.86 (m, 2H), 3.87 (s, 3H), 3.96 (t, J=4.88 Hz, 2H), 4.03-4.07 (m, 2H), 4.14-4.18 (m, 2H), 4.55 (t, J=4.88 Hz, 2H), 5.13 (s, 2H), 6.73 (s, 1H), 6.89-6.96 (m, 4H), 7.34 (t, J=7.57 Hz, 1H), 7.36-7.41 (m, 1H), 7.45-7.53 (m, 5H), 7.59 (d, J=7.81 Hz, 1H), 7.64 (ddd, J=8.42, 6.95, 1.71 Hz, 1H), 7.85-7.90 (m, 2H), 7.92 (dd, J=7.56, 1.22 Hz, 1H), 7.95-8.00 (m, 3H), 8.08 (d, J=8.79 Hz, 1H), 8.25 (dd, J=8.05, 1.71 Hz, 1H); $^{13}$C NMR (101 MHz, CHLOROFORM-d) δ ppm 25.18, 25.74, 28.37, 50.02, 51.93, 67.25, 68.18, 69.50, 69.73, 73.21, 100.73, 107.33, 114.21, 114.61, 117.57, 117.77, 121.88, 123.44, 124.00, 124.57, 125.59, 126.00, 126.79, 128.19, 128.86, 129.14, 129.66, 130.01, 130.42, 131.25, 131.69, 133.08, 133.24, 137.10, 138.97, 147.44, 155.02, 156.08, 157.81, 160.36, 162.80, 163.44, 166.67, 174.65, 177.61; LRMS (ESI) m/z 834 [M+H]$^+$, 856 [M+Na]$^+$; HRMS (ESI) calcd for $C_{49}H_{44}N_3O_{10}$ [M+H]$^+$ 834.3027, found 834.3041; calcd for $C_{49}H_{43}N_3O_{10}Na$ [M+Na]$^+$ 856.2846, found 856.2834.

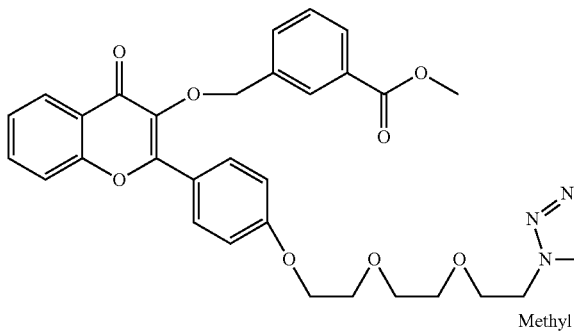

3-(((4-oxo-2-(4-(2-(2-(2-(4-(4-((4-oxo-2-phenyl-4H-chromen-7-yl)oxy)butyl)-1H-1,2,3-triazol-1-yl)ethoxy)ethoxy)ethoxy)phenyl)-4H-chromen-3-yl)oxy)methyl)benzoate (Ac12Az9)

This compound (78 mg) was obtained from Ac12 and Az9 in 89% yield according to the general procedure described above. $^1$H NMR (500 MHz, CHLOROFORM-d) δ ppm 1.84-1.93 (m, 4H), 2.74-2.82 (m, 2H), 3.63-3.67 (m, 2H), 3.68-3.73 (m, 2H), 3.84-3.87 (m, 2H), 3.87-3.90 (m, 5H), 4.04-4.09 (m, 2H), 4.15-4.20 (m, 2H), 4.52 (t, J=5.12 Hz, 2H), 5.14 (s, 2H), 6.74 (s, 1H), 6.89-6.97 (m, 4H), 7.34 (t, J=7.56 Hz, 1H), 7.39 (t, J=7.57 Hz, 1H), 7.46-7.54 (m, 5H), 7.59 (d, J=7.81 Hz, 1H), 7.65 (ddd, J=8.54, 7.08, 1.46 Hz, 1H), 7.86-7.90 (m, 2H), 7.92 (d, J=7.81 Hz, 1H), 7.95-8.01 (m, 3H), 8.09 (d, J=8.79 Hz, 1H), 8.26 (dd, J=7.81, 1.46 Hz, 1H); $^{13}$C NMR (101 MHz, CHLOROFORM-d) δ ppm 25.19, 25.80, 28.39, 50.00, 51.93, 67.39, 68.20, 69.49, 69.52, 70.44, 70.62, 73.19, 100.75, 107.33, 114.23, 114.60, 117.60, 117.79, 121.81, 123.31, 124.00, 124.55, 125.59, 126.01, 126.80, 128.20, 128.86, 129.14, 129.64, 130.01, 130.40, 131.26, 131.69, 133.08, 133.23, 137.10, 138.96, 147.36, 155.03, 156.17, 157.83, 160.49, 162.83, 163.47, 166.68, 174.68, 177.63; LRMS (ESI) m/z 878 [M+H]$^+$, 900 [M+Na]$^+$; HRMS (ESI) calcd for $C_{51}H_{48}N_3O_{11}$ [M+H]$^+$ 878.3289, found 878.3313; calcd for $C_{51}H_{47}N_3O_{11}Na$ [M+Na]$^+$ 900.3108, found 900.3151.

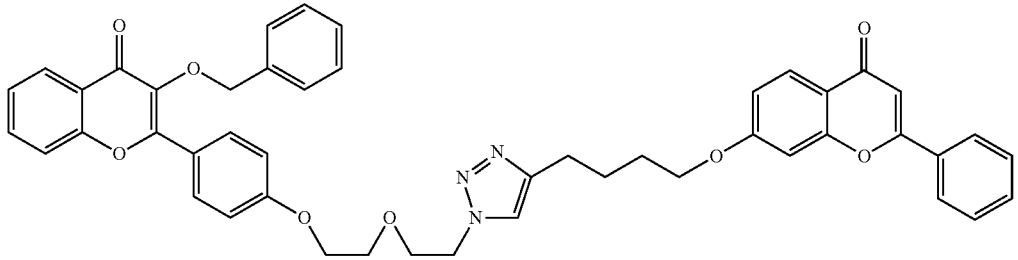 [SMILES: O=c1cc(-c2ccccc2)oc2cc(OCCCCc3cn(CCOCCOc4ccc(-c5oc6ccccc6c(=O)c5OCc5ccccc5)cc4)nn3)ccc12]

3-(Benzyloxy)-2-(4-(2-(2-(4-(4-((4-oxo-2-phenyl-4H-chromen-7-yl)oxy)butyl)-1H-1,2,3-triazol-1-yl)ethoxy)ethoxy)phenyl)-4H-chromen-4-one (Ac12Az10)

This compound (74 mg) was obtained from Ac12 and Az10 in 96% yield according to the general procedure described above. $^1$H NMR (500 MHz, CHLOROFORM-d) δ ppm 1.82-1.94 (m, 4H), 2.78-2.80 (m, 2H), 3.81-3.87 (m, 2H), 3.96 (t, J=4.88 Hz, 2H), 4.01-4.08 (m, 2H), 4.13-4.20 (m, 2H), 4.55 (t, J=4.88 Hz, 2H), 5.12 (s, 2H), 6.73 (s, 1H), 6.88-6.98 (m, 4H), 7.25-7.30 (m, 3H), 7.34-7.41 (m, 3H), 7.44-7.54 (m, 5H), 7.61-7.67 (m, 1H), 7.85-7.91 (m, 2H), 8.01-8.06 (m, 2H), 8.09 (d, J=8.75 Hz, 1H), 8.25 (dd, J=8.54, 1.22 Hz, 1H); $^{13}$C NMR (101 MHz, CHLOROFORM-d) δ ppm 25.22, 25.79, 28.40, 50.05, 67.30, 68.20, 69.55, 69.77, 73.82, 100.76, 107.40, 114.21, 114.64, 117.63, 117.77, 121.87, 123.70, 124.07, 124.53, 125.64, 126.05, 126.85, 128.00, 128.15, 128.66, 128.90, 130.46, 131.28, 131.76, 133.18, 136.75, 139.28, 147.47, 155.03, 155.80, 157.86, 160.33, 162.85, 163.48, 174.78, 177.66; LRMS (ESI) m/z 776 [M+H]$^+$, 798 [M+Na]$^+$; HRMS (ESI) calcd for $C_{47}H_{42}N_3O_8$ [M+H]$^+$ 776.2972, found 776.2946; calcd for $C_{47}H_{41}N_3O_8Na$ [M+Na]$^+$ 798.2791, found 798.2767.

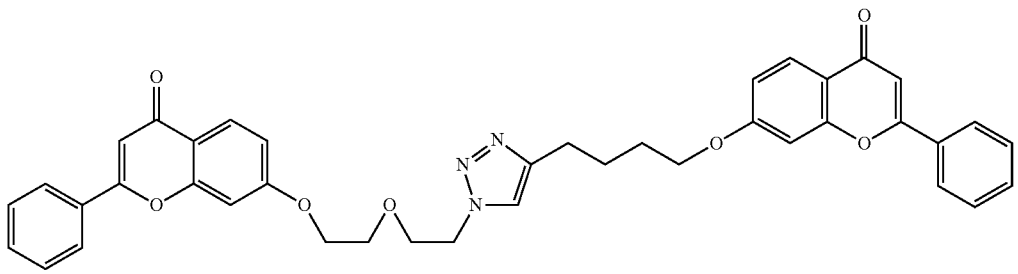 [SMILES: O=c1cc(-c2ccccc2)oc2cc(OCCCCc3cn(CCOCCOc4ccc5c(=O)cc(-c6ccccc6)oc5c4)nn3)ccc12]

7-(2-(2-(4-(4-((4-Oxo-2-phenyl-4H-chromen-7-yl)oxy)butyl)-1H-1,2,3-triazol-1-yl)ethoxy)ethoxy)-2-phenyl-4H-chromen-4-one (Ac12Az11)

This compound (30 mg) was obtained from Ac12 and Az11 in 45% yield according to the general procedure described above. $^1$H NMR (500 MHz, CHLOROFORM-d) δ ppm 1.87 (br. s., 4H), 2.78 (br. s., 2H), 3.85-3.87 (m, 2H), 3.96 (t, J=4.88 Hz, 2H), 4.04 (br. s., 2H), 4.18-4.22 (m, 2H), 4.55 (t, J=4.39 Hz, 2H), 6.72 (s, 1H), 6.73 (s, 1H), 6.86-7.00 (m, 4H), 7.45-7.55 (m, 7H), 7.83-7.90 (m, 4H), 8.07 (d, J=8.79 Hz, 1H), 8.13 (d, J=8.78 Hz, 1H); $^{13}$C NMR (101 MHz, CHLOROFORM-d) δ ppm 25.17, 25.71, 28.36, 50.10, 67.75, 68.18, 69.28, 69.74, 100.73, 101.08, 107.31, 107.36, 114.41, 114.62, 117.58, 117.97, 125.97, 126.02, 126.77, 127.01, 128.87, 128.89, 131.28, 131.37, 131.55, 131.70, 157.71, 157.81, 162.81, 162.92, 162.99, 163.45, 177.50, 177.64; LRMS (ESI) m/z 670 [M+H]$^+$; HRMS (ESI) calcd for $C_{40}H_{36}N_3O_7$ [M+H]$^+$ 670.2553, found 670.2565.

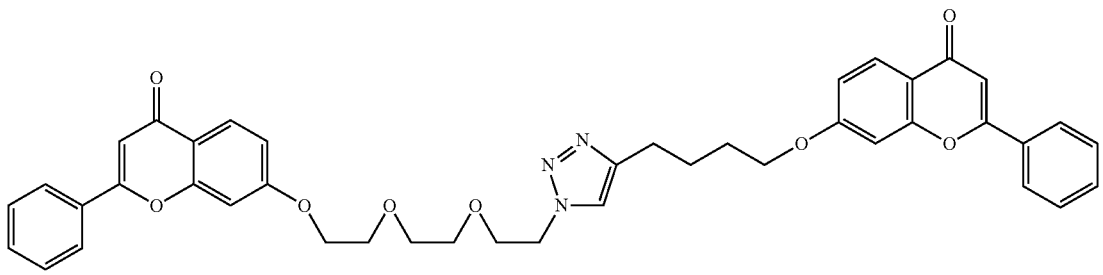 [SMILES: O=c1cc(-c2ccccc2)oc2cc(OCCCCc3cn(CCOCCOCCOc4ccc5c(=O)cc(-c6ccccc6)oc5c4)nn3)ccc12]

7-(2-(2-(2-(4-(4-((4-Oxo-2-phenyl-4H-chromen-7-yl)oxy)butyl)-1H-1,2,3-triazol-1-yl)ethoxy)ethoxy)ethoxy)-2-phenyl-4H-chromen-4-one (Ac12Az12)

This compound (17 mg) was obtained from Ac12 and Az12 in 24% yield according to the general procedure described above. $^1$H NMR (500 MHz, CHLOROFORM-d) δ ppm 1.85-1.91 (m, 4H), 2.80 (br. s., 2H), 3.62-3.68 (m, 2H), 3.68-3.72 (m, 2H), 3.86-3.90 (m, 4.70 Hz, 4H), 4.06 (s, 2H), 4.19-4.23 (m, 2H), 4.52 (t, J=5.12 Hz, 2H), 6.73 (s, 1H), 6.74 (s, 1H), 6.88-7.01 (m, 4H), 7.46-7.55 (m, 7H), 7.84-7.91 (m, 4H), 8.09 (d, J=8.79 Hz, 1H), 8.12 (d, J=8.79 Hz, 1H); $^{13}$C NMR (101 MHz, CHLOROFORM-d) δ ppm 25.26, 25.90, 28.48, 50.16, 68.05, 68.27, 69.41, 69.61, 70.54, 70.79, 100.84, 101.18, 107.48, 107.54, 114.59, 114.72, 117.73, 118.04, 121.92, 126.12, 126.14, 126.97, 127.15, 128.98, 128.99, 131.37, 131.44, 131.77, 131.85, 157.86, 157.97, 162.97, 163.05, 163.22, 163.57, 177.70, 177.80; LRMS (ESI) m/z 714 [M+H]$^+$; HRMS (ESI) calcd for $C_{42}H_{40}N_3O_8$ [M+H]$^+$ 714.2815, found 714.2818.

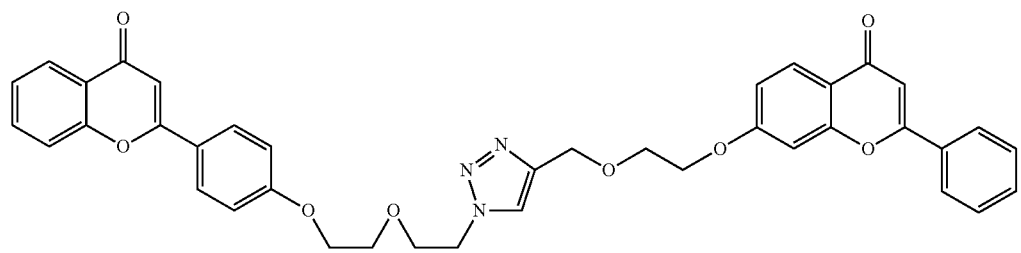 [SMILES: O=c1cc(-c2ccc(OCCOCCn3cc(COCCOc4ccc5c(=O)cc(-c6ccccc6)oc5c4)nn3)cc2)oc2ccccc12]

7-(2-((1-(2-(2-(4-(4-Oxo-4H-chromen-2-yl)phenoxy)ethoxy)ethyl)-1H-1,2,3-triazol-4-yl)methoxy)ethoxy)-2-phenyl-4H-chromen-4-one (Ac13Az1)

This compound (56 mg) was obtained from Ac13 and Az1 in 84% yield according to the general procedure described above. $^1$H NMR (500 MHz, CHLOROFORM-d) δ ppm 3.82-3.84 (m, 2H), 3.92-3.96 (m, 4H), 4.11-4.16 (m, 2H), 4.18-4.23 (m, 2H), 4.57 (t, J=4.88 Hz, 2H), 4.74 (s, 2H), 6.70 (d, J=3.90 Hz, 2H), 6.91 (d, J=2.44 Hz, 1H), 6.94 (dd, J=8.79, 2.44 Hz, 1H), 6.96-7.00 (m, 2H), 7.35-7.40 (m, 1H), 7.44-7.53 (m, 4H), 7.64 (ddd, J=8.42, 6.95, 1.71 Hz, 1H), 7.76 (s, 1H), 7.80-7.87 (m, 4H), 8.07 (d, J=8.79 Hz, 1H), 8.17 (dd, J=7.81, 1.46 Hz, 1H); $^{13}$C NMR (101 MHz, CHLOROFORM-d) δ ppm 50.25, 64.81, 67.40, 67.93, 68.43, 69.55, 69.66, 101.09, 106.25, 107.47, 114.70, 114.95, 117.87, 117.95, 123.80, 123.87, 124.41, 125.06, 125.61, 126.08, 126.98, 127.95, 128.95, 131.37, 131.75, 133.54, 144.73, 156.10, 157.80, 161.30, 162.97, 163.06, 163.22, 177.67, 178.20; LRMS (ESI) m/z 672 [M+H]$^+$; HRMS (ESI) calcd for $C_{39}H_{34}N_3O_8$ [M+H]$^+$ 672.2346, found 672.2334.

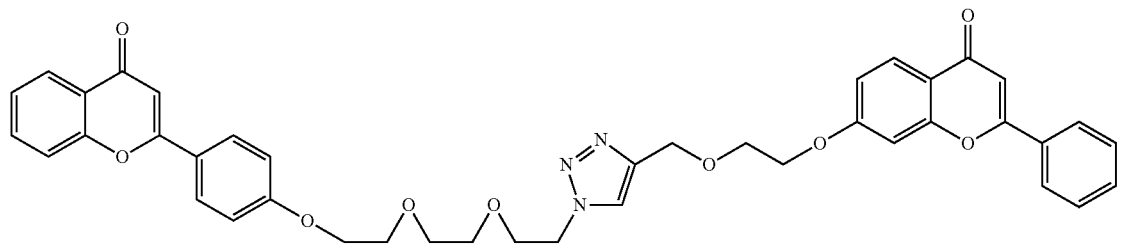 [SMILES: O=c1cc(-c2ccc(OCCOCCOCCn3cc(COCCOc4ccc5c(=O)cc(-c6ccccc6)oc5c4)nn3)cc2)oc2ccccc12]

7-(2-((1-(2-(2-(2-(4-(4-Oxo-4H-chromen-2-yl)phenoxy)ethoxy)ethoxy)ethyl)-1H-1,2,3-triazol-4-yl)methoxy)ethoxy)-2-phenyl-4H-chromen-4-one (Ac13Az2)

This compound (54 mg) was obtained from Ac13 and Az2 in 76% yield according to the general procedure described above. $^1$H NMR (500 MHz, CHLOROFORM-d) δ ppm 3.60-3.69 (m, 4H), 3.80-3.82 (m, 2H), 3.86-3.88 (m, 2H), 3.92-3.93 (m, 2H), 4.13-4.15 (m, 2H), 4.20-4.22 (m, 2H), 4.53 (t, J=4.88 Hz, 2H), 4.73 (s, 2H), 6.69 (d, J=11.2 Hz, 2H), 6.90 (s, 1H), 6.92-7.00 (m, 3H), 7.36 (t, J=7.57 Hz, 1H), 7.43-7.51 (m, 4H), 7.61-7.67 (m, 1H), 7.76-7.87 (m, 5H), 8.07 (d, J=8.79, 1H), 8.17 (d, J=8.0, 1H); $^{13}$C NMR (101 MHz, CHLOROFORM-d) δ ppm 50.22, 64.76, 67.54, 67.93, 68.40, 69.40, 69.48, 70.50, 70.66, 101.06, 106.13, 107.42, 114.65, 114.94, 117.86, 117.92, 123.77, 123.85, 124.19, 125.00, 125.56, 126.05, 126.96, 127.88, 128.92, 131.35, 131.70, 133.48, 144.57, 156.06, 157.77, 161.43, 162.93, 163.12, 163.19, 177.63, 178.18; LRMS (ESI) m/z 716 [M+H]$^+$, 738 [M+Na]$^+$; HRMS (ESI) calcd for $C_{41}H_{38}N_3O_9$ [M+H]$^+$ 716.2608, found 716.2574; calcd for $C_{41}H_{37}N_3O_9Na$ [M+Na]$^+$ 738.2427, found 738.2396.

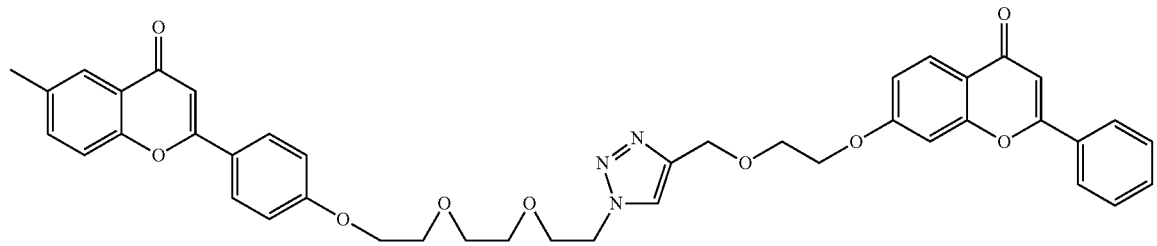 [SMILES: Cc1ccc2oc(-c3ccc(OCCOCCOCCn4cc(COCCOc5ccc6c(=O)cc(-c7ccccc7)oc6c5)nn4)cc3)cc(=O)c2c1]

6-Methyl-2-(4-(2-(2-(2-(4-((2-((4-oxo-2-phenyl-4H-chromen-7-yl)oxy)ethoxy)methyl)-1H-1,2,3-triazol-1-yl)ethoxy)ethoxy)ethoxy)phenyl)-4H-chromen-4-one (Ac13Az3)

This compound (47 mg) was obtained from Ac13 and Az3 in 65% yield according to the general procedure described above. $^1$H NMR (500 MHz, CHLOROFORM-d) δ ppm 3.60-3.69 (m, 4H), 3.78-3.83 (m, 2H), 3.87 (t, J=4.88 Hz, 2H), 3.90-3.92 (m, 2H), 4.11-4.16 (m, 2H), 4.18-4.22 (m, 2H), 4.53 (t, J=4.88 Hz, 2H), 4.73 (s, 2H), 6.65 (s, 1H), 6.69 (s, 1H), 6.88-6.99 (m, 4H), 7.34-7.39 (m, 1H), 7.41-7.51 (m, 4H), 7.76-7.86 (m, 5H), 7.94 (s, 1H), 8.06 (d, J=8.79 Hz, 1H); $^{13}$C NMR (101 MHz, CHLOROFORM-d) δ ppm 20.83, 50.21, 64.75, 67.52, 67.91, 68.37, 69.39, 69.47, 70.49, 70.64, 101.05, 105.97, 107.39, 114.63, 114.90, 117.60, 117.90, 123.46, 123.76, 124.30, 124.90, 126.03, 126.93, 127.83, 128.90, 131.33, 131.68, 134.67, 134.94, 144.55, 154.32, 157.75, 161.34, 162.91, 162.97, 163.18, 177.62, 178.29; LRMS (ESI) m/z 730 [M+H]$^+$, 752 [M+Na]$^+$; HRMS (ESI) calcd for $C_{42}H_{40}N_3O_9$ [M+H]$^+$ 730.2765, found 730.2753; calcd for $C_{42}H_{40}N_3O_9Na$ [M+Na]$^+$ 752.2584, found 752.2604.

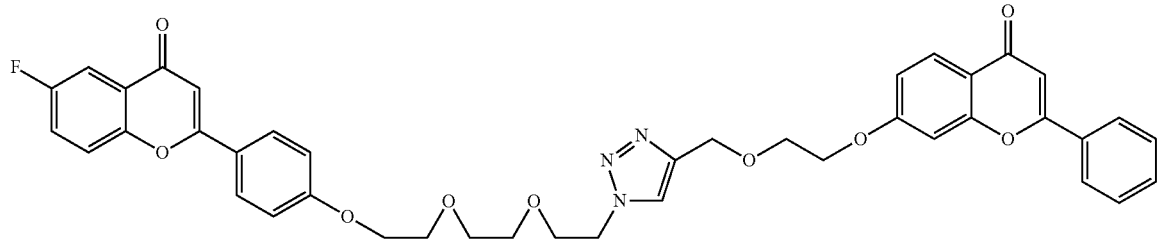 [SMILES: O=c1cc(-c2ccccc2)oc2cc(OCCOCc3cn(CCOCCOCCOc4ccc(-c5cc(=O)c6cc(F)ccc6o5)cc4)nn3)ccc12]

6-Fluoro-2-(4-(2-(2-(2-(4-((2-((4-oxo-2-phenyl-4H-chromen-7-yl)oxy)ethoxy)methyl)-1H-1,2,3-triazol-1-yl)ethoxy)ethoxy)ethoxy)phenyl)-4H-chromen-4-one (Ac13Az4)

This compound (48 mg) was obtained from Ac13 and Az4 in 65% yield according to the general procedure described above. $^1$H NMR (500 MHz, CHLOROFORM-d) δ ppm 3.60-3.70 (m, 4H), 3.78-3.83 (m, 2H), 3.88-3.89 (m, 2H), 3.95 (br. s., 2H), 4.11-4.17 (m, 2H), 4.22 (br. s., 2H), 4.50-4.58 (m, 2H), 4.73 (br. s., 2H), 6.66 (s, 1H), 6.71 (s, 1H), 6.88-6.99 (m, 4H), 7.32-7.38 (m, 1H), 7.43-7.51 (m, 4H), 7.76-7.86 (m, 6H), 8.07 (d, J=8.78 Hz, 1H); $^{13}$C NMR (101 MHz, CHLOROFORM-d) δ ppm 64.80, 64.82, 67.57, 67.94, 68.40, 69.36, 69.47, 70.50, 70.67, 101.05, 105.42, 107.41, 110.50 (d, J=23.23 Hz, C5), 114.66, 114.99, 119.92 (d, J=8.08 Hz, C8), 121.56 (d, J=25.25 Hz, C7), 123.86, 126.04, 126.95, 127.93, 128.92, 131.37, 131.67, 152.24 (d, J=2.22 Hz, C9), 157.78, 159.46 (d, J=247.45 Hz, C6), 161.58, 162.92, 163.19, 163.41, 177.31 (d, J=2.53 Hz, C4), 177.61; LRMS (ESI) m/z 734 [M+H]$^+$; HRMS (ESI) calcd for $C_{41}H_{37}N_3O_9F$ [M+H]$^+$ 734.2514, found 734.2546.

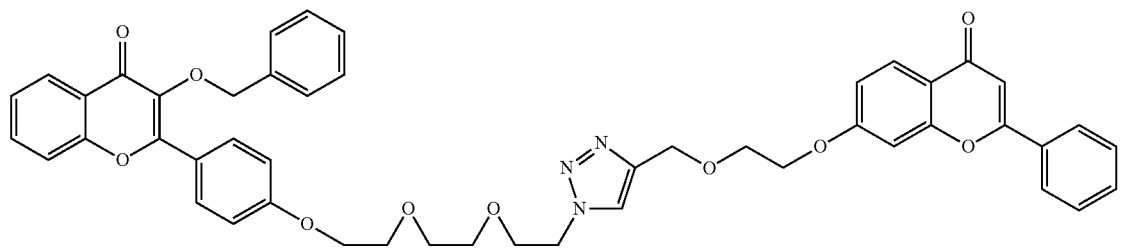 [SMILES: O=c1cc(-c2ccccc2)oc2cc(OCCOCc3cn(CCOCCOCCOc4ccc(-c5oc6ccccc6c(=O)c5OCc5ccccc5)cc4)nn3)ccc12]

3-(Benzyloxy)-2-(4-(2-(2-(2-(4-((2-((4-oxo-2-phenyl-4H-chromen-7-yl)oxy)ethoxy)methyl)-1H-1,2,3-triazol-1-yl)ethoxy)ethoxy)ethoxy)phenyl)-4H-chromen-4-one (Ac13Az5)

This compound (54 mg) was obtained from Ac13 and Az5 in 66% yield according to the general procedure described above. $^1$H NMR (500 MHz, CHLOROFORM-d) δ ppm 3.61-3.71 (m, 4H), 3.80-3.85 (m, 2H), 3.88 (t, J=5.12 Hz, 2H), 3.90-3.95 (m, 2H), 4.13-4.18 (m, 2H), 4.18-4.24 (m, 2H), 4.54 (t, J=5.12 Hz, 2H), 4.74 (s, 2H), 5.10 (s, 2H), 6.72 (s, 1H), 6.91-6.99 (m, 4H), 7.23-7.30 (m, 3H), 7.34-7.40 (m, 3H), 7.45-7.51 (m, 4H), 7.63 (ddd, J=8.54, 7.08, 1.95 Hz, 1H), 7.78 (s, 1H), 7.83-7.88 (m, 2H), 7.99-8.03 (m, 2H), 8.09 (d, J=8.79 Hz, 1H), 8.25 (dd, J=8.30, 1.46 Hz, 1H); $^{13}$C NMR (101 MHz, CHLOROFORM-d) δ ppm 50.24, 64.77, 67.46, 67.93, 68.40, 69.43, 69.57, 70.54, 70.70, 73.85, 101.10, 107.49, 114.29, 114.68, 117.83, 117.96, 123.59, 123.78, 124.14, 124.54, 125.70, 126.09, 126.99, 128.02, 128.19, 128.73, 128.95, 130.47, 131.36, 131.77, 133.19, 136.79, 139.29, 144.59, 155.10, 155.99, 157.81, 160.50, 162.96, 163.22, 174.86, 177.67; LRMS (ESI) m/z 822 [M+H]$^+$, 844 [M+Na]$^+$; HRMS (ESI) calcd for $C_{48}H_{44}N_3O_{10}$ [M+H]$^+$ 822.3027, found 822.3003; calcd for $C_{48}H_{44}N_3O_{10}Na$ [M+Na]$^+$ 844.2846, found 844.2825.

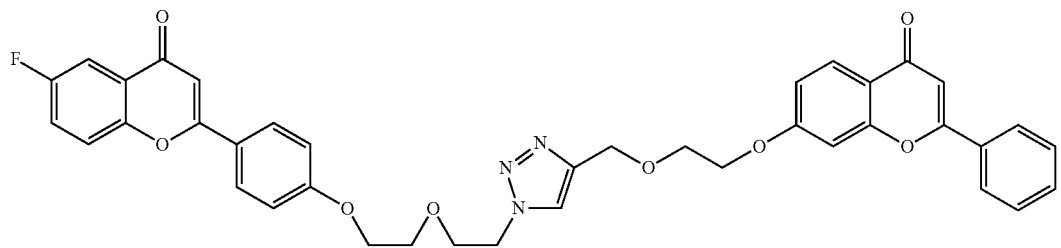 [SMILES: O=c1cc(-c2ccccc2)oc2cc(OCCOCc3cn(CCOCCOc4ccc(-c5cc(=O)c6cc(F)ccc6o5)cc4)nn3)ccc12]

6-Fluoro-2-(4-(2-(2-(4-((2-((4-oxo-2-phenyl-4H-chromen-7-yl)oxy)ethoxy)methyl)-1H-1,2,3-triazol-1-yl)ethoxy)ethoxy)phenyl)-4H-chromen-4-one (Ac13Az7)

This compound (30 mg) was obtained from Ac13 and Az7 in 44% yield according to the general procedure described above. $^1$H NMR (500 MHz, CHLOROFORM-d) δ ppm 3.83-3.83 (m, 2H), 3.95-3.97 (m, 4H), 4.14-4.15 (m, 2H), 4.22 (br. s., 2H), 4.59 (t, J=4.88 Hz, 2H), 4.75 (br. s., 2H), 6.69 (s, 1H), 6.72 (s, 1H), 6.90-7.01 (m, 4H), 7.36 (ddd, J=9.15, 7.44, 2.93 Hz, 1H), 7.47-7.52 (m, 4H), 7.78-7.87 (m, 6H), 8.08 (d, J=8.79 Hz, 1H); $^{13}$C NMR (101 MHz, CHLOROFORM-d) δ ppm 50.37, 64.85, 67.43, 67.96, 68.44, 69.55, 69.66, 101.09, 105.57, 107.48, 110.59 (d, J=24.24 Hz, C5), 114.72, 115.01, 119.94 (d, J=8.08 Hz, C8), 121.63 (d, J=26.26 Hz, C7), 124.14, 126.09, 127.01, 128.01, 128.98, 131.41, 131.74, 152.28 (d, J=1.46 Hz, C9), 157.81, 159.53 (d, J=247.45 Hz, C6), 161.45, 162.98, 163.23, 163.36, 177.34, 177.35 (d, J=2.02 Hz, C4), 177.66; LRMS (ESI) m/z 690 [M+H]$^+$; HRMS (ESI) calcd for $C_{39}H_{33}N_3O_8F$ [M+H]$^+$ 690.2252, found 690.2220.

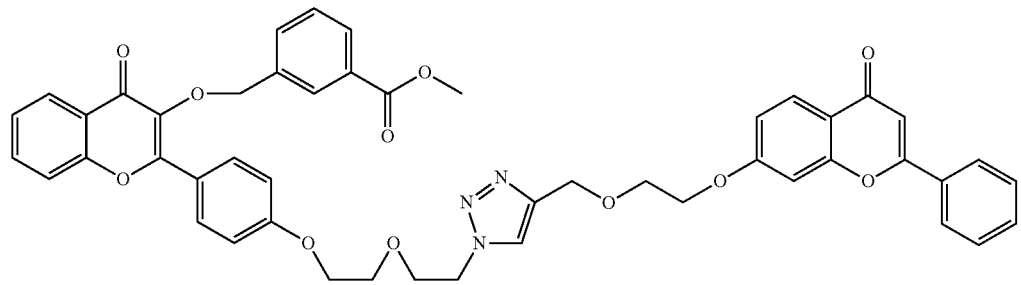 [SMILES: COC(=O)c1cccc(COc2c(-c3ccc(OCCOCCn4cc(COCCOc5ccc6c(=O)cc(-c7ccccc7)oc6c5)nn4)cc3)oc3ccccc3c2=O)c1]

Methyl 3-(((4-oxo-2-(4-(2-(2-(4-((2-((4-oxo-2-phenyl-4H-chromen-7-yl)oxy)ethoxy)methyl)-1H-1,2,3-triazol-1-yl)ethoxy)ethoxy)phenyl)-4H-chromen-3-yl)oxy)methyl)benzoate (Ac13Az8)

This compound (78 mg) was obtained from Ac13 and Az8 in 94% yield according to the general procedure described above. $^1$H NMR (500 MHz, CHLOROFORM-d) δ ppm 3.80-3.84 (m, 2H), 3.85 (s, 3H), 3.89-3.93 (m, 2H), 3.95 (t, J=4.88 Hz, 2H), 4.10-4.16 (m, 2H), 4.16-4.21 (m, 2H), 4.57 (t, J=4.88 Hz, 2H), 4.73 (s, 2H), 5.11 (s, 2H), 6.70 (s, 1H), 6.88-6.96 (m, 4H), 7.32 (t, J=7.57 Hz, 1H), 7.37 (t, J=7.57 Hz, 1H), 7.43-7.51 (m, 4H), 7.57 (d, J=7.81 Hz, 1H), 7.63 (ddd, J=8.54, 7.08, 1.95 Hz, 1H), 7.78 (br. s., 1H), 7.81-7.86 (m, 2H), 7.90 (d, J=7.81 Hz, 1H), 7.92-7.98 (m, 3H), 8.06 (d, J=9.27 Hz, 1H), 8.23 (dd, J=8.05, 1.71 Hz, 1H); $^{13}$C NMR (101 MHz, CHLOROFORM-d) δ ppm 50.51, 52.23, 65.01, 67.50, 68.15, 68.64, 69.83, 69.87, 73.51, 76.95, 77.26, 77.47, 77.58, 101.32, 107.70, 114.52, 114.94, 118.09, 123.78, 124.33, 124.88, 125.93, 126.32, 127.18, 128.51, 129.18, 129.44, 129.96, 130.33, 130.73, 131.59, 131.99, 133.40, 133.54, 137.42, 139.29, 155.35, 156.40, 158.02, 160.62, 163.18, 163.46, 166.99, 174.97, 177.87; LRMS (ESI) m/z 836 [M+H]$^+$, 858 [M+Na]$^+$; HRMS (ESI) calcd for $C_{48}H_{42}N_3O_{11}$ [M+H]$^+$ 836.2819, found 836.2792; calcd for $C_{48}H_{42}N_3O_{11}Na$ [M+Na]$^+$ 858.2639, found 858.2606.

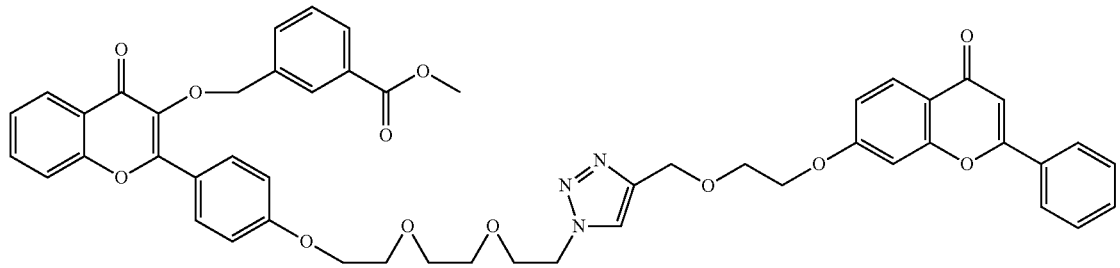 [SMILES: COC(=O)c1cccc(COc2c(-c3ccc(OCCOCCOCCn4cc(COCCOc5ccc6c(=O)cc(-c7ccccc7)oc6c5)nn4)cc3)oc3ccccc3c2=O)c1]

Methyl 3-(((4-oxo-2-(4-(2-(2-(2-(4-((2-((4-oxo-2-phenyl-4H-chromen-7-yl)oxy)ethoxy)methyl)-1H-1,2,3-triazol-1-yl)ethoxy)ethoxy)ethoxy)phenyl)-4H-chromen-3-yl)oxy)methyl)benzoate (Ac13Az9)

This compound (47 mg) was obtained from Ac13 and Az9 in 53% yield according to the general procedure described above. $^1$H NMR (500 MHz, CHLOROFORM-d) δ ppm 3.62-3.66 (m, 2H), 3.66-3.70 (m, 2H), 3.81-3.85 (m, 2H), 3.87 (s, 3H), 3.88 (t, J=4.75 Hz, 2H), 3.91-3.95 (m, 2H), 4.14-4.17 (m, 2H), 4.19-4.23 (m, 2H), 4.54 (t, J=5.12 Hz, 2H), 4.74 (s, 2H), 5.13 (s, 2H), 6.72 (s, 1H), 6.90-6.99 (m, 4H), 7.33 (t, J=7.57 Hz, 1H), 7.36-7.41 (m, 1H), 7.45-7.52 (m, 4H), 7.58 (d, J=7.32 Hz, 1H), 7.64 (ddd, J=8.42, 6.95, 1.71 Hz, 1H), 7.79 (br. s., 1H), 7.83-7.87 (m, 2H), 7.91 (d, J=7.81 Hz, 1H), 7.93-7.98 (m, 3H), 8.09 (d, J=8.79 Hz, 1H), 8.25 (dd, J=7.81, 1.46 Hz, 1H); $^{13}$C NMR (101 MHz, CHLOROFORM-d) δ ppm 50.29, 52.00, 64.76, 67.44, 67.93, 68.40, 69.42, 69.56, 70.53, 70.68, 73.27, 101.10, 107.48, 114.31, 114.69, 117.86, 123.39, 124.11, 124.62, 125.70, 126.09, 126.99, 128.27, 128.95, 129.21, 129.70, 130.09, 130.46, 131.36, 131.77, 133.16, 133.28, 137.18, 139.04, 155.12, 156.26, 157.81, 160.55, 162.97, 163.22, 166.76, 174.76, 177.66; LRMS (ESI) m/z 880 [M+H]$^+$; HRMS (ESI) calcd for $C_{50}H_{46}N_3O_{12}$ [M+H]$^+$ 880.3081, found 880.3043.

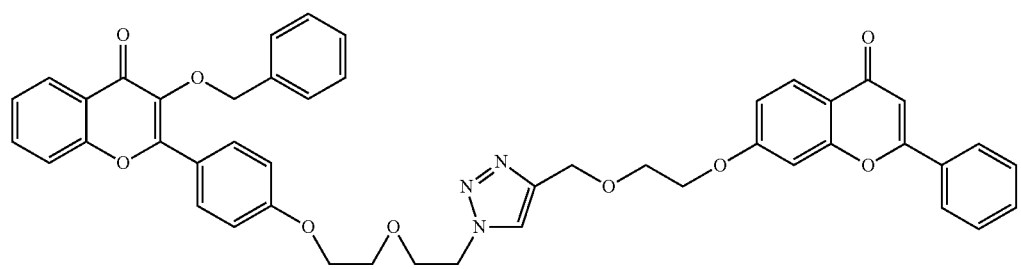 [SMILES: O=c1cc(-c2ccccc2)oc2cc(OCCOCc3cn(CCOCCOc4ccc(-c5oc6ccccc6c(=O)c5OCc5ccccc5)cc4)nn3)ccc12]

3-(Benzyloxy)-2-(4-(2-(2-(4-((2-((4-oxo-2-phenyl-4H-chromen-7-yl)oxy)ethoxy)methyl)-1H-1,2,3-triazol-1-yl)ethoxy)ethoxy)phenyl)-4H-chromen-4-one (Ac13Az10)

This compound (39 mg) was obtained from Ac13 and Az10 in 50% yield according to the general procedure described above. $^1$H NMR (500 MHz, CHLOROFORM-d) δ ppm 3.79-3.84 (m, 2H), 3.88-3.93 (m, 2H), 3.95 (t, J=4.88 Hz, 2H), 4.10-4.15 (m, 2H), 4.15-4.21 (m, 2H), 4.57 (t, J=4.88 Hz, 2H), 4.73 (s, 2H), 5.10 (s, 2H), 6.71 (s, 1H), 6.87-6.96 (m, 4H), 7.22-7.29 (m, 3H), 7.33-7.39 (m, 3H), 7.43-7.51 (m, 4H), 7.59-7.65 (m, 1H), 7.77 (br. s., 1H), 7.80-7.86 (m, 2H), 7.98-8.04 (m, 2H), 8.06 (d, J=8.75, 1H), 8.23 (dd, J=8.05, 1.71 Hz, 1H); $^{13}$C NMR (101 MHz, CHLOROFORM-d) δ ppm 50.27, 64.76, 67.26, 67.89, 68.40, 69.57, 69.61, 73.83, 101.07, 107.45, 114.23, 114.70, 117.80, 123.73, 124.11, 124.55, 125.67, 126.07, 126.94, 128.02, 128.18, 128.69, 128.92, 130.48, 131.34, 131.74, 133.20, 136.77, 139.30, 155.07, 155.84, 157.78, 160.31, 162.95, 163.21, 174.82, 177.63; LRMS (ESI) m/z 778 [M+H]$^+$; HRMS (ESI) calcd for C$_{46}$H$_{40}$N$_3$O$_9$ [M+H]$^+$ 778.2765, found 778.2791.

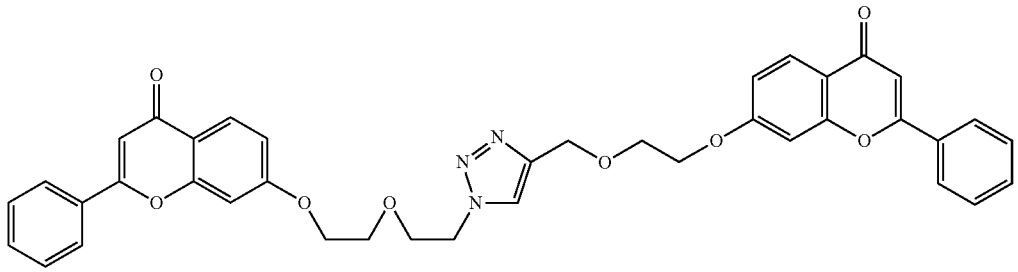 [SMILES: O=c1cc(-c2ccccc2)oc2cc(OCCOCCn3cc(COCCOc4ccc5c(=O)cc(-c6ccccc6)oc5c4)nn3)ccc12]

7-(2-((1-(2-(2-((4-Oxo-2-phenyl-4H-chromen-7-yl)oxy)ethoxy)ethyl)-1H-1,2,3-triazol-4-yl)methoxy)ethoxy)-2-phenyl-4H-chromen-4-one (Ac13Az11)

This compound (38 mg) was obtained from Ac13 and Az11 in 57% yield according to the general procedure described above. $^1$H NMR (500 MHz, CHLOROFORM-d) δ ppm 3.80-3.85 (m, 2H), 3.91 (br. s., 2H), 3.94 (t, J=4.88 Hz, 2H), 4.12-4.19 (m, 4H), 4.57 (t, J=4.88 Hz, 2H), 4.72 (s, 2H), 6.65 (s, 1H), 6.67 (s, 1H), 6.85 (dd, J=7.32, 2.44 Hz, 2H), 6.90 (dd, J=9.03, 2.20 Hz, 1H), 6.93 (dd, J=8.79, 1.95 Hz, 1H), 7.41-7.51 (m, 6H), 7.80 (ddd, J=7.69, 3.29, 1.71 Hz, 5H), 8.03 (d, J=8.78 Hz, 1H), 8.07 (d, J=9.27 Hz, 1H); $^{13}$C NMR (101 MHz, CHLOROFORM-d) δ ppm 50.24, 64.76, 67.69, 67.87, 68.41, 69.28, 69.59, 100.97, 101.03, 107.34, 107.37, 114.51, 114.68, 117.82, 117.97, 126.00, 126.02, 126.82, 127.00, 128.88, 128.90, 131.33, 131.37, 131.58, 131.64, 157.70, 162.86, 162.92, 162.95, 163.14, 177.52, 177.59; LRMS (ESI) m/z 672 [M+H]$^+$; HRMS (ESI) calcd for C$_{39}$H$_{34}$N$_3$O$_8$ [M+H]$^+$ 672.2346, found 672.2317.

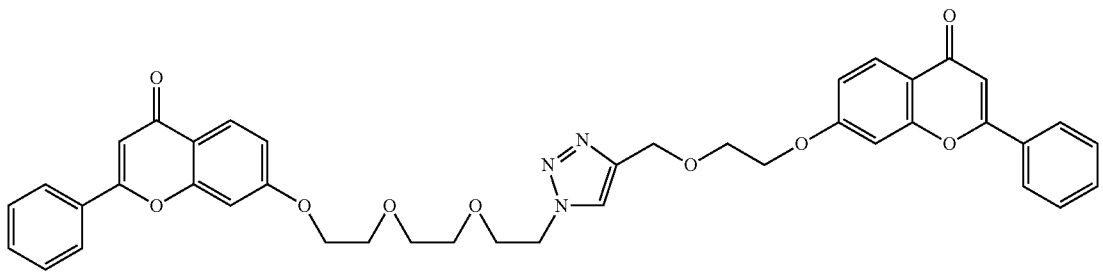 [SMILES: O=c1cc(-c2ccccc2)oc2cc(OCCOCCOCCn3cc(COCCOc4ccc5c(=O)cc(-c6ccccc6)oc5c4)nn3)ccc12]

7-(2-((1-(2-(2-(2-((4-Oxo-2-phenyl-4H-chromen-7-yl)oxy)ethoxy)ethoxy) ethyl)-1H-1,2,3-triazol-4-yl) methoxy)ethoxy)-2-phenyl-4H-chromen-4-one (Ac13Ac12)

This compound (32 mg) was obtained from Ac13 and Az12 in 45% yield according to the general procedure described above. $^1$H NMR (500 MHz, CHLOROFORM-d) δ ppm 3.60-3.66 (m, 2H), 3.66-3.70 (m, 2H), 3.81-3.86 (m, 2H), 3.88-3.90 (m, 2H), 3.94 (br. s., 2H), 4.17-4.25 (m, 4H), 4.53-4.55 (m, 2H), 4.73 (br. s., 2H), 6.71 (s, 2H), 6.87-6.98 (m, 4H), 7.43-7.54 (m, 6H), 7.80-7.88 (m, 5H), 8.08 (t, J=8.54 Hz, 2H); $^{13}$C NMR (101 MHz, CHLOROFORM-d) δ ppm 50.45, 64.80, 67.93, 67.99, 68.43, 69.36, 69.37, 70.51, 70.71, 101.07, 101.16, 107.44, 107.45, 114.58, 114.68, 118.01, 126.08, 126.96, 127.04, 128.94, 131.37, 131.72, 157.79, 157.80, 162.97, 163.18, 163.20, 177.63; LRMS (ESI) m/z 716 [M+H]$^+$; HRMS (ESI) calcd for $C_{41}H_{38}N_3O_9$ [M+H]$^+$ 716.2608, found 716.2577.

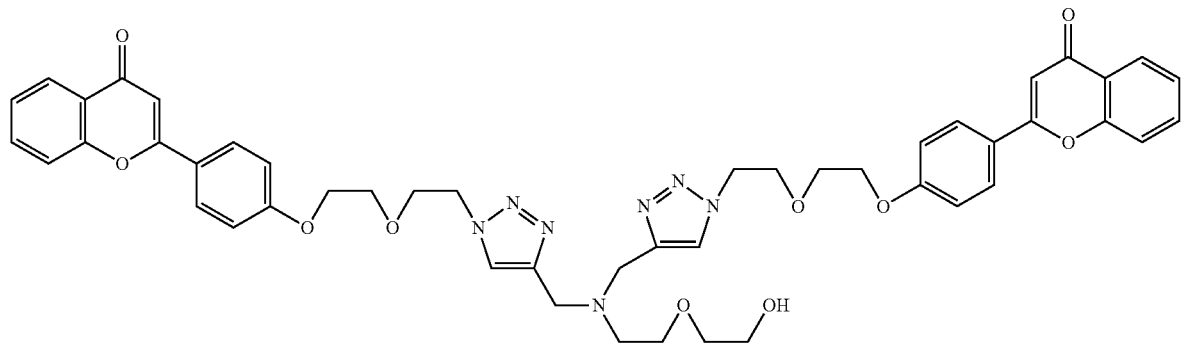 [SMILES: O=c1cc(-c2ccc(OCCOCCn3cc(CN(CCOCCO)Cc4cn(CCOCCOc5ccc(-c6cc(=O)c7ccccc7o6)cc5)nn4)nn3)cc2)oc2ccccc12]

2,2'-((((((4,4'-(((2-(2-(4-(4-Oxo-4H-chromen-2-yl) phenoxy)ethoxy)ethyl) azanediyl)bis(methylene))bis (1H-1,2,3-triazole-4,1-diyl))bis(ethane-2,1-diyl))bis (oxy)) bis(ethane-2,1-diyl))bis(oxy))bis(4,1-phenylene))bis(4H-chromen-4-one) (Ac14Az1)

This compound (63 mg) was obtained from Ac14 and Az1 in 71% yield according to the general procedure described above. $^1$H NMR (500 MHz, CHLOROFORM-d) δ ppm 2.71-2.73 (m, 2H) 3.52-3.56 (m, 2H) 3.64-3.70 (m, 4H) 3.79 (s, 4H) 3.80-3.85 (m, 4H) 3.96 (t, J=5.12 Hz, 4H) 4.15-4.17 (m, 4H) 4.56 (t, J=5.12 Hz, 4H) 6.72 (s, 2H) 6.97-7.02 (m, 4H) 7.37-7.42 (m, 2H) 7.53 (d, J=8.30 Hz, 2H) 7.67 (ddd, J=8.54, 7.08, 1.46 Hz, 2H) 7.82-7.86 (m, 4H) 7.88 (s, 2H) 8.20 (dd, J=7.81, 1.95 Hz, 2H); $^{13}$C NMR (126 MHz, CHLOROFORM-d) δ ppm 47.56, 50.11, 52.62, 61.67, 67.43, 68.39, 69.46, 69.62, 72.35, 106.08, 114.95, 117.89, 123.77, 124.17, 124.64, 125.04, 125.52, 127.93, 133.55, 143.38, 156.06, 161.32, 163.21, 178.30; LRMS (ESI) m/z 906 [M+Na]$^+$; HRMS (ESI) calcd for $C_{48}H_{49}N_7O_{10}Na$ [M+Na]$^+$ 906.3439, found 906.3398.

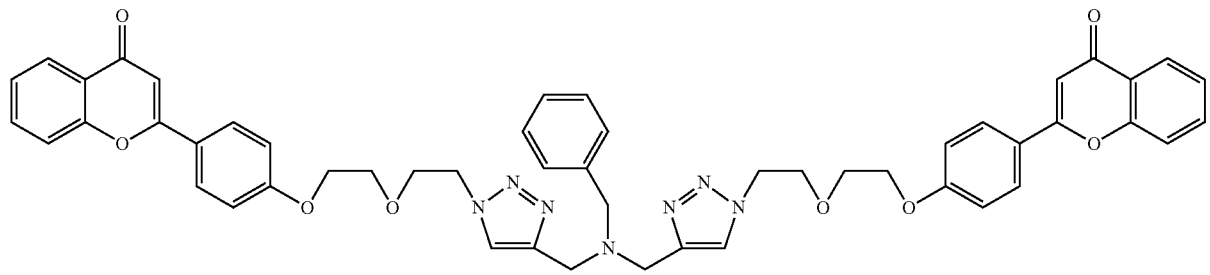 [SMILES: O=c1cc(-c2ccc(OCCOCCn3cc(CN(Cc4ccccc4)Cc4cn(CCOCCOc5ccc(-c6cc(=O)c7ccccc7o6)cc5)nn4)nn3)cc2)oc2ccccc12]

2,2'-((((((4,4'-(Benzylazanediyl)bis(methylene))bis (1H-1,2,3-triazole-4,1-diyl))bis(ethane-2,1-diyl))bis (oxy))bis(ethane-2,1-diyl))bis(oxy))bis(4,1-phenylene))bis (4H-chromen-4-one) (Ac15Az1)

This compound (88 mg) was obtained from Ac15 and Az1 in 99% yield according to the general procedure described above. $^1$H NMR (500 MHz, CHLOROFORM-d) δ ppm 3.62-3.74 (m, 2H), 3.75-3.81 (m, 2H), 3.93 (br. s., 2H), 4.06-4.12 (m, 2H), 4.52-4.54 (m, 2H), 6.65 (s, 1H), 6.91 (d, J=9.27 Hz, 2H), 7.11-7.18 (m, 1H), 7.22 (t, J=7.08 Hz, 1H), 7.29-7.39 (m, 2H), 7.48 (d, J=8.30 Hz, 1H), 7.63 (ddd, J=8.54, 7.08, 1.46 Hz, 1H), 7.68-7.79 (m, 3H), 8.15 (dd, J=7.81, 1.46 Hz, 1H); $^{13}$C NMR (101 MHz, CHLOROFORM-d) δ ppm 50.11, 67.34, 69.37, 69.55, 106.00, 114.84, 117.83, 123.74, 124.08, 124.94, 125.41, 126.89, 127.83, 127.89, 128.13, 128.73, 133.44, 155.97, 161.22, 163.06, 178.10; LRMS (ESI) m/z 886 [M+H]$^+$; HRMS (ESI) calcd for $C_{51}H_{48}N_7O_8$ [M+H]$^+$ 886.3564, found 886.3524.

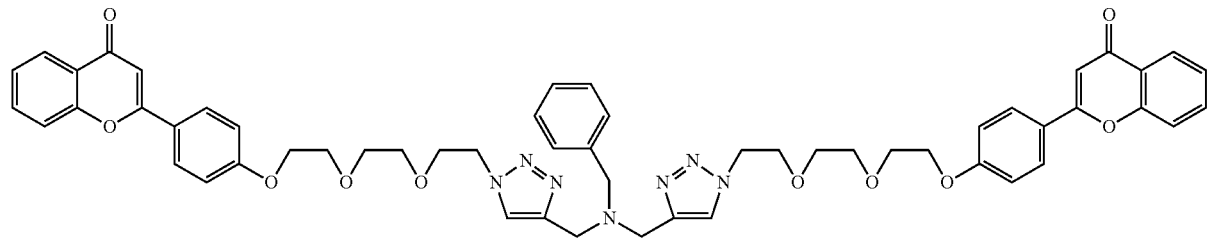 [SMILES: O=c1cc(-c2ccc(OCCOCCOCCn3cc(CN(Cc4ccccc4)Cc4cn(CCOCCOCCOc5ccc(-c6cc(=O)c7ccccc7o6)cc5)nn4)nn3)cc2)oc2ccccc12]

2,2'-(((((((4,4'-(Benzylazanediyl)bis(methylene))bis (1H-1,2,3-triazole-4,1-diyl))bis(ethane-2,1-diyl))bis (oxy))bis(ethane-2,1-diyl))bis(oxy))bis(ethane-2,1-diyl)) bis(oxy))bis(4,1-phenylene))bis(4H-chromen-4-one) (Ac15Az2)

This compound (48 mg) was obtained from Ac15 and Az2 in 49% yield according to the general procedure described above. $^1$H NMR (500 MHz, CHLOROFORM-d) δ ppm 3.60-3.90 (m, 10H), 4.10-4.18 (m, 2H), 4.53 (br. s., 2H), 6.72 (s, 1H), 6.99 (d, J=8.79 Hz, 2H), 7.17-7.33 (m, 2H), 7.33-7.43 (m, 2H), 7.50-7.56 (m, 1H), 7.64-7.70 (m, 1H), 7.72-7.89 (m, 3H), 8.20 (dd, J=7.81, 1.46 Hz, 1H); $^{13}$C NMR (101 MHz, CHLOROFORM-d) δ ppm 67.62, 69.53, 70.59, 70.72, 106.19, 115.01, 117.93, 124.19, 125.04, 125.60, 127.12, 127.94, 128.32, 133.52, 156.14, 161.50, 163.25, 178.26; LRMS (ESI) m/z 974 [M+H]$^+$; HRMS (ESI) calcd for $C_{55}H_{56}N_7O_{10}$ [M+H]$^+$ 974.4089, found 974.4064.

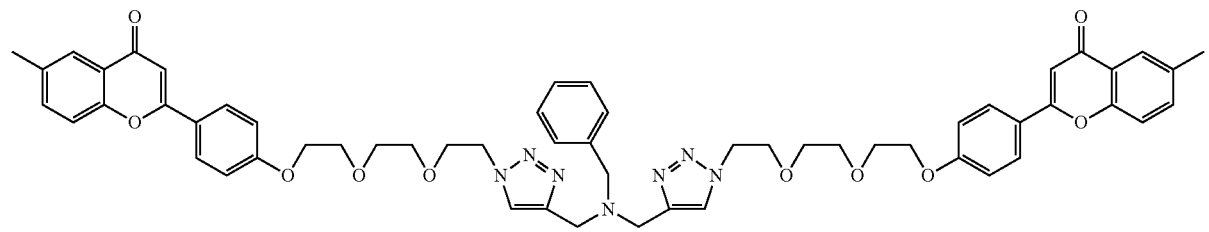

2,2'-(((((((4,4'-(Benzylazanediyl)bis(methylene))bis(1H-1,2,3-triazole-4,1-diyl))bis(ethane-2,1-diyl))bis(oxy))bis(ethane-2,1-diyl))bis(oxy))bis(ethane-2,1-diyl)) bis(oxy))bis(4,1-phenylene))bis(6-methyl-4H-chromen-4-one) (Ac15Az3)

This compound (99 mg) was obtained from Ac15 and Az3 in 99% yield according to the general procedure described above. $^1$H NMR (500 MHz, CHLOROFORM-d) δ ppm 2.41 (s, 3H), 3.59-3.70 (m, 5H), 3.73 (br. s., 1H), 3.76-3.81 (m, 2H), 3.87 (br. s., 2H), 4.10-4.12 (m, 2H), 4.51 (br. s., 2H), 6.66 (s, 1H), 6.95 (d, J=8.79 Hz, 2H), 7.14-7.23 (m, 1H), 7.23-7.31 (m, 1H), 7.31-7.47 (m, 3H), 7.70-7.82 (m, 3H), 7.95 (s, 1H); $^{13}$C NMR (101 MHz, CHLOROFORM-d) δ ppm 20.80, 67.50, 69.37, 69.43, 70.50, 70.62, 105.90, 114.87, 117.60, 123.43, 124.16, 124.83, 126.95, 127.80, 128.20, 128.84, 134.64, 134.89, 154.29, 161.33, 163.01, 178.27; LRMS (ESI) m/z 1002 [M+H]$^+$; HRMS (ESI) calcd for $C_{57}H_{60}N_7O_{10}$ [M+H]$^+$ 1002.4402, found 1002.4353.

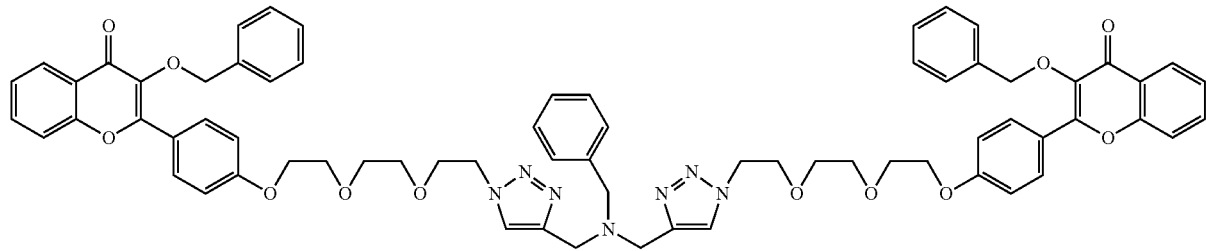 [SMILES: O=c1c(OCc2ccccc2)c(-c2ccc(OCCOCCOCCn3cc(CN(Cc4ccccc4)Cc4cn(CCOCCOCCOc5ccc(-c6oc7ccccc7c(=O)c6OCc6ccccc6)cc5)nn4)nn3)cc2)oc2ccccc12]

2,2'-(((((((4,4'-((Benzylazanediyl)bis(methylene))bis(1H-1,2,3-triazole-4,1-diyl))bis(ethane-2,1-diyl))bis(oxy))bis(ethane-2,1-diyl))bis(oxy))bis(ethane-2,1-diyl)) bis(oxy))bis(4,1-phenylene))bis(3-(benzyloxy)-4H-chromen-4-one) (Ac15Az5)

This compound (110 mg) was obtained from Ac15 and Az5 in 92% yield according to the general procedure described above. $^1$H NMR (500 MHz, CHLOROFORM-d) δ ppm 3.61-3.66 (m, 2H), 3.66-3.72 (m, 2H), 3.76 (br. s., 2H), 3.80-3.86 (m, 2H), 3.88 (t, J=5.12 Hz, 2H), 4.12-4.19 (m, 2H), 4.53 (t, J=4.88 Hz, 2H), 5.11 (s, 2H), 6.94 (d, J=9.27 Hz, 2H), 7.24-7.30 (m, 4H), 7.35-7.42 (m, 4H), 7.51 (d, J=7.81 Hz, 1H), 7.66 (ddd, J=8.54, 7.08, 1.95 Hz, 1H), 7.74 (br. s., 1H), 7.99-8.05 (m, 2H), 8.28 (dd, J=8.05, 1.71 Hz, 1H); $^{13}$C NMR (101 MHz, CHLOROFORM-d) δ ppm 50.10, 67.44, 69.47, 69.54, 70.56, 70.68, 73.83, 114.26, 117.83, 123.47, 124.11, 124.52, 125.64, 126.98, 127.99, 128.14, 128.23, 128.71, 128.88, 130.44, 133.17, 136.71, 139.23, 155.08, 156.09, 160.50, 174.85; LRMS (ESI) m/z 1186 [M+H]$^+$; HRMS (ESI) calcd for $C_{69}H_{68}N_7O_{12}$ [M+H]$^+$ 1186.4926, found 1186.4880.

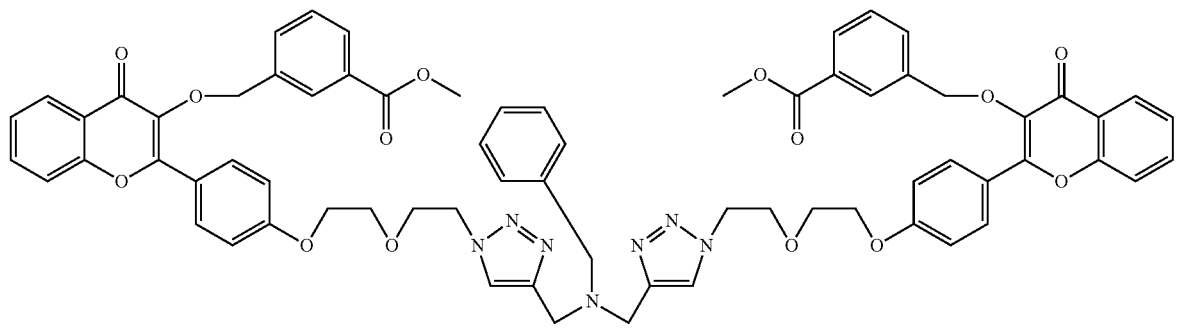 [SMILES: COC(=O)c1cccc(COc2c(-c3ccc(OCCOCCn4cc(CN(Cc5ccccc5)Cc5cn(CCOCCOc6ccc(-c7oc8ccccc8c(=O)c7OCc7cccc(C(=O)OC)c7)cc6)nn5)nn4)cc3)oc3ccccc3c2=O)c1]

Dimethyl 3,3'-(((2,2'-(((((4,4'-((benzylazanediyl)bis(methylene))bis(1H-1,2,3-triazole-4,1-diyl))bis(ethane-2,1-diyl))bis(oxy))bis(ethane-2,1-diyl))bis(oxy))bis(4,1-phenylene))bis(4-oxo-4H-chromene-3,2-diyl)bis(oxy))bis(methylene))dibenzoate (Ac15Az8)

This compound (120 mg) was obtained from Ac15 and Az8 in 98% yield according to the general procedure described above. $^1$H NMR (500 MHz, CHLOROFORM-d) δ ppm 3.74 (br. s., 2H), 3.80-3.82 (m, 2H), 3.86 (s, 3H), 3.94 (t, J=5.12 Hz, 2H), 4.10-4.15 (m, 2H), 4.54 (t, J=5.12 Hz, 2H), 5.12 (s, 2H), 6.87-6.93 (m, 2H), 7.17 (d, J=7.32 Hz, 1H), 7.24 (t, J=7.57 Hz, 1H), 7.32 (t, J=7.81 Hz, 1H), 7.35-7.42 (m, 2H), 7.49 (d, J=7.81 Hz, 1H), 7.56-7.60 (m, 1H), 7.65 (ddd, J=8.54, 7.08, 1.46 Hz, 1H), 7.75 (br. s., 1H), 7.89-7.98 (m, 4H), 8.26 (dd, J=8.05, 1.71 Hz, 1H); $^{13}$C NMR (101 MHz, CHLOROFORM-d) δ ppm 47.53, 50.11, 51.98, 57.43, 67.30, 69.55, 69.69, 73.27, 114.28, 117.88, 123.43, 124.10, 124.22, 124.63, 125.68, 126.99, 128.21, 128.25, 128.89, 129.20, 129.72, 130.07, 130.48, 133.16, 133.30, 137.14, 139.02, 144.38, 155.13, 156.31, 160.39, 166.73, 174.78; LRMS (ESI) m/z 1214 [M+H]$^+$; HRMS (ESI) calcd for $C_{69}H_{64}N_7O_{14}$ [M+H]$^+$ 1214.4511, found 1214.4476.

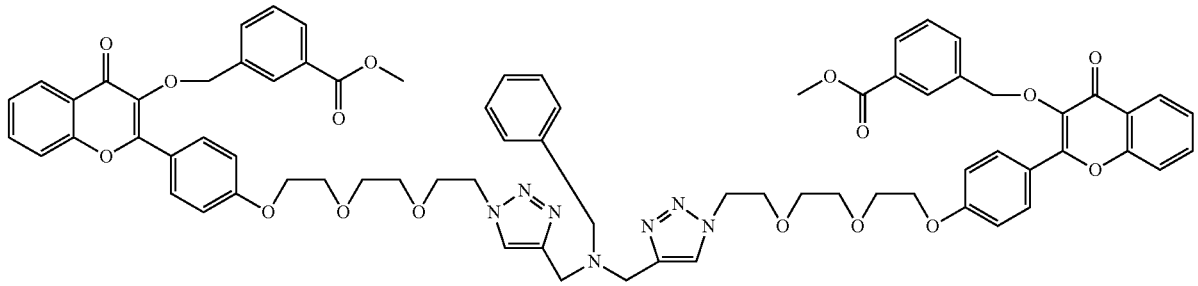 [SMILES: COC(=O)c1cccc(COc2c(-c3ccc(OCCOCCOCCn4cc(CN(Cc5ccccc5)Cc5cn(CCOCCOCCOc6ccc(-c7oc8ccccc8c(=O)c7OCc7cccc(C(=O)OC)c7)cc6)nn5)nn4)cc3)oc3ccccc3c2=O)c1]

Dimethyl 3,3'-(((2,2'-(((((((4,4'-((benzylazanediyl)bis(methylene))bis(1H-1,2,3-triazole-4,1-diyl)) bis(ethane-2,1-diyl))bis(oxy))bis(ethane-2,1-diyl))bis(oxy))bis(ethane-2,1-diyl))bis(oxy)) bis(4,1-phenylene))bis(4-oxo-4H-chromene-3,2-diyl))bis(oxy))bis(methylene))dibenzoate (Ac15Az9)

This compound (120 mg) was obtained from Ac15 and Az9 in 90% yield according to the general procedure described above. $^1$H NMR (500 MHz, CHLOROFORM-d) δ ppm 3.60-3.65 (m, 3H), 3.65-3.70 (m, 3H), 3.77 (br. s., 2H), 3.80-3.84 (m, 2H), 3.85-3.90 (m, 5H), 4.14 (t, J=4.64 Hz, 2H), 4.52 (t, J=5.12 Hz, 2H), 5.13 (s, 2H), 6.93 (d, J=8.79 Hz, 2H), 7.20-7.22 (d, J=6.83 Hz, 1H), 7.29 (t, J=7.08 Hz, 1H), 7.33 (t, J=7.81 Hz, 1H), 7.40 (t, J=7.57 Hz, 2H), 7.50 (d, J=8.79 Hz, 1H), 7.58 (d, J=7.32 Hz, 1H), 7.63-7.69 (m, 1H), 7.75 (br. s., 1H), 7.91 (d, J=7.81 Hz, 1H), 7.93-7.99 (m, 3H), 8.27 (d, J=7.81 Hz, 1H); $^{13}$C NMR (101 MHz, CHLOROFORM-d) δ ppm 50.20, 52.03, 67.49, 69.56, 69.61, 70.64, 70.75, 73.32, 114.36, 117.92, 123.38, 124.16, 124.66, 125.75, 128.29, 129.25, 129.76, 130.12, 130.51, 133.21, 133.31, 137.19, 139.07, 155.19, 156.42, 160.62, 166.80, 174.84; LRMS (ESI) m/z 1302 [M+H]$^+$; HRMS (ESI) calcd for $C_{73}H_{72}N_7O_{16}$ [M+H]$^+$ 1302.4980, found 1302.5036.

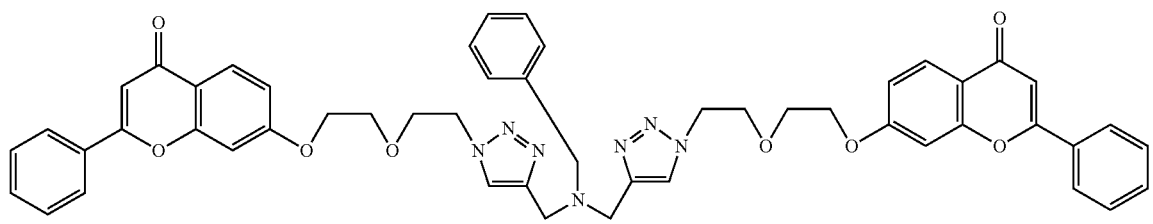 [SMILES: O=c1cc(-c2ccccc2)oc2cc(OCCOCCn3cc(CN(Cc4ccccc4)Cc4cn(CCOCCOc5ccc6c(=O)cc(-c7ccccc7)oc6c5)nn4)nn3)ccc12]

7,7'-(((((4,4'-((Benzylazanediyl)bis(methylene))bis (1H-1,2,3-triazole-4,1-diyl))bis(ethane-2,1-diyl))bis (oxy))bis(ethane-2,1-diyl))bis(oxy))bis(2-phenyl-4H-chromen-4-one) (Ac15Az11)

This compound (88 mg) was obtained from Ac15 and Az11 in 99% yield according to the general procedure described above. $^1$H NMR (500 MHz, CHLOROFORM-d) δ ppm 3.61-4.17 (m, 8H), 4.56 (br. s., 2H), 6.73 (s, 1H), 6.92 (br. s., 2H), 7.16 (br. s., 1H), 7.26 (d, J=1.46 Hz, 1H), 7.44-7.56 (m, 3H), 7.86 (d, J=7.81 Hz, 2H), 8.07 (d, J=8.30 Hz, 1H); $^{13}$C NMR (101 MHz, CHLOROFORM-d) δ ppm 67.89, 69.36, 101.25, 107.51, 114.56, 126.16, 127.10, 128.99, 131.42, 131.78, 157.83, 163.05, 177.68; LRMS (ESI) m/z 886 [M+H]$^+$; HRMS (ESI) calcd for $C_{51}H_{48}N_7O_8$ [M+H]$^+$ 886.3564, found 886.3521.

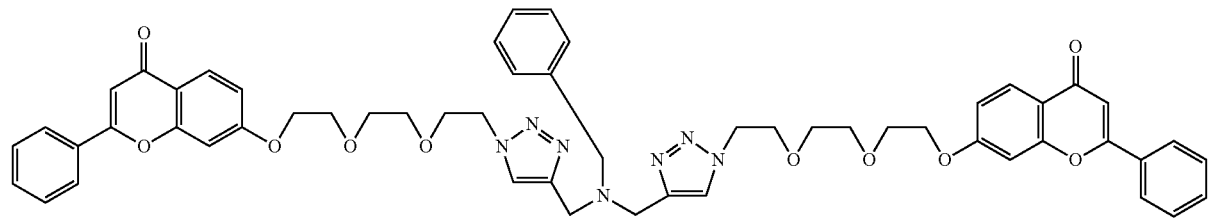 [SMILES: O=c1cc(-c2ccccc2)oc2cc(OCCOCCOCCn3cc(CN(Cc4ccccc4)Cc4cn(CCOCCOCCOc5ccc6c(=O)cc(-c7ccccc7)oc6c5)nn4)nn3)ccc12]

7,7'-(((((((4,4'-(Benzylazanediyl))bis(methylene))bis (1H-1,2,3-triazole-4, 1-diyl))bis(ethane-2,1-diyl))bis (oxy))bis(ethane-2,1-diyl))bis(oxy))bis(ethane-2,1-diyl)) bis(oxy))bis(2-phenyl-4H-chromen-4-one) (Ac15Az12)

This compound (58 mg) was obtained from Ac15 and Az12 in 60% yield according to the general procedure described above. $^1$H NMR (500 MHz, CHLOROFORM-d) δ ppm 3.59-3.65 (m, 2H), 3.65-3.71 (m, 2H), 3.77 (br. s., 2H), 3.81-3.86 (m, 2H), 3.87-3.89 (m, 2H), 4.16-4.22 (m, 2H), 4.52 (t, J=4.88 Hz, 2H), 6.74 (s, 1H), 6.91-6.99 (m, 2H), 7.19-7.22 (m, 1H), 7.28 (t, J=7.08 Hz, 1H), 7.39 (br. s., 1H), 7.46-7.55 (m, 3H), 7.77 (br. s., 1H), 7.85-7.91 (m, 2H), 8.10 (d, J=8.79 Hz, 1H); $^{13}$C NMR (101 MHz, CHLOROFORM-d) δ ppm 50.21, 68.06, 69.42, 69.52, 70.64, 70.79, 101.20, 107.53, 114.65, 117.98, 126.15, 127.05, 128.33, 128.98, 131.40, 131.83, 157.86, 163.04, 163.26, 177.74; LRMS (ESI) m/z 974 [M+H]$^+$; HRMS (ESI) calcd for $C_{55}H_{56}N_7O_{10}$ [M+H]$^+$ 974.4089, found 974.4063.

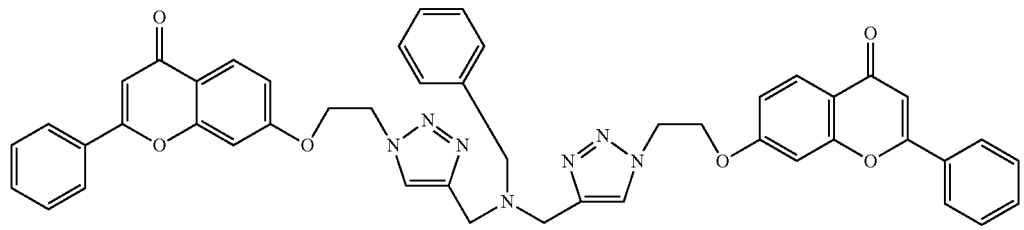 [SMILES: O=c1cc(-c2ccccc2)oc2cc(OCCn3cc(CN(Cc4ccccc4)Cc4cn(CCOc5ccc6c(=O)cc(-c7ccccc7)oc6c5)nn4)nn3)ccc12]

7,7'-(((4,4'-(Benzylazanediyl)bis(methylene))bis(1H-1,2,3-triazole-4,1-diyl))bis(ethane-2,1-diyl))bis (oxy))bis(2-phenyl-4H-chromen-4-one) (Ac15Az13)

This compound (69 mg) was obtained from Ac15 and Az13 in 87% yield according to the general procedure described above. $^1$H NMR (500 MHz, CHLOROFORM-d) δ ppm 3.75 (br. s., 2H), 4.50 (br. s., 2H), 4.83 (br. s., 2H), 6.73 (s, 1H), 6.94 (br. s., 2H), 7.31 (br. s., 1H), 7.46-7.56 (m, 3H), 7.86 (d, J=7.81 Hz, 2H), 8.10 (d, J=8.30 Hz, 1H); $^{13}$C NMR (101 MHz, CHLOROFORM-d) δ ppm 53.84, 69.47, 101.42, 107.51, 114.28, 126.14, 127.36, 128.48, 128.99, 131.49, 131.61, 157.71, 162.13, 163.14, 177.52; LRMS (ESI) m/z 798 [M+H]$^+$; HRMS (ESI) calcd for $C_{47}H_{40}N_7O_6$ [M+H]$^+$ 798.3040, found 798.3013.

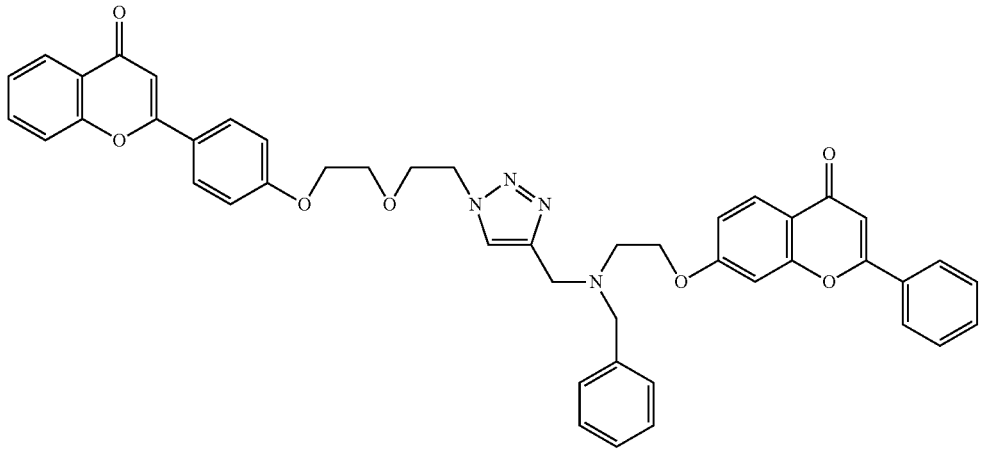 [SMILES: O=c1cc(-c2ccc(OCCOCCn3cc(CN(CCOc4ccc5c(=O)cc(-c6ccccc6)oc5c4)Cc4ccccc4)nn3)cc2)oc2ccccc12]

7-(2-(Benzyl((1-(2-(2-(4-(4-oxo-4H-chromen-2-yl)phenoxy)ethoxy)ethyl)-1H-1,2,3-triazol-4-yl)methyl)amino)ethoxy)-2-phenyl-4H-chromen-4-one (Ac16Az1)

This compound (69 mg) was obtained from Ac16 and Az1 in 90% yield according to the general procedure described above. $^1$H NMR (500 MHz, CHLOROFORM-d) δ ppm 2.98 (br. s., 2H), 3.71-3.85 (m, 4H), 3.95 (t, J=5.12 Hz, 4H), 4.06-4.12 (m, 2H), 4.14 (br. s., 2H), 4.57 (t, J=5.12 Hz, 2H), 6.67 (s, 1H), 6.71 (s, 1H), 6.83-6.95 (m, 4H), 7.20-7.25 (m, 1H), 7.29 (t, J=7.32 Hz, 2H), 7.36-7.39 (m, 3H), 7.43-7.52 (m, 4H), 7.62-7.67 (m, 1H), 7.71 (br. s., 1H), 7.75-7.81 (m, 2H), 7.82-7.87 (m, 2H), 8.06 (d, J=8.79 Hz, 1H), 8.14-8.20 (m, 1H); $^{13}$C NMR (101 MHz, CHLOROFORM-d) δ ppm 49.33, 50.21, 51.66, 58.89, 67.17, 67.42, 69.50, 69.76, 100.91, 106.18, 107.38, 114.64, 114.85, 117.76, 117.85, 123.84, 124.33, 125.03, 125.56, 126.05, 126.90, 127.20, 127.89, 128.32, 128.76, 128.92, 131.35, 131.69, 133.50, 156.05, 157.83, 161.22, 162.89, 163.00, 163.22, 177.65, 178.15; LRMS (ESI) m/z 761 [M+H]$^+$, 783 [M+Na]$^+$; HRMS (ESI) calcd for $C_{46}H_{41}N_4O_7$ [M+H]$^+$ 761.2975, found 761.2980; calcd for $C_{46}H_{40}N_4O_7Na$ [M+Na]$^+$ 783.2795, found 783.2794.

7-(2-(Benzyl((1-(2-(2-(2-(4-(4-oxo-4H-chromen-2-yl)phenoxy)ethoxy)ethoxy)ethyl)-1H-1,2,3-triazol-4-yl)methyl)amino)ethoxy)-2-phenyl-4H-chromen-4-one (Ac16Az2)

This compound (19 mg) was obtained from Ac16 and Az2 in 24% yield according to the general procedure described above. $^1$H NMR (500 MHz, CHLOROFORM-d) δ ppm 3.02 (br. s., 2H), 3.59-3.69 (m, 4H), 3.73-3.84 (m, 4H), 3.88 (t, J=5.0 Hz, 2H), 3.96 (br. s., 2H), 4.07-4.14 (m, 2H), 4.19 (br. s., 2H), 4.54 (t, J=5.12 Hz, 2H), 6.70 (s, 1H), 6.73 (s, 1H), 6.88-6.98 (m, 4H), 7.22-7.28 (m, 1H), 7.32 (t, J=7.57 Hz, 2H), 7.35-7.44 (m, 3H), 7.45-7.54 (m, 4H), 7.66 (ddd, J=8.66, 6.95, 1.46 Hz, 1H), 7.74 (br. s., 1H), 7.81 (d, J=9.25 Hz, 2H), 7.85-7.90 (m, 2H), 8.08 (d, J=8.79 Hz, 1H), 8.19 (dd, J=7.81, 1.46 Hz, 1H); $^{13}$C NMR (101 MHz, CHLOROFORM-d) δ ppm 49.28, 50.24, 51.69, 58.87, 67.22, 67.55, 69.51, 69.55, 70.56, 70.74, 100.98, 106.19, 107.44, 114.67, 114.95, 117.82, 117.89, 123.89, 124.24, 125.04, 125.61, 126.10, 126.96, 127.21, 127.92, 128.35, 128.81, 128.95, 131.37, 131.76, 133.52, 156.11, 157.89, 161.43, 162.95, 163.17, 163.25, 177.71, 178.24; LRMS (ESI) m/z 805 [M+H]$^+$, 827 [M+Na]$^+$; HRMS (ESI) calcd for $C_{48}H_{45}N_4O_8$ [M+H]$^+$ 805.3237, found 805.3260; calcd for $C_{48}H_{44}N_4O_8Na$ [M+Na]$^+$ 827.3057, found 827.3070.

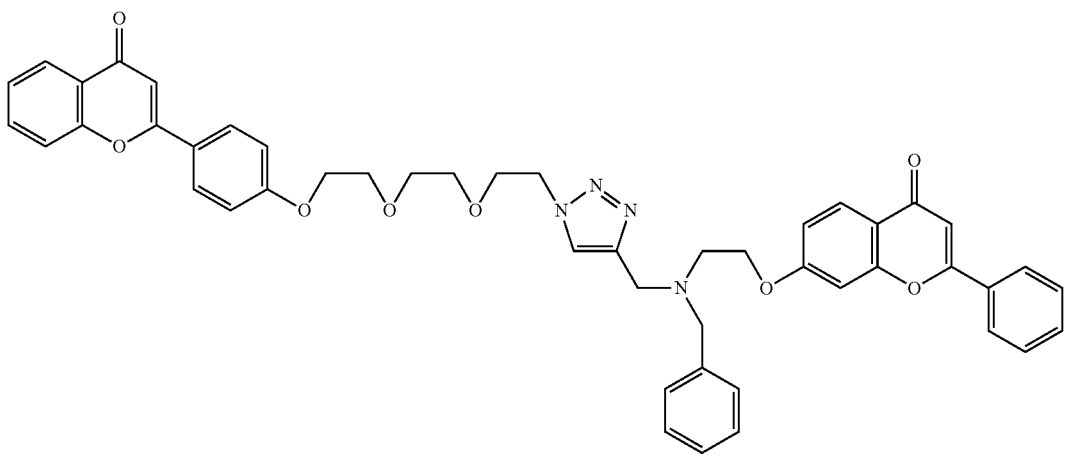 [SMILES: O=c1cc(-c2ccc(OCCOCCOCCn3cc(CN(CCOc4ccc5c(=O)cc(-c6ccccc6)oc5c4)Cc4ccccc4)nn3)cc2)oc2ccccc12]

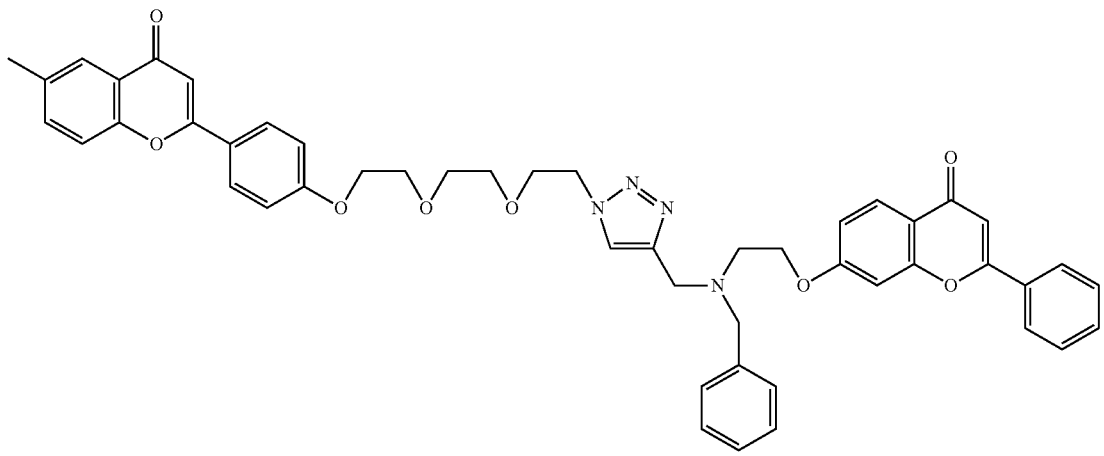 [SMILES: Cc1ccc2oc(-c3ccc(OCCOCCOCCn4cc(CN(CCOc5ccc6c(=O)cc(-c7ccccc7)oc6c5)Cc5ccccc5)nn4)cc3)cc(=O)c2c1]

7-(2-(Benzyl((1-(2-(2-(2-(4-(6-methyl-4-oxo-4H-chromen-2-yl)phenoxy)ethoxy)ethoxy)ethyl)-1H-1,2,3-triazol-4-yl)methyl)amino)ethoxy)-2-phenyl-4H-chromen-4-one (Ac16Az3)

This compound (28 mg) was obtained from Ac16 and Az3 in 34% yield according to the general procedure described above. $^1$H NMR (500 MHz, CHLOROFORM-d) δ ppm 2.38 (s, 3H), 2.94 (br. s., 2H), 3.45-3.68 (m, 6H), 3.68-3.76 (m, 3H), 3.82 (br. s., 3H), 4.05 (m, 2H), 4.11 (br. s., 2H), 4.48 (br. s., 2H), 6.62 (s, 1H), 6.67 (s, 1H), 6.81-6.92 (m, 4H), 7.16-7.21 (m, 2H), 7.26 (br. s., 2H), 7.31-7.37 (m, 2H), 7.37-7.48 (m, 5H), 7.74 (d, J=8.79 Hz, 2H), 7.78-7.83 (m, 2H), 7.91 (s, 1H), 8.02 (d, J=8.79 Hz, 1H); $^{13}$C NMR (101 MHz, CHLOROFORM-d) δ ppm 20.90, 67.58, 69.52, 69.55, 70.59, 70.76, 101.05, 106.10, 107.48, 114.66, 114.95, 117.67, 124.41, 125.01, 126.13, 127.03, 127.91, 128.44, 128.98, 131.40, 131.78, 134.75, 135.02, 154.42, 157.91, 161.37, 162.99, 163.05, 177.72, 178.39; LRMS (ESI) m/z 819 [M+H]$^+$, 841 [M+Na]$^+$; HRMS (ESI) calcd for $C_{49}H_{47}N_4O_8$ [M+H]$^+$ 819.3394, found 819.3392; calcd for $C_{49}H_{46}N_4O_8Na$ [M+Na]$^+$ 841.3213, found 841.3220.

7-(2-(Benzyl((1-(2-(2-(2-(4-(3-(benzyloxy)-4-oxo-4H-chromen-2-yl)phenoxy)ethoxy)ethoxy)ethyl)-1H-1,2,3-triazol-4-yl)methyl)amino)ethoxy)-2-phenyl-4H-chromen-4-one (Ac16Az5)

This compound (29 mg) was obtained from Ac16 and Az5 in 31% yield according to the general procedure described above. $^1$H NMR (500 MHz, CHLOROFORM-d) δ ppm 3.00 (br. s., 2H), 3.57-3.70 (m, 4H), 3.70-3.85 (m, 4H), 3.88-3.98 (m, 4H), 4.09-4.23 (m, 4H), 4.53 (t, J=4.88 Hz, 2H), 5.10 (s, 2H), 6.73 (s, 1H), 6.87-6.95 (m, 4H), 7.20-7.42 (m, 11H), 7.45-7.52 (m, 4H), 7.64 (td, J=7.81, 1.46 Hz, 1H), 7.70 (br. s., 1H), 7.86-7.59 (m, 2H), 8.00 (d, J=8.75 Hz, 2H), 8.08 (d, J=8.79 Hz, 1H), 8.25 (dd, J=8.05, 1.71 Hz, 1H); $^{13}$C NMR (101 MHz, CHLOROFORM-d) δ ppm 50.33, 67.44, 69.51, 69.57, 70.55, 70.72, 73.85, 100.98, 107.45, 114.26, 114.67, 117.83, 123.58, 124.14, 124.55, 125.70, 126.11, 126.94, 127.18, 128.02, 128.17, 128.34, 128.72, 128.79, 128.94, 130.47, 131.36, 131.77, 133.19, 136.77, 139.29, 155.10, 156.01, 157.89, 160.46, 162.95, 163.28, 174.87, 177.70; LRMS (ESI) m/z 911 [M+H]$^+$, 933 [M+Na]$^+$; HRMS (ESI) calcd for $C_{55}H_{51}N_4O_9$ [M+H]$^+$ 911.3656, found 911.3662; calcd for $C_{55}H_{50}N_4O_9Na$ [M+Na]$^+$ 933.3475, found 933.3487.

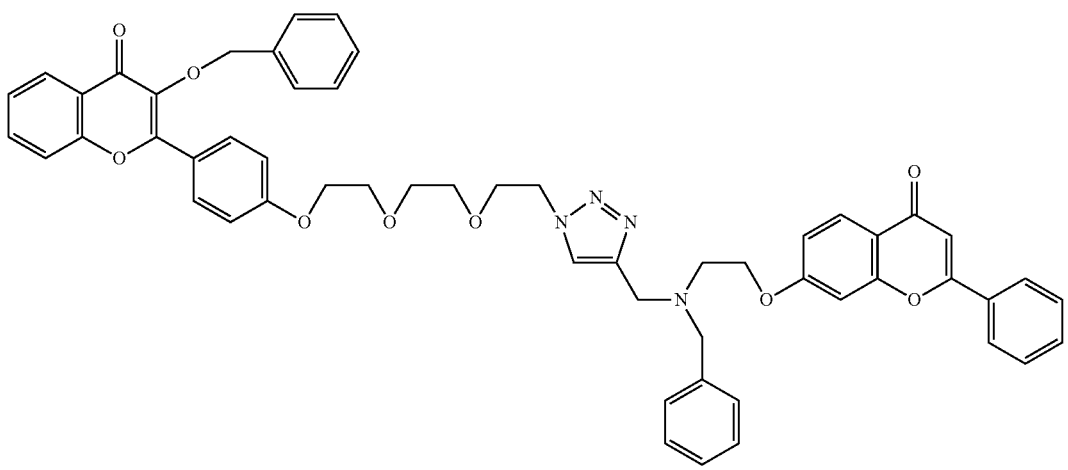 [SMILES: O=c1cc(-c2ccccc2)oc2cc(OCCN(Cc3ccccc3)Cc3cn(CCOCCOCCOc4ccc(-c5oc6ccccc6c(=O)c5OCc5ccccc5)cc4)nn3)ccc12]

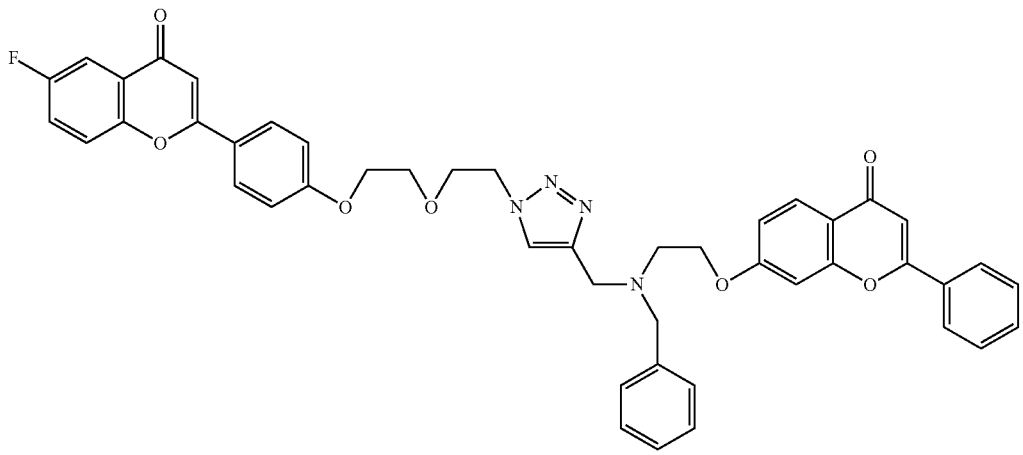 [SMILES: O=c1cc(-c2ccccc2)oc2cc(OCCN(Cc3ccccc3)Cc3cn(CCOCCOc4ccc(-c5cc(=O)c6cc(F)ccc6o5)cc4)nn3)ccc12]

7-(2-(Benzyl((1-(2-(2-(4-(6-fluoro-4-oxo-4H-chromen-2-yl)phenoxy)ethoxy)ethyl)-1H-1,2,3-triazol-4-yl)methyl)amino)ethoxy)-2-phenyl-4H-chromen-4-one (Ac16Az7)

This compound (20 mg) was obtained from Ac16 and Az7 in 25% yield according to the general procedure described above. $^1$H NMR (500 MHz, CHLOROFORM-d) δ ppm 2.99 (br. s., 2H), 3.68-3.92 (m, 4H), 3.92-4.05 (m, 4H), 4.08-4.27 (m, 4H), 4.58 (br. s., 2H), 6.66 (s, 1H), 6.72 (s, 1H), 6.85-6.96 (m, 4H), 7.21-7.44 (m, 7H), 7.45-7.53 (m, 4H), 7.77 (d, J=8.79 Hz, 2H), 7.80 (dd, J=8.05, 3.17 Hz, 1H), 7.82-7.88 (m, 2H), 8.07 (d, J=8.79 Hz, 1H); $^{13}$C NMR (101 MHz, CHLOROFORM-d) δ ppm 67.50, 69.55, 69.73, 101.00, 105.54, 107.45, 110.59 (d, J=24.24 Hz, C5), 114.62, 114.95, 119.94 (d, J=8.08 Hz, C8), 121.63 (d, J=25.25 Hz, C7), 124.09, 126.09, 127.03, 127.99, 128.97, 131.42, 131.69, 152.27, 152.28, 157.86, 159.53 (d, J=247.45 Hz, C6), 161.40, 162.97, 163.33, 177.37, 177.67; LRMS (ESI) m/z 799 [M+H]$^+$, 801 [M+Na]$^+$; HRMS (ESI) calcd for $C_{46}H_{40}N_4O_7F$ [M+H]$^+$ 799.2881, found 799.2916; calcd for $C_{46}H_{39}N_4O_7FNa$ [M+Na]$^+$ 801.2700, found 801.2738.

7-(2-(Benzyl((1-(2-(2-(2-((4-oxo-2-phenyl-4H-chromen-7-yl)oxy)ethoxy)ethoxy)ethyl)-1H-1,2,3-triazol-4-yl)methyl)amino)ethoxy)-2-phenyl-4H-chromen-4-one (Ac16Az12)

This compound (33 mg) was obtained from Ac16 and Az12 in 41% yield according to the general procedure described above. $^1$H NMR (500 MHz, CHLOROFORM-d) δ ppm 2.99 (br. s., 2H), 3.58-3.69 (m, 4H), 3.71-3.84 (m, 4H), 3.88 (t, J=5.12 Hz, 2H), 3.93 (br. s., 2H), 4.11-4.20 (m, 4H), 4.53 (t, J=5.12 Hz, 2H), 6.72 (s, 1H), 6.72 (s, 1H), 6.87-6.96 (m, 4H), 7.20-7.25 (m, 1H), 7.30 (t, J=7.57 Hz, 2H), 7.33-7.41 (m, 2H), 7.45-7.54 (m, 6H), 7.68 (br. s., 1H), 7.82-7.89 (m, 4H), 8.08 (dd, J=8.79, 2.93 Hz, 2H); $^{13}$C NMR (101 MHz, CHLOROFORM-d) δ ppm 49.28, 50.25, 51.69, 58.83, 67.24, 67.99, 69.38, 69.55, 70.57, 70.78, 100.97, 101.14, 107.45, 107.51, 114.56, 114.67, 117.83, 118.00, 123.80, 126.11, 126.96, 127.06, 127.20, 128.36, 128.78, 128.96, 131.37, 131.39, 131.77, 138.96, 157.80, 157.88, 162.95, 162.97, 163.16, 163.25, 177.65, 177.69; LRMS (ESI) m/z 805 [M+H]$^+$, 827 [M+Na]$^+$; HRMS (ESI) calcd for $C_{48}F_{145}N_4O_8$ [M+H]$^+$ 805.3237, found 805.3265; calcd for $C_{48}H_{44}N_4O_8Na$ [M+Na]$^+$ 827.3057, found 827.3078.

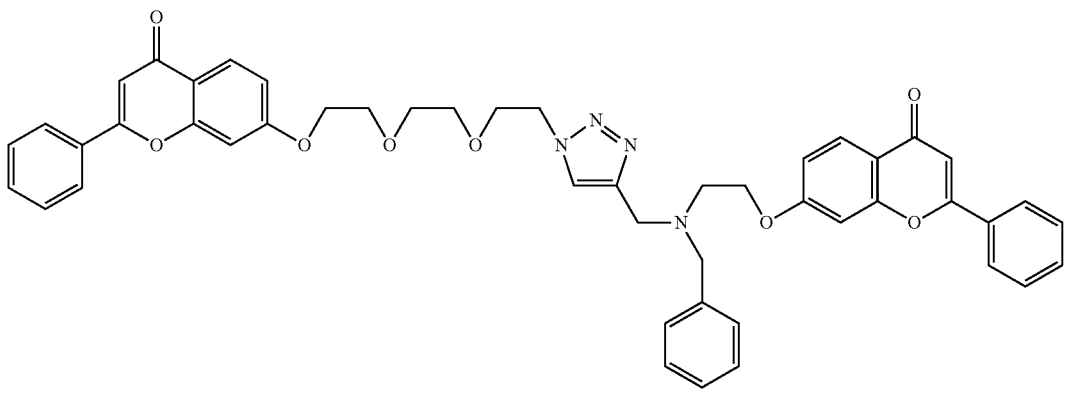 [SMILES: O=c1cc(-c2ccccc2)oc2cc(OCCOCCOCCn3cc(CN(CCOc4ccc5c(=O)cc(-c6ccccc6)oc5c4)Cc4ccccc4)nn3)ccc12]

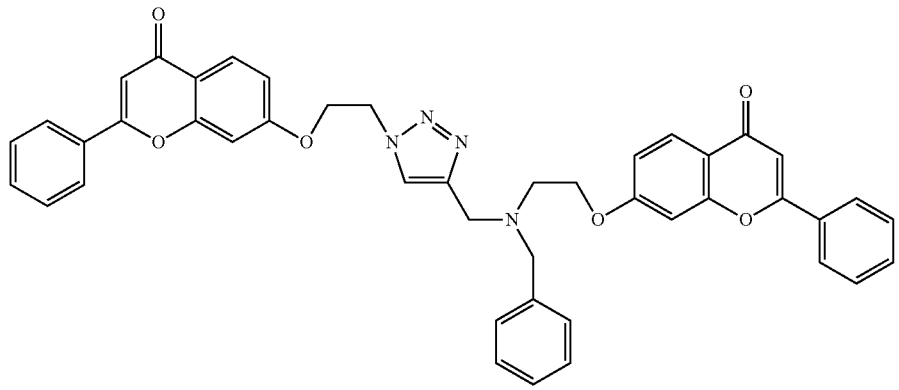 [SMILES: O=c1cc(-c2ccccc2)oc2cc(OCCN(Cc3ccccc3)Cc3cn(CCOc4ccc5c(=O)cc(-c6ccccc6)oc5c4)nn3)ccc12]

7-(2-(Benzyl((1-(2-((4-oxo-2-phenyl-4H-chromen-7-yl)oxy)ethyl)-1H-1,2,3-triazol-4-yl)methyl)amino)ethoxy)-2-phenyl-4H-chromen-4-one (Ac16Az13)

This compound (18 mg) was obtained from Ac16 and Az13 in 25% yield according to the general procedure described above. $^1$H NMR (500 MHz, CHLOROFORM-d) δ ppm 3.00 (br. s., 2H), 3.75 (br. s., 2H), 3.97 (br. s., 2H), 4.16 (br. s., 2H), 4.47 (t, J=4.88 Hz, 2H), 4.81 (t, J=4.64 Hz, 2H), 6.99 (s, 1H), 6.70 (s, 1H), 6.84-6.93 (m, 4H), 7.20-7.25 (m, 1H), 7.30 (t, J=7.32 Hz, 2H), 7.36 (br. s., 2H), 7.44-7.53 (m, 6H), 7.73 (br. s., 1H), 7.85 (dd, J=7.56, 1.71 Hz, 2H), 7.82 (dd, J=8.05, 1.22 Hz, 2H), 8.06 (dd, J=9.03, 2.20 Hz, 2H); $^{13}$C NMR (101 MHz, CHLOROFORM-d) δ ppm 49.48, 51.83, 58.83, 66.84, 67.21, 101.02, 101.34, 107.44, 107.51, 114.08, 114.59, 117.84, 118.54, 124.00, 126.09, 126.11, 126.96, 127.28, 127.39, 128.38, 128.73, 128.95, 128.98, 131.38, 131.49, 131.58, 131.76, 138.71, 157.67, 157.85, 162.08, 162.93, 163.09, 163.21, 177.44, 177.66; LRMS (ESI) m/z 717 [M+H]$^+$, 739 [M+Na]$^+$; HRMS (ESI) calcd for $C_4H_{37}N_4O_6$ [M+H]$^+$ 717.2713, found 717.2729; calcd for $C_{44}H_{36}N_4O_6Na$ [M+Na]$^+$ 739.2533, found 739.2541.

2,2',2''-(((((((4,4',4''-(nitrilotris(methylene))tris(1H-1,2,3-triazole-4,1-diyl))tris(ethane-2,1-diyl))tris(oxy))tris(ethane-2,1-diyl))tris(oxy))tris(ethane-2,1-diyl))tris(oxy))tris(benzene-4,1-diyl))tris(4H-chromen-4-one) (Ac17Az2)

This compound (21 mg) was obtained from Ac17 and Az2 in 31% yield according to the general procedure described above. $^1$H NMR (500 MHz, CHLOROFORM-d) δ ppm 3.60-3.67 (m, 2H), 3.67-3.74 (m, 2H), 3.79-3.98 (m, 6H), 4.15-4.20 (m, 2H), 4.54 (t, J=5.12 Hz, 2H), 6.72 (s, 1H), 6.98-7.03 (m, 2H), 7.35-7.42 (m, 1H), 7.50-7.55 (m, 1H), 7.63-7.70 (m, 1H), 7.82-7.88 (m, 2H), 8.06 (br. s., 1H), 8.16-8.23 (dd, J=8.0, 1.50 Hz, 1H); 13C NMR (101 MHz, CHLOROFORM-d) δ ppm 46.72, 50.32, 67.67, 69.44, 69.58, 70.70, 70.78, 106.20, 115.06, 117.94, 123.92, 124.19, 125.06, 125.63, 127.97, 133.53, 156.16, 161.58, 163.30, 178.29. LRMS (ESI) m/z 1317 [M+H]$^+$; HRMS (ESI) calcd for $C_{72}H_{73}N_{10}O_{15}$ [M+H]$^+$ 1317.5257, found 1317.5303.

Synthesis of Syn-Triazole Bridged Flavonoid Dimers (Scheme 3)

General Procedure for the Synthesis of Syn-Triazole Bridged Flavonoid Dimers Catalyzed by Ru(II) Catalyst.

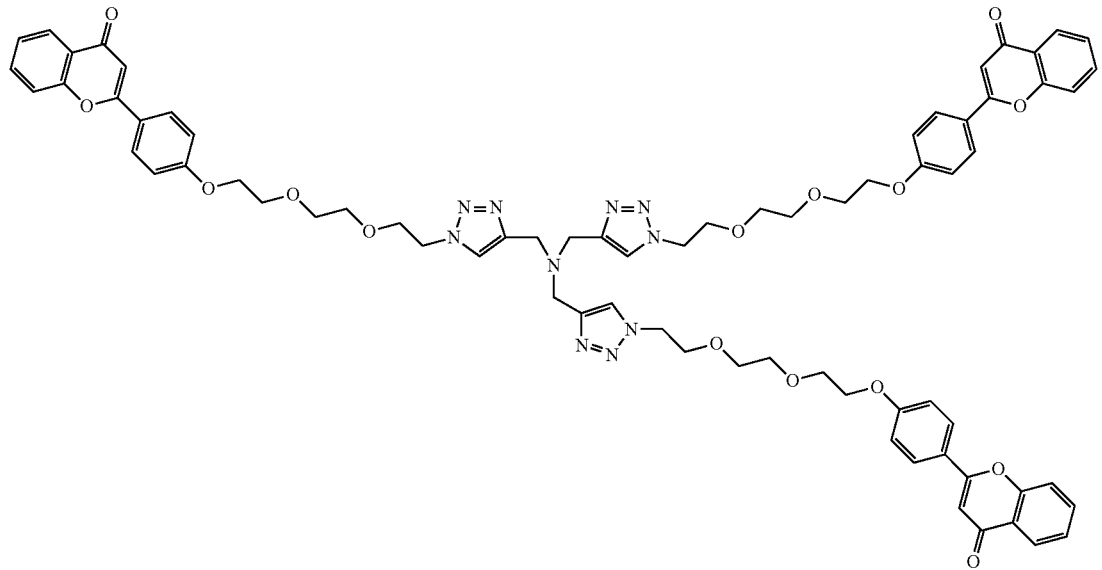 [SMILES: O=c1cc(-c2ccc(OCCOCCOCCn3cc(CN(Cc4cn(CCOCCOCCOc5ccc(-c6cc(=O)c7ccccc7o6)cc5)nn4)Cc4cn(CCOCCOCCOc5ccc(-c6cc(=O)c7ccccc7o6)cc5)nn4)nn3)cc2)oc2ccccc12]

The catalyst chloro(pentamethylcyclopentadienyl)bis(triphenylphosphine)ruthenium (II) (0.01 mmol) was added to a PhMe solution (2.0 mL) containing the azide (Az, 0.2 mmol) and the alkyne (Ac, 0.2 mmol). The reaction mixture was stirred overnight under reflux condition. Solvent was removed by evaporation, and the resulting crude mixture was purified by flash chromatography on silica gel using gradient of 10-50% of acetone with $CH_2Cl_2$ to afford the desired syn-compound.

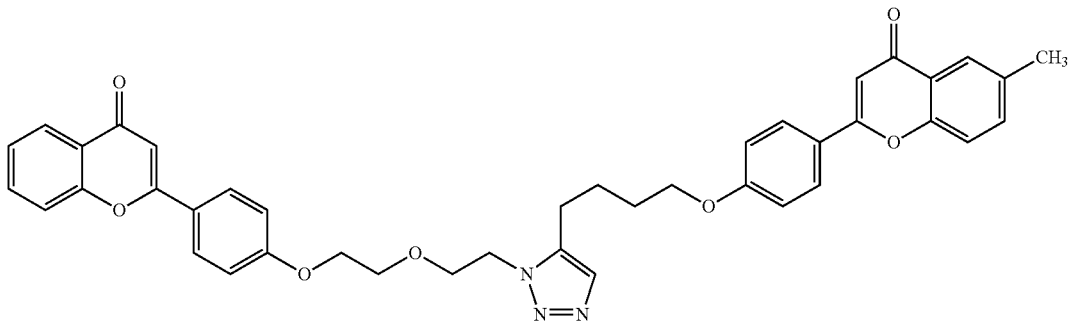

syn-Ac5Az1

6-Methyl-2-(4-(4-(1-(2-(2-(4-(4-oxo-4H-chromen-2-yl)phenoxy)ethoxy)ethyl)-1H-1,2,3-triazol-5-yl)butoxy)phenyl)-4H-chromen-4-one (syn-Ac5Az1)

This compound (100% syn, 46 mg) was obtained from Ac5 and Az1 in 67% yield according to the general procedure described above. $^1$H NMR (400 MHz, CHLOROFORM-d) δ ppm 1.74-1.88 (m, 4H), 2.45 (s, 3H), 2.76-2.79 (m, 2H), 3.73-3.80 (m, 2H), 3.88 (t, J=5.66 Hz, 2H), 4.02 (t, J=5.27 Hz, 2H), 4.04-4.09 (m, 2H), 4.48 (t, J=5.27 Hz, 2H), 6.62 (s, 1H), 6.69 (s, 1H), 6.88 (d, J=10.0 Hz, 2H), 6.95 (d, J=10.0 Hz, 2H), 7.30 (t, J=7.42 Hz, 1H), 7.36-7.42 (m, 1H), 7.43-7.50 (m, 3H), 7.61 (ddd, J=8.49, 7.12, 1.56 Hz, 1H), 7.75 (d, J=8.98 Hz, 2H), 7.81 (d, J=8.98 Hz, 2H), 7.96 (s, 1H), 8.11 (dd, J=8.00, 1.37 Hz, 1H); $^{13}$C NMR (101 MHz, CHLOROFORM-d) δ ppm 20.90, 22.96, 24.70, 28.70, 47.73, 67.45, 67.48, 69.66, 70.46, 105.96, 106.21, 114.69, 114.85, 117.70, 117.81, 123.53, 123.84, 124.13, 124.37, 124.96, 125.02, 125.58, 127.83, 127.94, 131.83, 133.53, 134.72, 134.99, 137.94, 154.36, 156.05, 161.34, 161.45, 162.93, 162.96, 178.17, 178.35. LRMS (ESI) m/z 684 [M+H]$^+$, 706 [M+Na]$^+$; HRMS (ESI) calcd for $C_{41}H_{38}N_3O_7$ [M+H]$^+$ 684.2710, found 684.2732; calcd for $C_{41}H_{37}N_3O_7Na$ [M+Na]$^+$ 706.2529, found 706.2553.

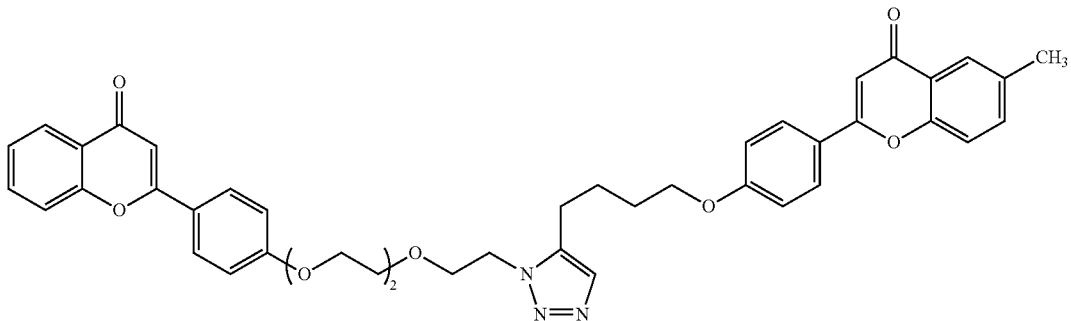

syn-Ac5Az2

6-Methyl-2-(4-(4-(1-(2-(2-(2-(4-(4-oxo-4H-chromen-2-yl)phenoxy)ethoxy) ethoxy)ethyl)-1H-1,2,3-triazol-5-yl)butoxy)phenyl)-4H-chromen-4-one (syn-Ac5Az2)

This compound (90% syn, 54 mg) was obtained from Ac5 and Az2 in 74% yield according to the general procedure described above. $^1$H NMR (500 MHz, CHLOROFORM-d) δ ppm 1.86-1.90 (m, 4H), 2.44 (s, 3H), 2.78-2.81 (m, 2H), 3.55-3.60 (m, 2H), 3.63-3.65 (m, 2H), 3.78-3.80 (m, 2H), 3.95 (t, J=5.37 Hz, 2H), 4.00-4.04 (m, 2H), 4.12-4.15 (m, 2H), 4.45 (t, J=5.37 Hz, 2H), 6.69 (s, 1H), 6.71 (s, 1H), 6.96 (d, J=10.0 Hz, 2H), 7.00 (d, J=10.0 Hz, 2H), 7.37 (t, J=7.81 Hz, 1H), 7.41 (d, J=10.0 Hz, 1H), 7.45-7.49 (m, 2H), 7.51 (d, J=10.0 Hz, 1H), 7.63-7.67 (m, 1H), 7.80-7.86 (m, 4H), 7.97 (s, 1H), 8.18 (dd, J=7.81, 1.46 Hz, 1H); $^{13}$C NMR (101 MHz, CHLOROFORM-d) δ ppm 20.92, 22.93, 24.78, 28.70, 47.73, 67.55, 67.65, 69.53, 70.13, 70.72, 70.77, 106.10, 106.26, 114.82, 115.01, 117.69, 117.91, 123.58, 123.93, 124.31, 125.06, 125.66, 127.96, 131.84, 133.55, 134.76, 135.04, 137.77, 154.44, 156.16, 161.52, 163.18, 163.17, 178.40; LRMS (ESI) m/z 728 [M+H]$^+$; HRMS (ESI) calcd for $C_{43}H_{42}N_3O_8$ [M+H]$^+$ 728.2972, found 728.2946.

Materials for Biological Studies.

Dimethyl sulfoxide (DMSO), vincristine, paclitaxel, DOX, verapamil, topotecan and phenazine methosulfate (PMS) were purchased from Sigma-Aldrich. Dulbecco's Modified Eagle's Medium (DMEM), Roswell Park Memorial Institute (RPMI) 1640 medium, trypsin-ethylenediaminetetraacetic acid (EDTA) and penicillin/streptomycin were purchased from Gibco BRL. Fetal bovine serum (FBS) was purchased from HyClone Laboratories. 3-(4,5-Dimethylthiazol-2-yl)-5-[3-(carboxymethoxy)phenyl]-2-(4-sulfophenyl)-2H-tetrazolium (MTS) was purchased from Promega. The human breast cancer cell lines MDA435/LCC6 and MDA435/LCC6MDR were kindly provided by Dr. Robert Clarke (Georgetown University, United States). The human ovarian carcinoma cell lines 2008/P and 2008/MRP1 were generous gifts from Prof. P. Borst (The Netherlands Cancer Institute, Amsterdam, Netherlands). The human embryonic kidney (HEK) 293 cell lines, HEK293/pcDNA3.1 (empty vector-transfected) and HEK293/R2 (BCRP-transfected) and MCF7-MX100 mitoxantrone selected cell lines were kindly provided by Dr. Kenneth To (The Chinese University of Hong Kong, Hong Kong). MCF7 was kindly provided by Prof. Thomas Leung (The Hong Kong Polytechnic University, Hong Kong).

Cell Culture.

MDA435/LCC6, MDA435/LCC6MDR cell lines were cultured in supplemented DMEM media with 10% heat inactivated FBS and 100 U/mL penicillin and 100 µg/mL of streptomycin. 2008/P and 2008/MRP1 cells or HEK293/pcDNA3.1 and HEK293/R2 or MCF7 and MCF7-MX100 were cultured in RPMI 1640 medium containing heat inactivated 10% FBS and 100 U/mL penicillin and 100 µg/mL of streptomycin. They were maintained at 37° C. in a humidified atmosphere with 5% $CO_2$. The cells were split constantly after a confluent monolayer has been formed. To split cells, the plate was washed briefly with phosphate-buffered saline (PBS), treated with 0.05% trypsin-EDTA and harvested by centrifugation.

Cell Proliferation Assay.

6,000 cells of LCC6 or LCC6MDR and paclitaxel were mixed with or without 1 µM modulator to a final volume of 200 µL in each well of 96-well plates. 4,000 cells of 2008/P or 2008/MRP1 and DOX or vincristine were co-incubated with or without 1 µM modulator to a final volume of 200 µL. 6,500 cells of HEK293/pcDNA3.1 or HEK293/R2 and topotecan were co-incubated with or without 1 µM modulator to a final volume of 200 µL. 7,500 cells of MCF7 or MCF7-MX100 and topotecan were co-incubated with or without 1 µM modulator to a final volume of 200 µL. The plates were then incubated for 5 days at 37° C. After 5 days, the % of survival or viability was determined by MTS according to procedures reported previously.[59,67] These results were represented as meant standard error of mean. $IC_{50}$ values were calculated from the dose-response curves of MTS assays (Prism 4.0).

Results and Discussions

Chemistry

Design.

With the success of applying bivalent approach in P-gp and MRP1 modulators as well as the appealing ease and chemoselectivity of click chemistry, we started to explore the cycloaddition reaction of azides with alkynes as the key dimerization process for construction of a triazole bridged flavonoid dimer library. With one flavonoid bearing an acetylene group and another flavonoid bearing an azido group, a triazole bridged flavonoid dimer would be easily obtained by employing Cu(I)-catalyzed azide-alkyne 1,3-dipolar cycloaddition (CuAAC). A bis-triazole bridged flavonoid dimer can be obtained by using a diacetylene compound "clicked" with two molecules of flavonoid bearing an azido group or a diazido compound "clicked" with two molecules of flavonoid bearing an acetylene group. More importantly, CuAAC was to be the crucial step affording an anti-1,2,3-triazole element for connecting flavonoid moieties. On the other hand, a ruthenium-catalyzed cycloaddition would afford the corresponding syn-1,2,3-triazole regioisomers[68,69].

Synthesis of Alkynes.

The synthesis of the required acetylene bearing flavonoids is shown in Scheme 1. Treatment of 4' or 7-hydroxyflavones (1a-e) with various haloalkynes afforded acetylene bearing flavonoids (Ac1-5, 12) in high yield. Base-catalyzed aldol condensation of aldehyde 2 with various 2-hydroxyl acetophenones afforded chalcones which was further converted to acetylenes (Ac6-10). 2-Phenylquinazolin-4(3H)-one derivative (Ac11) was obtained by treatment of 2-aminobenzamide (4) with aldehyde 2 in the present of catalytic amount of iodine. Acetylene bearing flavonoid (Ac13) was prepared in two steps: treatment of flavone 1a with bromoethanol followed by alkylation of the hydroxyl group with propargyl bromide in the presence of sodium hydride. Acetylene bearing flavonoid (Ac16) was obtained simply from 2-(benzyl(prop-2-yn-1-yl)amino)ethanol under Mitsunobu condition. Treatment of 2-(2-aminoethoxy)ethanol with propargyl bromide afforded the diacetylene (Ac14). Diacetylene Ac15 and triacetylene Ac17 are commercially available.

Synthesis of Azides.

The synthesis of the required azide bearing flavonoids is shown in Scheme 2. 4' or 7-Hydroxyflavones (1a, d-h) were conveniently converted to the corresponding azides (Az1-7, 10-13) with good yield in three steps: (1) alkylation of hydroxyl group of flavones with various hydroxyl halides such as bromoethanol, 2-(2-chloroethoxy)ethanol and 2-(2-(2-chloroethoxy)ethoxy)ethanol under basic medium; (2) mesylation of the hydroxyl flavones; (3) reaction of the mesylated flavones with excess sodium azide. All reactions proceeded smoothly to furnish the desired products. Azides Az8-9 were prepared to investigate the substituent effect on the benzyl group. Starting from compounds 5, debenzylation gave compounds 6 which was followed by alkylation with methyl 3-(bromomethyl)benzoate to furnish compound 7. Azides (Az8-9) were realized after the conversion of hydroxyl group to azido group. For the azides Az14-15 with amine-containing chain homolog, a Mitsunobu reaction of flavones 1a or 1e with 2,2'-(benzylimino)-diethanol was employed, followed by conversion of the hydroxyl group to azido group.

Fusion of Alkynes and Azides to Triazoles.

The syntheses of the flavonoid dimers were completed by a CuAAC between the azides and the alkynes as shown in Scheme 3. Treatment of acetylenes (Ac1-17) with azides (Az1-15) in the presence of catalytic amount of Cu(PPh$_3$)$_3$Br under THF refluxing temperature afforded the desired triazole bridged flavonoid dimers with anti-regiochemistry. Table 9 in FIG. 9 shows the flavonoid dimers thus synthesized. The dimeric nature of triazole bridge flavonoid dimers was evident from high-resolution mass spectrometric data. In the examples of Ac4Az1, Ac5Az5 and Ac5Az10, deprotection of the benzyl group were performed as shown in Scheme 4. In order to investigate whether the syn-isomer of triazole would give similar biological effect as the anti-isomer, ruthenium-catalyzed azide-alkyne 1,3-dipolar cycloaddition (RuAAC) was employed to prepare compound syn-Ac5Ac1 and syn-Ac5Ac2.

Biological Study

These new compounds were investigated for the P-gp-, MRP1- and BCRP-modulating potencies. Four different cell lines were employed in this study, P-gp-transfected human breast cancer cell line, LCC6MDR (IC$_{50}$=158.7±6.1 nM), displayed about 99.2-fold greater resistance to paclitaxel than the parental LCC6 cells (IC$_{50}$=1.6±0.3 nM) (Table 1 in FIGS. 1A-1P). MRP1-transfected ovarian cancer cell line, 2008/MRP1 (IC$_{50}$=419.9±17.4 nM) was about 8.4-fold more resistant to DOX than the parental 2008/P cells (IC$_{50}$=50.1±3.9 nM) (Table 1 in FIGS. 1A-1P). BCRP-transfected human embryonic kidney cell line, HEK293/R2 (IC$_{50}$=508.1±31.1 nM) was about 32.2-fold more resistant to topotecan than the wild type, HEK293/pcDNA3.1 cell line (IC$_{50}$=15.8±1.5 nM) (Table 1 in FIGS. 1A-1P). MCF7-MX100 is a mitoxantrone-selected breast cancer cell line in which the BCRP transporter protein was found to be overexpressed. MCF7-MX100 (IC$_{50}$=33.4±2.1 µM) exhibited about 104.4-fold more resistance to topotecan than the wild type MCF7 (IC$_{50}$=0.32±0.07 µM) (Table 1 in FIGS. 1A-1P). Relative Fold (RF) and % of reversion were employed as parameters for measuring the MDR reversal activity.[70,71] Verapamil (RF=3.6 in LCC6MDR), PSC388 (RF=88.2 in LCC6MDR) and cyclosporine A (RF=79.4 in LCC6MDR) are known P-gp inhibitors, whereas Ko143 (RF=21.2 in HEK293/R2 and RF=69.6 in MCF7-MX100) is a BCRP-specific modulator. Flavonoid dimer, 1d(5,7H-6Me) n=5 (RF=6.5 in 2008/MRP1) was reported previously to possess promising MRP1-modulating activity.[59] Here, all these compounds were used as positive controls in the cell proliferation assays. The triazole bridged flavonoid dimers would be considered as potent MDR chemosensitizers if they exhibit a relatively high RF values as the positive controls. The cytotoxicity and MDR reversal activity of these triazole dimers were listed in Table 1 in FIGS. 1A-1P and compared with the monomeric precursors as well. In general, they displayed varied level of toxicity towards normal fibroblasts L929 and MDR-reversal activity among the ABC transporter-overexpressed cancer cell lines.

Intrinsic Cytotoxicity of Triazole Bridged Dimers and their Monomers

In terms of intrinsic cytotoxicity, most of Ac monomers (Group A) are non-toxic to L929 cells as their IC$_{50}$ values were above 81 µM. Only Ac13 (IC$_{50}$=32.2 µM) and Ac16 (IC$_{50}$=58.2 µM) monomers showed moderate cytotoxicity towards L929. Az monomers (Group B) generally were more cytotoxic than the Ac monomers (Group A) as their IC$_{50}$ values for L929 cells were below 68 µM. When the Ac monomers were coupled with the Az monomers, the resultant triazole bridged dimers interestingly became less cytotoxic as compared to the Az monomers. Az1-2 triazole dimers (Group C), Ac5 triazole dimers (Group D), Ac12 triazole dimers (Group F), Ac13 triazole dimers (Group H), Ac15 triazole dimers (Group J) and Ac16 triazole dimers (Group K) were generally non-cytotoxic towards normal cells L929 because their IC$_{50}$ values were at least above 50 µM. From Groups C, D, F, H, J and K, only Ac4Az1, Ac11Az2, Ac5Az5OH, Ac5Az10OH, Ac13Az2 and Ac13Az12 displayed remarkable killing activity towards L929 cells as their IC$_{50}$ values were below 12.1 µM. Of 69 triazole dimers tested, 63 dimers generally exhibited no inherent cytotoxicity towards L929 cells (IC$_{50}$>50 µM), suggesting that these triazole dimers are potential MDR reversal candidates because of their low toxicity.

P-gp-Modulating Activity of the Alkyne-, Azide and Triazole-Containing Flavonoids In order to determine whether anticancer drug resistance reversal activity of these triazole dimers is due solely to the dimeric nature, their MDR reversal activities were compared with those of the corresponding monomeric precursors at doubled concentration (2.0 µM). Most Ac monomers (Group A) showed no Pgp-modulating activity as all RF values were close to or below the 1.0 except for Ac4 monomer. Az monomers (Group B) generally showed higher P-gp-modulating activity than Ac monomers (Group A), suggesting that Az monomers may bind to P-gp better than the Ac monomers (Group A). The Az monomers including Az5, Az9 and Az10 at 2.0 µM gave about 20.5% to 24.2% of reversion of sensitivity in LCC6MDR cells. Nevertheless, their reversal potencies were still weaker than the triazole dimers as shown below.

Among the different groups of triazole dimers, Ac5 triazole dimers (Group D) were the most potent group in chemo-sensitizing Pgp-overexpressed LCC6MDR cell line towards paclitaxel. Of the 18 triazole dimers tested, 9 compounds at 1.0 µM can reduce the IC$_{50}$ of paclitaxel of LCC6MDR from 158.7 nM to below 3.0 nM. Ac5Az4, Ac5Az5, Ac5Az7, Ac5Az8 and Ac5Az9 caused at least 94.1% of reversion of paclitaxel sensitivity in LCC6MDR cell line. Ac5Az1, Ac5Az3, Ac5Az11 and Ac5Az15 achieved about 55.2% to 69.6% of reversion. The group containing Ac12 triazole dimers (Group F) was the second most potent group in modulating P-gp-mediated drug resistance. Of the 11 triazole dimers investigated, 5 compounds showed promising P-gp-reversal activity. Ac12Az5 and Ac12Az9 at 1.0 µM can result in 80.0% and 88.9% of reversion of sensitivity in LCC6MDR resistant cell line, respectively. Ac12Az3, Ac12Az8 and Ac12Az10 resulted in about 53.3% to 72.7% of reversion. Az1-2 triazole dimers (Group C) were the third potent group because only 2 out of 12 dimers gave modest P-gp-modulating activity. Ac3Az1 and Ac7Az1 achieved 64.0% and 55.2% of reversion of sensitivity of LCC6MDR cells, respectively. Ac13 triazole dimers (Group H) were relatively poor P-gp-inhibitors because only 2 compounds, Ac13Az9 and Ac13Az10, showed modest P-gp-modulating activity. They resulted in about 59.3% and 50.0% of reversion, respectively. Ac16 triazole dimers (Group K) were also weak in chemo-sensitizing Pgp-overexpressed LCC6MDR towards paclitaxel as all of them exhibited below 39.0% of reversion. Ac15 triazole dimers (Group J) were the poorest P-gp inhibitors as all of them gave below 17.6% of reversion. Even at 0.5 µM lower concentration tested, Ac5 triazole dimers (Group D) were still the most potent group of P-gp inhibitor. A total of 6 compounds in Group D reversed $IC_{50}$ of paclitaxel of LCC6MDR from 158.7 nM to below 10.0 nM. From the above data, it is clear that the Ac5 structure is the most critical components for modulating P-gp transporter.

In order to demonstrate that the formation of dimer is necessary for P-gp-modulation, we compared the activity of the dimer Ac12-Az9 at 1.0 µM with a mixture of their respective monomer precursors Ac12 and Az9, each at 1.0 µM. The dimer Ac12Az9 is highly potent at 1.0 µM, with RF=88.2 and 88.9% reversion (Table 1 in FIGS. 1A-1P, Group F). In contrast, the mixture of their respective monomer precursors Ac12 and Az9 has a very weak P-gp-modulating activity (RF=8.8 and 8.9% reversion) (Table 1 in FIGS. 1A-1P, Group G). Same is true for Ac12Az10 in Group G (compared to monomers Ac12 and Az10) or Ac13Az9 in Group I (compared to monomers Ac13 and Az10) or Ac13Az10 in Group I (compared to monomers Ac13 and Az10). These results clearly indicate that bivalency approach is crucial for P-gp modulation.

MRP1-Modulating Activity of the Alkyne-, Azide and Triazole-Containing Flavonoids Similar to P-gp modulating activity, all Ac monomers (Group A) and Az monomers (Group B) displayed no or low MRP1-modulating activity even at doubled concentration (2.0 µM). On the other hand, the triazole dimers resulted in a very promising MRP1-inhibitory potency as compared to the monomers alone. Among the six groups of triazole dimers, Ac16 triazole dimers (Group K) were the most potent group of MRP1 chemosensitizers. Of the 7 compounds tested at 1.0 µM, 6 compounds exhibited significant MRP1-inhibitory potency except for Ac16Az13. Dimers Ac16Az1, Ac16Az2, Ac16Az3, Ac16Az7 and Ac16Az12 gave at least 204.5% of reversion of sensitivity of 2008/MRP1 towards DOX. They dramatically reduced the $IC_{50}$ of DOX of 2008/MRP1 from 419.9 nM to or below 25 nM. Ac16Az5, moderate MRP1-inhibitor, gave about 77.8% of reversion. Ac12 triazole dimers (Group F) were the second most potent group of MRP1 chemosensitizers. Of the 11 dimers tested at 1.0 µM concentration, 10 compounds exhibited significant MRP1-inhibitory potency except for Ac12Az10. Dimers Ac12Az1 to Ac12z4, Ac12Az7, Ac12Az11 and Ac12Az12 caused remarkably 80.4% to 104.2% of reversion of sensitivity of 2008/MRP1 towards DOX. They dramatically reduced the $IC_{50}$ of DOX of 2008/MRP1 from 412.8 nM to or below 62.3 nM. Dimers Ac12Az5, Ac12Az8 and Ac12Az9 gave modest MRP1-mediated resistance reversal potency and achieved about 51.8% to 58.3% of reversion. The Az1-2 triazole dimers (Group C) belonged to the third most active group of MRP1 inhibitors. Of the 12 dimers investigated, 6 compounds caused a pronounced re-sensitization of 2008/MRP1 towards DOX. Dimers Ac1Az1, Ac2Az1, Ac3Az1 and Ac4 (5OH)Az1 achieved at least 92.3% of reversion at 1.0 µM. Dimers Ac8Az1 and Ac10Az1 showed moderate reversal potency and caused about 52.5% and 54.8% of reversion, respectively. The Ac5 triazole dimers (Group D) were the fourth promising group in re-sensitizing the MRP1-overexpressed 2008/MRP1 towards DOX. A total of 6 compounds gave significant MRP1-inhibitory activity. Dimers Ac5Az4, Ac5Az7 and Ac5Az15 caused at least 95.1% of reversion at 1.0 µM. The modest MRP1 inhibitors including Ac5Az2, Ac5Az3 and Ac5Az9 with at least 53.9% of reversion was noted. Of the nine Ac15 triazole dimers (Group J), only 3 compounds gave remarkable chemosensitization effect: Ac15Az1, Ac15Az2 and Ac15Az3 notably caused at least 98.6% of reversion.

The Ac13 triazole dimers (Group H) appeared to be the poorest group of MRP1-inhibitor. Only 1 compound of 11 dimers gave modest MRP1-modulating activity: Ac13Az8 in Group H caused about 55.9% of reversion. The above data demonstrates that coupling Ac16 monomer with more diverse Az monomers may be a reasonable direction for identifying more potent MRP1 chemosensitizers. Combining 1.0 µM of Ac5 monomer with 1.0 µM of Az4 or Az7 monomers (Group E) and Ac12 monomer with Az2, Az3, Az4 or Az7 monomers (Group G) showed about 6.7- to 10.4-fold poorer MRP1-mediated resistance reversal potency as compared to their respective dimer counterparts. These combined monomers just gave about 10% of reversion. Once again, the bivalent nature of the triazole dimers is a necessary and efficient design for increasing their affinity to inhibit the function of both P-gp and MRP1 transporters.

Other than DOX resistance reversal potency, the effect of all triazole dimers on re-sensitization of 2008/MRP1 towards another anticancer drug, vincristine, were also studied. Here, 2008/MRP1 displayed only about 2.4-fold more resistance to vincristine than the parental wild type 2008/P. Nevertheless, many of the triazole dimers showed very promising MRP1-mediated vincristine resistance reversal potency and remarkably caused over 100% of reversion of sensitivity of 2008/MRP1 towards vincristine. At 1.0 µM concentration of most triazole dimers, the 2008/MRP1 became several-fold more sensitive to the vincristine than the wild type 2008/P.

The mechanism of that hypersensitization with the triazole dimers has not yet been elucidated. It is possible that there may be a synergy resulting from the MRP1-inhibition and an unknown cytotoxic effect of triazole dimers together with the vincristine. Majority of the triazole dimers alone showed no inherent cytotoxicity towards 2008/P and 2008/MRP1 cells. For the Ac12 triazole dimers (Group F), 5 (Ac12Az1 to Ac12Az4 and Ac12Az7) out of 11 dimers dramatically reduced the $IC_{50}$ of vincristine of 2008/MRP1 from 123.2 nM to below 10.0 nM and with RF values ranging from 14.0 to 24.6. Of the 18 Ac5 triazole dimers (Group D) tested, 2 compounds (Ac5Az4 and Ac5Az15) showed remarkable vincristine resistance reversal potency and caused the $IC_{50}$ of vincristine of 2008/MRP1 below 10.0 nM. No potent vincristine resistance reversal agent was found in Group H and Group J as all of them gave $IC_{50}$ of vincristine of 2008/MRP1 above 13.0 nM. Combining of 1.0 µM of Ac12 with 1.0 µM of Az2 or Az3 or Az4 monomers (Group G) showed 15.8- to 20.5-fold weaker vincristine resistance reversal potency as compared to their respective triazole dimers, possibly suggesting that bivalent nature of triazole dimers is not only essential for inhibition of MRP1 transporter, but also for the unknown synergistic cancer killing effect with vincristine. Importantly, that pronounced hypersensitivity towards vincristine induced by our triazole dimers may provide an opportunity for use in treating MDR tumors.

BCRP-Modulating Activity of the Alkyne-, Azide and Triazole-Containing Flavonoids In contrast to their P-gp and MRP1-modulating activities, Ac monomers (Group A) and Az monomers (Group B) unexpectedly displayed remarkable BCRP-modulating activity. At 2.0 µM concentration, Ac4 monomer from Group A achieved about 42.1% of reversion of sensitivity in HEK293/R2 towards topotecan. No such high level of reversal activity of Ac4 monomer was observed in LCC6MDR or 2008/MRP1, respectively. Of the 12 Az monomers (Group B) investigated, 5 of them have potent BCRP modulating activity. Az9 monomer at 2.0 μM gave a 100% of reversion which is as potent as some of the dimers (see below). Az5, Az6, Az8 and Az10 monomers gave modest BCRP modulating activity with 52.7% to 75.6% of reversion at 2.0 μM.

Among different groups of triazole dimers, Ac12 triazole dimers (Group F) were the most potent group in re-sensitizing BCRP-overexpressed HEK293/R2 cell line towards topotecan. Of the 11 triazole dimers, all of them displayed significant BCRP-modulating activity. Dimers Ac12Az5 and Ac12Az8 to Ac12Az12 caused about 80.6% to 122.5% of reversion and with $IC_{50}$ of topotecan of HEK293/R2 below 20.0 nM. Dimers Ac12Az1 to Ac12Az4 and Ac12Az5 achieved about 61.2% to 77.8% of reversion. The Ac15 triazole dimers (Group J) were the second most active group of BCRP inhibitors in which 7 out of 9 dimers showed remarkable BCRP-chemosensitization effect. Dimers Ac15Az1, Ac15Az3, Ac15Az5, Ac15Az8 and Ac15Az9 achieved about 87.3% to 110.5% of reversion at 1.0 μM. Dimers Ac15Az11 and Ac15Az12 were moderate reversal agents and gave about 77.5% and 79.4% of reversion, respectively.

The Ac13 triazole dimers (Group H) were the third most potent group of BCRP inhibitors. A total of 5 compounds with pronounced BCRP-inhibitory potency were found. Dimers Ac13Az5, Ac13Az8 to Ac13Az10 at 1.0 μM caused at least 85.9% of reversion of sensitivity of HEK293/R2 towards topotecan. Dimers Ac13Az11 and Ac13Az12 were modest BCRP inhibitors and gave about 56.4% and 68.1% of reversion, respectively. The Ac5 triazole dimers (Group D) were the less potent in reversing BCRP-mediated topotecan resistance. Of the 18 triazole dimers, 7 compounds were found to exhibit promising BCRP-modulating activity. Dimer Ac5Az12 achieved about 80.2% of reversion. Other modest reversal agents including Ac5Az4, Ac5Az5 and Ac5Az8 to Ac5Az10 and Ac5Az11 with at least 54.9% of reversion was noted.

The Az1-2 triazole dimers (Group C) were also weak in chemo-sensitizing HEK293/R2 towards topotecan as 5 out of 12 dimers gave modest BCRP inhibitory potency. Dimers Ac1Az1, Ac3Az1, Ac4(5OH)Az1, Ac10Az1 and Ac11Az1 caused about 50.5% to 74.2% of reversion. The Ac16 triazole dimers (Group K) were the poorest group of BCRP inhibitors as all of them gave below 40.0% of reversion. Generally, Az8 and Az9 monomers appeared to be the crucial components for making active BCRP inhibitor as coupling Ac12, Ac13 or Ac15 monomers with them resulted in remarkably potent BCRP-modulating activity with over 100% reversion.

Combining 1.0 μM of Ac5 monomer with 1.0 μM of Az5 or Az8 monomers (Group E), Ac12 monomer with Az8, Az9 or Az10 monomers (Group G) and Ac13 monomers with Az8, Az9 or Az10 monomers (Group I) showed promising BCRP-modulating activity with at least 35.1% of reversion. Ac12 or Ac13 monomers with Az9 monomer even gave 81.4% and 87.8% of reversion, respectively. Such high level of reversal activity of those combined monomers might result from their potent Az monomers Az5, Az8, Az9 and Az10. Nevertheless, those combined monomers were still about 1.3- to 2.8-fold weaker than their dimer counterparts in reversing topotecan resistance in HEK293/R2 cell line. Unlike the P-gp and MRP1 chemosensitizers, these results demonstrated that the bivalency approach is sufficient but not required for BCRP modulation.

Mitoxantrone selected cell line MCF7-MX100, which overexpressed BCRP, was also employed to study the BCRP-modulating activities of the triazole flavonoid dimers. Ac4 monomer and some Az monomers (Az8, Az9 and Az10) gave certain level of BCRP-modulating activity with about 17.8% to 45.7% of reversion. For Az1-2 monomers (Group C), only 1 out of 12 dimers exhibited modest BCRP-modulating activity. Ac3Az1 achieved about 53.3% reversion of sensitivity in MCF7-MX100 towards topotecan. For the Ac5 triazole dimers (Group D), Ac5Az10 exhibited potent BCRP modulating activity and achieved about 80.0% of reversion of sensitivity of MCF7-MX100 towards topotecan. Dimers Ac5Az8 and Ac5Az9 were moderate BCRP inhibitors and gave about 64.0% of reversion.

For the Ac12 (Group F), Ac13 (Group H) and Ac15 (Group J) triazole dimers, only Ac12Az8 to Ac12Az10, Ac13Az8 to Ac13Az10, Ac15Az8 and Ac15Az9 were screened with BCRP-mediated resistance reversal potency using MCF7-MX100 cell line. All of these triazole dimers exhibited significant BCRP inhibitory potency in HEK293/R2 cell line. Dimers Ac12Az8, Ac12Az9, Ac13Az8 and Ac13Az9 achieved about 80.0% of reversion, whereas Ac12Az10, Ac13Az10, Ac15Az8 and Ac15Az9 caused at least 53.3% of reversion. For the Ac16 triazole dimers (Group K), Ac16Az1 gave significant BCRP-modulating activity with 80.0% of reversion. The moderate BCRP inhibitors, A16Az2, Ac16Az3, Ac16Az5, Ac16Az7 and Ac16Az12 caused about 53.3% to 64.0% of reversion. For the combined monomers (Groups E, G and I), Ac5 or Ac12 or Ac13 monomers with Az9 monomer displayed significant BCRP-mediated resistance reversal potency with 64.0% of reversion.

Their BCRP reversal activity was nearly as strong as their respective dimers. Such high level of reversal potency was mainly resulted from the potent Az9 monomer. For other combined monomers, they also exhibited about 2.2- to 4.0-fold lower BCRP-modulating activity as compared to their dimer counterparts except for Ac5 monomer with Az8 monomer which displayed about 7.4-fold lower chemosensitization effect than Ac5Az8.

Overall, exploiting bivalency was found to be useful though not critical in designing effective BCRP inhibitor. However, we cannot exclude the possibility that monovalent azide especially Az9 is also a good candidate to reverse the BCRP-mediated drug resistance. The mechanisms for re-sensitization of HEK293/R2 and MCF7-MX100 towards topotecan by bivalent triazole and monovalent azide have not been studied. However, it is likely that the triazole dimers inhibit the transport activity of BCRP transporter in a manner similar to that observed in the modulation of P-gp and MRP1 transporters by the synthetic flavonoid dimers previously studied.[57-59]

The possible reason responsible for the difference in MDR reversal activity of monomeric azides (e.g. Az9) among P-gp, MRP1 and BCRP transporters may be due to the structural difference of P-gp and MRP1 with respect to the BCRP transporters. P-gp and MRP1 are composed of two hydrophobic membrane domains (TMDs) and two hydrophilic nucleotide binding domains (NBDs). They are arranged in two repeated halves with 12 and 17 TM α-helices, respectively, forming a funnel facing the outside of the cell membrane.[3-6] In contrast, BCRP is a half ABC transporter with one NBD followed by one TMD.[9,10] It is suggested that BCRP requires homodimerization to exert its activity. A homotetrameric configuration of BCRP has also been proposed.[10,72] The substrate specificity of BCRP is overlapping with, but distinct from that of P-gp and MRP1.[9,]

TM6 and TM12 of P-gp are reported to be involved in drug binding.[74] Interestingly, arginine at position 482 of BCRP which is located within TM3 near the cytosolic membrane interface has been demonstrated to be important in substrate binding and transport activity.[75] Therefore, it is possible that an alternative substrate binding is solely applicable to BCRP but not for P-gp and MRP1 transporters. Whether monomeric azide binds to the alternative substrate recognition site of BCRP or inhibits the BCRP dimerization process remains to be investigated.

Effect of Anti or Syn Orientation of Triazole Dimers on MDR Reversal Activity

Interestingly, both the anti-regioisomers Ac5Az1 (RF=69.0) and Ac5Az2 (RF=48.1) showed higher P-gp-modulating activity than the syn-Ac5Az1 (RF=30.5) and syn-Ac5Az2 (RF=3.0) (Table 1 in FIGS. 1A-1P). These results suggested that the orientation of the triazole dimers is important in controlling binding affinity of the triazole dimers toward P-gp. Syn-Ac5Az2 showed poorer MRP1 inhibitory activity than the anti-isomer Ac5Az2. However, similar MRP1-reversal potency was noted in both the anti-isomer Ac5Az1 and syn-Ac5Az1. Thus, the importance of orientation of the triazole dimers on MRP1-modulating activity may be compound-dependent. On the other hand, the orientation of the triazole dimers appears to have no effect on controlling the BCRP-modulating activity as the RF values were very similar for the anti-isomer Ac5Az1 (RF=10.6) and syn-Ac5Az1 (RF=11.6). Similarly, the anti-isomer Ac5Az2 (RF=13.5) and syn-Ac5Az2 (RF=9.3) (Table 1) have similar potencies.

Selectivity of the Alkyne-, Azide and Triazole-Containing Flavonoids

Of the 69 triazole dimers and 21 monomers tested, they exhibited different potency against P-gp-, BCRP- and MRP1-mediated drug resistance. Generally, the triazole dimers library can be divided into mono-selective, dual-selective and multi-selective ABC transporter modulators. Table 2 in summarizes the selectivity of different active triazole dimers and some monomeric azides for the ABC transporters. Of the 56 active triazole compounds found, 2 compounds (Ac7Az1 and Ac5Az1) show mono-Pgp selectivity; 10 compounds (Ac2Az1, Ac8Az1, Ac5Az2, Ac15Az2, Ac16Az1, Ac16Az2, Ac16Az3, Ac16Az5, Ac16Az7 and Ac16Az12) show mono-MRP1 selectivity and 16 compounds (Az5, Az6, Az8, Az9, Az10, Ac11Az1, Ac5Az10, Ac5Az12, Ac13Az5, Ac13Az11, Ac13Az12, Ac15Az5, Ac15Az8, Ac15Az9, Ac5Az11 and Ac15Az12) show mono-BCRP selectivity. A total of 3 compounds (Ac5Az3, Ac5Az7 and Ac5Az15) have P-gp and MRP1-dual-selectivity; 6 compounds (Ac5Az5, Ac5Az8, Ac5Az11, Ac12Az10, Ac13Az9 and Ac13Az10) have Pgp- and BCRP-dual selectivity and 12 compounds (Ac1Az1, Ac4(5OH) Az1, Ac10Az1, Ac12Az1, Ac12Az2, Ac12Az4, Ac12Az7, Ac12Az11, Ac12Az12, Ac13Az8, Ac15Az1 and Ac15Az3) have MRP1- and BCRP-dual selectivity. Finally, a total of 7 compounds (Ac3Az1, Ac5Az4, Ac5Az9, Ac12Az3, Ac12Az5, Ac12Az8, and Ac12Az9) show multi-selectivity towards P-gp, MRP1 and BCRP transporters. About 57% and 32% of the triazole dimers were highly selective for the MRP1 and P-gp transporters, respectively. Overall, 73% of the active triazole dimers efficiently inhibited BCRP-mediated drug resistance. From the study, it seems that the simple monomeric azides could be a highly BCRP-selective inhibitor. Some of the bivalent triazoles showed multi-selectivity for ABC transporters. It is possible that differently selective (mono-, dual- and multi-) inhibitors of drug transporters could be potentially useful tools for investigation of complicated drug-resistance phenotypes and eventually, for treatment of drug-resistant cancers caused by overexpression of ABC transporters.

Effective Concentration ($EC_{50}$) and Therapeutic Index of the Alkene-, Azide and Triazole-Containing Flavonoids A good MDR chemosensitizer should possess high potency and non-cytotoxicity to normal cells. Here, we have determined $EC_{50}$ and therapeutic index (a ratio of cytotoxicity against L929 or Raw264.7 cells to the $EC_{50}$ of the modulators) of these dimers and monomers. Table 3 in FIGS. 3A-3D summarizes the $EC_{50}$ and therapeutic index of the active triazole compounds. Verapamil, PSC833, cyclosporine A, 1d(5,7H-6Me)n=5 and Ko143 have been included as positive P-gp, MRP1 and BCRP controls for comparison. In general, the active bivalent triazoles are safe MDR chemosensitizer because of their high value of therapeutic index. The $EC_{50}$ of active bivalent triazole for reversing paclitaxel resistance of LCC6MDR ranged from 141 to 340 nM and their therapeutic index were at least above 263.2, indicating that they are highly selective to re-sensitize LCC6MDR cells towards paclitaxel at the nanomolar range and caused no cytotoxicity to L929 cells. Overall, they possessed more selective P-gp modulating activity than the first generation of P-gp inhibitor verapamil, but displayed weaker selectivity as compared to cyclosporine A and PSC833. The $EC_{50}$ values of bivalent triazoles for lowering DOX and vincristine resistance of 2008/MRP1 ranged from 78 to 590 nM and 82 to 550 nM, respectively. The $EC_{50}$ values of the most active bivalent triazoles were comparable to the previous synthesized active flavonoid dimer, 1d(5, 7H-6Me)n=5. At such nanomolar concentration, they selectively reversed the DOX and vincristine resistance of 2008/MRP1 without inducing cytotoxicity to the L929 cells as indicated by their high therapeutic index.

Finally, most of the active triazole dimers were found to be more selective for the BCRP transporter than the P-gp and MRP1 transporters as their $EC_{50}$ values for reversing topotecan resistance of HEK293/R2 and MCF7-MX100 were in the low nM range. In HEK293/R2 and MCF7-MX100, a total of 11 compounds (Ac3Az1, Ac5Az8, Ac5Az9, Ac5Az10, Ac12Az8, Ac12Az9, Ac13Az8, Ac13Az9, Ac15Az8, Ac15Az9 and Az9) were as potent as the BCRP-inhibitor Ko143 because they possessed $EC_{50}$ values at or below 10 nM. Overall, their therapeutic indices were higher than that of Ko143 except for Az9. Therefore, the bivalent triazoles are not only superior to the Ko143 in re-sensitization of HEK293/R2 and MCF7-MX100 towards topotecan, but also highly selective for the BCRP transporter.

Summary Comments

In summary, various bioactive alkyne-, azide and triazole-containing flavonoids have been efficiently synthesized. The trizole-containing flavonoids were prepared by the cycloaddition of azide- (Az) with alkyne-containing flavonoids (Ac). These flavonoids displayed promising MDR reversal activity against P-gp-, MRP1- and BCRP-mediated drug resistance. Tables 4 to 8 (shown in FIGS. 4A-4B, 5, 6 7, 8) summarize the MDR reversal activity of different combinations of Ac monomers and Az monomers. For the P-gp modulating activity, the Ac5 monomer was found to be a good lead component for making potent P-gp chemosensitizer as compared to other Ac12, Ac13, Ac15 and Ac16 monomers because the triazoles of Ac5 monomer and various Az monomers exhibited high RF values (Table 4 in FIGS. 4A-4B). For MRP1-modulating activity, Ac16 monomer was demonstrated to be important component for reversing MRP1-mediated DOX drug resistance in 2008/

MRP1 (Table 5 in FIG. 5). Moreover, the combinations of Ac12 monomer with various Az monomers or Az1 monomer with various Ac monomers resulted in relatively potent DOX resistance and vincristine resistance reversal activity (Table 5 in FIG. 5 and Table 6). For the BCRP-modulating activity, Az8, Az9 and Az10 monomers were demonstrated to be potent components for generating BCRP inhibitor because coupling them with any Ac monomer (Ac5, Ac12, Ac13 and Ac15) resulted in a significant BCRP-inhibitory potency in both HEK293/R2 and MCF7-MX100 cells (Table 7 in FIG. 7 and Table 8 in FIG. 8).

Moreover, the active bivalent triazoles showed different levels of selectivity for various transporters. Overall, they can be divided into mono-selective, dual-selective and multi-selective modulators for the P-gp, MRP1 and BCRP transporters (Table 2 in FIGS. 2A-2D). The $EC_{50}$ values for reversing paclitaxel resistance of LCC6MDR (141-340 nM), DOX (78-590 nM) and vincristine (82-550 nM) resistance of 2008/MRP1 were at a nanomolar range (Table 3 in FIGS. 3A-3D). Interestingly, active bivalent triazoles or monomeric azide Az9 showed $EC_{50}$ values for lowering topotecan resistance of HEK293/R2 and MCF7-MX100 at or below 10 nM (Table 3 in FIGS. 3A-3D), indicating that the bivalent triazoles more selectively inhibit BCRP than the P-gp and MRP1. Most of the bivalent triazoles are notably safe MDR chemosensitizers as indicated by their high therapeutic index values (Table 3 in FIGS. 3A-3D). The present study demonstrates that the potential and importance of developing bioactive triazole flavonoid dimers to treat MDR cancers.

Drug resistance in cancer patients renders many patients unresponsive to chemotherapeutic treatments. This new invention can generate a new class of highly potent compounds that can inhibit the mechanism which would otherwise pumps the drugs out of cancer cells, resulting in cancer drug resistance.

Many brain tumors are difficult to treat because of low accumulation of cancer drugs in the brain, mainly due to the drug pump present in the blood brain barrier. Flavonoids developed here can be used to inhibit the pumps and therefore increasing the cancer drug concentration in the brain. This could make an otherwise ineffective cancer drug effective in treating brain tumor.

The approach of the present invention is to target the binding sites of ABC transporter using dimeric flavonoids. We have previously reported that, by using a bivalent approach, synthetic apigenin homodimers with polyethylene glycol (PEG) linker can modulate the P-gp and MRP1 transporters in human cancer[57-59] and parasitic protozoan Leishmania.[60,61] Their reversal activities were much more potent than the monomeric apigenin. These results indicate that the bivalent approach is successful in enhancing the reversal activity of P-gp- and MRP1-mediated resistance. Moreover, the modulating activity of the flavonoid dimers in human MDR cancer cells has recently been optimized by structural modification of the flavonoid ring[58] as well as the PEG linker.

The "click chemistry" is a rapid and versatile strategy for conjugating two molecular fragments under very mild reaction condition. It has been proved to be advantageous in yielding bioactive triazoles in numerous biological settings.[62-65] In this study, a novel series of triazole bridged flavonoid dimers derived from the precursor alkyne- and azide-containing flavonoids has been efficiently synthesized using "click chemistry" approach and their MDR reversal activities have been evaluated on the P-gp-, BCRP-, and MRP1-overexpressed tumor cell lines.

REFERENCES

1. Szakacs, G.; Paterson, J. K.; Ludwig, J. A.; Booth-Genthe, C.; Gottesman, M. M. Targeting multidrug resistance in cancer. *Nat Rev Drug Discov* 2006, 5, 219-34.
2. Perez-Tomas, R. Multidrug resistance: retrospect and prospects in anti-cancer drug treatment. *Curr Med Chem* 2006, 13, 1859-76.
3. Eckford, P. D.; Sharom, F. J. ABC efflux pump-based resistance to chemotherapy drugs. *Chem Rev* 2009, 109, 2989-3011.
4. Gros, P.; Croop, J.; Housman, D. Mammalian multidrug resistance gene: complete cDNA sequence indicates strong homology to bacterial transport proteins. *Cell* 1986, 47, 371-80.
5. Lockhart, A. C.; Tirona, R. G.; Kim, R. B. Pharmacogenetics of ATP-binding cassette transporters in cancer and chemotherapy. *Mol Cancer Ther* 2003, 2, 685-98.
6. Rosenberg, M. F.; Callaghan, R.; Ford, R. C.; Higgins, C. F. Structure of the multidrug resistance P-glycoprotein to 2.5 nm resolution determined by electron microscopy and image analysis. *J Biol Chem* 1997, 272, 10685-94.
7. Hipfner, D. R.; Almquist, K. C.; Leslie, E. M.; Gerlach, J. H.; Grant, C. E.; Deeley, R. G.; Cole, S. P. Membrane topology of the multidrug resistance protein (MRP). A study of glycosylation-site mutants reveals an extracytosolic NH2 terminus. *J Biol Chem* 1997, 272, 23623-30.
8. Kast, C.; Gros, P. Epitope insertion favors a six transmembrane domain model for the carboxy-terminal portion of the multidrug resistance-associated protein. *Biochemistry* 1998, 37, 2305-13.
9. Polgar, O.; Robey, R. W.; Bates, S. E. ABCG2: structure, function and role in drug response. *Expert Opin Drug Metab Toxicol* 2008, 4, 1-15.
10. Xu, J.; Liu, Y.; Yang, Y.; Bates, S.; Zhang, J. T. Characterization of oligomeric human half-ABC transporter ATP-binding cassette G2. *J Biol Chem* 2004, 279, 19781-9.
11. Honorat, M.; Faison, P.; Terreux, R.; Di Pietro, A.; Dumontet, C.; Payen, L. Multidrug resistance ABC transporter structure predictions by homology modeling approaches. *Curr Drug Metab* 2011, 12, 268-77.
12. Klepsch, F.; Jabeen, I.; Chiba, P.; Ecker, G. F. Pharmacoinformatic approaches to design natural product type ligands of ABC-transporters. *Curr Pharm Des* 2010, 16, 1742-52.
13. McDevitt, C. A.; Callaghan, R. How can we best use structural information on P-glycoprotein to design inhibitors? *Pharmacol Ther* 2007, 113, 429-41.
14. Saito, H.; An, R.; Hirano, H.; Ishikawa, T. Emerging new technology: QSAR analysis and MO Calculation to characterize interactions of protein kinase inhibitors with the human ABC transporter, ABCG2 (BCRP). *Drug Metab Pharmacokinet* 2010, 25, 72-83.
15. Hollt, V.; Kouba, M.; Dietel, M.; Vogt, G. Stereoisomers of calcium antagonists which differ markedly in their potencies as calcium blockers are equally effective in modulating drug transport by P-glycoprotein. *Biochem Pharmacol* 1992, 43, 2601-8.
16. Tsuruo, T.; Iida, H.; Nojiri, M.; Tsukagoshi, S.; Sakurai, Y. Circumvention of vincristine and Adriamycin resistance in vitro and in vivo by calcium influx blockers. *Cancer Res* 1983, 43, 2905-10.

17. Tsuruo, T.; Iida, H.; Tsukagoshi, S.; Sakurai, Y. Overcoming of vincristine resistance in P388 leukemia in vivo and in vitro through enhanced cytotoxicity of vincristine and vinblastine by verapamil. *Cancer Res* 1981, 41, 1967-72.
18. Tsuruo, T.; Iida, H.; Kitatani, Y.; Yokota, K.; Tsukagoshi, S.; Sakurai, Y. Effects of quinidine and related compounds on cytotoxicity and cellular accumulation of vincristine and adriamycin in drug-resistant tumor cells. *Cancer Res* 1984, 44, 4303-7.
19. Ganapathi, R.; Grabowski, D.; Turinic, R.; Valenzuela, R. Correlation between potency of calmodulin inhibitors and effects on cellular levels and cytotoxic activity of doxorubicin (adriamycin) in resistant P388 mouse leukemia cells. *Eur J Cancer Clin Oncol* 1984, 20, 799-806.
20. Tsuruo, T.; Iida, H.; Tsukagoshi, S.; Sakurai, Y. Increased accumulation of vincristine and adriamycin in drug-resistant P388 tumor cells following incubation with calcium antagonists and calmodulin inhibitors. *Cancer Res* 1982, 42, 4730-3.
21. Chao, N. J.; Aihara, M.; Blume, K. G.; Sikic, B. I. Modulation of etoposide (VP-16) cytotoxicity by verapamil or cyclosporine in multidrug-resistant human leukemic cell lines and normal bone marrow. *Exp Hematol* 1990, 18, 1193-8.
22. Slater, L. M.; Sweet, P.; Stupecky, M.; Gupta, S. Cyclosporin A reverses vincristine and daunorubicin resistance in acute lymphatic leukemia in vitro. *J Clin Invest* 1986, 77, 1405-8.
23. Slater, L. M.; Sweet, P.; Stupecky, M.; Wetzel, M. W.; Gupta, S. Cyclosporin A corrects daunorubicin resistance in Ehrlich ascites carcinoma. *Br J Cancer* 1986, 54, 235-8.
24. Twentyman, P. R.; Fox, N. E.; White, D. J. Cyclosporin A and its analogues as modifiers of adriamycin and vincristine resistance in a multi-drug resistant human lung cancer cell line. *Br J Cancer* 1987, 56, 55-7.
25. Barnes, K. M.; Dickstein, B.; Cutler, G. B., Jr.; Fojo, T.; Bates, S. E. Steroid treatment, accumulation, and antagonism of P-glycoprotein in multidrug-resistant cells. *Biochemistry* 1996, 35, 4820-7.
26. Gruol, D. J.; Zee, M. C.; Trotter, J.; Bourgeois, S. Reversal of multidrug resistance by RU 486. *Cancer Res* 1994, 54, 3088-91.
27. Ueda, K.; Okamura, N.; Hirai, M.; Tanigawara, Y.; Saeki, T.; Kioka, N.; Komano, T.; Hori, R. Human P-glycoprotein transports cortisol, aldosterone, and dexamethasone, but not progesterone. *J Biol Chem* 1992, 267, 24248-52.
28. Pirker, R.; FitzGerald, D. J.; Raschack, M.; Frank, Z.; Willingham, M. C.; Pastan, I. Enhancement of the activity of immunotoxins by analogues of verapamil. *Cancer Res* 1989, 49, 4791-5.
29. Twentyman, P. R.; Bleehen, N. M. Resistance modification by PSC-833, a novel non-immunosuppressive cyclosporin [corrected]. *Eur J Cancer* 1991, 27, 1639-42.
30. Hofmann, J.; Wolf, A.; Spitaler, M.; Bock, G.; Drach, J.; Ludescher, C.; Grunicke, H. Reversal of multidrug resistance by B859-35, a metabolite of B859-35, niguldipine, verapamil and nitrendipine. *J Cancer Res Clin Oncol* 1992, 118, 361-6.
31. Germann, U. A.; Ford, P. J.; Shlyakhter, D.; Mason, V. S.; Harding, M. W. Chemosensitization and drug accumulation effects of VX-710, verapamil, cyclosporin A, MS-209 and GF120918 in multidrug resistant HL60/ADR cells expressing the multidrug resistance-associated protein MRP. *Anticancer Drugs* 1997, 8, 141-55.
32. Germann, U. A.; Shlyakhter, D.; Mason, V. S.; Zelle, R. E.; Duffy, J. P.; Galullo, V.; Armistead, D. M.; Saunders, J. O.; Boger, J.; Harding, M. W. Cellular and biochemical characterization of VX-710 as a chemosensitizer: reversal of P-glycoprotein-mediated multidrug resistance in vitro. *Anticancer Drugs* 1997, 8, 125-40.
33. Krishna, R.; Mayer, L. D. Multidrug resistance (MDR) in cancer. Mechanisms, reversal using modulators of MDR and the role of MDR modulators in influencing the pharmacokinetics of anticancer drugs. *Eur J Pharm Sci* 2000, 11, 265-83.
34. Thomas, H.; Coley, H. M. Overcoming multidrug resistance in cancer: an update on the clinical strategy of inhibiting p-glycoprotein. *Cancer Control* 2003, 10, 159-65.
35. Gekeler, V.; Ise, W.; Sanders, K. H.; Ulrich, W. R.; Beck, J. The leukotriene LTD4 receptor antagonist MK571 specifically modulates MRP associated multidrug resistance. *Biochem Biophys Res Commun* 1995, 208, 345-52.
36. Payen, L.; Delugin, L.; Courtois, A.; Trinquart, Y.; Guillouzo, A.; Fardel, O. The sulphonylurea glibenclamide inhibits multidrug resistance protein (MRP1) activity in human lung cancer cells. *Br J Pharmacol* 2001, 132, 778-84.
37. Gollapudi, S.; Kim, C. H.; Tran, B. N.; Sangha, S.; Gupta, S. Probenecid reverses multidrug resistance in multidrug resistance-associated protein-overexpressing HL60/AR and H69/AR cells but not in P-glycoprotein-overexpressing HL60/Tax and P388/ADR cells. *Cancer Chemother Pharmacol* 1997, 40, 150-8.
38. Draper, M. P.; Martell, R. L.; Levy, S. B. Indomethacin-mediated reversal of multidrug resistance and drug efflux in human and murine cell lines overexpressing MRP, but not P-glycoprotein. *Br J Cancer* 1997, 75, 810-5.
39. Duffy, C. P.; Elliott, C. J.; O'Connor, R. A.; Heenan, M. M.; Coyle, S.; Cleary, I. M.; Kavanagh, K.; Verhaegen, S.; O'Loughlin, C. M.; NicAmhlaoibh, R.; Clynes, M. Enhancement of chemotherapeutic drug toxicity to human tumour cells in vitro by a subset of non-steroidal anti-inflammatory drugs (NSAIDs). *Eur J Cancer* 1998, 34, 1250-9.
40. Li, Y.; Hayman, E.; Plesescu, M.; Rrakash, S. Synthesis of potent BCRP inhibitor-Ko143. *Tetrahedron Lett* 2008, 49, 1480-1483.
41. Wang, L.; Leggas, M.; Goswami, M.; Empey, P. E.; McNamara, P. J. N-(4-[2-(1,2,3,4-tetrahydro-6,7-dimethoxy-2-isoquinolinyl)ethyl]-phenyl)-9,10-dihydro-5-methoxy-9-oxo-4-acridine carboxamide (GF120918) as a chemical ATP-binding cassette transporter family G member 2 (Abcg2) knockout model to study nitrofurantoin transfer into milk. *Drug Metab Dispos* 2008, 36, 2591-6.
42. Kuhnle, M.; Egger, M.; Muller, C.; Mahringer, A.; Bernhardt, G.; Fricker, G.; Konig, B.; Buschauer, A. Potent and selective inhibitors of breast cancer resistance protein (ABCG2) derived from the p-glycoprotein (ABCB1) modulator tariquidar. *J Med Chem* 2009, 52, 1190-7.
43. Harborne, J. B. Nature, distribution and function of plant flavonoids. *Prog Clin Biol Res* 1986, 213, 15-24.
44. Castro, A. F.; Altenberg, G. A. Inhibition of drug transport by genistein in multidrug-resistant cells expressing P-glycoprotein. *Biochem Pharmacol* 1997, 53, 89-93.
45. de Castro, W. V.; Mertens-Talcott, S.; Derendorf, H.; Butterweck, V. Effect of grapefruit juice, naringin, naringenin, and bergamottin on the intestinal carrier-mediated transport of talinolol in rats. *J Agric Food Chem* 2008, 56, 4840-5.
46. Limtrakul, P.; Khantamat, O.; Pintha, K. Inhibition of P-glycoprotein function and expression by kaempferol and quercetin. *J Chemother* 2005, 17, 86-95.
47. Mitsunaga, Y.; Takanaga, H.; Matsuo, H.; Naito, M.; Tsuruo, T.; Ohtani, H.; Sawada, Y. Effect of bioflavonoids on vincristine transport across blood-brain barrier. *Eur J Pharmacol* 2000, 395, 193-201.
48. Zhang, S.; Morris, M. E. Effect of the flavonoids biochanin A and silymarin on the P-glycoprotein-mediated transport of digoxin and vinblastine in human intestinal Caco-2 cells. *Pharm Res* 2003, 20, 1184-91.
49. Zhang, S.; Sagawa, K.; Arnold, R. D.; Tseng, E.; Wang, X.; Morris, M. E. Interactions between the flavonoid biochanin A and P-glycoprotein substrates in rats: in vitro and in vivo. *J Pharm Sci* 2010, 99, 430-41.
50. Leslie, E. M.; Mao, Q.; Oleschuk, C. J.; Deeley, R. G.; Cole, S. P. Modulation of multidrug resistance protein 1 (MRP1/ABCC1) transport and atpase activities by interaction with dietary flavonoids. *Mol Pharmacol* 2001, 59, 1171-80.
51. Nguyen, H.; Zhang, S.; Morris, M. E. Effect of flavonoids on MRP1-mediated transport in Panc-1 cells. *J Pharm Sci* 2003, 92, 250-7.
52. van Zanden, J. J.; Wortelboer, H. M.; Bijlsma, S.; Punt, A.; Usta, M.; Bladeren, P. J.; Rietjens, I. M.; Cnubben, N. H. Quantitative structure activity relationship studies on the flavonoid mediated inhibition of multidrug resistance proteins 1 and 2. *Biochem Pharmacol* 2005, 69, 699-708.
53. Cooray, H. C.; Janvilisri, T.; van Veen, H. W.; Hladky, S. B.; Barrand, M. A. Interaction of the breast cancer resistance protein with plant polyphenols. *Biochem Biophys Res Commun* 2004, 317, 269-75.
54. Imai, Y.; Tsukahara, S.; Asada, S.; Sugimoto, Y. Phytoestrogens/flavonoids reverse breast cancer resistance protein/ABCG2-mediated multidrug resistance. *Cancer Res* 2004, 64, 4346-52.
55. Yoshikawa, M.; Ikegami, Y.; Sano, K.; Yoshida, H.; Mitomo, H.; Sawada, S.; Ishikawa, T. Transport of SN-38 by the wild type of human ABC transporter ABCG2 and its inhibition by quercetin, a natural flavonoid. *J Exp Ther Oncol* 2004, 4, 25-35.
56. Zhang, S.; Yang, X.; Morris, M. E. Flavonoids are inhibitors of breast cancer resistance protein (ABCG2)-mediated transport. *Mol Pharmacol* 2004, 65, 1208-16.
57. Chan, K. F.; Zhao, Y.; Burkett, B. A.; Wong, I. L.; Chow, L. M.; Chan, T. H. Flavonoid dimers as bivalent modulators for P-glycoprotein-based multidrug resistance: synthetic apigenin homodimers linked with defined-length poly(ethylene glycol) spacers increase drug retention and enhance chemosensitivity in resistant cancer cells. *J Med Chem* 2006, 49, 6742-59.
58. Chan, K. F.; Zhao, Y.; Chow, T. W.; Yan, C. S.; Ma, D. L.; Burkett, B. A.; Wong, I. L.; Chow, L. M.; Chan, T. H. Flavonoid dimers as bivalent modulators for p-glycoprotein-based multidrug resistance: structure-activity relationships. *ChemMedChem* 2009, 4, 594-614.
59. Wong, I. L.; Chan, K. F.; Tsang, K. H.; Lam, C. Y.; Zhao, Y.; Chan, T. H.; Chow, L. M. Modulation of multidrug resistance protein 1 (MRP1/ABCC1)-mediated multidrug resistance by bivalent apigenin homodimers and their derivatives. *J Med Chem* 2009, 52, 5311-22.
60. Wong, I. L.; Chan, K. F.; Burkett, B. A.; Zhao, Y.; Chai, Y.; Sun, H.; Chan, T. H.; Chow, L. M. Flavonoid dimers as bivalent modulators for pentamidine and sodium stiboglucanate resistance in *leishmania*. *Antimicrob Agents Chemother* 2007, 51, 930-40.
61. Wong, I. L.; Chan, K. F.; Zhao, Y.; Chan, T. H.; Chow, L. M. Quinacrine and a novel apigenin dimer can synergistically increase the pentamidine susceptibility of the protozoan parasite *Leishmania*. *J Antimicrob Chemother* 2009, 63, 1179-90.
62. Boechat, N.; Ferreira, V. F.; Ferreira, S. B.; Ferreira, M. D.; da Silva, F. D.; Bastos, M. M.; Costa, M. D.; Lourenco, M. C.; Pinto, A. C.; Krettli, A. U.; Aguiar, A. C.; Teixeira, B. M.; da Silva, N. V.; Martins, P. R.; Bezerra, F. A.; Camilo, A. L.; da Silva, G. P.; Costa, C. C. Novel 1,2,3-Triazole Derivatives for Use against *Mycobacterium tuberculosis* H37Rv (ATCC 27294) Strain. *J Med Chem* 2011, 54, 5988-5999.
63. Kumar, S.; Arya, D. P. Recognition of HIV TAR RNA by triazole linked neomycin dimers. *Bioorg Med Chem Lett* 2011, 21, 4788-92.
64. Wangler, C.; Schafer, M.; Schirrmacher, R.; Bartenstein, P.; Wangler, B. DOTA derivatives for site-specific biomolecule-modification via click chemistry: synthesis and comparison of reaction characteristics. *Bioorg Med Chem* 2011, 19, 3864-74.
65. Zhang, H. L.; He, X. P.; Sheng, L.; Yao, Y.; Zhang, W.; Shi, X. X.; Li, J.; Chen, G. R. Synthesis of novel 6-triazologlycolipids via click chemistry and their preliminary cytotoxicity assessments. *Mol Divers* 2011.
66. Gujadhur, R.; Venkataraman, D.; Kintigh, J. T. Formation of aryl-nitrogen bonds using a soluble copper(I) catalyst. *Tetrahedron Lett.* 2001, 42, 4791-4793.
67. Zhang, P. Y.; Wong, I. L.; Yan, C. S.; Zhang, X. Y.; Jiang, T.; Chow, L. M.; Wan, S. B. Design and syntheses of permethyl ningalin B analogues: potent multidrug resistance (MDR) reversal agents of cancer cells. *J Med Chem* 2010, 53, 5108-20.
68. Zhang, L.; Chen, X.; Xue, P.; Sun, H. H.; Williams, I. D.; Sharpless, K. B.; Fokin, V. V.; Jia, G. Ruthenium-catalyzed cycloaddition of alkynes and organic azides. *J Am Chem Soc* 2005, 127, 15998-9.
69. Rasmussen, L. K.; Boren, B. C.; Fokin, V. V. Ruthenium-catalyzed cycloaddition of aryl azides and alkynes. *Org Lett* 2007, 9, 5337-9.
70. Soenen, D. R.; Hwang, I.; Hedrick, M. P.; Boger, D. L. Multidrug resistance reversal activity of key ningalin analogues. *Bioorg Med Chem Lett* 2003, 13, 1777-81.
71. Tao, H.; Hwang, I.; Boger, D. L. Multidrug resistance reversal activity of permethyl ningalin B amide derivatives. *Bioorg Med Chem Lett* 2004, 14, 5979-81.
72. McDevitt, C. A.; Collins, R. F.; Conway, M.; Modok, S.; Storm, J.; Kerr, I. D.; Ford, R. C.; Callaghan, R. Purification and 3D structural analysis of oligomeric human multidrug transporter ABCG2. *Structure* 2006, 14, 1623-32.
73. Mao, Q.; Unadkat, J. D. Role of the breast cancer resistance protein (ABCG2) in drug transport. *AAPS J* 2005, 7, E118-33.
74. Loo, T. W.; Clarke, D. M. Determining the dimensions of the drug-binding domain of human P-glycoprotein using thiol cross-linking compounds as molecular rulers. *J Biol Chem* 2001, 276, 36877-80.
75. Honjo, Y.; Hrycyna, C. A.; Yan, Q. W.; Medina-Perez, W. Y.; Robey, R. W.; van de Laar, A.; Litman, T.; Dean, M.; Bates, S. E. Acquired mutations in the MXR/BCRP/ABCP gene alter substrate specificity in MXR/BCRP/ABCP-overexpressing cells. *Cancer Res* 2001, 61, 6635-9.

The IC$_{50}$ value was determined after exposure to a series of anti-cancer drugs including paclitaxel, DOX, vincristine and topotecan with different triazole, azide or acetylene compounds using LCC6MDR, 2008/MRP1, HEK293/R2 and MCF7-MX100 cells, as described in the experiment section. Relative fold (RF)=(IC$_{50}$ without modulator)/(IC$_{50}$ with modulator), % of reversion=(IC$_{50}$ of wild type)/(IC$_{50}$ of resistant cells with modulators)×100%. Positive controls including verapamil, cyclosporine A, PSC833, 1d(5,7H-6Me)n=5 and Ko143 were included for comparison. N=1-8 independent experiments and values were presented as mean±standard error of mean.[a] All compounds were dissolved in DMSO for testing and the final % of DMSO was 0.05% and 0.1%.[b] The triazole dimers were tested at 1.0 μM.[c] The triazole dimers were tested at 0.5 μM.[d] The monomers were tested at 2.0 μM.[e] 1.0 μM of Ac monomer and 1.0 μM of Az monomer were combined for testing.[f] LCC6MDR, HEK293/R2, MCF7-MX100 and 2008/MRP1 were used without modulators.[g] LCC6, 2008/P, HEK293/pcDNA3.1 and MCF7 were used without modulators. For cytotoxicity assay, IC$_{50}$ of different triazole compounds for LCC6, LCC6MDR, 2008/P, 2008/MRP1 and L929 cell lines were determined. N=1-3 independent experiment and the values were presented as mean±standard error of mean. L929: mouse fibroblasts. ND=not determined.

The selectivity of active triazole compounds for various ABC transporters was determined from the Table 1 shown in FIGS. 1A-1P. It would be considered as strongly selective if it causes >80% of reversion. It would be considered as moderately selective if it results in 79-50% of reversion. Overall, the active triazole compounds can be divided into mono-, dual- and multi-selective for P-gp, MRP1 and BCRP transporters.

EC$_{50}$ values were presented as mean±standard error of mean. N=1-4 independent experiments. Therapeutic index= (IC$_{50}$ of triazoles towards L929 fibroblasts or Raw264.7 cells)/(EC$_{50}$ of triazoles for reversing drug resistance). ND=not determined.

The P-gp modulating activity of different triazole dimers was measured as relative fold (RF). RF=(IC$_{50}$ without modulator)/(IC$_{50}$ with modulator). A color gradient was used to discriminate a low-to-high reversal activity of dimers. The pale color represents the low RF values and the dark color represents the high RF values. ND=not determined.

The DOX resistance reversal activity of different triazole dimers was measured as relative fold (RF). RF=(IC$_{50}$ without modulator)/(IC$_{50}$ with modulator). A color gradient was used to discriminate a low-to-high reversal activity of dimers. The pale color represents the low RF values and the dark color represents the high RF values. ND=not determined.

The vincrisitine resistance reversal activity of different triazole dimers was measured as relative fold (RF). RF= (IC$_{50}$ without modulator)/(IC$_{50}$ with modulator). A color gradient was used to discriminate a low-to-high reversal activity of dimers. The pale color represents the low RF values and the dark color represents the high RF values. ND=not determined.

The BCRP-modulating activity of different triazole dimers was measured as relative fold (RF). RF=(IC$_{50}$ without modulator)/(IC$_{50}$ with modulator). A color gradient was used to discriminate a low-to-high reversal activity of dimers. The pale color represents the low RF values and the dark color represents the high RF values. ND=not determined.

The BCRP-modulating activity of different triazole dimers was measured as relative fold (RF). RF=(IC$_{50}$ without modulator)/(IC$_{50}$ with modulator). A color gradient was used to discriminate a low-to-high reversal activity of dimers. The pale color represents the low RF values and the dark color represents the high RF values. ND=not determined.

Scheme 1. Synthesis of acetylenes Ac1 to Ac14, Ac16 and structures of Ac15 and Ac17.[a]

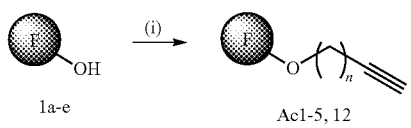

1a-e    Ac1-5, 12

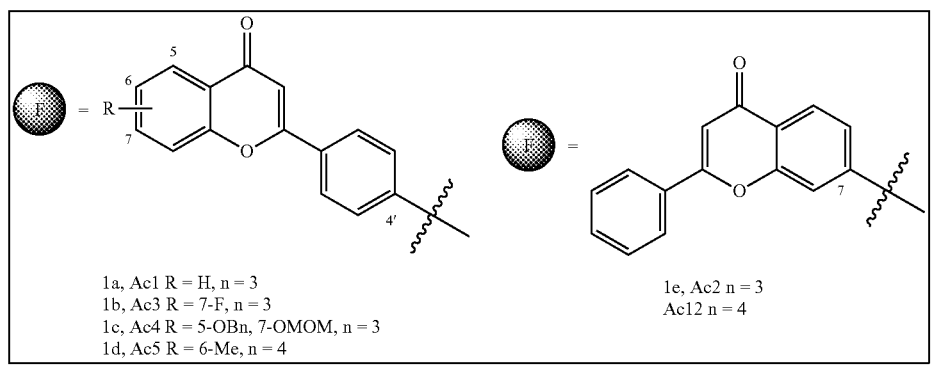

1a, Ac1 R = H, n = 3
1b, Ac3 R = 7-F, n = 3
1c, Ac4 R = 5-OBn, 7-OMOM, n = 3
1d, Ac5 R = 6-Me, n = 4

1e, Ac2 n = 3
Ac12 n = 4

-continued
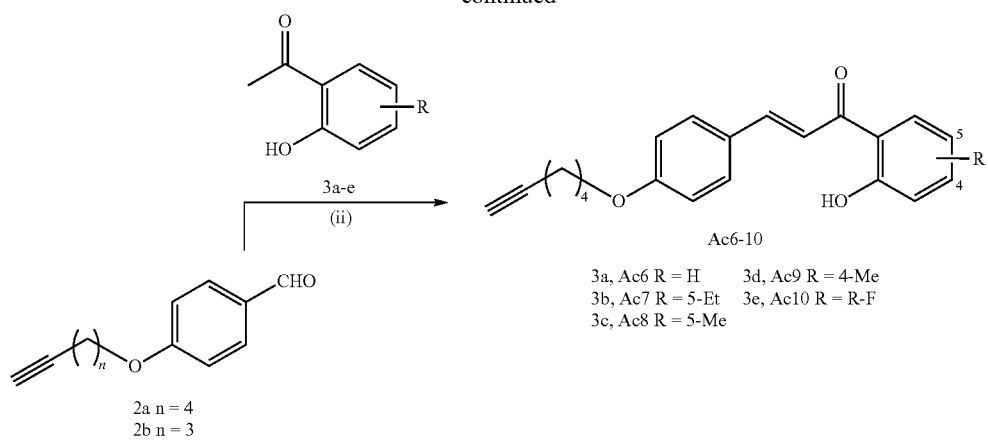
3a, Ac6 R = H    3d, Ac9 R = 4-Me
3b, Ac7 R = 5-Et  3e, Ac10 R = R-F
3c, Ac8 R = 5-Me
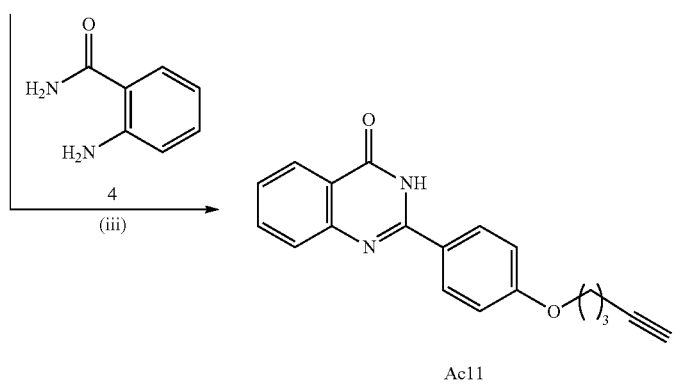
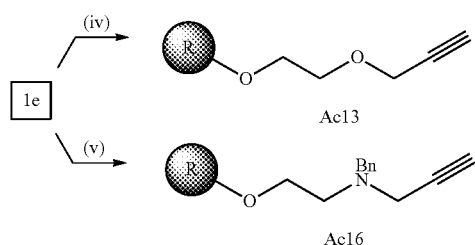
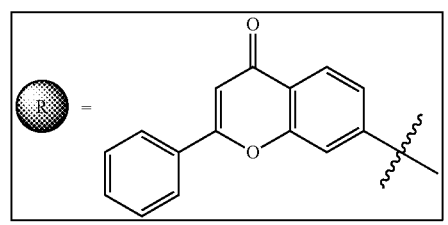
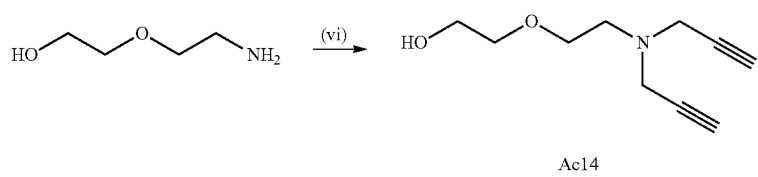

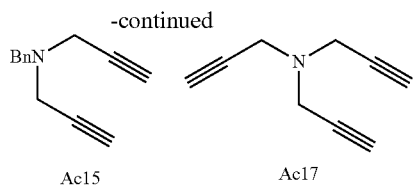

Ac15  Ac17

<sup>a</sup>Reagents and condition:
(i) K₂CO₃, 6-chloro-1-hexyne or 5-chloro-1-pentyne, DMF, reflux;
(ii) KOH, EtOH, rt;
(iii) I₂, DSMO, 150° C.;
(iv) (a) K₂CO₃, 2-bromoethanol, DMF, reflux; (b) NaH, propargyl bromide solution, anhy. THF;
(v) 2-(benzyl(prop-2-yn-1-yl)amino)ethanol, PPh₃, DIAD, THF;
(vi) propargyl bromide solution, acetone, rt;

Ac15 and Ac17 are commercially available. Ac15 can also be prepared by mixing 2 equiv. of propargyl bromide with benzyl amine.

Scheme 2. Synthesis of azides Az1 to Az15.<sup>a</sup>

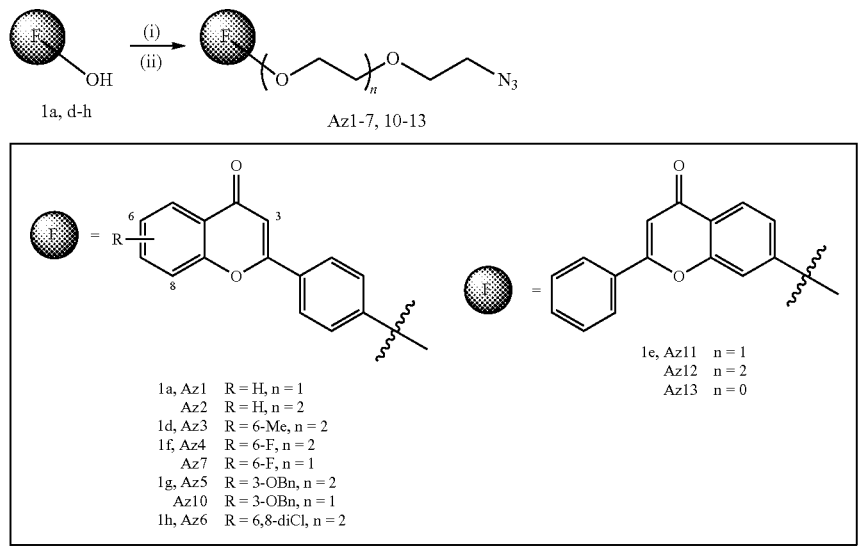

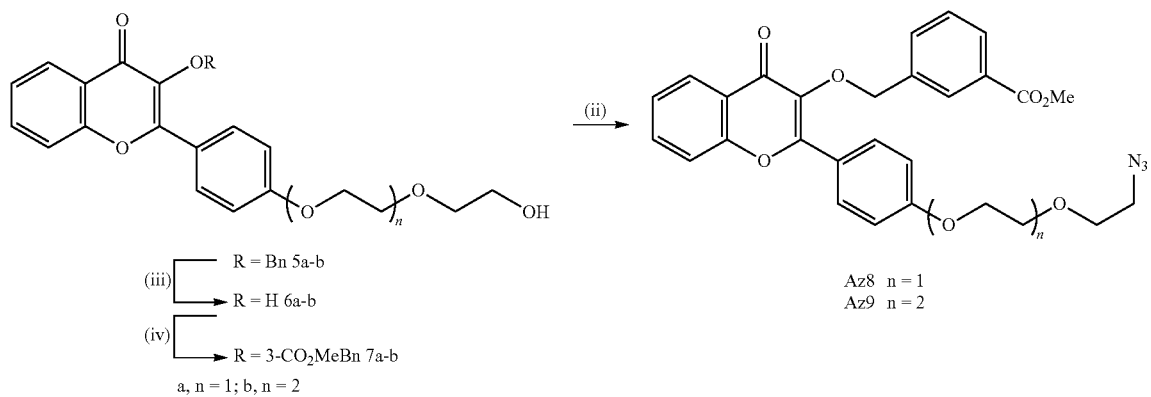

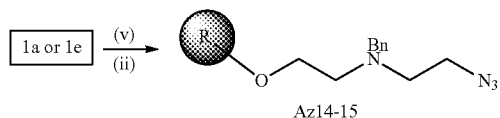

-continued

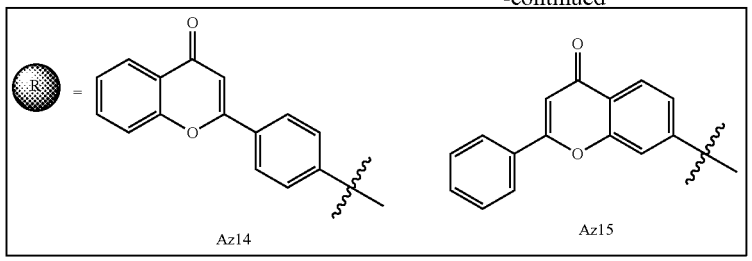

<sup>a</sup>Reagents and condition: (i) K₂CO₃, 2-bromoethanol or 2-(2-chloroethoxy)ethanol or 2-(2-(2-chloroethoxy)ethoxy)ethanol, DMF, reflux; (ii) (a) methanesulfonyl chloride, NEt₃, DCM, 0° C.; (b) NaN₃, ACN; (iii) H₂, Pd/C, MeOH, rt; (iv) K₂CO₃, methyl 3-(bromomethyl)benzoate, acetone, reflux; (v) 2,2′-(benzylimino)-diethanol, PPh₃, DIAD, THF;

Scheme 3. Synthesis of triazole bridged flavonoid dimers.<sup>a</sup>

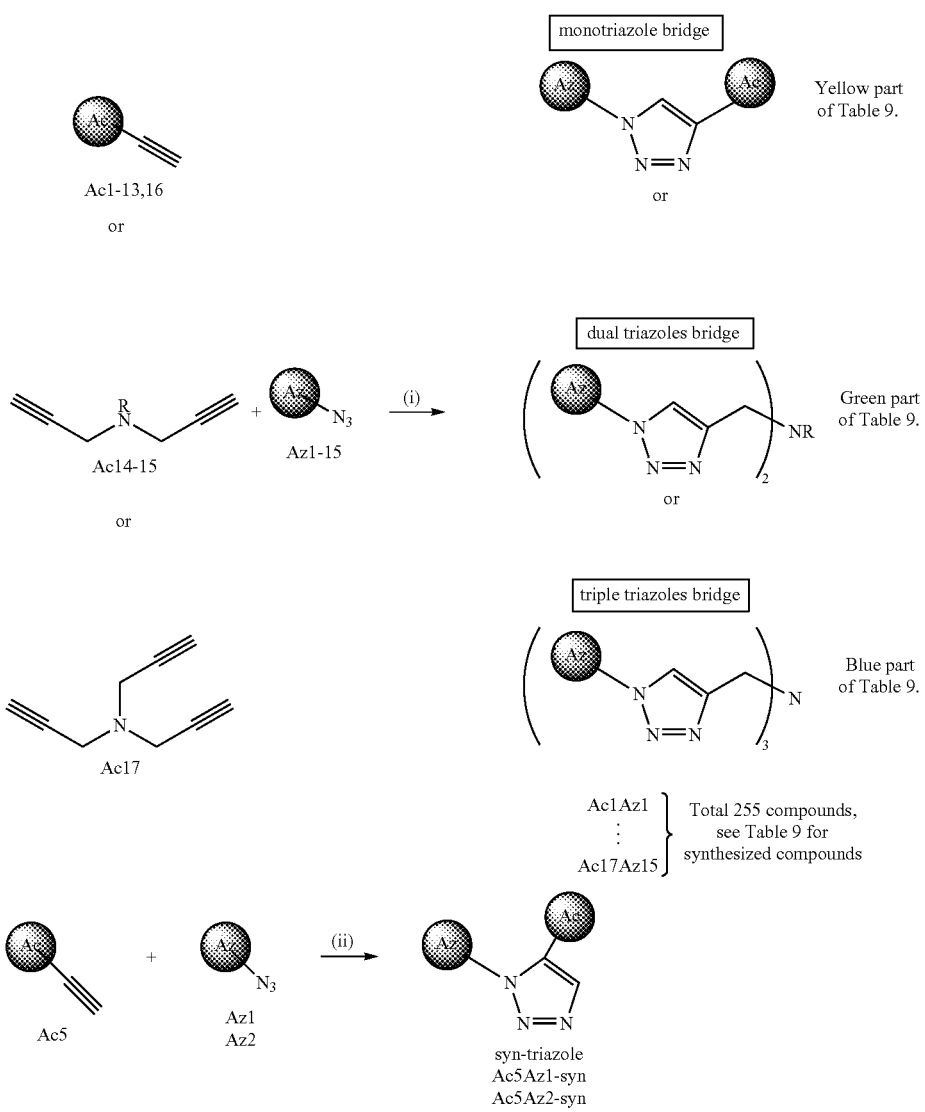

<sup>a</sup>Reagents and condition: (i) cat. Cu(PPh₃)₃Br, THF, reflux, 12 hr; (ii) cat. Cp*RuCl(PPh₃)₂, PhMe, reflux, 12 hr.

Scheme 4. Deprotection of triazole bridged flavonoid dimers.[a]

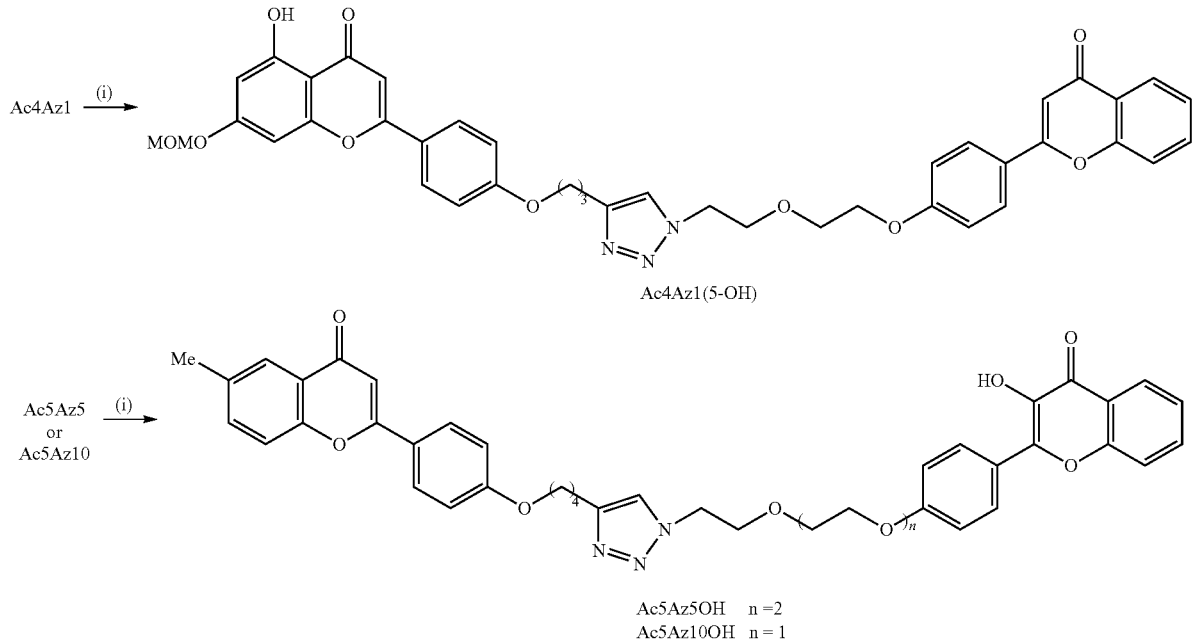

[a]Reagents and condition: (i) H₂, Pd/C, MeOH, rt.

The invention claimed is:

1. A compound of formula I:

flavonoid-linker-X     I wherein

X is CCH or $N_3$;

the flavonoid is selected from the group consisting of, flavone, flavonol, flavanone, anthocyanin, and isoflavonoid; and the linker is a group having at least one carbon atom and an oxygen atom, wherein the flavonoid is connected to the linker by the oxygen atom, wherein the linker is a group having a plurality of alkylene units, a group having a plurality of ethylene glycol units, a group having a plurality of propylene glycol units, a group having a plurality of amino ethylene units, or a combination thereof.

2. The compound of claim 1, wherein X is CCH.

3. The compound of claim 1, wherein X is $N_3$.

4. A method of reducing P-glycoprotein based multidrug resistance including the step of administering an effective amount of a compound of formula I as defined in claim 1.

5. A method of reducing MRP1-based multidrug resistance including the step of administering an effective amount of a compound of formula I as defined in claim 1.

6. A method of reducing BCRP-based multidrug resistance including the step of administering an effective amount of a compound of formula I as defined in claim 1.

7. A method of reducing resistance of a drug caused by overexpression of ABC transporters including the step of administering an effective amount of a compound of formula I as defined in claim 1.

8. A method of treating drug-resistance cancers caused by overexpression of ABC transporters including the step of administering an effective amount of a compound of formula I as defined in claim 1.

9. The compound of claim 1 being: Methyl 3-(((2-(4-(2-(2-(2-azidoethoxy)ethoxy)ethoxy)phenyl)-4-oxo-4H-chromen-3-yl)oxy)methyl)benzoate.

* * * * *

UNITED STATES PATENT AND TRADEMARK OFFICE
CERTIFICATE OF CORRECTION

PATENT NO. : 10,208,025 B2
APPLICATION NO. : 15/296471
DATED : February 19, 2019
INVENTOR(S) : Chow et al.

It is certified that error appears in the above-identified patent and that said Letters Patent is hereby corrected as shown below:

On the Title Page

Page 3, Item (56), References Cited, Other Publications:
"Szakacs et al., "Targeting multidrug resistance in cancer," *Nature Reviews* 5:219-234, 2006." should read --Szakács et al., "Targeting multidrug resistance in cancer," *Nature Reviews* 5:219-234, 2006.--

Page 3, Item (56), References Cited, Other Publications:
"Wang et al., "N-(4-[2-(1,2,3,4-Tetrahydro-6, 7-dimethoxy-2-isoquinolinypethyl]-phenyl)-9, 10-dihydro-5-methoxy-9-oxo-4-acridine Carboxamide (GF120918) as a Chemical ATP-Binding Cassette Transporter Family G Member 2 (Abcg2) Knockout Model to Study Nitrofurantoin Transfer into Milk," *Drug Metabolism and Disposition* 36(12):2591-2596, 2008." should read --Wang et al., "*N*-(4-[2-(1,2,3,4-Tetrahydro-6, 7-dimethoxy-2-isoquinolinyl)ethyl]-phenyl)-9, 10-dihydro-5-methoxy-9-oxo-4-acridine Carboxamide (GF120918) As a Chemical ATP-Binding Cassette Transporter Family G Member 2 (Abcg2) Knockout Model to Study Nitrofurantoin Transfer into Milk," *Drug Metabolism and Disposition* 36(12):2591-2596, 2008.--

Signed and Sealed this
Eighth Day of September, 2020

Andrei Iancu
*Director of the United States Patent and Trademark Office*